(12) United States Patent
Babu et al.

(10) Patent No.: US 11,638,706 B2
(45) Date of Patent: May 2, 2023

(54) METHODS FOR TREATING HUNTINGTON'S DISEASE

(71) Applicant: PTC Therapeutics, Inc., South Plainfield, NJ (US)

(72) Inventors: Suresh Babu, Pennington, NJ (US); Anuradha Bhattacharyya, Edison, NJ (US); Seongwoo Hwang, Edison, NJ (US); Minakshi Jani, Iselin, NJ (US); Young-choon Moon, Belle Mead, NJ (US); Nadiya Sydorenko, Princeton, NJ (US)

(73) Assignee: PTC Therapeutics, Inc., South Plainfield, NJ (US)

( * ) Notice: Subject to any disclaimer, the term of this patent is extended or adjusted under 35 U.S.C. 154(b) by 0 days.

(21) Appl. No.: 17/093,194

(22) Filed: Nov. 9, 2020

(65) Prior Publication Data

US 2021/0275526 A1 Sep. 9, 2021

Related U.S. Application Data

(60) Continuation of application No. 16/710,515, filed on Dec. 11, 2019, now Pat. No. 10,881,658, which is a
(Continued)

(51) Int. Cl.
| | | |
|---|---|---|
| *C07D 417/14* | (2006.01) | |
| *A61K 31/4468* | (2006.01) | |
| *A61K 31/506* | (2006.01) | |
| *A61K 31/433* | (2006.01) | |
| *C07D 403/14* | (2006.01) | |
| *C07D 405/14* | (2006.01) | |
| *C07D 401/12* | (2006.01) | |
| *C07D 417/04* | (2006.01) | |
| *C07D 487/04* | (2006.01) | |
| *C07D 401/04* | (2006.01) | |
| *C07D 409/14* | (2006.01) | |
| *C07D 487/10* | (2006.01) | |
| *C07D 237/20* | (2006.01) | |
| *C07D 471/10* | (2006.01) | |
| *C07D 413/14* | (2006.01) | |
| *C07D 487/08* | (2006.01) | |
| *C07D 405/12* | (2006.01) | |

(Continued)

(52) U.S. Cl.
CPC .......... *A61K 31/506* (2013.01); *A61K 31/415* (2013.01); *A61K 31/433* (2013.01); *A61K 31/4439* (2013.01); *A61K 31/4709* (2013.01); *A61K 31/50* (2013.01); *A61K 31/501* (2013.01); *A61K 31/517* (2013.01); *A61K 31/5377* (2013.01); *A61K 31/5513* (2013.01); *A61P 25/28* (2018.01); *C07D 237/20* (2013.01); *C07D 401/04* (2013.01); *C07D 401/12* (2013.01); *C07D 401/14* (2013.01); *C07D 403/10* (2013.01); *C07D 403/12* (2013.01); *C07D 403/14* (2013.01); *C07D 405/12* (2013.01); *C07D 405/14* (2013.01); *C07D 409/14* (2013.01); *C07D 413/14* (2013.01); *C07D 417/04* (2013.01); *C07D 417/10* (2013.01); *C07D 417/12* (2013.01); *C07D 417/14* (2013.01); *C07D 471/08* (2013.01); *C07D 471/10* (2013.01); *C07D 487/04* (2013.01); *C07D 487/08* (2013.01); *C07D 487/10* (2013.01); *G01N 33/6896* (2013.01); *G01N 2800/2835* (2013.01)

(58) Field of Classification Search
CPC .... C07D 417/14; A61K 31/4468; A61P 25/00
USPC .......................................... 546/209; 514/326
See application file for complete search history.

(56) References Cited

U.S. PATENT DOCUMENTS

| | | | |
|---|---|---|---|
| 3,558,618 | A | 1/1971 | Trepanier |
| 4,122,274 | A | 10/1978 | Juby |

(Continued)

FOREIGN PATENT DOCUMENTS

| | | |
|---|---|---|
| DE | 2345064 A1 | 4/1974 |
| EP | 1227084 A1 | 7/2002 |

(Continued)

OTHER PUBLICATIONS

Chloé Copin et al, "SnAr versus Buchwald-Hartwig Amination/Amidation in the Imidazo[2,1-b][1,3,4]thiadiazole Series", European Journal of Organic Chemistry, vol. 2015(31), Sep. 29, 2015, p. 6932-6942.

(Continued)

*Primary Examiner* — Charanjit Aulakh
(74) *Attorney, Agent, or Firm* — Hoffmann & Baron, LLP

(57) ABSTRACT

The present description relates to compounds, forms, and pharmaceutical compositions thereof and methods of using such compounds, forms, or compositions thereof for treating or ameliorating Huntington's disease.

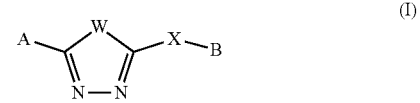

In particular, the present description relates to substituted monocyclic heteroaryl compounds of Formula (I), forms and pharmaceutical compositions thereof and methods of using such compounds, forms, or compositions thereof for treating or ameliorating Huntington's disease.

8 Claims, No Drawings

Related U.S. Application Data division of application No. 15/781,303, filed as application No. PCT/US2016/066042 on Dec. 11, 2016, now Pat. No. 10,874,672.

(60) Provisional application No. 62/265,652, filed on Dec. 10, 2015.

(51) Int. Cl.

| | |
|---|---|
| *C07D 403/10* | (2006.01) |
| *C07D 471/08* | (2006.01) |
| *C07D 403/12* | (2006.01) |
| *C07D 417/10* | (2006.01) |
| *C07D 401/14* | (2006.01) |
| *C07D 417/12* | (2006.01) |
| *A61K 31/50* | (2006.01) |
| *A61K 31/415* | (2006.01) |
| *A61P 25/28* | (2006.01) |
| *A61K 31/4439* | (2006.01) |
| *A61K 31/4709* | (2006.01) |
| *A61K 31/501* | (2006.01) |
| *A61K 31/517* | (2006.01) |
| *A61K 31/5377* | (2006.01) |
| *A61K 31/5513* | (2006.01) |
| *G01N 33/68* | (2006.01) |

(56) References Cited

U.S. PATENT DOCUMENTS

| | | | |
|---|---|---|---|
| 4,342,870 A | 8/1982 | Kennis et al. | |
| 5,089,633 A | 2/1992 | Powers et al. | |
| 5,599,816 A | 2/1997 | Chu et al. | |
| 5,627,274 A | 5/1997 | Kole et al. | |
| 5,665,593 A | 9/1997 | Kole et al. | |
| 5,916,808 A | 6/1999 | Kole et al. | |
| 5,916,916 A | 6/1999 | Hauser et al. | |
| 5,976,879 A | 11/1999 | Kole et al. | |
| 6,172,216 B1 | 1/2001 | Bennett et al. | |
| 6,210,892 B1 | 4/2001 | Bennett et al. | |
| 6,214,986 B1 | 4/2001 | Bennett et al. | |
| 6,468,607 B1 | 10/2002 | Takehara et al. | |
| 6,630,488 B1 | 10/2003 | Lamothe et al. | |
| 6,977,255 B2 | 12/2005 | Robertson et al. | |
| 7,326,711 B2 | 2/2008 | Wang et al. | |
| 7,399,767 B2 | 7/2008 | Zhang et al. | |
| 7,569,337 B2 | 8/2009 | Auberson | |
| 7,655,657 B2 | 2/2010 | Stoner et al. | |
| 7,897,792 B2 | 3/2011 | Iikuea et al. | |
| 7,910,578 B2 | 3/2011 | Peters et al. | |
| 8,143,274 B2 | 3/2012 | Hattori et al. | |
| 8,314,119 B2 | 11/2012 | Schrimpf et al. | |
| 8,337,941 B2 | 12/2012 | Gubernator et al. | |
| 8,563,550 B2 | 10/2013 | Pevarello et al. | |
| 8,633,019 B2 | 1/2014 | Paushkin et al. | |
| 8,846,661 B2 | 9/2014 | Schrimpf et al. | |
| 8,921,361 B2 | 12/2014 | Cmiljanovic et al. | |
| 9,040,712 B2* | 5/2015 | Axford | C07D 487/20 548/136 |
| 9,371,336 B2 | 6/2016 | Lee et al. | |
| 9,399,649 B2 | 7/2016 | Chen et al. | |
| 9,617,268 B2 | 4/2017 | Woll et al. | |
| 9,969,754 B2 | 5/2018 | Ratni et al. | |
| 2002/0099208 A1 | 7/2002 | Yu et al. | |
| 2003/0004164 A1 | 1/2003 | Bebbington et al. | |
| 2003/0199526 A1 | 10/2003 | Choquette et al. | |
| 2005/0054836 A1 | 3/2005 | Krainer et al. | |
| 2005/0074801 A1 | 4/2005 | Monia et al. | |
| 2005/0159597 A1 | 7/2005 | Ji et al. | |
| 2006/0172962 A1 | 8/2006 | Vickers et al. | |
| 2006/0205741 A1 | 9/2006 | Zhang et al. | |
| 2007/0078144 A1 | 4/2007 | Stockwell et al. | |
| 2007/0105807 A1 | 5/2007 | Sazani et al. | |
| 2007/0191374 A1 | 8/2007 | Hodgetts | |
| 2008/0171792 A1 | 7/2008 | Jobdevairakkam et al. |
| 2008/0255162 A1 | 10/2008 | Bruendl et al. |
| 2009/0163464 A1 | 6/2009 | Black et al. |
| 2009/0163515 A1 | 6/2009 | Birault et al. |
| 2009/0170793 A1 | 7/2009 | Gaur |
| 2009/0264433 A1 | 10/2009 | Russell et al. |
| 2010/0004233 A1 | 1/2010 | Iikura et al. |
| 2010/0035279 A1 | 2/2010 | Gubernator et al. |
| 2010/0267721 A1 | 10/2010 | Hohlweg et al. |
| 2011/0086833 A1 | 4/2011 | Paushkin et al. |
| 2011/0118289 A1 | 5/2011 | Giordani et al. |
| 2012/0083495 A1 | 4/2012 | Heemskerk et al. |
| 2014/0051672 A1 | 2/2014 | Cheung et al. |
| 2014/0121197 A1 | 5/2014 | Burli et al. |
| 2014/0206661 A1 | 7/2014 | Axford et al. |
| 2014/0329825 A1 | 11/2014 | Heback et al. |
| 2015/0005289 A1 | 1/2015 | Qi et al. |
| 2015/0018301 A1 | 1/2015 | Lee et al. |
| 2015/0057218 A1 | 2/2015 | Zhong et al. |
| 2015/0080383 A1 | 3/2015 | Yang et al. |
| 2015/0119380 A1 | 4/2015 | Woll et al. |
| 2016/0244762 A1 | 8/2016 | Vorechovsky et al. |
| 2017/0000794 A1 | 1/2017 | Naryshkin |
| 2017/0001995 A1 | 1/2017 | Metzger et al. |
| 2017/0002016 A1 | 1/2017 | Shishido et al. |
| 2017/0096411 A1 | 4/2017 | Vechorkin et al. |
| 2017/0121197 A1 | 5/2017 | Tale |
| 2017/0355989 A1 | 12/2017 | Konstantinova et al. |
| 2018/0118748 A1 | 5/2018 | Slaugenhaupt et al. |
| 2018/0161456 A1 | 6/2018 | Naryshkin et al. |
| 2019/0264267 A1 | 8/2019 | Yang et al. |
| 2020/0056173 A1 | 2/2020 | Vargeese et al. |
| 2020/0080083 A1 | 3/2020 | Vargeese et al. |

FOREIGN PATENT DOCUMENTS

| | | |
|---|---|---|
| EP | 2560008 A2 | 2/2013 |
| EP | 2841428 B1 | 8/2018 |
| FR | 2914188 A1 | 10/2008 |
| GB | 1047935 | 11/1966 |
| GB | 1383409 | 2/1975 |
| JP | S58-52307 A | 3/1983 |
| JP | 2006219453 A | 8/2006 |
| WO | 1993/023398 A1 | 11/1993 |
| WO | 1994/026887 A1 | 11/1994 |
| WO | 1996/039407 A1 | 12/1996 |
| WO | 1998/025930 A1 | 6/1998 |
| WO | 2001/053266 A1 | 7/2001 |
| WO | 2002/062290 A2 | 8/2002 |
| WO | 2002/087589 A1 | 11/2002 |
| WO | 2004/009558 A1 | 1/2004 |
| WO | 2004/029053 A1 | 4/2004 |
| WO | 2004/113335 A2 | 12/2004 |
| WO | 2005/012288 A1 | 2/2005 |
| WO | 2005/019215 A1 | 3/2005 |
| WO | 2005/061513 A1 | 7/2005 |
| WO | 2005/066166 A2 | 7/2005 |
| WO | 2005/072720 A1 | 8/2005 |
| WO | 2005/105801 A1 | 11/2005 |
| WO | 2007/003604 A2 | 1/2007 |
| WO | 2007/018738 A1 | 2/2007 |
| WO | 2007/047913 A2 | 4/2007 |
| WO | 2007/089584 A2 | 8/2007 |
| WO | 2007/089611 A2 | 8/2007 |
| WO | 2007/090073 A2 | 8/2007 |
| WO | 2007/109211 A2 | 9/2007 |
| WO | 2007/130383 A2 | 11/2007 |
| WO | 2007/133561 A2 | 11/2007 |
| WO | 2007/133756 A2 | 11/2007 |
| WO | 2007/135121 A1 | 11/2007 |
| WO | 2008/011109 A2 | 1/2008 |
| WO | 2008/049864 A1 | 5/2008 |
| WO | 2008/077188 A1 | 7/2008 |
| WO | 2009/042907 A1 | 4/2009 |
| WO | 2009/114874 A2 | 9/2009 |
| WO | 2009/126635 A1 | 10/2009 |
| WO | 2009/151546 A2 | 12/2009 |
| WO | 2009/156861 A2 | 12/2009 |
| WO | 2010/000032 A1 | 1/2010 |

(56) References Cited

FOREIGN PATENT DOCUMENTS

| | | |
|---|---|---|
| WO | 2010/019236 A1 | 2/2010 |
| WO | 2010/071819 A1 | 6/2010 |
| WO | 2010/093425 A1 | 8/2010 |
| WO | 2010/130934 A2 | 11/2010 |
| WO | 2010/145208 A1 | 12/2010 |
| WO | 2011/032045 A1 | 3/2011 |
| WO | 2011/050245 A1 | 4/2011 |
| WO | 2011/057204 A2 | 5/2011 |
| WO | 2011/062853 A1 | 5/2011 |
| WO | 2011/085990 A1 | 7/2011 |
| WO | 2011/097641 A1 | 8/2011 |
| WO | 2011/097643 A1 | 8/2011 |
| WO | 2011/097644 A2 | 8/2011 |
| WO | 2012/012467 A2 | 1/2012 |
| WO | 2012/075393 A2 | 6/2012 |
| WO | 2012/104823 A2 | 8/2012 |
| WO | 2012/109395 A1 | 8/2012 |
| WO | 2012/116965 A1 | 9/2012 |
| WO | 2013/019938 A1 | 2/2013 |
| WO | 2013/020993 A1 | 2/2013 |
| WO | 2013/022990 A1 | 2/2013 |
| WO | 2013/033223 A1 | 3/2013 |
| WO | 2013/059606 A1 | 4/2013 |
| WO | 2013/068769 A1 | 5/2013 |
| WO | 2013/101974 A1 | 7/2013 |
| WO | 2013/112788 A1 | 8/2013 |
| WO | 2013/119916 A1 | 8/2013 |
| WO | 2013/130689 A1 | 9/2013 |
| WO | 2013/142236 A1 | 9/2013 |
| WO | 2013/163190 A1 | 10/2013 |
| WO | 2014/012050 A2 | 1/2014 |
| WO | 2014/028459 A1 | 2/2014 |
| WO | 2014/059341 A2 | 4/2014 |
| WO | 2014/059356 A2 | 4/2014 |
| WO | 2014/116845 A1 | 7/2014 |
| WO | 2014/121287 A2 | 8/2014 |
| WO | 2014/135244 A1 | 9/2014 |
| WO | 2014/184163 A1 | 11/2014 |
| WO | 2014/209841 A2 | 12/2014 |
| WO | 2015/024876 A2 | 12/2014 |
| WO | 2015/017589 A1 | 2/2015 |
| WO | 2015/095446 A1 | 6/2015 |
| WO | 2015/095449 A1 | 6/2015 |
| WO | 2015/105657 A1 | 7/2015 |
| WO | 2015/107425 A2 | 7/2015 |
| WO | 2015/107494 A1 | 7/2015 |
| WO | 2015/110446 A1 | 7/2015 |
| WO | 2017/080967 A1 | 7/2015 |
| WO | 2015/173181 A1 | 11/2015 |
| WO | 2015/197503 A1 | 12/2015 |
| WO | 2016/131776 A1 | 8/2016 |
| WO | 2016/170163 A1 | 10/2016 |
| WO | 2016/184832 A1 | 11/2016 |
| WO | 2017/023987 A1 | 2/2017 |
| WO | 2017/081111 A1 | 5/2017 |
| WO | 2017/097728 A1 | 6/2017 |
| WO | 2017/100726 A1 | 6/2017 |
| WO | 2017/175068 A1 | 10/2017 |
| WO | 2017/189829 A1 | 11/2017 |
| WO | 2017/210134 A1 | 12/2017 |
| WO | 2018/081091 A1 | 5/2018 |
| WO | 2018/187209 A1 | 10/2018 |
| WO | 2018/218133 A1 | 11/2018 |
| WO | 2018/226622 A1 | 12/2018 |
| WO | 2019/005980 A1 | 1/2019 |
| WO | 2019/005993 A1 | 1/2019 |
| WO | 2019/028440 A1 | 2/2019 |
| WO | 2019/165073 A1 | 8/2019 |
| WO | 2019/183364 A1 | 9/2019 |
| WO | 2019/183367 A1 | 9/2019 |
| WO | 2019/191092 A1 | 10/2019 |
| WO | 2019/191229 A1 | 10/2019 |
| WO | 2020/005873 A1 | 1/2020 |
| WO | 2020/005877 A1 | 1/2020 |
| WO | 2020/005882 A1 | 1/2020 |
| WO | 2020/231977 A1 | 11/2020 |
| WO | 2021/007378 A1 | 1/2021 |
| WO | 2021/084495 A1 | 5/2021 |

OTHER PUBLICATIONS

Database Registry, Chemical Abstracts Service, Feb. 22, 2018, Database Accession No. 2178867-25-7.
Database Registry, Chemical Abstracts Service, Sep. 18, 2017, Database Accession No. 2128311-64-6.
Database Registry, Chemical Abstracts Service, Sep. 24, 2017, Database Accession No. 2130300-22-8.
Database Registry, Chemical Abstracts Service, Sep. 25, 2017, Database Accession No. 2130694-60-7.
Fascio Mirta L et al, "Synthesis and antiviral activity of some imidazo[1,2-b][1,3,4]thiadiazole carbohydrate derivatives", Carbohydrate Research, vol. 480, May 21, 2019, p. 61-66.
Ingo Knepper et al., "3-Acylindoles as versatile starting materials for pyridine ring annulation: synthesis of 1-deazapurine isosteres", Tetrahedron.vol. 67(29):5293-5303, May 14, 2011.
K.K. Abdul Khader et al., "Regioselective synthesis of C-2 substituted imidazo[4,5-b]pyridines utilizing palladium catalysed C-N bond forming reactions with enolizable heterocy", Tetrahedron Letters, vol. 55(10):1778-1783, Feb. 1, 2014.
Mariusz Mojzych et al., "Synthesis of pyrazolo[4,3-e][1,2,4]triazine sulfonamides, novel Sildenafil analogs with tyrosinase inhibitory activity", Bioorganic & Medicinal Chemistry, vol. 22, pp. 6616-6624, Oct. 18, 2014.
Mazzone G et al, "Sintesi e valutazione biologica preliminare di imidazo[2,1-b]-1,3-4-tiadazoli-2,6-diarilsostituti", Farmaco, Edizione Scientifica, Societa Chimica Italiana, Pavia, IT,vol. 39(7), Jan. 1, 1984, p. 585-598. English Abstract Only.
Patel Harun M et al, "2,5,6-Trisubstituted imidazo[2,1-b][1,3,4]thiadiazoles: Search for antihyperlipidemic agents", European Journal of Medicinal Chemistry, Editions Scientifique Elsevier, Paris, FR, vol. 65, Apr. 18, 2013, p. 119-133.
ISR in PCT/US2019/038889, dated Aug. 8, 2019.
WO in PCT/US2019/038889, dated Aug. 8, 2019.
ISR in PCT/US2019/038895, dated Aug. 14, 2019.
WO in PCT/US2019/038895, dated Aug. 14, 2019.
ISR in PCT/US19/38900, dated Aug. 20, 2019.
WO in PCT/US19/38900, dated Aug. 20, 2019.
J. S. Nair et al: "Synthesis and Fluorescence Properties of 3-Benzoxa- and Thiazol-2-ylquinoline-5 or 7-maleimides.", Cheminform, vol. 36, No. 2, Sep. 1, 2004 (Sep. 1, 2004), pp. 1944-1949.
Naik et al: "Studies in the Vilsmeier-Haack reaction: Part XVI., Synthesis of 7-amino-3-hetrarylquinoline fluorophore and derivatives", Indian Journal of Chemistry, Council of Scientific and Industrial Research (CS I R), DE, vol. 15B, No. 6, Jan. 1, 1977 (Jan. 1, 1977), pp. 506-508.
USPTO, Office Action dated Feb. 4, 2021 in U.S. Appl. No. 16/617,450. See whole document in general and compounds on pp. 10-14 and 15-18 in particular.
Potkin et al., "New directions in therapeutics for Huntington disease", Future Neurology, vol. 13(2):101-121, May 2018.
Wermuth, "The Practice of Medicinal Chemistry", 2nd ed., 2003, Chapters 9-10.
H. Kubinyi, "3D QSAR in Drug Design—Theory Methods and Applications", pp. vii-ix and pp. 243-244, 1998.
Brunhilde Wirth et al., "Moving towards treatments for spinal muscular atrophy: hopes and limits", Expert Opinion on Emerging drugs, 20(3):353-356, Apr. 28, 2015.
Cheung et al., "Discovery of Small Molecule Splicing Modulators of Survival Motor Neuron-2 (SMN2) for the Treatment of Spinal Muscular Atrophy (SMA)", J. Med. Chem. vol. 61(24):11021-11036, Aug. 15, 2018 (received), Nov. 8, 2018 (published), pp. A-P.
Chiara Zanetta et al., "Molecular Therapeutic Strategies for Spinal Muscular Atrophies: Current and Future Clinical Trials", Clinical Therapeutics, 36(1):128-140, Dec. 17, 2013.
Coady et al., 2010, "Trans-splicing-mediated improvement in a severe mouse model of spinal muscular atrophy", J. Neurosci., vol. 30(1), pp. 126-130, 2010.

(56) References Cited

OTHER PUBLICATIONS

Combrink et al., "Respiratory syncytial virus fusion inhibitors. Part 6: An examination of the effect of structural variation for the benzimidazol-2-one heterocycle moiety", Bioorganic & Medicinal Chemistry Letters, 17(17):4784-4790, Aug. 4, 2007.
European Patent Office, Communication pursuant to Article 94(3) EPC, European Application No. 14877918.4, dated Mar. 23, 2018.
Greene, Protective Groups in Organic Synthesis, 1991, Wiley, New York, pp. v-xxi and 1-17.
Higuchi and V. Stella, "Pro-drugs as novel delivery systems", vol. 14 of the A.C.S., Symposium Series and in Bioreversible Carriers in Drug Design, ed., Edward B. Roche, American Pharmaceutical Association and Pergamon Press (1975).
Hua et al., "Peripheral SMN restoration is essential for long-term rescue of a severe SMA mouse model", Nature, vol. 478(7367), pp. 123-126, 2012.
Jarecki et al., "Diverse small-molecule modulators of SMN expression found by high-throughput compound screening: early leads towards a therapeutic for spinal muscular atrophy", Human molecular genetics, 14(14):2003-2018, 2005.
Knight et al., "Isoform-specific phosphoinositide 3-kinase inhibitors from an arylmorpholine scaffold", *Bioorganic & Medicinal Chemistry*, vol. 12(17):4749-4759, 2004.
Kocar, Transformations of 3-aminopyridazines. Synthesis of 4-oxo-4H-pyrimido [1,2-b]pyridazine and 1-(substituted pyridazin-3-yl)-1H-1,2,3-triazole derivatives, Arkivoc, vol. 8, 2002, 143-156.
Lazarev et al., "Factors Affecting Aggregate Formation in Cell Models of Huntington's Disease and Amyotrophic Lateral Sclerosis", *Acta Naturae*, vol. 5(2):81-89, Apr. 2013.
Le et al., "SMND7, the major product of the centromeric survival motor neuron (SMN2) gene, extends survival in mice with spinal muscular atrophy and associates with full-length SMN, Human Molecular Genetics", vol. 14(5), pp. 845-857, 2005.
Liu et al., "A novel nuclear structure containing the survival of motor neurons protein", EMBO J. vol. 15(14), pp. 3555-3565 (1996).
MacDonald et al., "Quantification Assays for Total and Polyglutamine-Expanded Huntington Proteins", PLOS One, 2014, vol. 9(5), published May 9, 2014, pp. 1-17.
Makhortova et al., "A screen for regulators of survival of motor neuron proteins levels", Nature chemical biology, vol. 7(8):544-552, 2011.
Markus Riessland et al., "The benzamide M344, a novel histone deacetylase inhibitor, significantly increases SMN2 RNA/protein levels in spinal muscular atrophy cells", Hum Genet 120:101-110, May 26, 2006.
Naryshkin et al., "SMN2 splicing modifiers improve motor function and longevity in mice with spinal muscular atrophy", Science, vol. 345(6197):688-693, 2014 (including supplementary materials).
Palacino et al., "SMN2 splice modulators enhance U1-pre-mRNA association and rescue SMA mice", Nature: Chemical Biology, pp. 511-517 and 5 Supplemental Pages +S1-S20, vol. 11, Jun. 1, 2015.
Passini et al., "Antisense Oligonucleotides delivered to the mouse CNS ameliorate symptoms of severe spinal muscular atrophy", Sci Transl. Med., vol. 3(72), 2001.
Peng, Lijie et al., "Identification of pyrido[1,2-alpha]pyrimidine-4-ones as new molecules improving the transcriptional functions of estrogen-related receptor alpha", Journal of medicinal chemistry, vol. 54(21):7729-7733, 2011.
Pryor et al., "Huntingtin promotes mTORC1 signaling in the pathogenesis of Huntington's disease", Sci. Signal, dated Oct. 28, 2014, 2014, vol. 7, Issue 349, ra103, pp. 1-12.
PubChem/NCBI Database accession No. CID 377422 [online], 2005, retrieved on Jul. 4, 2016, URL http://pubchem.nci.nlm.nih.gov/compound/377422.
Seisuke Mimori et al., "Protective Effects of 4-phenylbutyrate derivatives on the neuronal cell death and endoplasmic reticulum stress," Biological & Pharmaceutical Bulletin of Japan, 35(1):84-90, Jan. 1, 2012.
Shao, Ning et al., "Synthesis and structure-activity relationship (SAR) study of 4-azabenzoxazole analogues as H3 antagonists", Bioorganic & Medicinal chemistry letters, vol. 22(5):2075-2078, 2012.
Sin et al., "Respiratory syncytial virus fusion inhibitors. Part 7: Structure-activity relationships associated with a series of isatin oximes that demonstrate antiviral activity in vivo", Bioorganic & Medicinal Chemistry Letters, 19(16):4857-4862, Aug. 15, 2009.
Yuo et al., 2008, "5-(N-ethyl-N-isopropyl)-amiloride enhances SMN2 exon 7 inclusion and protein expression in spinal muscular atrophy cells", Annals of neurology, vol. 63(1):26-34, 2008.
Pubchem, Substance Record for SID 249779947, Mar. 31, 2015, "4H-Quinolizin-4one1; Hydrobromide".
International Search Report for PCT/US2013/025292, dated Aug. 30, 2013.
Written Opinion of the International Searching Authority in PCT/US2013/025292, dated Aug. 30, 2013.
International Search Report in PCT/US2016/066042, dated Mar. 16, 2017.
Written Opinion of the International Searching Authority in PCT/US2016/066042, dated Mar. 16, 2017.
International Search Report in PCT/US2018/035954, dated Oct. 1, 2018.
Written Opinion of the International Searching Authority in PCT/US2018/035954, dated Oct. 1, 2018.
International Search Report in PCT/US2018/039775, dated Oct. 29, 2018.
Written Opinion of the International Searching Authority in PCT/US2018/039775, dated Oct. 29, 2018.
International Search Report in PCT/US2018/039794, dated Oct. 25, 2018.
Written Opinion of the International Searching Authority in PCT/US2018/039794, dated Oct. 25, 2018.
International Search Report in PCT/US2019/024068, dated Jul. 10, 2019.
Written Opinion in PCT/US2019/024068, dated Jul. 10, 2019.
International Search Report in PCT/US2019/024278, dated May 28, 2019.
Written Opinion in PCT/US2019/024278, dated May 28, 2019.
International Search Report for PCT/EP2012/065499, dated Sep. 28, 2012.
Written Opinion of the International Searching Authority in PCT/EP2012/065499, dated Sep. 28, 2012.
International Search Report for PCT/EP2014/059699, dated Aug. 25, 2014.
Written Opinion of the International Searching Authority in PCT/EP2014/059699, dated Aug. 25, 2014.
International Search Report for PCT/EP2015/051066, dated Feb. 19, 2015.
Written Opinion of the International Searching Authority in PCT/EP2015/051066, dated Feb. 19, 2015.
International Search Report for PCT/EP2015/060343, dated Jul. 13, 2015.
Written Opinion of the International Searching Authority in PCT/EP2015/060343, dated Jul. 13, 2015.
International Search Report for PCT/EP2016/060952, dated Jun. 29, 2016.
Written Opinion of the International Searching Authority in PCT/EP2016/060952, dated Jun. 29, 2016.
International Search Report in PCT/EP2016/076905, dated Feb. 9, 2017.
Written Opinion of the International Searching Authority in PCT/EP2016/076905, dated Feb. 9, 2017.
Written Opinion of the International Searching Authority in PCT/EP2016/077190, dated Mar. 1, 2017.
International Search Report in PCT/EP2016/077190, dated Mar. 1, 2017.
International Search Report for PCT/EP2016/079816, dated Jan. 19, 2017.
Written Opinion of the International Searching Authority in PCT/EP2016/079816, dated Jan. 19, 2017.
International Search Report for PCT/US20/41300, dated Oct. 16, 2020.

(56) References Cited

OTHER PUBLICATIONS

Written Opinion of the International Searching Authority in PCT/US20/41300, dated Oct. 16, 2020.
Andreassi, C. et al. 2001. Human Molecular Genetics 10, 2841-2849. "Aclarubicin treatment restores SMN levels to cells derived from type I spinal muscular atrophy patients."
Artursson P., et al. 1991. Biochem Biophys Res Comm 175, 880-5. "Correlation between oral drug absorption in humans and apparent drug permeability coefficients in human intestinal epithelial (Caco-2) cells."
Baldo, B. et al. 2012. J. Biol. Chem. 287, 1406-1414. "A Screen for enhancers of clearance identifies huntingtin as a heat shock protein 90 (Hsp90) client protein."
Barbaro, B.A. et al. 2015. Human Molecular Genetics 24, 913-925 (published online Oct. 9, 2014). "Comparative study of naturally occurring huntingtin fragments in *Drosophila* points to exon 1 as the most pathogenic species in Huntington's disease."
Bates, G.P. et al. 2015. Nature Reviews, Disease Primers 1, 15005 (published online Apr. 23, 2015). "Huntington disease."
Bengart, P. et al. 2004. Nucleic Acids Res. 32, W154-W159. "Riboswitch finder—a tool for indentification of riboswitch RNAs."
Bhattacharyya, A. et al. 2007 Drug Discovery Today 12, 553-560. "Mining the GEMS—a novel platform technology targeting post-transcriptional control mechanisms."
Bibillo, A and Eickbush, T.H. 2002. J. Biol. Chem. 277, 34836-34845. "High Processivity of the Reverse Transcriptase from a Non-long Terminal Repeat Retrotransposon."
Carroll, J.B. et al. 2015. Lancet Neurol 14, 1135-1142 (No. 11—Nov. 2015). "Treating the whole body in Huntongton's disease."
Cartegni, L. et al. 2003. Nucleic Acids Res. 31, 3568-3571. "ESEfinder: a web resource to identify exonic splicing enhancers."
Crooks, G. E., et al. 2004. Genome Research 14, 1188-1190. "WebLogo: a sequence logo generator."
Daguenet et al. 2015. EMBO reports 16, 1640-1655 (published online Nov. 13, 2015). "The pathogenicity of splicing defects: mechanistic insights into pre-mRNA processing inform novel therapeutic approaches."
DiFiglia, et al 1997. Science 277, 1990-1993. "Aggregation of Huntingtin in Neuronal Intranuclear Inclusions and Dystrophic Neurites in Brain".
Dobin, A. et al. 2013. Bioinformatics 29, 15-21. "STAR: ultrafast universal RNA-seq aligner."
Evers, M.M. et al. 2015. Molecular Neurodegeneration 10, Article No. 21 (published online Apr. 28, 2015). "Making (anti-) sense out of huntingtin levels in Huntington disease."
Fardaei, M. et al. 2002. Human Molecular Genetics 11, 805-814. "Three proteins, MBNL, MBLL and MBXL, co-localize in vivo with nuclear foci of expanded-repeat transcripts in DM1 and DM2 cells."
Fernandez-Nogales, M. et al. 2014. Nature Medicine 20, 881-885. "Huntington's disease is a four-repeat tauopathy with tau nuclear rods."
Gipson, T. A. et al. 2013. RNA Biology 10, 1647-1652. "Aberrantly spliced HTT, a new player in Huntington's disease pathogenesis."
Gray, M. et al. 2008. J. Neurosci. 28, 6182-6195. "Full-length human mutant huntingtin with a stable polyglutamine repeat can elicit progressive and selective neuropathogenesis in BACHD mice."
Griffiths-Jones, S. et al. 2005. Nucleic Acids Res. 33, D121-D124. "Rfam: annotating non-coding RNAs in complete genomes."
Griffiths-Jones, S. et al. 2006. Nucleic Acids Res. 34, D140-D144. "miRBase: microRNA sequences, targets and gene nomenclature."
Grillo, G. et al. 2003. Nucleic Acids Res. 31, 3608-3612. "PatSearch: a program for the detection of patterns and structural motifs in nucleotide sequences."
Grimson, A. et al. 2007. Molecular Cell 27, 91-105. "MicroRNA Targeting Specificity in Mammals: Determinants beyond Seed Pairing."
Heemskerk, J. et al. 2002. Nature Neuroscience Supplement 5, 1027-1029. "From chemical to drug: neurodegeneration drug screening and the ethics of clinical trials."
Heemskerk, J, et al. 2002. Trends Neurosci. 25, 494-496. "Teaching old drugs new tricks."
Heemskerk, J. et al. 2005. Chapter 16—"Therapeutics Development for Hereditary Disorders" in ed. Waxman, S. From Neuroscience to Neurology: Neuroscience, Molecular Medicine, and the Therapeutic Transformation of Neurology, pp. 285-291.
Hernandez-Imas, E. et al. 2015. PLoS One 10, e141735 (published online Oct. 28, 2015). "Functional Analysis of Mutations in Exon 9 of NF1 Revales the Presence of Several Elements Regulating Splicing."
Hodges, A. et al. 2006. Human Molecular Genetics 15, 965-977. "Regional and cellular gene expression changes in human Huntington's disease brain."
Hua et al. 2007. PLoS Biol 5, e73. Enhancement of SMN2 Exon 7 "Inclusion by Antisense Oligonucleotides Targeting the Exon."
Hua et al. 2008. American J. of Human Genetics 82, 834-848. "Antisense Masking of an hnRNP A1/A2 Intronic Splicing Silencer Corrects SMN2 Splicing in Transgenic Mice."
Hughes, A.C. et al. 2014. J. Mol. Biol. 426, 1428-1438. "Identification of Novel Alternative Splicing Events inthe Huntingtin Gene and Assessment of the Functional Consequences Using Structural Protein Homology Modelling."
The Huntington's Disease Collaborate Research Group, 1993, Cell, 72, pp. 971-983 (1993). "A novel gene containing a trinucleotide repeat that is expanded and unstable on Huntongtn's Disease chromosomes."
Janas, A. M. 2015. "A Stem Cell Model of the Motor Circuit Reveals Distinct Requirements for SMN in Motor Neuron Survival and Function."
Jacobs, G.H. et al. 2006. Nucleic Acids Res. 34, suppl_1, D37-D40. "Transterm—extended search facilities and improved integration with other databases."
Kanadia, R.N. et al. 2003. Science 302, 1978-1980. "A Muscleblind Knockout Model for Myotonic Dystrophy."
Kaplan, A. et al. 2012. Prog. Neurobiol. 99(3), 262-280. "Therapeutic approaches to preventing cell death in Huntington disease."
Kim, D. et al. 2013. Genome Biology 14, Article No. R36. "TopHat2: accurate alignment of transcriptomes in the presence of insertions, deletions and gene fusions."
Kordasiewicz, H.B. et al. 2012. Neuron, 74, 1031-1044. "Sustained Therapeutic Reversal of Huntington's Disease by Transient Repression of Huntingtin Synthesis".
Kuhn, A. et al. 2007. Human Molecular Genetics 16, 1845-1861. "Mutant huntingtin's effects on striatal gene expression in mice recapitulate changes observed in human Huntington's disease brain and do not differ with mutant huntingtin length or wild-type huntingtin dosage."
Labadorf, A.T. et al. 2015. Plos One 10(10): e0141298 (published online Oct. 23, 2015). "Evidence of Extensive Alternative Splicing in Post Mortem Human Brain HTT Transcription by mRNA Sequencing."
Labadorf, A. et al. 2015. PLoS One 10(12): e0143563 (published online Dec. 4, 2015). "RNA Sequence Analysis of Human Huntington Disease Brain Reveals an Extensive Increase in Inflammatory and Developmental Gene Expression."
Labbadia, J. et al. 2013. Trends Biochem. Sci. 38, 378-385. "Huntington's disease: underlying molecular mechanisms and emerging concepts."
Landles, C. et al. 2010. J. Bio. Chem. 285, 8808-8823. "Protoelysis of Mutant Huntington Produces an Exon 1 Fragment That Accumulates as an Aggregated Protein in Neuronal Nuclei in Huntington Disease."
Lei, et al. 2005. Nucleic Acids Res 33, 3897-3909. "Exonization of AluYa5 in the human ACE gene requires mutations in both 3' and 5' splice sites and is facilitated by a conserved splicing enhancer."
Liang, Y. et al. 2009. Brain Res. 2009 1286, 221-229. "ATF3 plays a protective role against toxicity by N-terminal fragment of mutant huntingtin in stable PC12 cell line."
Love, M. I. et al. 2014. Genome Biolog 15, 550. "Moderated estimation of fold change and dispersion for RNA-seq data with DESeq2."

(56) References Cited

OTHER PUBLICATIONS

Lunkes, A. et al. 2002. Molecular Cell 10, 259-269. "Proteases Acting on Mutant Huntingtin Generate Cleaved Products that Differentially Build Up Cytoplasmic and Nuclear Inclusions."
Macke, T.J. 2001. Nucleic Acids Res. 29, 4724-4735. "RNAMotif, an RNA secondary structure definition and search algorithm."
Mahmood, I. et al. 1996. Xenobiotica 26, 887-895. "Interspecies scaling: predicting clearance of drugs in humans. Three different approaches."
Mahmood, I. 2006. Pharm. Sci. 95, 1810-1821. "Prediction of human drug clearance from animal data: Application of the rule of exponents and 'fu corrected intercept method' (FCIM)."
Mahmoudi, S. et al. 2010. PLoS Biology 8(11), e1000521. "WRAP53 is Essential for Cajal Body and for Targeting the Survival of Motor Neuron Complex to Cajal Bodies."
Mangiarini, L. 1996. Cell 87, 493-506. "Exon 1 of the HD Gene with an Expanded CAG Repeat Is Sufficient to Cause a Progressive Neurological Phenotype in Transgenic Mice."
Mantione, K.J. et al. 2014. Med. Sci. Monit. Basic Res. 20, 138-141. "Comparing Bioinformation Gene Expression Profiling Methods: Microarray and RNA-Seq."
Mendoza, L.G. et al. 1999. BioTechniques 27, 778-788. "Hight-Throughput Microarray-Based Enzyme-Linked Immunosorbent Assay (ELISA)."
Mielcarek, M. et al. 2014. PLOS Genetics 10: 8 e1004550. "Dysfunction of the CNS-Heart Axis in Mouse Models of Huntington's Disease."
Mignone, F. et al. 2005. Nucleic Acids Res. 33, D141-D146. "UTRdb and UTRsite: a collection of sequences and regulatory motifs of the untranslated regions of eukaryotic mRNAs."
Mort, M. et al. 2015. J. of Huntington's Disease 4(2 of 4), 161-171, "Huntingtin Exists as Multiple Splice Forms in Human Brain."
Neuder, A. et al. 2014. BMC Medical Genomics 7:60. "A common gene expression signature in Huntington's disease patient brain regions."
Paganetti, P. et al. 2009. ChemBioChem 10, 1678-1688. "Development of Method for the High-Throughput Quantification of Cellular Proteins."
Pouladi, M. et al. 2013. Nature Review Neuroscience 14, 709-721. "Choosing an animal model for the study of Huntington's disease."
Ratovitski, T. et al. 2012. Cell Cycle 11, 2006-2021. "Huntingtin protein interactions altered by polyglutamine expansion as determined by quantitative proteomic analysis."
Reiner, A. et al. 2011. International Review of Neurobiology 98, 325-372. "Genetics and neuropathology of Huntington's disease."
Ruzo, A. et al. 2015. PLoS One 10, e0127678 (published online May 26, 2015). "Discovery of Novel Isoforms of Huntingtin Reveals a New Hominid-Specific Exon."
Sadeghian, H. et al. 2011. Arch. Neurol. 68, 650-652. "Huntington Chorea Presenting with Motor Neuron Disease."
Sathasivam, K. et al. 2013. Proc. Natl. Acad. Sci. 110, 2366-2370. "Aberrant splicing of HTT generates the pathogenic exon 1 protein in Huntington disease."
Schilling, G. et al. 2007. J Neuropathol. Exp. Neurol. 66, 313-320. "Characterization of Huntingtin Pathologic Fragments in Human Huntington Disease, Transgenic Mice, and Cell Models."
Schwab, C. et al. 2008. J. Neuropathol Exp Neurol 67, 1159-1165. "Colocalization of Transactivation-Responsive DNA-Binding Protein 43 and Huntingtin in Inclusions of Huntington Disease."
Shlyakhtenko, L.S. et al. 2007. Nanomedicine: Nanotech., Bio., and Med. 3, 192-197. "Single-molecule selection and recovery of structure-specific antibodies using atomic force microscopy."
Southwell, A.L. et al. 2013. Hum. Mol. Genet. 22, 18-34. "A fully humanized transgenic mouse model of Huntington disease."
Stanek, L.M. et al. 2014. Human Gene Therapy 25, 461-474. "Silencing Mutant Huntingtin by Adeno-Associated Virus-Mediated RNA Interference Ameliorates Disease Manifestations in the YAC128 Mouse Model of Huntington's Disease."

Stoilov, P. et al. 2008. Proc. Natl. Acad. Sci. 105, 11218-11223. "A high-throughput screening strategy identifies cardiotonic steroids as alternative splicing modulators."
Taylor et al. 1999. Nat. Biotechnol. 17, 1097-1100 "Induction of endogenous Bcl-xS through the control of Bcl-x pre-mRNA splicing by antisense oligonucleotides."
Van der Burg, J.M.M. et al. 2009. The Lancet (Neurology) 8, 765-774, "Beyond the brain: widespread pathology in Huntington's disease."
Varma, H. et al. 2008. Comb Chem High Throughput Screen 11, 238-248. "High Throughput Screening for Neurodegeneration and Complex Disease Phenotypes."
Vickers et al., 2006. J. Immunol. 176, 3652-3661 "Modification of MyD88 mRNA splicing and inhibition of IL-1 beta signaling in cell culture and in mice with a 2'-O-methoxyethyl-modified oligonucleotide."
Wachter, A. 2014. Trends in Genetics 30, 172-181. "Gene regulation by structured mRNA elements."
Weiland, M. et al. 2012. Methods 56, 351-357. "Engineering of ribozyme-based riboswitches for mammalian cells."
Wild, E.J. et al. 2014. Movement Disorders 29, 1434-1445. "Targets for Future Clinical Trials in Huntington's Disease: What's in the Pipeline?"
Wilton et al. 1999. Neuromuscul. Disord. 9, 330-338. "Specific removal of the nonsense mutation from the mdx dystrophin mRNA using antisense oligonucleotides."
Xiong, H.Y. et al. 2015. Science 347, 1254806 (published online Dec. 18, 2014.) "The human splicing code reveals new insights into the genetic determinants of disease."
Yen, L. et al. 2004. Nature 431, 471-6. "Exogenous control of mammalian gene expression through modulation of RNA self-cleavage."
Yeo, G. et al. 2004. J. Comput. Biol. 11, 377-394. "Maximum entropy modeling of short sequence motifs with applications to RNA splicing signals."
Younis et al. 2010. Molecular and Cellular Biology 30, 1718-1728. "Rapid-Response Splicing Reporter Screens Identify Differential Regulators of Constitutive and Alternative Splicing."
Yu, S. et al. 2014. Trends in Pharmacological Sci. 35, 53-62. "Drugging unconventional targets: insights from Huntington's disease."
Zona, S. et al. 2014. Biochimica et Biophysica Acta 1839, 1316-1322. "FOXM1: An emerging master regulator of DNA damage response and genotoxic agent resistance."
Nair, A.B. et al. 2016. J. Basic and Clinical Pharmacy 7, 27-31. "A simple and practical guide for dose conversion between animals and human."
Neuder, A. et al. 2017. Scientific Reports 7, 1307 (published online May 2, 2017). "The pathogenic exon 1 HTT protein is produced by incomplete splicing in Huntington's disease patients."
Nopoulos, P. C. 2016. Dialogues Clin Neurosci 18, 91-98. "Huntington disease: a single-gene degenerative disorder of the striatum."
Ratni, H. et al. 2016. J. Med. Chem. 59, 6086-6100. "Specific Correction of Alternative Survival Motor Neuron 2 Splicing by Small Molecules: Discovery of a Potential Novel Medicine To Treat Spinal Muscular Atrophy."
Rüb, U. et al. 2016. Brain Pathol. 26, 726-740. "Huntington's disease (HD): the neuropathology of a multisystem neurodegenerative disorder of the human brain."
Saudou, F. et al. 2016. Neuron 89, 910-926. "The Biology of Huntingtin."
Wang, G. et al. 2016. Proc. Natl. Acad. Sci. 113, 3359-3364. "Ablation of huntingtin in adult neurons is nondeleterious but its depletion in young mice causes acute pancreatitis."
Woll, M.G. et al. 2016. J. Med. Chem. 59, 6070-6085. "Discovery and Optimization of Small Molecule Splicing Modifiers of Survival Motor Neuron 2 as a Treatment for Spinal Muscular Atrophy."
International Search Report for PCT/EP2015/063894, dated Aug. 6, 2015.
Written Opinion of the International Searching Authority in PCT/EP2015/063894, dated Aug. 6, 2015.
International Search Report for PCT/US20/32446, dated Jul. 7, 2020.

(56) References Cited

OTHER PUBLICATIONS

Written Opinion of the International Searching Authority in PCT/US20/32446, dated Jul. 7, 2020.
Chemical Abstracts Registry No. 2107242-04-04, indexed in the Registry file on STN CAS Online Aug. 2, 2017. (Year: 2017).
Daldin et al., "Polyglutamine expansion affects huntingtin conformation in multiple Huntington's disease models", Scientific Reports, vol. 7, 15 pages, 2017.
Gleave et al., "Synthesis and evaluation of 3-amino-6-aryl-pyridazines as selective CB2 agonists for the treatment of inflammatory pain", Bioorganic & Medicinal Chemistry Letters, vol. 20, pp. 465-468, 2010.

* cited by examiner

METHODS FOR TREATING HUNTINGTON'S DISEASE

CROSS-REFERENCE TO RELATED APPLICATIONS

This application is a Continuation of U.S. patent application Ser. No. 16/710,515, filed Dec. 11, 2019, now U.S. Pat. No. 10,881,658, issued Jan. 5, 2021, which in turn is a Divisional of U.S. patent application Ser. No. 15/781,303, filed Jun. 4, 2018, now U.S. Pat. No. 10,874,672, issued Dec. 29, 2020, which is the U.S. National Stage filing under 35 U.S.C. § 371 of International Application No. PCT/US2016/066042, filed Dec. 11, 2016, which in turn claims priority to U.S. Provisional Application No. 62/265,652, filed Dec. 10, 2015, the entire contents of which are incorporated by reference herein.

FIELD OF THE INVENTION

The present description relates to compounds, forms, and pharmaceutical compositions thereof and methods of using such compounds, forms, or compositions thereof for treating or ameliorating Huntington's disease. In particular, the present description relates to substituted monocyclic heteroaryl compounds, forms and pharmaceutical compositions thereof and methods of using such compounds, forms, or compositions thereof for treating or ameliorating Huntington's disease.

BACKGROUND

Huntington's disease (HD) is a progressive, autosomal dominant neurodegenerative disorder of the brain, having symptoms characterized by involuntary movements, cognitive impairment, and mental deterioration. Death, typically caused by pneumonia or coronary artery disease, usually occurs 13 to 15 years after the onset of symptoms. The prevalence of HD is between three and seven individuals per 100,000 in populations of western European descent. In North America, an estimated 30,000 people have HD, while an additional 200,000 people are at risk of inheriting the disease from an affected parent. The disease is caused by an expansion of uninterrupted trinucleotide CAG repeats in the "mutant" huntingtin (Htt) gene, leading to production of HTT (Htt protein) with an expanded poly-glutamine (polyQ) stretch, also known as a "CAG repeat" sequence. There are no current small molecule therapies targeting the underlying cause of the disease, leaving a high unmet need for medications that can be used for treating or ameliorating HD. Consequently, there remains a need to identify and provide small molecule compounds for treating or ameliorating HD.

All other documents referred to herein are incorporated by reference into the present application as though fully set forth herein.

SUMMARY

The present description relates to methods for treating or ameliorating HD in a subject in need thereof comprising administering to the subject an effective amount of a compound of Formula (I):

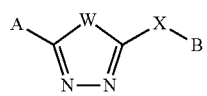

(I)

wherein W, X, A and B are as defined herein, or forms and compositions thereof.

In particular, the present description relates to a use of a compound of Formula (I) or a form or composition thereof in a method for treating or ameliorating HD in a subject in need thereof comprising, administering an effective amount of the compound or a form or composition thereof, to the subject.

The present description further relates to the use of a compound of Formula (I) or a form thereof in combination with agents having additive or synergistic activity, thus providing a combination product for the treatment of HD.

DETAILED DESCRIPTION

The present description relates to a method or use of a compound for treating or ameliorating HD in a subject in need thereof comprising administering to the subject an effective amount of a compound of Formula (I):

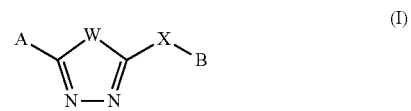

(I)

or a form thereof, wherein

W is CH=CH or S;

X is $CH_2$, $CH(C_{1-4}alkyl)$, $C(C_{1-4}alkyl)_2$, CH=CH, O, NRs, or a bond;

A is aryl, heteroaryl, heterocyclyl, or $C_{9-10}$cycloalkyl, wherein aryl is selected from phenyl and naphthyl, each optionally substituted with 1, 2, 3, or 4 substituents each selected from $R_1$, wherein heteroaryl is a monocyclic, bicyclic or polycyclic aromatic carbon atom ring structure radical in which one or more carbon atom ring members have been replaced, where allowed by structural stability, with one or more heteroatoms, such as an O, S, or N atom, each optionally substituted with 1, 2, 3, 4, or 5 substituents each selected from $R_1$, wherein heterocyclyl is a saturated or partially unsaturated monocyclic, bicyclic or tricyclic ring system having 1, 2, or 3 heteroatom ring members independently selected from N, O, or S, each optionally substituted with 1, 2, 3, 4, or 5 substituents each selected from $R_2$, and wherein $C_{9-10}$cycloalkyl is a saturated or partially unsaturated bicyclic ring system optionally substituted with 1, 2, 3, 4, or 5 substituents each selected from $R_2$;

B is heterocyclyl, wherein heterocyclyl is a saturated or partially unsaturated monocyclic, bicyclic or polycyclic ring system having 1, 2, or 3 heteroatom ring members independently selected from N, O, or S, each optionally substituted with 1, 2, 3, 4, or 5 substituents each selected from $R_4$;

$R_1$ is halogen, hydroxyl, cyano, $C_{1-4}$alkyl, halo-$C_{1-4}$alkyl, amino, $C_{1-4}$alkyl-amino, $(C_{1-4}alkyl)_2$-amino, amino-$C_{1-4}$alkyl, $C_{1-4}$alkyl-amino-$C_{1-4}$alkyl, $(C_{1-4}alkyl)_2$-amino-$C_{1-4}$alkyl, amino-carbonyl, $C_{1-4}$alkyl-amino-carbonyl, $(C_{1-4}alkyl)_2$-amino-carbonyl, $C_{1-4}$alkyl-amino-carbonyl-$C_{1-4}$alkyl, $(C_{1-4}alkyl)_2$-amino-carbonyl-$C_{1-4}$alkyl, $C_{1-4}$alkyl-carbonyl-amino, $C_{1-4}$alkyl-carbonyl-amino-$C_{1-4}$alkyl, hydroxyl-$C_{1-4}$alkyl, $C_{1-4}$alkyl-carbonyl, $C_{1-4}$alkoxy, halo-$C_{1-4}$alkoxy, amino-$C_{1-4}$alkoxy, hydroxyl-$C_{1-4}$alkoxy, $C_{1-4}$alkyl-$C_{1-4}$alkoxy, $C_{1-4}$alkyl-amino-$C_{1-4}$alkoxy, $(C_{1-4}alkyl)_2$-amino-$C_{1-4}$alkoxy, $C_{1-4}$alkyl-carbonyl-amino-$C_{1-4}$alkoxy, $C_{1-4}$alkoxy-$C_{1-4}$alkoxy, $C_{1-4}$alkoxy-carbonyl, $C_{1-4}$alkoxy-carbonyl-amino, $C_{1-4}$alkoxy-carbonyl-amino-$C_{1-4}$alkoxy, $C_{2-4}$alkenyl, $C_{2-4}$alkenyl-amino-carbonyl, $C_{3-7}$cycloalkyl, $C_{3-7}$cycloalkyl-$C_{1-4}$alkoxy, $C_{3-7}$cycloalkenyl, heteroaryl, heteroaryl-$C_{1-4}$alkyl, heteroaryl-$C_{1-4}$alkyl-amino, heteroaryl-$C_{1-4}$alkyl-amino-carbonyl, heteroaryl-$C_{1-4}$alkyl-carbonyl-amino, heteroaryl-$C_{1-4}$alkyl-amino-carbonyl-$C_{1-4}$alkyl, heteroaryl-$C_{1-4}$alkyl-carbonyl-amino-$C_{1-4}$ alkyl, heterocyclyl, heterocyclyl-$C_{1-4}$alkyl, heterocyclyl-$C_{1-4}$alkoxy, phenyl, or phenyl-$C_{1-4}$alkoxy, wherein heteroaryl is a monocyclic, bicyclic or polycyclic aromatic carbon atom ring structure radical in which one or more carbon atom ring members have been replaced, where allowed by structural stability, with one or more heteroatoms such as an O, S, or N atom, wherein heterocyclyl is a saturated or partially unsaturated monocyclic or bicyclic ring system having 1, 2, or 3 heteroatom ring members selected from N, O, and S, and wherein each instance of phenyl, heteroaryl or heterocyclyl is optionally substituted with 1, or 2 substituents each selected from $R_3$;

$R_2$ is halogen, hydroxyl, cyano, oxo, hydroxyl-imino, $C_{1-4}$alkyl, halo-$C_{1-4}$alkyl, amino, $C_{1-4}$alkyl-amino, ($C_{1-4}$alkyl)$_2$-amino, amino-$C_{1-4}$alkyl, $C_{1-4}$alkyl-amino-$C_{1-4}$alkyl, ($C_{1-4}$alkyl)$_2$-amino-$C_{1-4}$alkyl, amino-carbonyl, hydroxyl-$C_{1-4}$alkyl, $C_{1-4}$alkoxy, $C_{1-4}$alkoxy-carbonyl, $C_{2-4}$alkenyl, $C_{3-7}$cycloalkyl, or heterocyclyl-$C_{1-4}$alkyl, wherein heterocyclyl is a saturated or partially unsaturated monocyclic or bicyclic ring system having 1, 2, or 3 heteroatom ring members selected from N, O, and S, and wherein each instance of heterocyclyl is optionally substituted with 1, or 2 substituents each selected from $R_3$;

$R_3$ is halogen, hydroxyl, nitro, oxo, hydroxyl-imino, $C_{1-4}$alkyl, halo-$C_{1-4}$alkyl, amino, $C_{1-4}$alkyl-amino, ($C_{1-4}$alkyl)$_2$-amino, amino-$C_{1-4}$alkyl, $C_{1-4}$alkyl-amino-$C_{1-4}$alkyl, ($C_{1-4}$alkyl)$_2$-amino-$C_{1-4}$alkyl, amino-carbonyl, $C_{1-4}$alkyl-amino-carbonyl, ($C_{1-4}$alkyl)$_2$-amino-carbonyl, $C_{1-4}$alkyl-amino-carbonyl-$C_{1-4}$alkyl, ($C_{1-4}$alkyl)$_2$-amino-carbonyl-$C_{1-4}$alkyl, $C_{1-4}$alkyl-carbonyl-amino, $C_{1-4}$alkyl-carbonyl-amino-$C_{1-4}$alkyl, hydroxyl-$C_{1-4}$alkyl, $C_{1-4}$alkyl-carbonyl, $C_{1-4}$alkoxy, halo-$C_{1-4}$alkoxy, amino-$C_{1-4}$alkoxy, hydroxyl-$C_{1-4}$alkoxy, $C_{1-4}$alkyl-$C_{1-4}$alkoxy, $C_{1-4}$alkyl-amino-$C_{1-4}$alkoxy, ($C_{1-4}$alkyl)$_2$-amino-$C_{1-4}$alkoxy, $C_{1-4}$alkyl-carbonyl-amino-$C_{1-4}$alkoxy, $C_{1-4}$alkoxy-$C_{1-4}$alkoxy, $C_{1-4}$alkoxy-carbonyl, $C_{1-4}$alkoxy-carbonyl-amino, $C_{1-4}$alkoxy-carbonyl-amino-$C_{1-4}$alkoxy, $C_{2-4}$alkenyl, $C_{2-4}$alkenyl-amino-carbonyl, $C_{3-7}$cycloalkyl, $C_{3-7}$cycloalkyl-$C_{1-4}$alkoxy, $C_{3-7}$cycloalkenyl, heteroaryl, heteroaryl-$C_{1-4}$alkyl, heteroaryl-$C_{1-4}$alkyl-amino, heteroaryl-$C_{1-4}$alkyl-amino-carbonyl, heteroaryl-$C_{1-4}$alkyl-carbonyl-amino, heteroaryl-$C_{1-4}$alkyl-amino-carbonyl-$C_{1-4}$alkyl, heteroaryl-$C_{1-4}$alkyl-carbonyl-amino-$C_{1-4}$ alkyl, heterocyclyl, heterocyclyl-$C_{1-4}$alkyl, phenyl, or phenyl-$C_{1-4}$alkoxy;

$R_4$ is independently selected from halogen, $C_{1-4}$alkyl, hydroxyl-$C_{1-4}$alkyl, amino, $C_{1-4}$alkyl-amino, ($C_{1-4}$alkyl)$_2$-amino or hydroxyl-$C_{1-4}$alkyl-amino; and $R_5$ is hydrogen, $C_{1-4}$alkyl, or hydroxyl-$C_{1-4}$alkyl;

wherein a form of the compound is selected from the group consisting of a prodrug, salt, hydrate, solvate, clathrate, isotopologue, racemate, enantiomer, diastereomer, stereoisomer, polymorph and tautomer form thereof.

An embodiment of the present description further relates to a method or use of a compound for treating or ameliorating HD in a subject in need thereof comprising administering to the subject an effective amount of a compound of Formula (I) selected from a compound of Formula (Ia) and Formula (Ib):

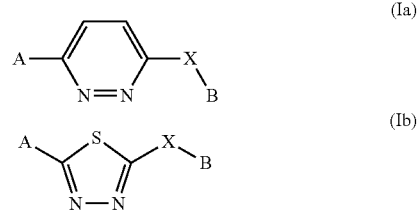

or a form thereof, wherein

X is $CH_2$, $CH(C_{1-4}$alkyl), $C(C_{1-4}$alkyl)$_2$, CH=CH, O, NRs, or a bond;

A is aryl, heteroaryl, heterocyclyl, or $C_{9-10}$cycloalkyl, wherein aryl is selected from phenyl and naphthyl, each optionally substituted with 1, 2, 3, or 4 substituents each selected from $R_1$, wherein heteroaryl is a monocyclic, bicyclic or polycyclic aromatic carbon atom ring structure radical in which one or more carbon atom ring members have been replaced, where allowed by structural stability, with one or more heteroatoms, such as an O, S, or N atom, each optionally substituted with 1, 2, 3, 4, or 5 substituents each selected from $R_1$, wherein heterocyclyl is a saturated or partially unsaturated monocyclic, bicyclic or tricyclic ring system having 1, 2, or 3 heteroatom ring members independently selected from N, O, or S, each optionally substituted with 1, 2, 3, 4, or 5 substituents each selected from $R_2$, and wherein $C_{9-10}$cycloalkyl is a saturated or partially unsaturated bicyclic ring system optionally substituted with 1, 2, 3, 4, or 5 substituents each selected from $R_2$;

B is heterocyclyl, wherein heterocyclyl is a saturated or partially unsaturated monocyclic, bicyclic or polycyclic ring system having 1, 2, or 3 heteroatom ring members independently selected from N, O, or S, each optionally substituted with 1, 2, 3, 4, or 5 substituents each selected from $R_4$;

$R_1$ is halogen, hydroxyl, cyano, $C_{1-4}$alkyl, halo-$C_{1-4}$alkyl, amino, $C_{1-4}$alkyl-amino, ($C_{1-4}$alkyl)$_2$-amino, amino-$C_{1-4}$ alkyl, $C_{1-4}$alkyl-amino-$C_{1-4}$alkyl, ($C_{1-4}$alkyl)$_2$-amino-$C_{1-4}$alkyl, amino-carbonyl, $C_{1-4}$alkyl-amino-carbonyl, $C_{1-4}$alkyl-amino-carbonyl-$C_{1-4}$alkyl, $C_{1-4}$alkyl-carbonyl-amino, $C_{1-4}$alkyl-carbonyl-amino-$C_{1-4}$alkyl, hydroxyl-$C_{1-4}$alkyl, $C_{1-4}$alkyl-carbonyl, $C_{1-4}$alkoxy, halo-$C_{1-4}$alkoxy, amino-$C_{1-4}$alkoxy, hydroxyl-$C_{1-4}$alkoxy, $C_{1-4}$alkyl-$C_{1-4}$alkoxy, $C_{1-4}$alkyl-amino-$C_{1-4}$alkoxy, ($C_{1-4}$alkyl)$_2$-amino-$C_{1-4}$alkoxy, $C_{1-4}$alkyl-carbonyl-amino-$C_{1-4}$alkoxy, $C_{1-4}$alkoxy-$C_{1-4}$alkoxy, $C_{1-4}$alkoxy-carbonyl, $C_{1-4}$alkoxy-carbonyl-amino, $C_{1-4}$alkoxy-carbonyl-amino-$C_{1-4}$alkoxy, $C_{2-4}$alkenyl, $C_{2-4}$alkenyl-amino-carbonyl, $C_{3-7}$cycloalkyl, $C_{3-7}$cycloalkyl-$C_{1-4}$alkoxy, $C_{3-7}$cycloalkenyl, heteroaryl, heteroaryl-$C_{1-4}$alkyl, heteroaryl-$C_{1-4}$alkyl-amino, heteroaryl-$C_{1-4}$alkyl-amino-carbonyl, heteroaryl-$C_{1-4}$alkyl-carbonyl-amino, heteroaryl-$C_{1-4}$alkyl-amino-carbonyl-$C_{1-4}$alkyl, heteroaryl-$C_{1-4}$alkyl-carbonyl-amino-$C_{1-4}$alkyl, heterocyclyl, heterocyclyl-$C_{1-4}$alkyl, heterocyclyl-$C_{1-4}$alkoxy, phenyl, or phenyl-$C_{1-4}$alkoxy, wherein heteroaryl is a monocyclic, bicyclic or polycyclic aromatic carbon atom ring structure radical in which one or more carbon atom ring members have been replaced, where allowed by structural stability, with one or more heteroatoms such as an O, S, or N atom, wherein heterocyclyl is a saturated or partially unsaturated monocyclic or bicyclic ring system having 1, 2, or 3 heteroatom ring members selected from N, O, and S, and wherein each instance of phenyl, heteroaryl or heterocyclyl is optionally substituted with 1, or 2 substituents each selected from $R_3$;

$R_2$ is halogen, hydroxyl, cyano, oxo, hydroxyl-imino, $C_{1-4}$alkyl, halo-$C_{1-4}$alkyl, amino, $C_{1-4}$alkyl-amino, ($C_{1-4}$alkyl)$_2$-amino, amino-$C_{1-4}$alkyl, amino-carbonyl, hydroxyl-$C_{1-4}$alkyl, $C_{1-4}$alkoxy, $C_{1-4}$alkoxy-carbonyl, $C_{2-4}$alkenyl, $C_{3-7}$cycloalkyl, or heterocyclyl-$C_{1-4}$alkyl;

$R_3$ is halogen, hydroxyl, nitro, oxo, hydroxyl-imino, $C_{1-4}$alkyl, amino, $C_{1-4}$alkyl-amino, ($C_{1-4}$alkyl)$_2$-amino, amino-$C_{1-4}$alkyl, $C_{1-4}$alkyl-amino-$C_{1-4}$alkyl, ($C_{1-4}$alkyl)$_2$-amino-$C_{1-4}$alkyl, amino-carbonyl, $C_{1-4}$alkyl-amino-carbonyl, $C_{1-4}$alkyl-amino-carbonyl-$C_{1-4}$alkyl, $C_{1-4}$alkyl-carbonyl-amino, $C_{1-4}$alkyl-carbonyl-amino-$C_{1-4}$alkyl, hydroxyl-$C_{1-4}$alkyl, $C_{1-4}$alkyl-carbonyl, $C_{1-4}$alkoxy, halo-$C_{1-4}$alkoxy, amino-$C_{1-4}$alkoxy, hydroxyl-$C_{1-4}$alkoxy, $C_{1-4}$alkyl-$C_{1-4}$alkoxy, $C_{1-4}$alkyl-amino-$C_{1-4}$alkoxy, ($C_{1-4}$alkyl)$_2$-amino-$C_{1-4}$alkoxy, $C_{1-4}$alkyl-carbonyl-amino-$C_{1-4}$alkoxy, $C_{1-4}$alkoxy-$C_{1-4}$alkoxy, $C_{1-4}$alkoxy-carbonyl, $C_{1-4}$alkoxy-carbonyl-amino, $C_{1-4}$alkoxy-carbonyl-amino-$C_{1-4}$alkoxy, $C_{2-4}$alkenyl, $C_{2-4}$alkenyl-amino-carbonyl, $C_{3-7}$cycloalkyl, $C_{3-7}$cycloalkyl-$C_{1-4}$alkoxy, $C_{3-7}$cycloalkenyl, heteroaryl, heteroaryl-$C_{1-4}$alkyl, heteroaryl-$C_{1-4}$alkyl-amino, heteroaryl-$C_{1-4}$alkyl-amino-carbonyl, heteroaryl-$C_{1-4}$alkyl-carbonyl-amino, heteroaryl-$C_{1-4}$alkyl-amino-carbonyl-$C_{1-4}$alkyl, heteroaryl-$C_{1-4}$alkyl-carbonyl-amino-$C_{1-4}$alkyl, heterocyclyl, heterocyclyl-$C_{1-4}$alkyl, phenyl, or phenyl-$C_{1-4}$alkoxy;

$R_4$ is independently selected from halogen, $C_{1-4}$alkyl, hydroxyl-$C_{1-4}$alkyl, amino, $C_{1-4}$alkyl-amino, ($C_{1-4}$alkyl)$_2$-amino or hydroxyl-$C_{1-4}$alkyl-amino; and $R_5$ is hydrogen, $C_{1-4}$alkyl, or hydroxyl-$C_{1-4}$alkyl;

wherein a form of the compound is selected from the group consisting of a prodrug, salt, hydrate, solvate, clathrate, isotopologue, racemate, enantiomer, diastereomer, stereoisomer, polymorph and tautomer form thereof.

Another embodiment of the present description further relates to methods for treating or ameliorating HD in a subject in need thereof comprising administering to the subject an effective amount of a compound of Formula (I) selected from a compound of Formula (Ia) and Formula (Ib):

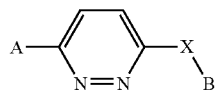

(Ia)

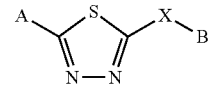

(Ib)

or a form thereof, wherein

X is O, NH, N(CH$_3$) or a bond;

A is aryl, heteroaryl or heterocyclyl, wherein aryl is selected from the group consisting of

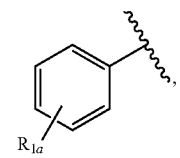

a1

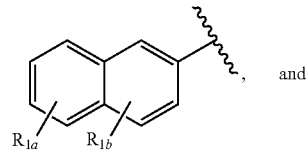

a2

, and

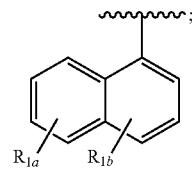

a3

;

wherein heteroaryl is selected from the group consisting of

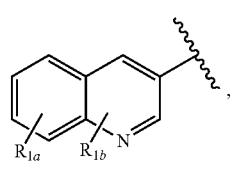

a4

,

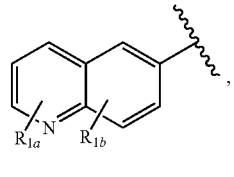

a5

,

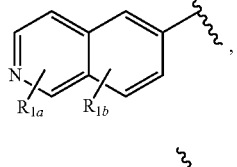

a6

,

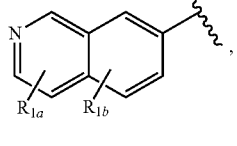

a7

,

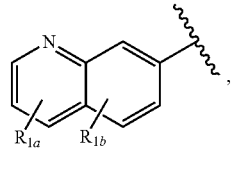

a8

,

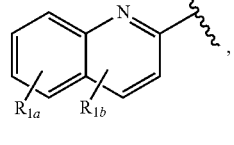

a9

,

-continued
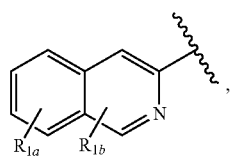, a10
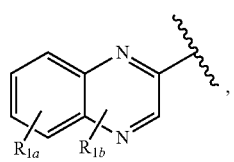, a11
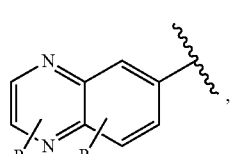, a12
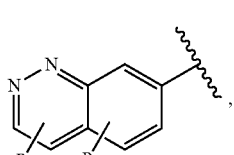, a13
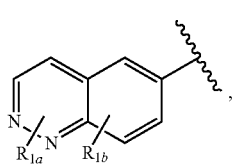, a14
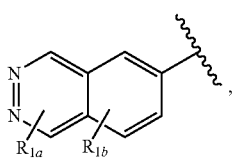, a15
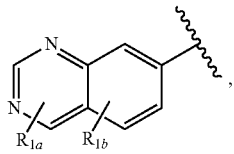, a16
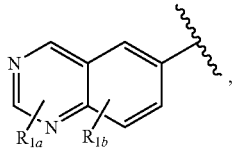, a17
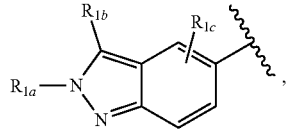, a18
-continued
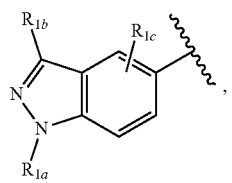, a19
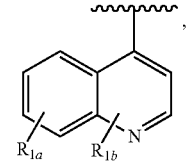, a20
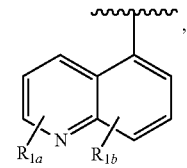, a21
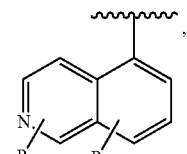, a22
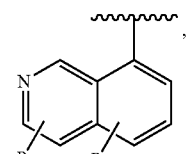, a23
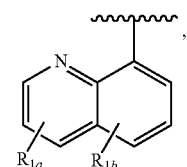, a24
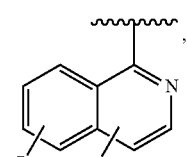, a25
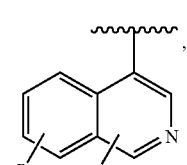, a26
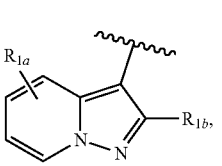, a27

-continued
a28 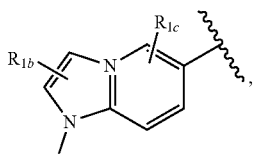
a29 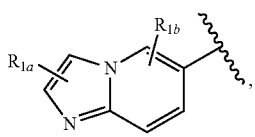
a30 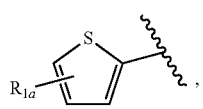
a31 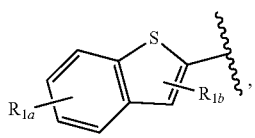
a32 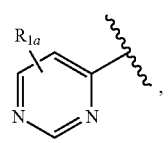
a33 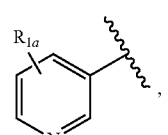
a34 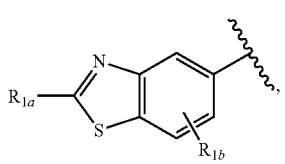
a35 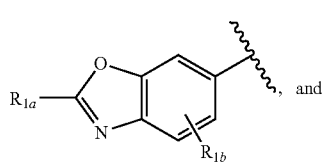, and
a36 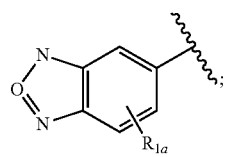;
wherein heterocyclyl is selected from the group consisting of
a37 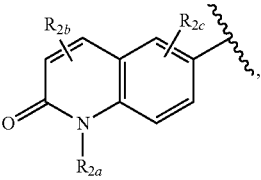
a38 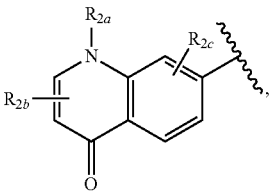
a39 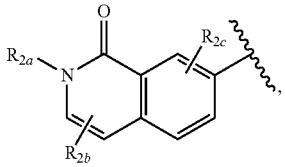
a40 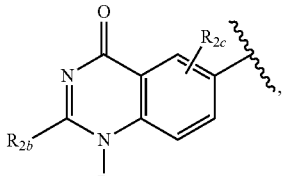
a41 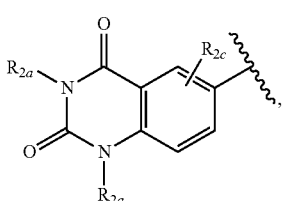
a42 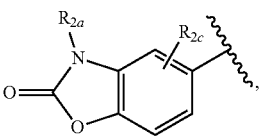
a43 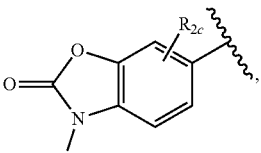
a44 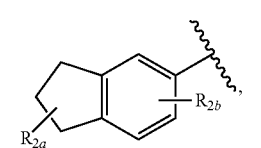

-continued
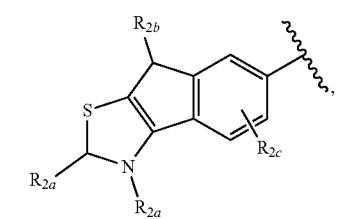
a45
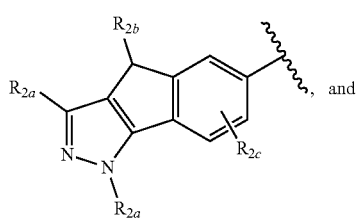
a46, and
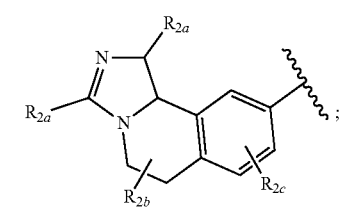
a47;
B is heterocyclyl selected from the group consisting of
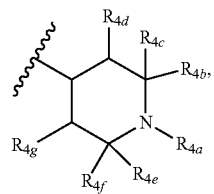
b1
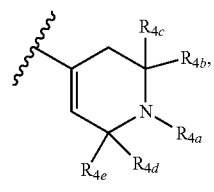
b2
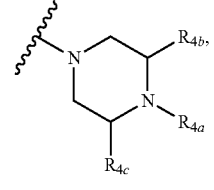
b3
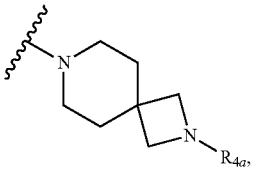
b4
-continued
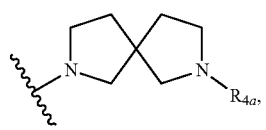
b5
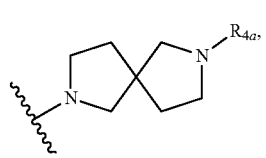
b6
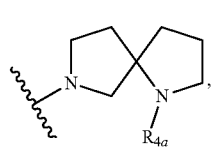
b7
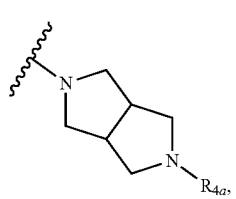
b8
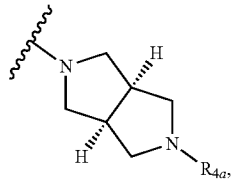
b9
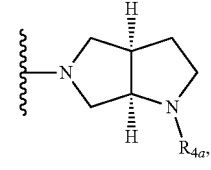
b10
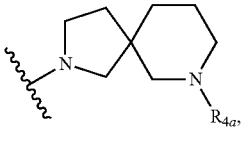
b11
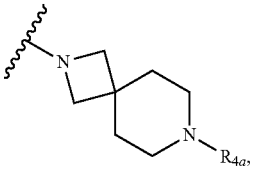
b12
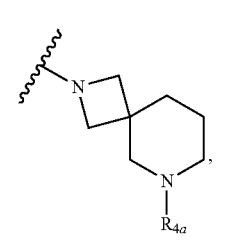
b13

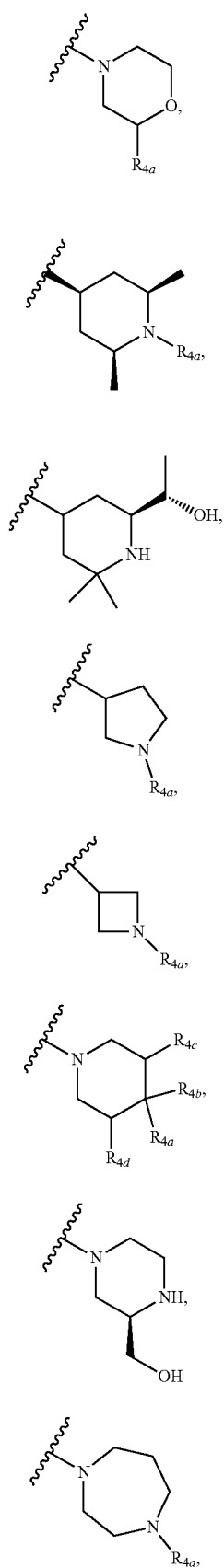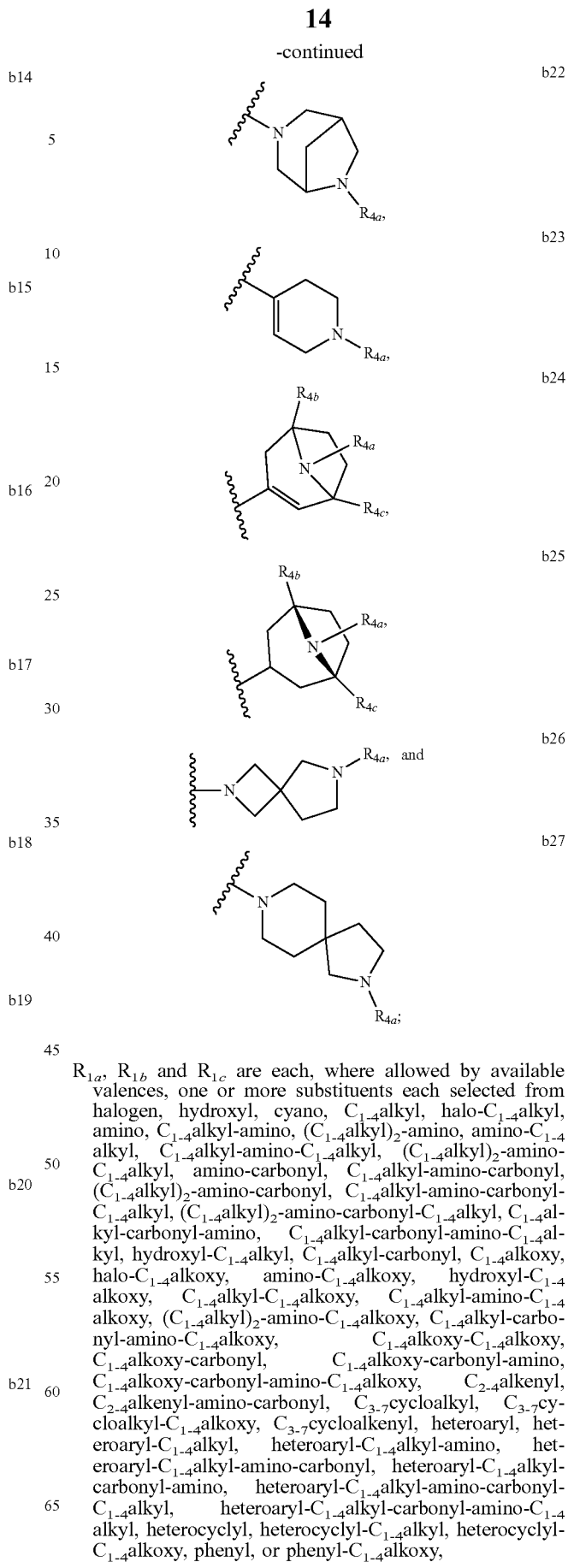

$R_{1a}$, $R_{1b}$ and $R_{1c}$ are each, where allowed by available valences, one or more substituents each selected from halogen, hydroxyl, cyano, $C_{1-4}$alkyl, halo-$C_{1-4}$alkyl, amino, $C_{1-4}$alkyl-amino, $(C_{1-4}$alkyl$)_2$-amino, amino-$C_{1-4}$alkyl, $C_{1-4}$alkyl-amino-$C_{1-4}$alkyl, $(C_{1-4}$alkyl$)_2$-amino-$C_{1-4}$alkyl, amino-carbonyl, $C_{1-4}$alkyl-amino-carbonyl, $(C_{1-4}$alkyl$)_2$-amino-carbonyl, $C_{1-4}$alkyl-amino-carbonyl-$C_{1-4}$alkyl, $(C_{1-4}$alkyl$)_2$-amino-carbonyl-$C_{1-4}$alkyl, $C_{1-4}$alkyl-carbonyl-amino, $C_{1-4}$alkyl-carbonyl-amino-$C_{1-4}$alkyl, hydroxyl-$C_{1-4}$alkyl, $C_{1-4}$alkyl-carbonyl, $C_{1-4}$alkoxy, halo-$C_{1-4}$alkoxy, amino-$C_{1-4}$alkoxy, hydroxyl-$C_{1-4}$alkoxy, $C_{1-4}$alkyl-$C_{1-4}$alkoxy, $C_{1-4}$alkyl-amino-$C_{1-4}$alkoxy, $(C_{1-4}$alkyl$)_2$-amino-$C_{1-4}$alkoxy, $C_{1-4}$alkyl-carbonyl-amino-$C_{1-4}$alkoxy, $C_{1-4}$alkoxy-$C_{1-4}$alkoxy, $C_{1-4}$alkoxy-carbonyl, $C_{1-4}$alkoxy-carbonyl-amino, $C_{1-4}$alkoxy-carbonyl-amino-$C_{1-4}$alkoxy, $C_{2-4}$alkenyl, $C_{2-4}$alkenyl-amino-carbonyl, $C_{3-7}$cycloalkyl, $C_{3-7}$cycloalkyl-$C_{1-4}$alkoxy, $C_{3-7}$cycloalkenyl, heteroaryl, heteroaryl-$C_{1-4}$alkyl, heteroaryl-$C_{1-4}$alkyl-amino, heteroaryl-$C_{1-4}$alkyl-amino-carbonyl, heteroaryl-$C_{1-4}$alkyl-carbonyl-amino, heteroaryl-$C_{1-4}$alkyl-amino-carbonyl-$C_{1-4}$alkyl, heteroaryl-$C_{1-4}$alkyl-carbonyl-amino-$C_{1-4}$alkyl, heterocyclyl, heterocyclyl-$C_{1-4}$alkyl, heterocyclyl-$C_{1-4}$alkoxy, phenyl, or phenyl-$C_{1-4}$alkoxy, wherein heteroaryl is a monocyclic, bicyclic or polycyclic aromatic carbon atom ring structure radical in which one or more carbon atom ring members have been replaced, where allowed by structural stability, with one or more heteroatoms such as an O, S, or N atom, wherein heterocyclyl is a saturated or partially unsaturated monocyclic or bicyclic ring system having 1, 2, or 3 heteroatom ring members selected from N, O, and S, and wherein each instance of phenyl, heteroaryl or heterocyclyl is optionally substituted with 1, or 2 substituents each selected from $R_3$;

$R_{2a}$, $R_{2b}$ and $R_{2c}$ are each, where allowed by available valences, one or more substituents each selected from halogen, hydroxyl, cyano, oxo, hydroxyl-imino, $C_{1-4}$alkyl, halo-$C_{1-4}$alkyl, amino, $C_{1-4}$alkyl-amino, $(C_{1-4}$alkyl$)_2$-amino, amino-$C_{1-4}$alkyl, $C_{1-4}$alkyl-amino-$C_{1-4}$alkyl, $(C_{1-4}$alkyl$)_2$-amino-$C_{1-4}$alkyl, amino-carbonyl, hydroxyl-$C_{1-4}$alkyl, $C_{1-4}$alkoxy, $C_{1-4}$alkoxy-carbonyl, $C_{2-4}$alkenyl, $C_{3-7}$cycloalkyl, or heterocyclyl-$C_{1-4}$alkyl, wherein heterocyclyl is a saturated or partially unsaturated monocyclic or bicyclic ring system having 1, 2, or 3 heteroatom ring members selected from N, O, and S, and wherein each instance of heterocyclyl is optionally substituted with 1, or 2 substituents each selected from $R_3$;

$R_3$ is halogen, hydroxyl, nitro, oxo, hydroxyl-imino, $C_{1-4}$alkyl, amino, $C_{1-4}$alkyl-amino, $(C_{1-4}$alkyl$)_2$-amino, amino-$C_{1-4}$alkyl, $C_{1-4}$alkyl-amino-$C_{1-4}$alkyl, $(C_{1-4}$alkyl$)_2$-amino-$C_{1-4}$alkyl, amino-carbonyl, $C_{1-4}$alkyl-amino-carbonyl, $(C_{1-4}$alkyl$)_2$-amino-carbonyl, $C_{1-4}$alkyl-amino-carbonyl-$C_{1-4}$alkyl, $(C_{1-4}$alkyl$)_2$-amino-carbonyl-$C_{1-4}$alkyl, $C_{1-4}$alkyl-carbonyl-amino, $C_{1-4}$alkyl-carbonyl-amino-$C_{1-4}$alkyl, hydroxyl-$C_{1-4}$alkyl, $C_{1-4}$alkyl-carbonyl, $C_{1-4}$alkoxy, halo-$C_{1-4}$alkoxy, amino-$C_{1-4}$alkoxy, hydroxyl-$C_{1-4}$alkoxy, $C_{1-4}$alkyl-$C_{1-4}$alkoxy, $C_{1-4}$alkyl-amino-$C_{1-4}$alkoxy, $(C_{1-4}$alkyl$)_2$-amino-$C_{1-4}$alkoxy, $C_{1-4}$alkyl-carbonyl-amino-$C_{1-4}$alkoxy, $C_{1-4}$alkoxy-$C_{1-4}$alkoxy, $C_{1-4}$alkoxy-carbonyl, $C_{1-4}$alkoxy-carbonyl-amino, $C_{1-4}$alkoxy-carbonyl-amino-$C_{1-4}$alkoxy, $C_{2-4}$alkenyl, $C_{2-4}$alkenyl-amino-carbonyl, $C_{3-7}$cycloalkyl, $C_{3-7}$cycloalkyl-$C_{1-4}$alkoxy, $C_{3-7}$cycloalkenyl, heteroaryl, heteroaryl-$C_{1-4}$alkyl, heteroaryl-$C_{1-4}$alkyl-amino, heteroaryl-$C_{1-4}$alkyl-amino-carbonyl, heteroaryl-$C_{1-4}$alkyl-carbonyl-amino, heteroaryl-$C_{1-4}$alkyl-amino-carbonyl-$C_{1-4}$alkyl, heteroaryl-$C_{1-4}$alkyl-carbonyl-amino-$C_{1-4}$alkyl, heterocyclyl, heterocyclyl-$C_{1-4}$alkyl, phenyl, or phenyl-$C_{1-4}$alkoxy; and $R_{4a}$, $R_{4b}$, $R_{4c}$, $R_{4d}$, $R_{4e}$, $R_{4f}$ and $R_{4g}$ are independently selected from halogen, $C_{1-4}$alkyl, hydroxyl-$C_{1-4}$alkyl, amino, $C_{1-4}$alkyl-amino, $(C_{1-4}$alkyl$)_2$-amino or hydroxyl-$C_{1-4}$alkyl-amino;

wherein a form of the compound is selected from the group consisting of a prodrug, salt, hydrate, solvate, clathrate, isotopologue, racemate, enantiomer, diastereomer, stereoisomer, polymorph and tautomer form thereof.

Another aspect of the present description relates to a compound of Formula (I) selected from a compound of Formula (Ia11), Formula (Ia15), Formula (Ia18) or Formula (Ib1):

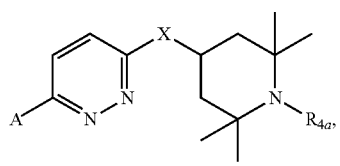

(Ia11)

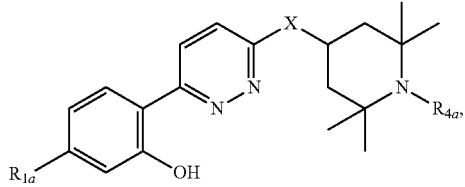

(Ia15)

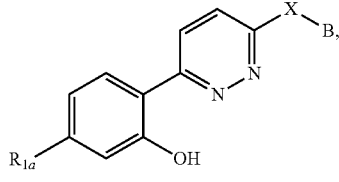

(Ia18)

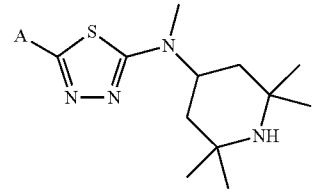

(Ib1)

or a form thereof, wherein (when present),

X is selected from O, $NR_5$, or a bond;

A is selected from phenyl, thiophenyl, indazolyl, pyridinyl, pyrimidinyl or phenoxy, wherein phenyl and phenoxy are each optionally substituted with 1, 2 or 3 substituents each selected from $R_{1a}$, wherein thiophenyl, indazolyl, pyridinyl, pyrimidinyl are each optionally substituted with 1 or 2 substituents each selected from $R_{1a}$;

B is selected from 1H-pyrazolyl, piperidinyl, 1,2,3,6-tetrahydropyridinyl, (1R,5S)-8-azabicyclo[3.2.1]octyl, 8-azabicyclo[3.2.1]oct-2-enyl, 2,6-diazaspiro[3.4]octyl or 2,7-diazaspiro[3.5]nonyl, each optionally substituted with 1 or 2 substituents each selected from $R_{4a}$;

$R_{1a}$ is selected from halogen, hydroxyl, $C_{1-4}$alkyl, halo-$C_{1-4}$alkyl, amino, $C_{1-4}$alkoxy, or heteroaryl, wherein heteroaryl is a monocyclic, bicyclic or polycyclic aromatic carbon atom ring structure radical in which one or more carbon atom ring members have been replaced, where allowed by structural stability, with one or more heteroatoms such as an O, S, or N atom, optionally substituted with 1 or 2 substituents each selected from R3a;

$R_{3a}$ is selected from nitro or $C_{1-4}$alkyl; and, $R_{4a}$ is $C_{1-4}$alkyl;

$R_{5a}$ is hydrogen, $C_{1-4}$alkyl, or hydroxyl-$C_{1-4}$alkyl;

wherein a form of the compound is selected from the group consisting of a prodrug, salt, hydrate, solvate, clathrate, isotopologue, racemate, enantiomer, diastereomer, stereoisomer, polymorph and tautomer form thereof.

Another aspect of the present description relates to a compound of Formula (I) selected from a compound of Formula (Ia11), Formula (Ia15), Formula (Ia18) or Formula (Ib1):

or a form thereof, wherein (when present), $R_{1a}$ is selected from fluoro, chloro, hydroxyl, methyl, difluoromethyl, amino, methoxy or 1H-pyrazolyl or 1H-imidazol-1-yl, wherein 1H-pyrazolyl is optionally substituted with 1 or 2 substituents each selected from $R_{3a}$;

$R_{3a}$ is selected from nitro or methyl or amino; and, $R_{4a}$ is methyl or ethyl;

$R_{5a}$ is hydrogen or methyl;

wherein a form of the compound is selected from the group consisting of a prodrug, salt, hydrate, solvate, clathrate, isotopologue, racemate, enantiomer, diastereomer, stereoisomer, polymorph and tautomer form thereof.

Another embodiment of the method of the present description includes the use of a compound of Formula (Ia) or a form thereof selected from a compound of Formula (Ia1) or a form thereof, wherein substituents $R_{1a}$, $R_{1b}$, and X, when present, are indicated in the table below with multiple substituents separated by a comma; and, "--" indicates that one or more $R_{1a}$, $R_{1b}$, and X substituents are not present:

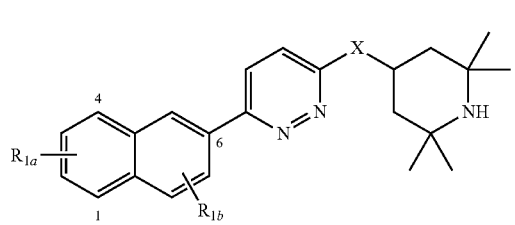

(Ia1)

| Cpd | $R_{1a}$ | $R_{1b}$ | X |
|---|---|---|---|
| 1 | — | — | NH |
| 8 | 2-OH | — | N(CH$_3$) |
| 40 | 1-CH$_2$CH=CH$_2$, 2-OH | — | N(CH$_3$) |
| 106 | 1-Br, 2-OH | 7-OH | N(CH$_3$) |
| 107 | 1-Cl, 2-OH | 7-OH | N(CH$_3$) |

Another embodiment of the method of the present description includes the use of a compound of Formula (Ia) or a form thereof selected from a compound of Formula (Ia2) or a form thereof, wherein substituents $R_{1a}$, $R_{1b}$, and $R_{4a}$, when present, are indicated in the table below with multiple substituents separated by a comma; and, "--" indicates that one or more $R_{1a}$, $R_{1b}$, and $R_{4a}$ substituents are not present:

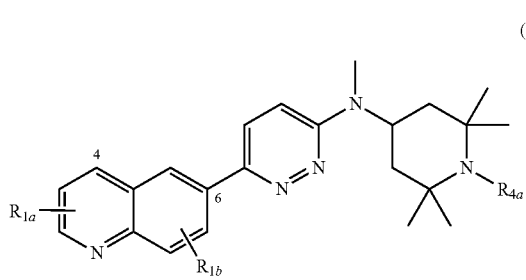

(Ia2)

| Cpd | $R_{1a}$ | $R_{1b}$ | $R_{4a}$ |
|---|---|---|---|
| 13 | — | — | — |
| 207 | — | 7-OH | — |
| 208 | — | 7-OH | CH$_3$ |
| 210 | 2-CH$_3$ | 7-OH | — |

-continued

| Cpd | $R_{1a}$ | $R_{1b}$ | $R_{4a}$ |
|---|---|---|---|
| 222 | 3-Cl | 7-OH | — |
| 223 | 3-Br | 7-OH | — |
| 224 | 3-CN | 7-OH | — |
| 225 | 3-(1-CH$_3$-1H-imidazol-4-yl) | 7-OH | — |
| 226 | 3-(1H-imidazol-1-yl) | 7-OH | — |
| 227 | 3-OH | 7-OH | — |
| 228 | 3-CH$_2$CH$_3$ | 7-OH | — |
| 229 | 3-CH(CH$_3$)$_2$ | 7-OH | — |
| 232 | 2-CH$_3$, 4-OCH$_3$, | 7-OH | — |
| 233 | 2-CH$_3$, 4-(pyrrolidin-1-yl) | 7-OH | — |
| 234 | 2-CH$_3$, 4-(morpholin-4-yl) | 7-OH | — |
| 235 | 2-CH$_3$, 4-N(CH$_3$)$_2$ | 7-OH | — |
| 236 | 2-CH$_3$, 4-OCH$_2$CH$_3$ | 7-OH | — |
| 237 | 2-CH$_3$, 4-(1-CH$_3$-1H-pyrazol-4-yl) | 7-OH | — |
| 240 | 3-(tetrahydro-2H-pyran-4-yl) | 7-OH | — |
| 249 | 4-OCH$_3$ | 7-OH | — |
| 250 | 2-CH$_3$, 4-(azetidin-1-yl) | 7-OH | — |
| 251 | 2-CH$_3$, 4-CN | 7-OH | — |
| 252 | 2-CH$_3$, 4-cyclopropyl | 7-OH | — |
| 253 | 2-CH$_3$, 4-(3,6-dihydro-2H-pyran-4-yl) | 7-OH | — |
| 254 | 2-CH$_3$, 4-(tetrahydro-2H-pyran-4-yl) | 7-OH | — |
| 255 | 2-CH$_3$, 4-(oxetan-3-yl) | 7-OH | — |
| 256 | 4-N(CH$_3$)$_2$ | 7-OH | — |
| 262 | 2-CN | 7-OH | — |
| 265 | 2-C(O)NH$_2$ | 7-OH | — |
| 293 | 3-Cl | 7-OH | — |
| 294 | 3-CH(CH$_3$)$_2$ | 7-OH | — |
| 296 | 2-CH$_3$, 4-Cl | 7-OH | — |

Another embodiment of the method of the present description includes the use of a compound of Formula (Ia) or a form thereof selected from a compound of Formula (Ia3) or a form thereof, wherein substituents $R_{1a}$, $R_{1b}$ and X, when present, are indicated in the table below with multiple substituents separated by a comma; and, "--" indicates that one or more $R_{1a}$, $R_{1b}$ and X substituents are not present:

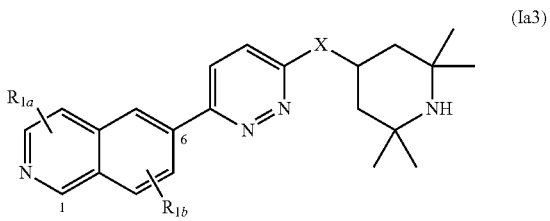

(Ia3)

| Cpd | $R_{1a}$ | $R_{1b}$ | X |
|---|---|---|---|
| 11 | — | — | O |
| 15 | — | — | N(CH$_3$) |
| 218 | — | 7-OH | N(CH$_3$) |
| 261 | 1-CN | 7-OH | N(CH$_3$) |
| 272 | 1-CH$_3$ | 7-OH | N(CH$_3$) |

-continued

| Cpd | $R_{1a}$ | $R_{1b}$ | X |
|---|---|---|---|
| 275 | 1-CN, 3-CH$_3$ | 7-OH | N(CH$_3$) |
| 292 | 3-(OCH$_2$-phenyl) | — | N(CH$_3$) |

Another embodiment of the method of the present description includes the use of a compound of Formula (Ia) or a form thereof selected from a compound of Formula (Ia4) or a form thereof, wherein substituents X, $R_{1a}$, $R_{1b}$ and $R_{4a}$, when present, are indicated in the table below; and, "--" indicates that one or more X, $R_{1a}$, $R_{1b}$ and $R_{4a}$ substituents are not present:

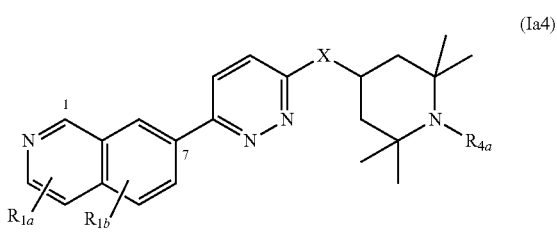

(Ia4)

| Cpd | $R_{1a}$ | $R_{1b}$ | X | $R_{4a}$ |
|---|---|---|---|---|
| 10 | — | — | O | — |
| 14 | — | — | N(CH$_3$) | — |
| 159 | 1-(OCH$_2$-phenyl) | — | N(CH$_3$) | — |
| 211 | — | 6-OH | N(CH$_3$) | CH$_3$ |
| 212 | — | 6-OH | N(CH$_3$) | — |
| 213 | — | 6-OH | O | — |
| 215 | 1-cyclopropyl | 6-OH | N(CH$_3$) | — |
| 216 | 1-OH | 6-OH | N(CH$_3$) | — |
| 217 | 1-CN | 6-OH | N(CH$_3$) | — |
| 264 | 1-C(O)NH$_2$ | 6-OH | N(CH$_3$) | — |
| 273 | 1-CH3 | 6-OH | N(CH$_3$) | — |
| 274 | 1,3-(CH$_3$)$_2$ | 6-OH | N(CH$_3$) | — |
| 276 | 1-NH$_2$ | 6-OH | N(CH$_3$) | — |
| 283 | 1-OCH$_2$CH$_3$ | 6-OH | N(CH$_3$) | — |
| 284 | 1-OH | 6-OH | O | — |
| 285 | 3-phenyl | 6-OH | N(CH$_3$) | — |
| 286 | 3-CH$_3$ | 6-OH | N(CH$_3$) | — |
| 287 | 3-cyclopropyl | 6-OH | N(CH$_3$) | — |
| 288 | 3-CH(CH$_3$)$_2$ | 6-OH | N(CH$_3$) | — |
| 289 | 3-(CH$_2$)$_2$CH$_3$ | 6-OH | N(CH$_3$) | — |
| 290 | 3-CH(CH$_3$)$_2$ | 6-OH | O | — |

Another embodiment of the method of the present description includes the use of a compound of Formula (Ia) or a form thereof selected from a compound of Formula (Ia5) or a form thereof, wherein substituents $R_{1a}$ and $R_{1b}$, when present, are indicated in the table below with multiple substituents separated by a comma; and, "--" indicates that one or more $R_{1a}$ and $R_{1b}$ substituents are not present:

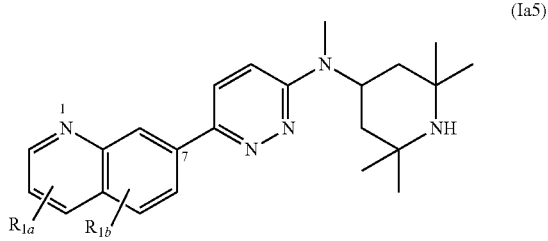

(Ia5)

| Cpd | $R_{1a}$ | $R_{1b}$ |
|---|---|---|
| 12 | — | — |
| 220 | — | 6-OH |
| 221 | 2-CH$_3$ | 6-OH |
| 238 | 4-OCH$_3$ | 6-OH |
| 241 | 3-Cl | 6-OH |
| 242 | 3-Br | 6-OH |
| 243 | 3-CH$_3$ | 6-OH |
| 244 | 3-CH$_3$ | 5-Br, 6-OH |
| 263 | 2-CN | 6-OH |
| 266 | 2-C(O)NH$_2$ | 6-OH |
| 267 | 2-CO$_2$CH$_3$ | 6-OH |
| 297 | 4-Cl | 6-OH |
| 300 | — | 6-OH |

Another embodiment of the method of the present description includes the use of a compound of Formula (Ia) or a form thereof selected from a compound of Formula (Ia6) or a form thereof, wherein substituents $R_{1a}$, when present, are indicated in the table below; and, "--" indicates that one or more $R_{1a}$ substituents are not present:

(Ia6)

| Cpd | $R_{1a}$ |
|---|---|
| 239 | — |
| 246 | 2,3-(CH$_3$)$_2$ |
| 247 | 2-CH$_3$ |
| 248 | 3-CH$_3$ |

Another embodiment of the method of the present description includes the use of a compound of Formula (Ia) or a form thereof selected from a compound of Formula (Ia7) or a form thereof, wherein substituents $R_{1a}$, when present, are indicated in the table below; and, "--" indicates that one or more $R_{1a}$ substituents are not present:

(Ia7)

| Cpd | $R_{1a}$ |
|---|---|
| 258 | — |
| 260 | 2-CH$_3$ |

Another embodiment of the method of the present description includes the use of a compound of Formula (Ia) or a form thereof selected from a compound of Formula (Ia8) or a form thereof, wherein substituents $R_{1a}$ and B, when present, are indicated in the table below; and, "--" indicates that one or more $R_{1a}$ and B substituents are not present:

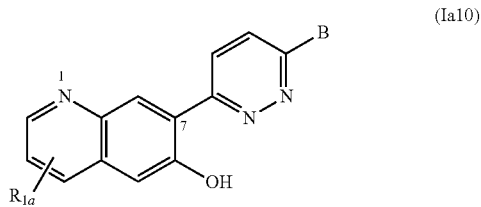

| Cpd | $R_{1a}$ | B |
|---|---|---|
| 209 | — | 6-((3aR,6aS)-5-$CH_3$-hexahydropyrrolo[3,4-c]pyrrol-2(1H)-yl) |
| 269 | 2-CN | piperazin-1-yl |

Another embodiment of the method of the present description includes the use of a compound of Formula (Ia) or a form thereof selected from a compound of Formula (Ia9) or a form thereof, wherein substituents $R_{1a}$ and B, when present, are indicated in the table below; and, "--" indicates that one or more $R_{1a}$ and B substituents are not present:

| Cpd | $R_{1a}$ | B |
|---|---|---|
| 214 | — | 6-((3aR,6aS)-5-$CH_3$-hexahydropyrrolo[3,4-c]pyrrol-2(1H)-yl) |
| 270 | — | piperazin-1-yl |
| 291 | 3-$CH_3$ | piperazin-1-yl |

Another embodiment of the method of the present description includes the use of a compound of Formula (Ia) or a form thereof selected from a compound of Formula (Ia10) or a form thereof, wherein substituents $R_{1a}$ and B, when present, are indicated in the table below; and, "--" indicates that one or more $R_{1a}$ and B substituents are not present:

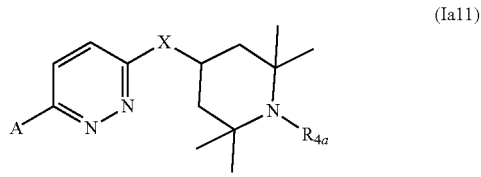

| Cpd | $R_{1a}$ | B |
|---|---|---|
| 268 | 2-CN | piperazin-1-yl |
| 271 | — | 1,2,3,6-tetrahydropyridin-4-yl |

Another embodiment of the method of the present description includes the use of a compound of Formula (Ia) or a form thereof selected from a compound of Formula (Ia11) or a form thereof, wherein substituents A, X and $R_{4a}$, when present, are indicated in the table below; and, "--" indicates that one or more A, X and $R_{4a}$ substituents are not present:

| Cpd | A | X | $R_{4a}$ |
|---|---|---|---|
| 2 | benzo[b]thiophen-2-yl | N($CH_3$) | — |
| 4 | 5-CN-benzo[b]thiophen-2-yl | N($CH_3$) | — |
| 5 | quinolin-3-yl | NH | — |
| 6 | benzo[b]thiophen-2-yl | O | — |
| 9 | benzo[b]thiophen-2-yl | NH | — |
| 16 | imidazo[1,2-a]pyridin-6-yl | N($CH_3$) | — |
| 17 | 6-phenyl-pyridin-3-yl | N($CH_3$) | — |
| 18 | 6-(1H-pyrrol-1-yl)-pyridin-3-yl | N($CH_3$) | — |
| 19 | 6-(1H-pyrazol-1-yl)-pyridin-3-yl | N($CH_3$) | — |
| 20 | quinoxalin-2-yl | N($CH_3$) | — |
| 21 | quinolin-3-yl | N($CH_3$) | — |
| 22 | phthalazin-6-yl | N($CH_3$) | — |
| 23 | benzo[c][1,2,5]oxadiazol-5-yl | NH | — |
| 24 | benzo[d]thiazol-5-yl | NH | — |
| 25 | 2-$CH_3$-benzo[d]oxazol-6-yl | NH | — |
| 30 | 2-(4-CN-phenol) | N($CH_3$) | — |
| 32 | 2-(4-$CF_3$-phenol) | N($CH_3$) | — |
| 33 | 6-(2-F-phenol) | N($CH_3$) | — |
| 34 | 2-[3,5-($OCH_3$)$_2$-phenol] | N($CH_3$) | — |
| 35 | 2-[4,5-($OCH_3$)$_2$-phenol] | N($CH_3$) | — |
| 37 | 2-(4,5-$F_2$-phenol) | N($CH_3$) | — |
| 41 | benzo[b]thiophen-2-yl | NH | $CH_3$ |
| 53 | 2-[4-(1H-pyrazol-1-yl)-phenol] | N($CH_3$) | — |
| 115 | 2-[3-OH-5-(1H-pyrazol-4-yl)-phenol] | N($CH_3$) | — |
| 116 | 2-[3-$OCH_3$-5-(1H-pyrazol-4-yl)-phenol] | N($CH_3$) | — |
| 117 | 2-[5-(1H-pyrazol-4-yl)-3-$OCF_3$-phenol] | NH | — |
| 118 | 2-[5-(1-$CH_3$-1H-pyrazol-4-yl)-3-$OCF_3$-phenol] | N($CH_3$) | — |
| 119 | 2-[5-(1H-pyrazol-4-yl)-3-$OCF_3$-phenol] | N($CH_3$) | — |
| 120 | 2-[5-(1-$CH_3$-pyridin-2(1H)-one)-3-$OCF_3$-phenol] | N($CH_3$) | — |
| 121 | 2-[3-$OCH_3$-5-(1-$CH_3$-1H-pyrazol-4-yl)-phenol] | N($CH_3$) | — |
| 122 | 2-[3-$OCH_3$-5-(5,6,7,8-tetrahydroimidazo-[1,2-a]pyridin-3-yl)-phenol] | N($CH_3$) | — |
| 123 | 2-[3-$OCH_3$-5-(pyridin-3-yl)-phenol] | N($CH_3$) | — |
| 124 | 2-[3-$OCH_3$-5-(1-cyclopentyl-1H-pyrazol-4-yl)-phenol] | N($CH_3$) | — |

-continued

| Cpd | A | X | R$_{4a}$ |
|---|---|---|---|
| 125 | 2-[5-(3-OCH$_3$-phenyl)-3-OCH$_3$-phenol] | N(CH$_3$) | — |
| 126 | 2-[3-benzyloxy-5-(5-CH$_3$-oxazol-2-yl)-phenol] | N(CH$_3$) | — |
| 127 | 2-[3-OCH$_2$CH$_3$-5-(5-CH$_3$-oxazol-2-yl)-phenol] | N(CH$_3$) | — |
| 128 | 2-[3-(OCH$_2$-cyclopropyl)-5-(5-CH$_3$-oxazol-2-yl)-phenol] | N(CH$_3$) | — |
| 129 | 5-(2-CH$_3$-1H-benzo[d]imidazol-6-ol) | N(CH$_3$) | — |
| 134 | 2-[4-(1H-pyrazol-4-yl)-phenol] | N(CH$_3$) | — |
| 135 | 2-[4-(4,5,6,7-tetrahydropyrazolo[1,5-a]pyridin-3-yl)-phenol] | N(CH$_3$) | — |
| 136 | 2-[4-(4,5,6,7-tetrahydropyrazolo[1,5-a]pyrazin-3-yl)-phenol] | N(CH$_3$) | — |
| 137 | 2-[4-(1H-indol-2-yl)-phenol] | N(CH$_3$) | — |
| 138 | 2-[4-(cyclopent-1-en-1-yl)-phenol] | N(CH$_3$) | — |
| 139 | 2-[4-(1H-pyrazol-3-yl)-phenol] | N(CH$_3$) | — |
| 140 | 2-[4-(2-OH-pyridin-4-yl)-phenol] | N(CH$_3$) | — |
| 141 | 2[4-(1-CH$_3$-pyridin-2(1H)-one)-phenol] | O | — |
| 142 | 2-[4-(2-OH-pyridin-4-yl)-phenol] | O | — |
| 144 | 2-[4-Cl-5-(1H-pyrazol-4-yl)-phenol] | N(CH$_3$) | — |
| 145 | 2-[4-F-5-(1H-pyrazol-4-yl)-phenol] | N(CH$_3$) | — |
| 146 | 2-[5-F-4-(1H-imidazol-4-yl)-phenol] | N(CH$_3$) | — |
| 147 | 2-[5-F-4-(1H-pyrazol-4-yl)-phenol] | N(CH$_3$) | — |
| 148 | 2-[5-F-(1H-pyrazol-5-yl)-phenol] | N(CH$_3$) | — |
| 149 | 6-OH-1-oxo-2,3-dihydro-1H-inden-5-yl | N(CH$_3$) | — |
| 150 | 6-(1,4-dihydroindeno[1,2-c]-1H-pyrazol-7-ol) | N(CH$_3$) | — |
| 151 | 6-OH-1-OH-imino-2,3-dihydro-1H-inden-5-yl | N(CH$_3$) | — |
| 152 | 6-OH-1-OH-2,3-dihydro-1H-inden-5-yl | N(CH$_3$) | — |
| 153 | 6-(2-NH$_2$-8H-indeno[1,2-d]thiazol-5-ol) | N(CH$_3$) | — |
| 154 | 9-(5,6-dihydroimidazo[5,1-a]isoquinolin-8-ol) | N(CH$_3$) | — |
| 155 | 2-{4-[C(O)NHCH$_2$-(1-CH$_3$-1H-pyrazol-4-yl)]-phenol} | N(CH$_3$) | — |
| 156 | 2-[4-(4-CH$_2$OH-1H-pyrazol-1-yl)-phenol] | N(CH$_3$) | — |
| 158 | 2-(OCH$_2$-phenyl)-isoquinolin-6-yl | N(CH$_3$) | — |
| 160 | 2-[3-F-5-(2-OCH$_3$-pyridin-4-yl)-phenol] | N(CH$_3$) | — |
| 161 | 4-[1-(4-pyridin-2(1H)-one)-3-F-5-OH-phenyl] | N(CH$_3$) | — |
| 162 | 4-{1-[4-(1-CH$_3$-pyridin-2(1H)-one)]-3-F-5-OH-phenyl} | N(CH$_3$) | — |
| 163 | 4-{1-[5-(1-CH$_3$-pyridin-2(1H)-one)]-3-F-5-OH-phenyl} | N(CH$_3$) | — |
| 164 | 2-[3-F-5-(1H-pyrazol-4-yl)-phenol] | O | — |
| 165 | 2-(5-Cl-3-F-phenol) | N(CH$_3$) | — |
| 166 | 2-[3-F-5-(1H-pyrazol-4-yl)-phenol] | N(CH$_3$) | — |
| 167 | 2-[3-F-5-(1-CH$_3$-1H-pyrazol-4-yl)-phenol] | N(CH$_3$) | — |
| 219 | 8-(quinolin-7-ol) | N(CH$_3$) | — |
| 230 | 6-(7-OH-quinolin-2(1H)-one) | N(CH$_3$) | — |
| 231 | 6-(7-OH-1-CH$_3$-quinolin-2(1H)-one) | N(CH$_3$) | — |
| 245 | 7-(6-OH-1-CH$_3$-quinolin-4(1H)-one) | N(CH$_3$) | — |
| 257 | 6-(7-OH-quinazolin-4(1H)-one) | N(CH$_3$) | — |
| 259 | 6-(7-OH-1-CH$_3$-3,4-dihydroquinolin-2(1H)-one) | N(CH$_3$) | — |
| 277 | 7-OH-1,3-(CH$_3$)$_2$-quinazolin-6-yl-2,4(1H,3H)-dione | N(CH$_3$) | — |
| 278 | 6-OH-benzo[d]oxazol-5-yl-2(3H)-one | N(CH$_3$) | — |
| 279 | 2-CH$_3$-6-OH-2H-indazol-5-yl | N(CH$_3$) | — |
| 280 | 1-CH$_3$-6-OH-1H-indazol-5-yl | N(CH$_3$) | — |
| 281 | 7-(6-OH-2-CH$_3$-isoquinolin-1(2H)-one) | N(CH$_3$) | — |
| 282 | 7-(6-OH-2-CH$_2$CH$_3$-isoquinolin-1(2H)-one) | O | — |

Another embodiment of the present description includes a compound of Formula (Ia) or a form thereof selected from a compound of Formula (Ia11) or a form thereof, wherein substituents A, X and R$_{4a}$, when present, are indicated in the table below; and, "--" indicates that one or more A, X and R$_{4a}$ substituents are not present:

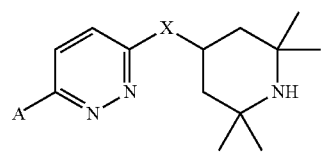

(Ia11)

| Cpd | A | X |
|---|---|---|
| 420 | 2-OCH$_3$-4-(4-NO$_2$-1H-pyrazol-1-yl)phenyl | N(CH$_3$) |
| 428 | 2,5-F$_2$-4-(1H-pyrazol-4-yl)phenyl | N(CH$_3$) |
| 430 | 2,3-F$_2$-4-(1H-pyrazol-4-yl)phenyl | N(CH$_3$) |
| 431 | 2,5-F$_2$-4-(1H-pyrazol-4-yl)phenyl | O |
| 434 | 2-OCH$_3$-4-(1H-pyrazol-4-yl)phenyl | N(CH$_3$) |
| 435 | 4-(1H-pyrazol-4-yl)phenyl | O |
| 437 | 2-F-4-(1H-pyrazol-4-yl)phenyl | O |
| 438 | 4-(1-CH$_3$-1H-pyrazol-4-yl)thiophen-2-yl | O |
| 440 | 2-F-4-OH-phenyl | N(CH$_3$) |
| 442 | 2-CH$_3$-2H-indazol-5-yl | N(CH$_3$) |
| 443 | 2-CH$_3$-2H-indazol-5-yl | O |
| 444 | 4-Cl-2-OCH$_3$-phenyl | O |
| 445 | 2-CH$_3$-pyrazolo[1,5-a]pyridin-3-yl | N(CH$_3$) |
| 446 | imidazo[1,2-a]pyridin-6-yl | O |
| 447 | 2-OCH$_3$-4-(1H-pyrazol-1-yl)phenyl | O |
| 448 | 5-(1H-pyrazol-4-yl)thiophen-2-yl | O |
| 449 | 5-(1-CH$_3$-1H-pyrazol-4-yl)thiophen-2-yl | O |
| 450 | 4-(1H-pyrazol-4-yl)thiophen-2-yl | O |
| 451 | 2-OH-4-[3,5-(CH$_3$)$_2$-1H-pyrazol-4-yl]phenyl | O |
| 452 | 2-F-4-(1H-pyrazol-4-yl)phenyl | N(CH$_3$) |
| 453 | 2-OCH$_3$-4-OH-phenyl | O |
| 454 | 2-OCH$_3$-4-(4-NO$_2$-1H-pyrazol-1-yl)phenyl | O |
| 455 | 2,4-(OH)$_2$-phenyl | O |
| 456 | 2-Cl-4-(1H-pyrazol-4-yl)phenyl | N(CH$_3$) |
| 457 | 5-amino-2-(lH-pyrazol-4-yl)pyrimidin-4-yl | O |
| 458 | 2,6-F$_2$-4-(1H-pyrazol-4-yl)phenyl | O |
| 464 | 2-(CHF$_2$)-4-(1H-pyrazol-4-yl)phenyl | O |
| 465 | 2-(CHF$_2$)-4-(1H-pyrazol-4-yl)phenyl | N(CH$_3$) |

Another embodiment of the method of the present description includes the use of a compound of Formula (Ia) or a form thereof selected from a compound of Formula (Ia11) or a form thereof, wherein substituents A, X and R$_{4a}$, when present, are indicated in the table below; and, "--" indicates that one or more A, X and R$_{4a}$ substituents are not present:

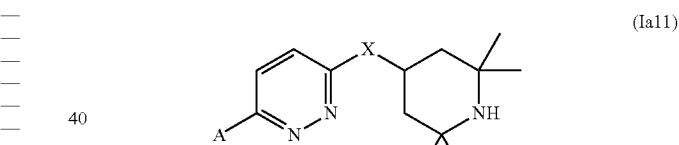

(Ia11)

| Cpd | A | X |
|---|---|---|
| 420 | 2-OCH$_3$-4-(4-NO$_2$-1H-pyrazol-1-yl)phenyl | N(CH$_3$) |
| 428 | 2,5-F$_2$-4-(1H-pyrazol-4-yl)phenyl | N(CH$_3$) |
| 430 | 2,3-F$_2$-4-(1H-pyrazol-4-yl)phenyl | N(CH$_3$) |
| 431 | 2,5-F$_2$-4-(1H-pyrazol-4-yl)phenyl | O |
| 434 | 2-OCH$_3$-4-(1H-pyrazol-4-yl)phenyl | N(CH$_3$) |
| 435 | 4-(1H-pyrazol-4-yl)phenyl | O |
| 437 | 2-F-4-(1H-pyrazol-4-yl)phenyl | O |
| 438 | 4-(1-CH$_3$-1H-pyrazol-4-yl)thiophen-2-yl | O |
| 440 | 2-F-4-OH-phenyl | N(CH$_3$) |
| 442 | 2-CH$_3$-2H-indazol-5-yl | N(CH$_3$) |
| 443 | 2-CH$_3$-2H-indazol-5-yl | O |
| 444 | 4-Cl-2-OCH$_3$-phenyl | O |
| 445 | 2-CH$_3$-pyrazolo[1,5-a]pyridin-3-yl | N(CH$_3$) |
| 446 | imidazo[1,2-a]pyridin-6-yl | O |
| 447 | 2-OCH$_3$-4-(1H-pyrazol-1-yl)phenyl | O |
| 448 | 5-(1H-pyrazol-4-yl)thiophen-2-yl | O |
| 449 | 5-(1-CH$_3$-1H-pyrazol-4-yl)thiophen-2-yl | O |
| 450 | 4-(1H-pyrazol-4-yl)thiophen-2-yl | O |
| 451 | 2-OH-4-[3,5-(CH$_3$)$_2$-1H-pyrazol-4-yl]phenyl | O |
| 452 | 2-F-4-(1H-pyrazol-4-yl)phenyl | N(CH$_3$) |
| 453 | 2-OCH$_3$-4-OH-phenyl | O |
| 454 | 2-OCH$_3$-4-(4-NO$_2$-1H-pyrazol-1-yl)phenyl | O |
| 455 | 2,4-(OH)$_2$-phenyl | O |
| 456 | 2-Cl-4-(1H-pyrazol-4-yl)phenyl | N(CH$_3$) |

-continued

| Cpd | A | X |
|---|---|---|
| 457 | 5-amino-2-(1H-pyrazol-4-yl)pyrimidin-4-yl | O |
| 458 | 2,6-F₂-4-(1H-pyrazol-4-yl)phenyl | O |
| 464 | 2-(CHF₂)-4-(1H-pyrazol-4-yl)phenyl | O |
| 465 | 2-(CHF₂)-4-(1H-pyrazol-4-yl)phenyl | N(CH₃) |

Another embodiment of the method of the present description includes the use of a compound of Formula (Ia) or a form thereof selected from a compound of Formula (Ia12) or a form thereof, wherein substituents X, $R_{1a}$ and B, when present, are indicated in the table below; and, "--" indicates that one or more X, $R_{1a}$ and B substituents are not present:

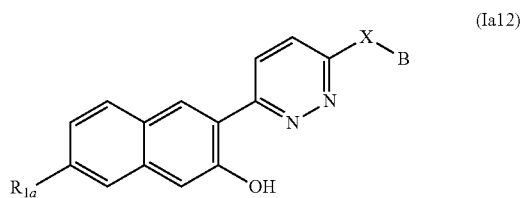
(Ia12)

| Cpd | $R_{1a}$ | X | B |
|---|---|---|---|
| 66 | H | NH | azetidin-3-yl |
| 82 | OH | — | piperazin-1-yl |
| 85 | H | — | 1,2,3,6-tetrahydropyridin-4-yl |
| 86 | OH | — | 1,2,3,6-tetrahydropyridin-4-yl |
| 87 | OH | — | 2,2,6,6-tetramethyl-(1,2,3,6-tetrahydropyridin-4-yl) |
| 88 | OH | — | 1-CH₃-(1,2,3,6-tetrahydropyridin-4-yl) |
| 89 | OH | — | piperidin-4-yl |
| 99 | H | CH₂ | piperidin-4-yl |

Another embodiment of the method of the present description includes the use of a compound of Formula (Ia) or a form thereof selected from a compound of Formula (Ia13) or a form thereof, wherein substituents X, $R_{1a}$ and $R_{4a}$, when present, are indicated in the table below; and, "--" indicates that one or more X, $R_{1a}$ and $R_{4a}$ substituents are not present:

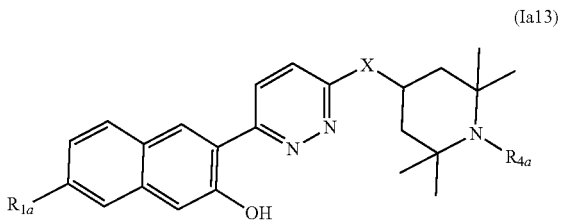
(Ia13)

| Cpd | X | $R_{1a}$ | $R_{4a}$ |
|---|---|---|---|
| 26 | N(CH₃) | H | — |
| 28 | NH | H | — |
| 31 | O | H | — |
| 90 | O | OH | — |
| 91 | N(CH₃) | OH | — |
| 92 | NH | OH | — |
| 93 | N(CH₃) | O(CH₂)₃NHCO₂C(CH₃)₃ | — |
| 94 | N(CH₃) | O(CH₂)₃NH₂ | — |
| 95 | N(CH₃) | O(CH₂)₃NHCO₂CH₃ | — |
| 96 | N(CH₃) | O(CH₂)₃OH | — |
| 97 | N(CH₃) | O(CH₂)₃OCH₃ | — |
| 98 | O | O(CH₂)₃-morpholin-4-yl | — |
| 103 | N(CH₃) | CN | — |
| 104 | N(CH₃) | CH₂-1-piperidinyl | — |
| 105 | N(CH₃) | CH₂-pyrrolidin-1-yl | — |
| 108 | N(CH₃) | OCH₃ | — |
| 109 | N(CH₃) | OCH₃ | CH₃ |
| 110 | N(CH₃) | 3,6-dihydro-2H-pyran-4-yl | — |
| 111 | N(CH₃) | tetrahydro-2H-pyran-4-yl | — |
| 112 | N(CH₃) | CHF₂ | — |
| 113 | N(CH₃) | OC(CH₃)₂(CH₂)₂OH | — |
| 114 | N(CH₃) | O(CH₂)₂C(CH₃)₂OH | — |

Another embodiment of the method of the present description includes the use of a compound of Formula (Ia) or a form thereof selected from a compound of Formula (Ia14) or a form thereof, wherein substituents X and B, when present, are indicated in the table below; and, "--" indicates that one or more X and B substituents are not present:

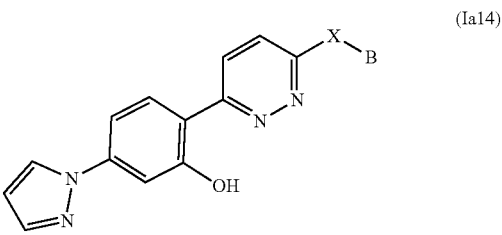
(Ia14)

| Cpd | X | B |
|---|---|---|
| 55 | O | piperidin-4-yl |
| 56 | O | (2S,4R,6R)-2,6-(CH₃)₂-piperidin-4-yl |
| 57 | O | 2,6-(CH₃)₂-piperidin-4-yl |
| 58 | O | pyrrolidin-3-yl |
| 59 | O | 2-CH₃-piperidin-4-yl |
| 60 | OCH₂ | 1H-pyrrolidin-3-yl |
| 61 | O | 3-F-piperidin-4-yl |
| 65 | — | piperazin-1-yl |
| 67 | NH | azetidin-3-yl |
| 68 | — | 3,5-(CH₃)₂-piperazin-1-yl |
| 69 | — | 7-CH₃-2,7-diazaspiro[4.4]non-2-yl |
| 70 | — | [1,4]diazepan-1-yl |
| 71 | — | 4-CH₂CH₂OH-piperazin-1-yl |
| 72 | — | 2,7-diazaspiro[3.5]non-7-yl |
| 73 | — | 2,7-diazaspiro[3.5]non-7-yl |
| 74 | — | 3-CH₂OH-piperazin-1-yl |
| 75 | — | 1,7-diazaspiro[4.4]non-7-yl |
| 76 | — | 4-NH₂-4-CH₃-piperidin-1-yl |
| 77 | — | 3-N(CH₃)₂-piperidin-1-yl |
| 79 | — | 3,3-(CH₃)₂-piperazin-1-yl |
| 80 | — | 7-CH₂CH₂OH-2,7-diazaspiro[4.4]-nonan-2-yl |
| 83 | — | 1,2,3,6-tetrahydropyridin-4-yl |
| 84 | — | piperidin-4-yl |
| 102 | O | (6S)-6-[(S)-CH(OH)CH₃]-2,2-(CH₃)₂-piperidin-4-yl |
| 133 | O | 2,2-(CH₃)₂-piperidin-4-yl |

Another embodiment of the method of the present description includes the use of a compound of Formula (Ia) or a form thereof selected from a compound of Formula (Ia15) or a form thereof, wherein substituents X, $R_{1a}$ and $R_{4a}$, when present, are indicated in the table below; and, "--" indicates that one or more X, $R_{1a}$ and $R_{4a}$ substituents are not present:

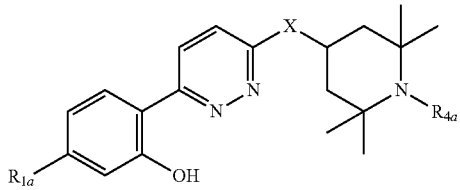

(Ia15)

| Cpd | X | $R_{1a}$ | $R_{4a}$ |
|---|---|---|---|
| 3 | NH | H | — |
| 7 | N(CH$_3$) | H | — |
| 27 | N(CH$_3$) | Cl | CH$_3$ |
| 29 | NH | Cl | CH$_3$ |
| 36 | N(CH$_3$) | OCH$_3$ | — |
| 38 | N(CH$_3$) | F | — |
| 39 | N(CH$_3$) | CN | — |
| 42 | N(CH$_3$) | C(O)NHCH$_2$CH=CH$_2$ | — |
| 43 | N(CH$_3$) | 1H-pyrazol-1-yl | — |
| 44 | N(CH$_3$) | 5-CH$_3$-oxazol-2-yl | — |
| 45 | N(CH$_3$) | 4-CH$_2$OH-1H-pyrazole-1-yl | — |
| 46 | N(CH$_3$) | 1H-imidazole-1-yl | — |
| 47 | N(CH$_3$) | 4-NH$_2$-1H-pyrazol-1-yl | — |
| 48 | N(CH$_3$) | 1H-pyrazol-4-yl | — |
| 49 | N(CH$_3$) | 3-NH$_2$-1H-pyrazol-1-yl | — |
| 50 | N(CH$_3$) | 1-(CH$_2$CH$_2$-morpholin-4-yl)-1H-pyrazol-4-yl | — |
| 51 | N(CH$_3$) | 1-CH$_3$-1H-pyrazol-4-yl | — |
| 52 | N(CH$_3$) | 5-NH$_2$-1H-pyrazol-1-yl | — |
| 54 | N(CH$_2$CH$_2$OH) | 1H-pyrazol-1-yl | — |
| 62 | O | 1H-pyrazol-1-yl | CH$_3$ |
| 63 | O | 1H-pyrazol-1-yl | — |
| 64 | O | 1H-pyrazol-4-yl | — |
| 78 | NH | 1H-pyrazol-1-yl | CH$_3$ |
| 100 | CH$_2$ | 1H-pyrazol-1-yl | — |
| 130 | N(CH$_3$) | Cl | — |
| 131 | NH | 1H-pyrazol-1-yl | — |
| 132 | NH | CN | — |
| 143 | N(CH$_3$) | 1H-indazol-7-yl | — |
| 157 | CH$_2$ | 1H-pyrazol-4-yl | — |
| 168 | N(CH$_3$) | 5-OCH$_3$-pyridin-3-yl | — |
| 169 | N(CH$_3$) | 5-pyridin-2-ol | — |
| 170 | N(CH$_3$) | 4-pyridin-2-ol | — |
| 171 | N(CH$_3$) | 6-OCH$_3$-pyridin-3-yl | — |
| 172 | N(CH$_3$) | 5-(3-CF$_3$-pyridin-2-ol) | — |
| 173 | N(CH$_3$) | 5-(1-CH$_3$-pyridin-2(1H)-one) | — |
| 174 | N(CH$_3$) | 4-(1-CH$_3$-pyridin-2(1H)-one) | — |
| 175 | N(CH$_3$) | 2-OCH$_3$-pyridin-4-yl | — |
| 176 | O | 4-pyridin-2-ol | — |
| 177 | N(CH$_3$) | 6-N(CH$_3$)$_2$-pyridin-3-yl | — |
| 178 | O | 4-(1-CH$_3$-pyridin-2(1H)-one) | — |
| 179 | N(CH$_3$) | pyrimidin-5-yl | — |
| 180 | N(CH$_3$) | 5-pyridin-3-ol | — |
| 181 | N(CH$_3$) | 4-(1-cyclopropyl-pyridin-2(1H)-one) | — |
| 182 | N(CH$_3$) | 1,2,3,6-tetrahydropyridin-4-yl | — |
| 183 | N(CH$_3$) | cyclopent-1-en-1-yl | — |
| 184 | N(CH$_3$) | 3,6-dihydro-2H-pyran-4-yl | — |
| 185 | N(CH$_3$) | imidazo[1,5-a]pyridin-7-yl | — |
| 186 | N(CH$_3$) | imidazo[1,2-a]pyridin-7-yl | — |
| 187 | N(CH$_3$) | 2-CH$_3$-pyridin-4-yl | — |
| 188 | N(CH$_3$) | 1H-imidazol-2-yl | — |
| 189 | N(CH$_3$) | 1H-imidazol-4-yl | — |
| 190 | N(CH$_3$) | imidazo[1,2-a]pyrazin-3-yl | — |
| 191 | N(CH$_3$) | 5,6,7,8-tetrahydroimidazo[1,2-a]pyrazin-3-yl | — |
| 192 | N(CH$_3$) | 4-CH$_3$-1H-imidazol-2-yl | — |
| 193 | N(CH$_3$) | 1-CH$_3$-1H-imidazol-4-yl | — |
| 194 | N(CH$_3$) | 1-CH$_3$-1H-imidazol-5-yl | — |
| 195 | N(CH$_3$) | 4-NO$_2$-1H-imidazol-2-yl | — |

-continued

| Cpd | X | $R_{1a}$ | $R_{4a}$ |
|---|---|---|---|
| 196 | N(CH$_3$) | 2-CH$_3$-1H-imidazol-4-yl | — |
| 197 | N(CH$_3$) | 1,2-(CH$_3$)$_2$-1H-imidazol-4-yl | — |
| 198 | N(CH$_3$) | 4-C(O)NH$_2$-1H-pyrazol-1-yl | — |
| 206 | N(CH$_3$) | H | — |

Another embodiment of the present description includes a compound of Formula (Ia) or a form thereof selected from a compound of Formula (Ia15) or a form thereof, wherein substituents X, $R_{1a}$ and $R_{4a}$, when present, are indicated in the table below; and, "--" indicates that one or more X, $R_{1a}$ and $R_{4a}$ substituents are not present:

(Ia15)

| Cpd | X | $R_{1a}$ | $R_{4a}$ |
|---|---|---|---|
| 413 | NH | 1H-pyrazol-4-yl | — |
| 414 | O | 1-CH$_3$-1H-pyrazol-4-yl | — |
| 416 | N(CH$_3$) | 5-CH$_3$-1H-pyrazol-4-yl | — |
| 417 | O | 1H-imidazol-1-yl | — |
| 418 | O | 5-CH$_3$-1H-pyrazol-4-yl | — |
| 419 | N(CH$_3$) | 4-NO$_2$-1H-pyrazol-1-yl | — |
| 421 | O | 4-NH$_2$-1H-pyrazol-1-yl | — |
| 423 | O | 4-NO$_2$-1H-pyrazol-1-yl | — |
| 460 | N(CH$_3$) | 1H-pyrazol-4-yl | — |
| 461 | O | 1H-pyrazol-4-yl | — |

Another embodiment of the method of the present description includes the use of a compound of Formula (Ia) or a form thereof selected from a compound of Formula (Ia15) or a form thereof, wherein substituents X, $R_{1a}$ and $R_{4a}$, when present, are indicated in the table below; and, "--" indicates that one or more X, $R_{1a}$ and $R_{4a}$ substituents are not present:

(Ia15)

| Cpd | X | $R_{1a}$ |
|---|---|---|
| 413 | NH | 1H-pyrazol-4-yl |
| 414 | O | 1-CH$_3$-1H-pyrazol-4-yl |
| 416 | N(CH$_3$) | 5-CH$_3$-1H-pyrazol-4-yl |
| 417 | O | 1H-imidazol-1-yl |
| 418 | O | 5-CH$_3$-1H-pyrazol-4-yl |
| 419 | N(CH$_3$) | 4-NO$_2$-1H-pyrazol-1-yl |
| 421 | O | 4-NH$_2$-1H-pyrazol-1-yl |

| Cpd | X | R_{1a} |
|---|---|---|
| 423 | O | 4-NO$_2$-1H-pyrazol-1-yl |
| 460 | N(CH$_3$) | 1H-pyrazol-4-yl |
| 461 | O | 1H-pyrazol-4-yl |

Another embodiment of the method of the present description includes the use of a compound of Formula (Ia) or a form thereof selected from a compound of Formula (Ia16) or a form thereof, wherein substituents $R_{1a}$ and $R_{4a}$, when present, are indicated in the table below; and, "--" indicates that one or more $R_{1a}$ and $R_{4a}$ substituents are not present:

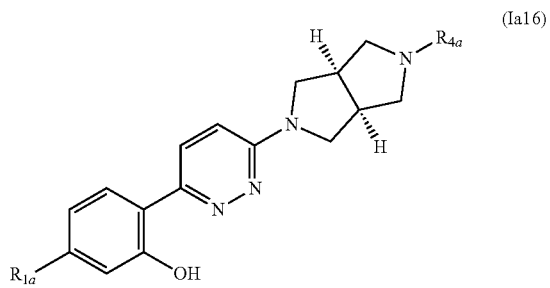

(Ia16)

| Cpd | R_{1a} | R_{4a} |
|---|---|---|
| 81 | 1H-pyrazol-1-yl | — |
| 199 | 1H-pyrazol-4-yl | (CH$_2$)$_2$OH |
| 200 | 1H-pyrazol-4-yl | — |
| 201 | 1H-pyrazol-4-yl | CH$_3$ |
| 202 | 4-(1-CH$_3$-pyridin-2(1H)-one) | CH$_3$ |
| 203 | 4-(1-CH$_3$-pyridin-2(1H)-one) | CH$_3$ |

Another embodiment of the method of the present description includes the use of a compound of Formula (Ia) or a form thereof selected from a compound of Formula (Ia17) or a form thereof, wherein substituent $R_{1a}$, when present, is indicated in the table below; and, "--" indicates that one or more $R_{1a}$ substituents are not present:

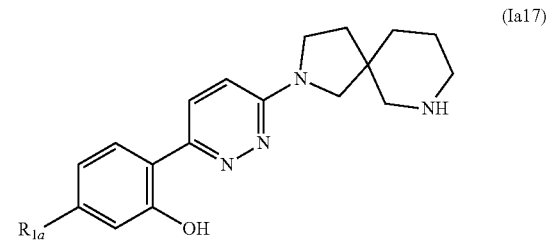

(Ia17)

| Cpd | R_{1a} |
|---|---|
| 204 | 1H-pyrazol-4-yl |
| 205 | 4-(1-CH$_3$-pyridin-2(1H)-one) |

Another embodiment of the present description includes a compound of Formula (Ia) or a form thereof selected from a compound of Formula (Ia18) or a form thereof, wherein substituents X and B, when present, are indicated in the table below; and, "--" indicates that one or more X and B substituents are not present:

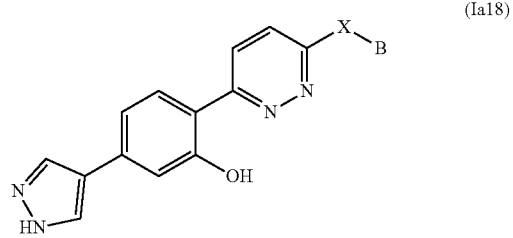

(Ia18)

| Cpd | X | B |
|---|---|---|
| 411 | N(CH$_3$) | (1R,5S)-8-azabicyclo[3.2.1]oct-3-yl |
| 412 | NH | (1R,5S)-8-azabicyclo[3.2.1]oct-3-yl |
| 415 | O | (1R,5S)-8-azabicyclo[3.2.1]oct-3-yl |
| 422 | — | 1-CH$_3$-(1,2,3,6-tetrahydropyridin-4-yl) |
| 424 | — | 1,2,3,6-tetrahydropyridin-4-yl |
| 425 | — | 1-CH$_3$CH$_2$-(1,2,3,6-tetrahydropyridin-4-yl) |
| 426 | N(CH$_3$) | piperidin-4-yl |
| 427 | NH | piperidin-4-yl |
| 429 | — | 8-azabicyclo[3.2.1]oct-2-en-3-yl |
| 432 | O | piperidin-4-yl |
| 433 | NH | (1R,5S)-8-azabicyclo[3.2.1]oct-3-yl |
| 436 | O | 2,6-(CH$_3$)$_2$-piperidin-4-yl |
| 439 | — | 2,7-diazaspiro[3.5]non-2-yl |
| 441 | O | 2,6-(CH$_3$)$_2$-piperidin-4-yl |
| 459 | — | 2,6-diazaspiro[3.4]oct-2-yl |

Another embodiment of the method of the present description includes the use of a compound of Formula (Ia) or a form thereof selected from a compound of Formula (Ia18) or a form thereof, wherein substituents X, $R_{1a}$ and B, when present, are indicated in the table below; and, "--" indicates that one or more X, $R_{1a}$ and B substituents are not present:

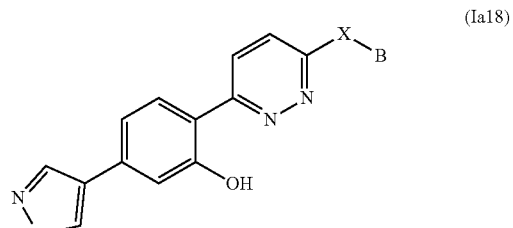

(Ia18)

| Cpd | X | B |
|---|---|---|
| 411 | N(CH$_3$) | (1R,5S)-8-azabicyclo[3.2.1]oct-3-yl |
| 412 | NH | (1R,5S)-8-azabicyclo[3.2.1]oct-3-yl |
| 415 | O | (1R,5S)-8-azabicyclo[3.2.1]oct-3-yl |
| 422 | — | 1-CH$_3$-(1,2,3,6-tetrahydropyridin-4-yl) |
| 424 | — | 1,2,3,6-tetrahydropyridin-4-yl |
| 425 | — | 1-CH$_3$CH$_2$-(1,2,3,6-tetrahydropyridin-4-yl) |
| 426 | N(CH$_3$) | piperidin-4-yl |
| 427 | NH | piperidin-4-yl |
| 429 | — | 8-azabicyclo[3.2.1]oct-2-en-3-yl |
| 432 | O | piperidin-4-yl |
| 433 | NH | (1R,5S)-8-azabicyclo[3.2.1]oct-3-yl |
| 436 | O | 2,6-(CH$_3$)$_2$-piperidin-4-yl |
| 439 | — | 2,7-diazaspiro[3.5]non-2-yl |

| Cpd | X | B |
|---|---|---|
| 441 | O | 2,6-(CH₃)₂-piperidin-4-yl |
| 459 | — | 2,6-diazaspiro[3.4]oct-2-yl |

Another embodiment of the method of the present description includes the use of a compound of Formula (Ib) or a form thereof selected from a compound of Formula (Ib1) or a form thereof, wherein substituent A is indicated in the table below:

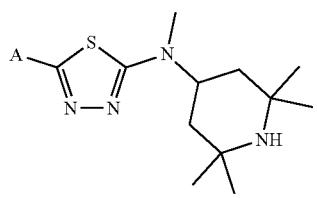
(Ib1)

| Cpd | A |
|---|---|
| 302 | 6-(naphthalen-2-ol) |
| 320 | 6-(naphthalen-2,7-diol) |
| 331 | 7-OCH₃-quinolin-6-yl |
| 332 | 7-OH-quinolin-6-yl |
| 337 | 2-CN-7-OCH₃-quinolin-6-yl |
| 355 | 3-F-5-(1H-pyrazol-4-yl)-pyridin-2-yl |
| 364 | 2-(6-OCH₃-3,4-dihydroisoquinolin-1(2H)-one) |
| 392 | 6-OH-1-oxo-2,3-dihydro-1H-inden-5-yl |
| 401 | 3-(4-OCH₃-1-CH₃-quinolin-2(1H)-one) |
| 402 | 3-(4-OH-1-CH₃-quinolin-2(1H)-one) |
| 403 | 3-(quinolin-2(1H)-one) |
| 404 | 3-(1-OCH₃-quinolin-2(1H)-one) |
| 408 | 5-CN-benzo[b]thiophen-2-yl |
| 409 | 3-Cl-benzo[b]thiophen-2-yl |

Another embodiment of the present description includes a compound of Formula (Ib) or a form thereof selected from a compound of Formula (Ib1) or a form thereof, wherein substituent A is indicated in the table below: c

| Cpd | A |
|---|---|
| 462 | 3-(1H-pyrazol-4-yl)phenoxy |
| 463 | 4-(1H-pyrazol-4-yl)phenoxy |

Another embodiment of the method of the present description includes the use of a compound of Formula (Ib) or a form thereof selected from a compound of Formula (Ib1) or a form thereof, wherein substituent A is indicated in the table below:

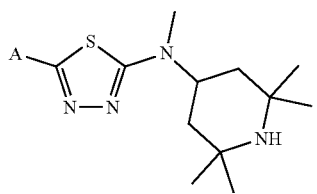
(Ib1)

| Cpd | A |
|---|---|
| 462 | 3-(1H-pyrazol-4-yl)phenoxy |
| 463 | 4-(1H-pyrazol-4-yl)phenoxy |

Another embodiment of the method of the present description includes the use of a compound of Formula (Ib) or a form thereof selected from a compound of Formula (Ib2) or a form thereof, wherein substituent A is indicated in the table below:

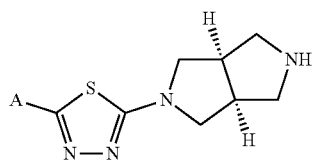
(Ib2)

| Cpd | A |
|---|---|
| 321 | 6-naphthalen-2,7-diol |

Another embodiment of the method of the present description includes the use of a compound of Formula (Ib) or a form thereof selected from a compound of Formula (Ib3) or a form thereof, wherein substituents $R_{1a}$, $R_{1b}$ and B, when present, are indicated in the table below; and, "—" indicates that one or more $R_{1a}$, $R_{1b}$ and B substituents are not present:

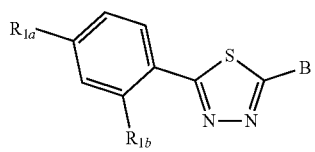
(Ib3)

| Cpd | $R_{1a}$ | $R_{1b}$ | B |
|---|---|---|---|
| 329 | 1H-pyrazol-1-yl | OCH₃ | 1,2,3,6-tetrahydropyridin-4-yl |
| 330 | 1H-pyrazol-1-yl | OH | piperazin-1-yl |
| 381 | 1H-pyrazol-1-yl | Cl | 5-((3aR,6aR)-1-CH₃-hexahydropyrrolo[3,4-b]pyrrol-5(1H)-yl) |
| 382 | 1H-pyrazol-1-yl | Cl | 2-NHCH(CH₃)₂-morpholin-4-yl |
| 383 | 1H-pyrazol-1-yl | Cl | 2-OCH₃-2,7-diazaspiro[4.5]decan-7-yl |
| 385 | 1-CH₃-1H-pyrazol-4-yl | OCH₃ | 5-((3aR,6aS)-5-CH₃-hexahydropyrrolo[3,4-c]pyrrol-2(1H)-yl) |

-continued

| Cpd | $R_{1a}$ | $R_{1b}$ | B |
|---|---|---|---|
| 394 | 1-CH$_3$-1H-pyrazol-4-yl | OH | 5-((3aR,6aS)-5-CH$_3$-hexahydropyrrolo[3,4-c]pyrrol-2(1H)-yl) |
| 406 | 1H-pyrazol-1-yl | Cl | 2,7-diazaspiro[4.5]decan-2-yl |
| 407 | 1H-pyrazol-1-yl | Cl | (3R)-3-(R)-CH$_2$OH)-piperazin-1-yl |

Another embodiment of the present description includes the use of a compound of Formula (Ib) or a form thereof selected from a compound of Formula (Ib4) or a form thereof, wherein substituents $R_{1a}$, $R_{1b}$, $R_{1c}$, $R_{1d}$ (each representative of the scope of $R_1$) and X, when present, are indicated in the table below; and, "--" indicates that one or more $R_{1a}$, $R_{1b}$, $R_{1c}$, $R_{1d}$ and X substituents are not present:

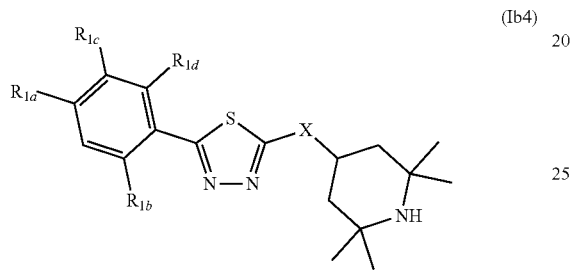

(Ib4)

| Cpd | $R_{1a}$ | $R_{1b}$ | $R_{1c}$ | $R_{1d}$ | X |
|---|---|---|---|---|---|
| 301 | 1H-pyrazol-1-yl | OCH$_3$ | H | H | N(CH$_3$) |
| 305 | 1H-pyrazol-1-yl | OCH$_3$ | H | H | N(CH$_3$) |
| 306 | 1-CH$_3$-1H-pyrazol-4-yl | OCH$_3$ | H | H | N(CH$_3$) |
| 307 | 1H-pyrazol-4-yl | OCH$_3$ | H | H | N(CH$_3$) |
| 308 | 4-(1-CH$_3$-pyridin-2(1H)-one) | OCH$_3$ | H | H | N(CH$_3$) |
| 309 | 5-pyridin-2-ol | OCH$_3$ | H | H | N(CH$_3$) |
| 310 | 5-(1-CH$_3$-pyridin-2(1H)-one) | OCH$_3$ | H | H | N(CH$_3$) |
| 311 | 1-CH$_3$-1H-pyrazol-4-yl | CH$_3$ | H | H | N(CH$_3$) |
| 312 | 4-(1-CH$_3$-pyridin-2(1H)-one) | OCF$_3$ | H | H | N(CH$_3$) |
| 313 | 3,5-(CH$_3$)$_2$-1H-pyrazol-4-yl | OCH$_3$ | H | H | N(CH$_3$) |
| 314 | 1-CH$_3$-1H-pyrazol-4-yl | CF$_3$ | H | H | N(CH$_3$) |
| 315 | 1-CH$_3$-1H-pyrazol-4-yl | OH | H | H | N(CH$_3$) |
| 316 | 1H-pyrazol-1-yl | OH | H | H | N(CH$_3$) |
| 317 | 5-(1-CH$_3$-pyridin-2(1H)-one) | OH | H | H | N(CH$_3$) |
| 318 | 4-(1-CH$_3$-pyridin-2(1H)-one) | OH | H | H | N(CH$_3$) |
| 319 | 5-pyridin-2-ol | OH | H | H | N(CH$_3$) |
| 324 | H | OH | 1H-pyrazol-1-yl | H | N(CH$_3$) |
| 325 | 1-CH$_3$-1H-pyrazol-4-yl | H | H | Cl | N(CH$_3$) |
| 326 | 1-CH$_3$-1H-pyrazol-4-yl | OH | H | Cl | N(CH$_3$) |
| 327 | 1-CH$_3$-1H-pyrazol-4-yl | H | H | Cl | N(CH$_3$) |
| 328 | 5-CH$_3$-oxazol-2-yl | OH | H | OCH$_3$ | N(CH$_3$) |
| 333 | CN | OCH$_3$ | H | H | N(CH$_3$) |
| 334 | CN | F | H | H | N(CH$_3$) |
| 335 | CO$_2$CH$_3$ | F | H | H | N(CH$_3$) |
| 336 | 3-NHCH$_3$-1H-pyrazol-1-yl | OCH$_3$ | H | H | N(CH$_3$) |
| 338 | 4-(1-CH$_3$-pyridin-2(1H)-one) | OCH$_3$ | H | H | N(CH$_3$) |
| 339 | 4-(1-CH$_3$-pyridin-2(1H)-one) | Cl | H | H | N(CH$_3$) |
| 340 | 1H-pyrazol-4-yl | Cl | H | H | N(CH$_3$) |
| 341 | 4,5,6,7-tetrahydropyrazolo[1,5-a]pyridin-3-yl | Cl | H | H | N(CH$_3$) |
| 343 | 1-CH$_3$-1H-pyrazol-4-yl | Cl | H | H | O |
| 344 | 6-OCH$_3$-pyridin-3-yl | Cl | H | H | N(CH$_3$) |
| 345 | 6-NH$_2$-pyridin-3-yl | F | H | H | N(CH$_3$) |
| 346 | 3-CH$_3$-1H-pyrazol-5-yl | F | H | H | N(CH$_3$) |
| 347 | 1H-pyrazol-5-yl | F | H | H | N(CH$_3$) |
| 348 | 1H-pyrazol-4-yl | H | F | F | N(CH$_3$) |
| 349 | 1H-pyrazol-5-yl | H | F | F | N(CH$_3$) |
| 350 | 1H-pyrazol-4-yl | F | F | H | N(CH$_3$) |
| 351 | 1H-pyrazol-5-yl | F | F | H | N(CH$_3$) |

-continued

| Cpd | $R_{1a}$ | $R_{1b}$ | $R_{1c}$ | $R_{1d}$ | X |
|---|---|---|---|---|---|
| 352 | 1H-pyrazol-4-yl | F | H | F | $N(CH_3)$ |
| 354 | 1H-pyrazol-4-yl | Cl | F | H | $N(CH_3)$ |
| 356 | 2-$NH_2$-pyrimidin-4-yl | Cl | H | H | $N(CH_3)$ |
| 357 | H | Cl | 2-$NH_2$-pyrimidin-4-yl | H | $N(CH_3)$ |
| 358 | 2,4-$(CH_3)_2$-thiazol-5-yl | F | F | H | $N(CH_3)$ |
| 359 | 2,4-$(CH_3)_2$-thiazol-5-yl | H | F | F | $N(CH_3)$ |
| 360 | 4-(1-$CH_3$-pyridin-2(1H)-one) | OH | H | $OCF_3$ | $N(CH_3)$ |
| 361 | 1H-pyrazol-4-yl | $OCH_3$ | H | F | $N(CH_3)$ |
| 363 | 1H-pyrazol-4-yl | $OCH_3$ | F | F | $N(CH_3)$ |
| 365 | 1H-pyrazol-1-yl | Cl | H | H | $N(CH_3)$ |
| 366 | 1H-1,2,3-triazol-1-yl | Cl | H | H | $N(CH_3)$ |
| 367 | 2H-1,2,3-triazol-2-yl | Cl | H | H | $N(CH_3)$ |
| 368 | 1H-1,2,4-triazol-1-yl | Cl | H | H | $N(CH_3)$ |
| 369 | 3-$NH_2$-1H-pyrazol-1-yl | Cl | H | H | $N(CH_3)$ |
| 371 | 1H-imidazol-1-yl | Cl | H | H | $N(CH_3)$ |
| 372 | 1H-imidazol-1-yl | F | H | H | $N(CH_3)$ |
| 373 | 1H-pyrazol-5-yl | $OCH_3$ | H | H | $N(CH_3)$ |
| 374 | 2,4-$(CH_3)_2$-thiazol-5-yl | $OCH_3$ | H | H | $N(CH_3)$ |
| 375 | pyridin-3-yl | $OCH_3$ | H | H | $N(CH_3)$ |
| 376 | 1H-pyrazol-4-yl | F | H | H | $N(CH_3)$ |
| 377 | 2-$OCH_3$-pyridin-4-yl | $OCH_3$ | H | H | $N(CH_3)$ |
| 378 | 6-$OCH_3$-pyridin-3-yl | $OCH_3$ | H | H | $N(CH_3)$ |
| 387 | 1H-pyrazol-1-yl | OH | H | H | $N(CH_3)$ |
| 388 | 5-(pyridin-2(1H)-one) | Cl | H | H | $N(CH_3)$ |
| 389 | 3-$NHCH_3$-1H-pyrazol-1-yl | OH | H | H | $N(CH_3)$ |
| 390 | 1H-pyrazol-4-yl | OH | H | F | $N(CH_3)$ |
| 391 | 1H-pyrazol-4-yl | OH | F | F | $N(CH_3)$ |
| 393 | 1H-pyrazol-4-yl | OH | H | H | $N(CH_3)$ |
| 397 | 1H-pyrazol-4-yl | OH | H | Cl | $N(CH_3)$ |
| 398 | 1H-pyrazol-1-yl | $OCH_3$ | H | H | $CH_2$ |
| 410 | 1H-pyrazol-4-yl | $OCH_3$ | H | H | $N(CH_3)$ |

Another embodiment of the method of the present description includes the use of a compound of Formula (Ib) or a form thereof selected from a compound of Formula (Ib5) or a form thereof, wherein substituents $R_{1a}$, $R_{1b}$, $R_{1c}$, $R_{1d}$ (each representative of the scope of $R_1$) and $R_{4a}$, when present, are indicated in the table below; and, "--" indicates that one or more $R_{1a}$, $R_{1b}$, $R_{1c}$, $R_{1d}$ and $R_{4a}$ substituents are not present:

or a form thereof selected from a compound of Formula (Ib6) or a form thereof, wherein substituents $R_{1a}$, $R_{1b}$, $R_{1c}$ and $R_{1d}$ (each representative of the scope of $R_1$), when present, are indicated in the table below; and, "--" indicates that one or more $R_{1a}$, $R_{1b}$, $R_{1c}$ and $R_{1d}$ substituents are not present:

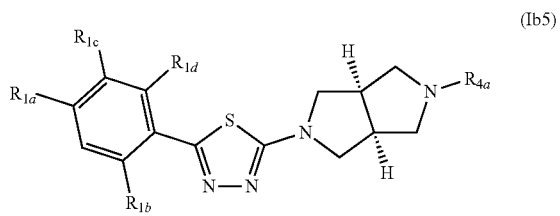

(Ib5)

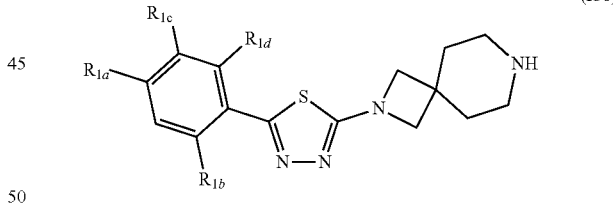

(Ib6)

| Cpd | $R_{1a}$ | $R_{1b}$ | $R_{1c}$ | $R_{1d}$ | $R_{4a}$ |
|---|---|---|---|---|---|
| 353 | 1H-pyrazol-4-yl | F | F | H | — |
| 362 | 1H-pyrazol-4-yl | $OCH_3$ | H | F | $CH_3$ |
| 370 | 1H-imidazol-1-yl | Cl | H | H | $CH_3$ |
| 379 | 1-$CH_3$-1H-pyrazol-4-yl | Cl | H | H | $CH_3$ |
| 380 | 1H-pyrazol-4-yl | Cl | H | H | $CH_3$ |
| 384 | 1H-pyrazol-4-yl | F | H | H | $CH_3$ |
| 396 | 1H-pyrazol-4-yl | F | H | OH | — |
| 405 | 1H-pyrazol-4-yl | Cl | H | H | — |

| Cpd | $R_{1a}$ | $R_{1b}$ | $R_{1c}$ | $R_{1d}$ |
|---|---|---|---|---|
| 386 | 1-$CH_3$-1H-pyrazol-4-yl | $OCH_3$ | H | H |
| 395 | 1-$CH_3$-1H-pyrazol-4-yl | OH | H | H |
| 399 | 1H-pyrazol-4-yl | H | F | F |
| 400 | 1H-pyrazol-4-yl | OH | H | F |

Another embodiment of the method of the present description includes the use of a compound of Formula (Ib) or a form thereof selected from a compound of Formula (Ib7) or a form thereof, wherein substituent $R_{1b}$, when present, is indicated in the table below:

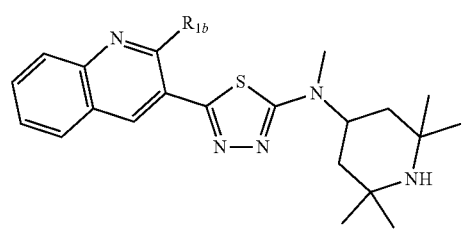

(Ib7)

| Cpd | R$_{1b}$ |
|-----|----------|
| 304 | OCH$_3$ |
| 322 | OH |

Another embodiment of the method of the present description includes the use of a compound of Formula (Ib) or a form thereof selected from a compound of Formula (Ib8) or a form thereof, wherein substituent R$_{1b}$, when present, is indicated in the table below:

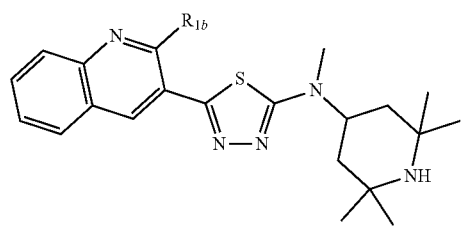

(Ib8)

| (Ib8) | |
|-------|---|
| Cpd | R$_{1b}$ |
| 303 | OCH$_3$ |
| 323 | OH |

An embodiment of the use of a compound of Formula (I) or a form thereof includes a method of use of a compound of Formula (I) or a form thereof for treating or ameliorating HD in a subject in need thereof, comprising administering an effective amount of the compound of Formula (I) or a form thereof to the subject, selected from the group consisting of:

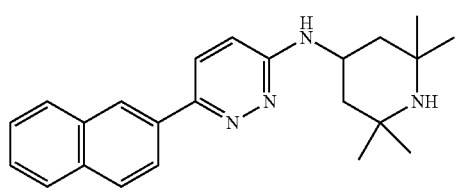

1

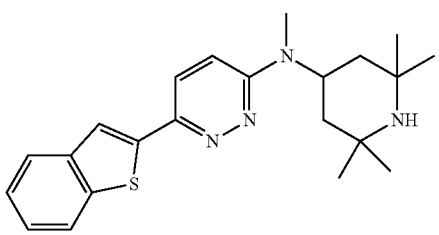

2

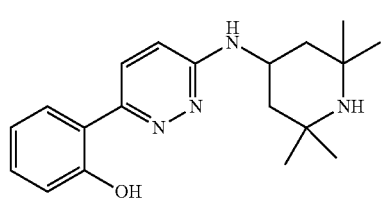

3

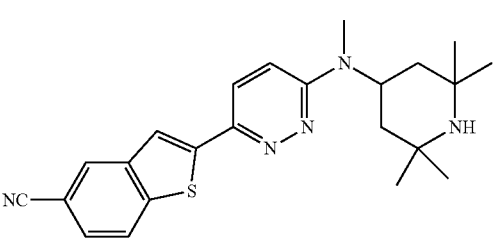

4

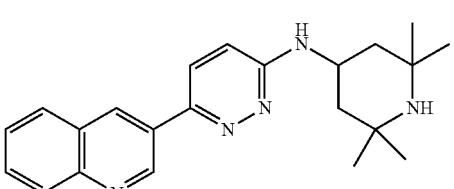

5

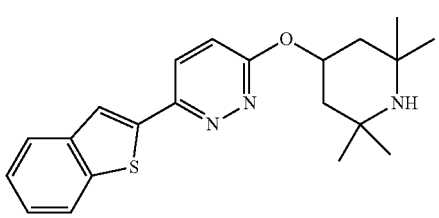

6

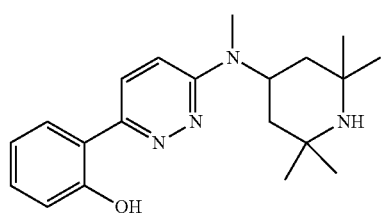

7

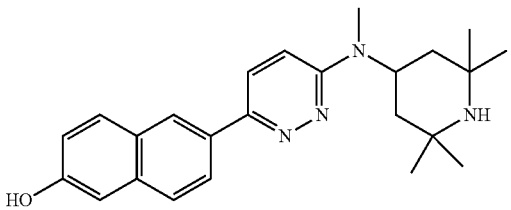

8

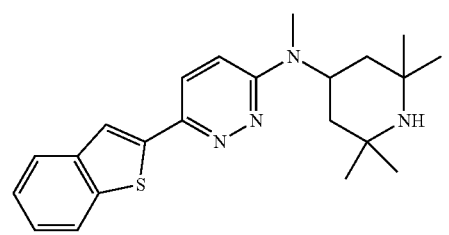
9
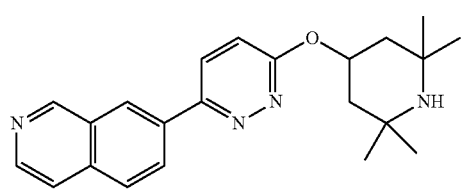
10
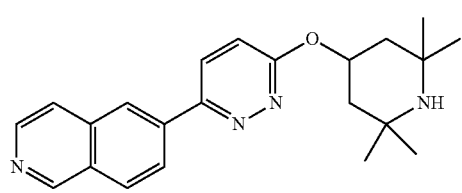
11
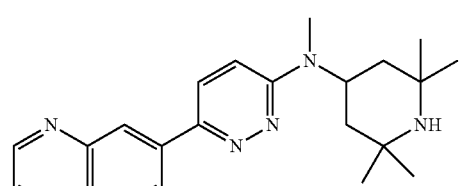
12
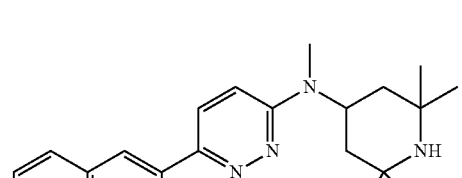
13
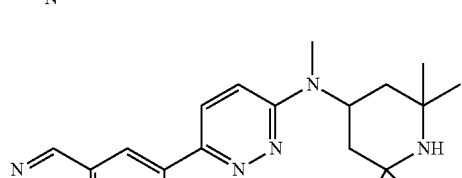
14
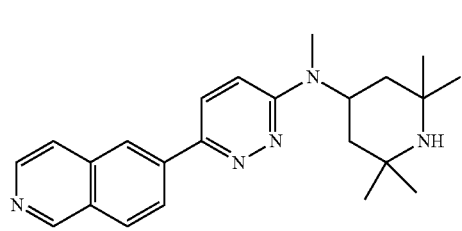
15
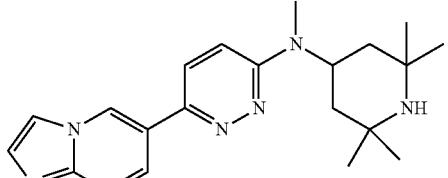
16
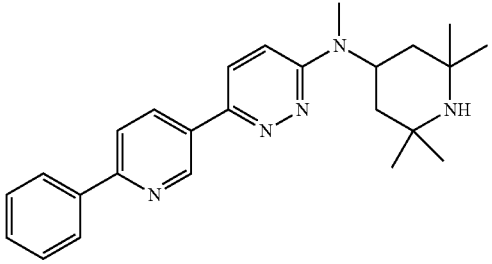
17
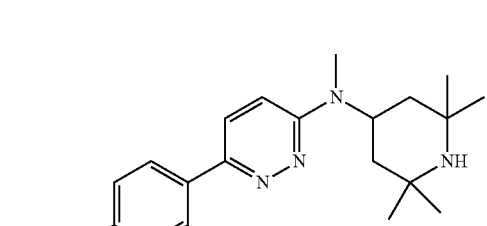
18
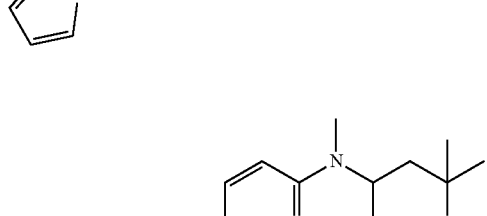
19
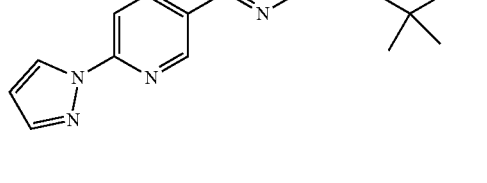
20
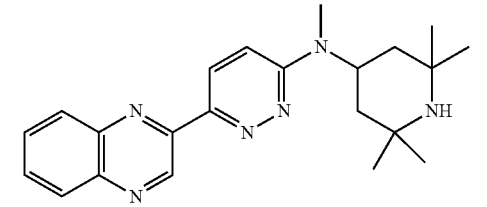
20
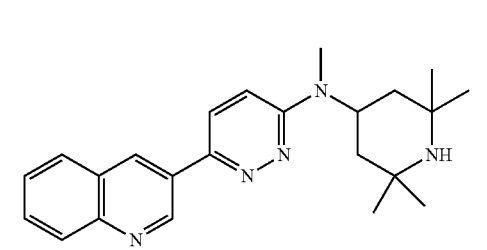
21

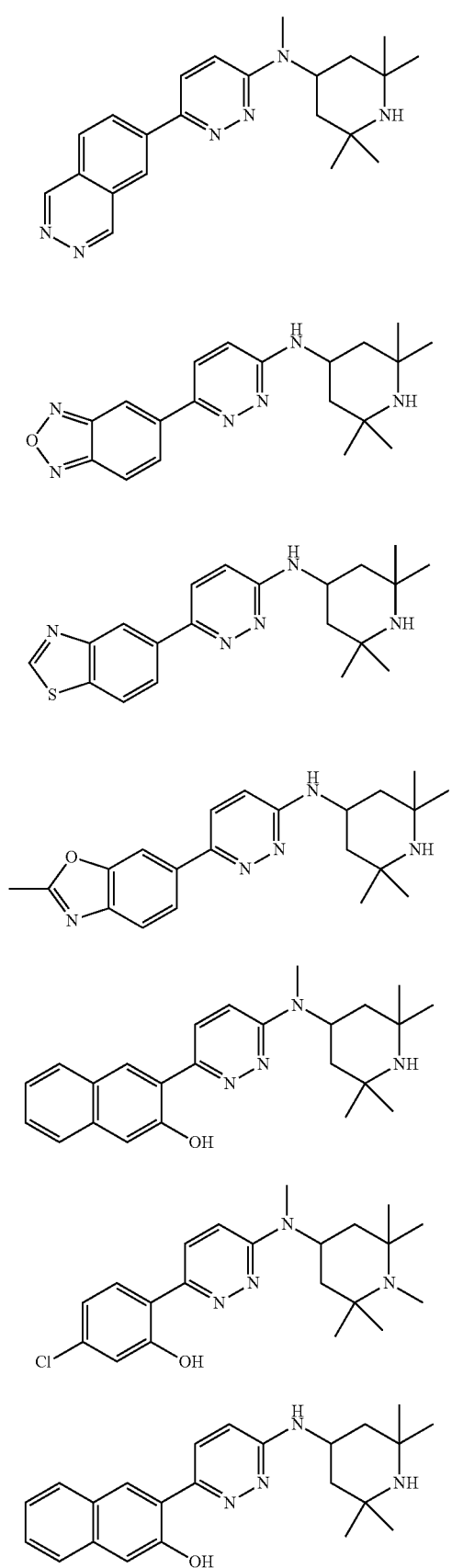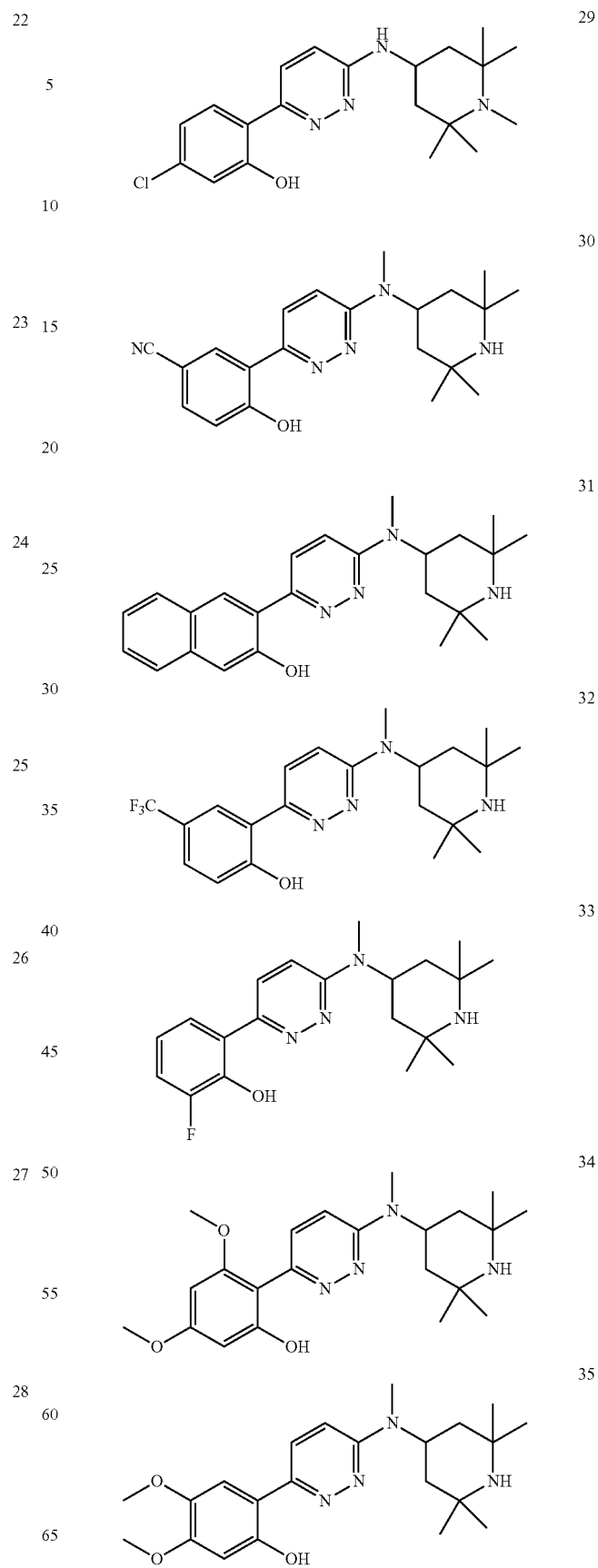

36 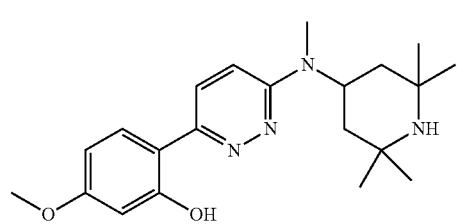
37 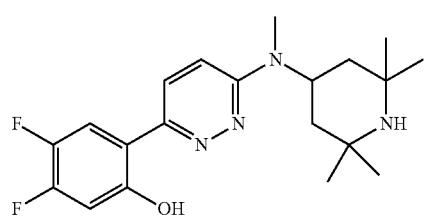
38 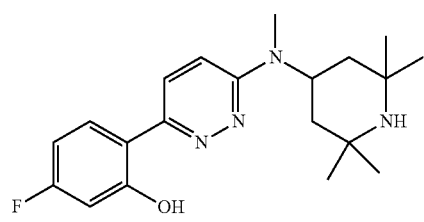
39 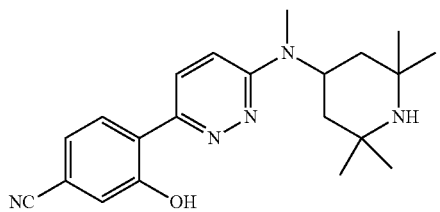
40 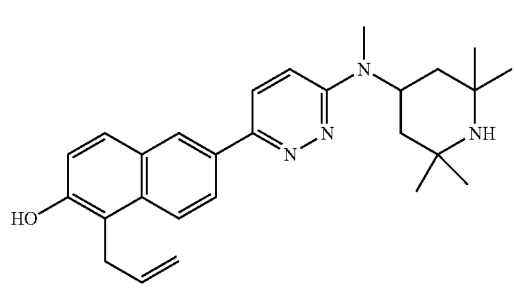
41 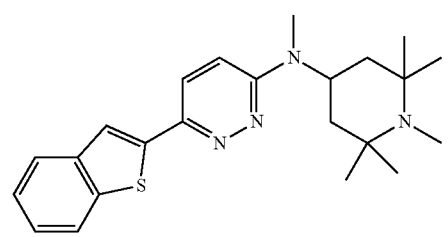
42 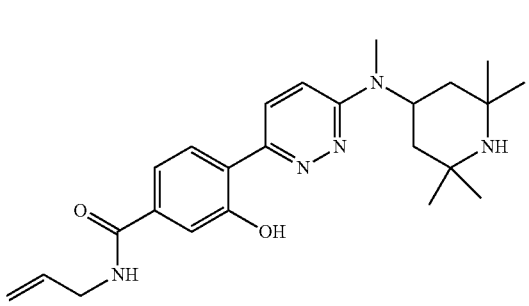
43 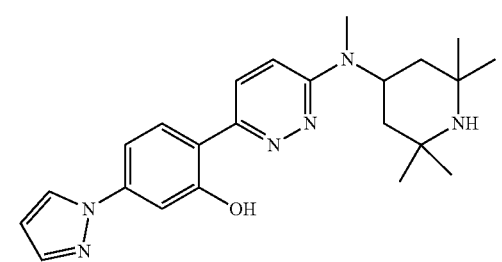
44 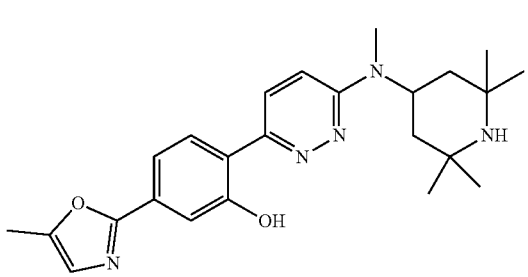
45 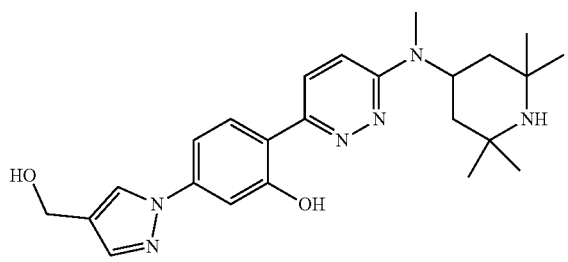
46 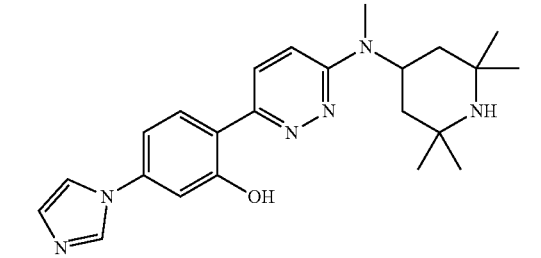
47 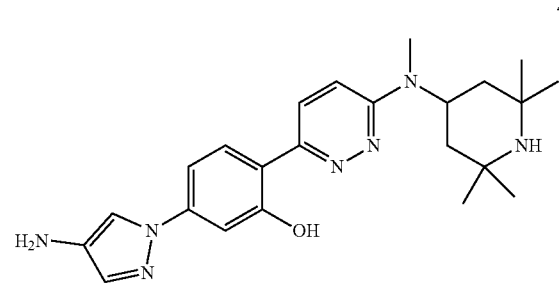

48
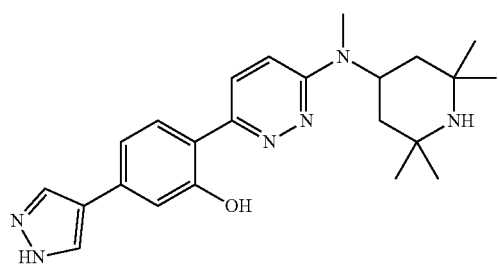
49
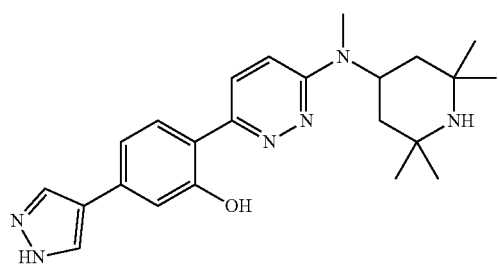
50
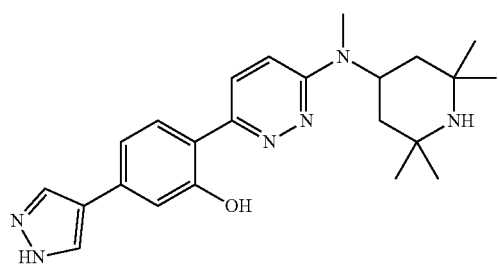
51
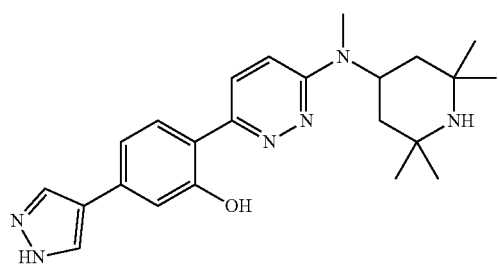
52
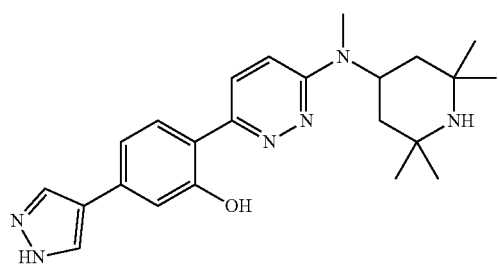
53
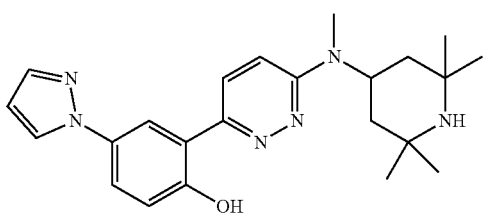
54
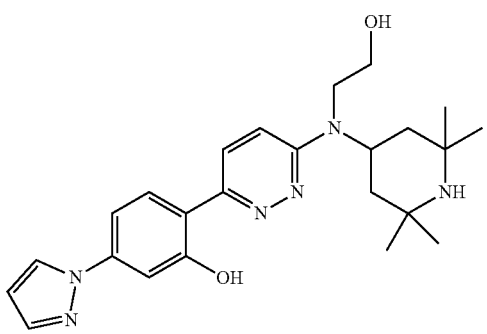
55
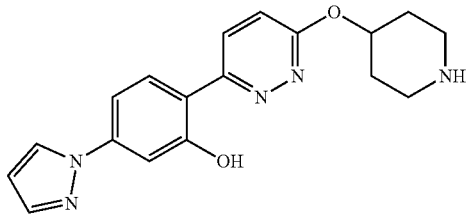
56
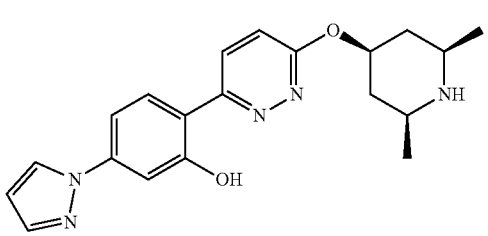
57
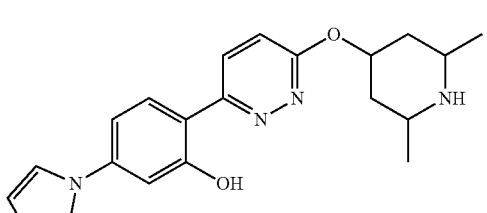
58
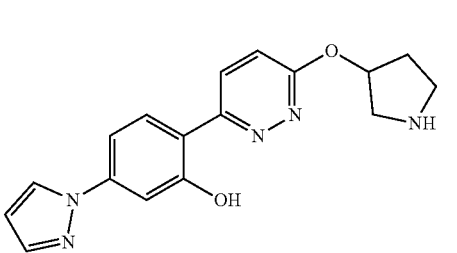

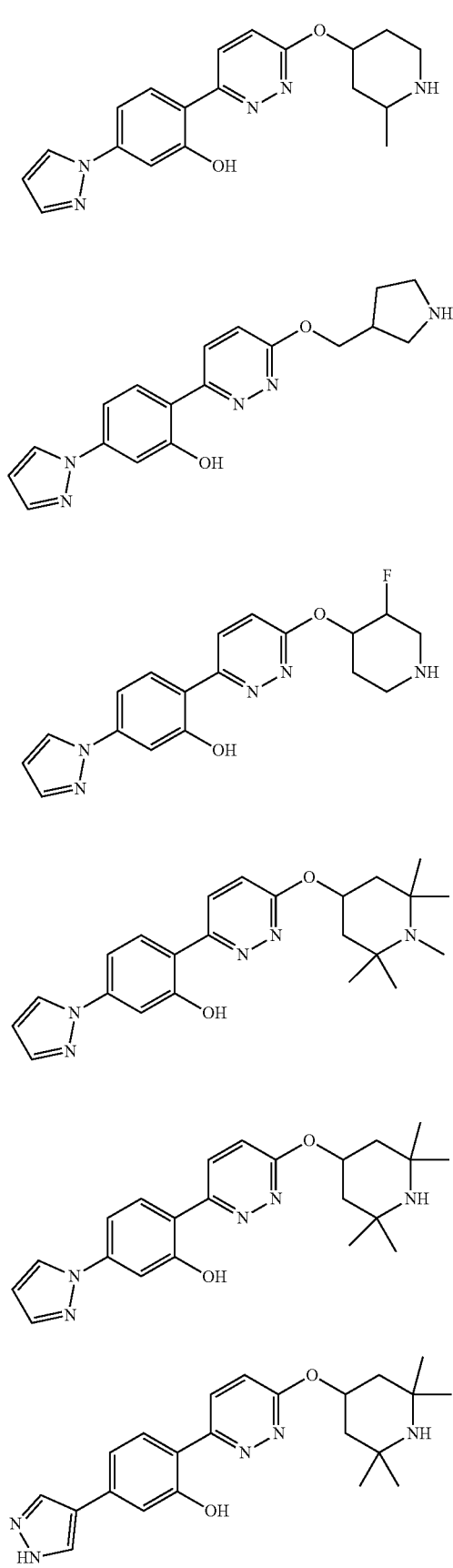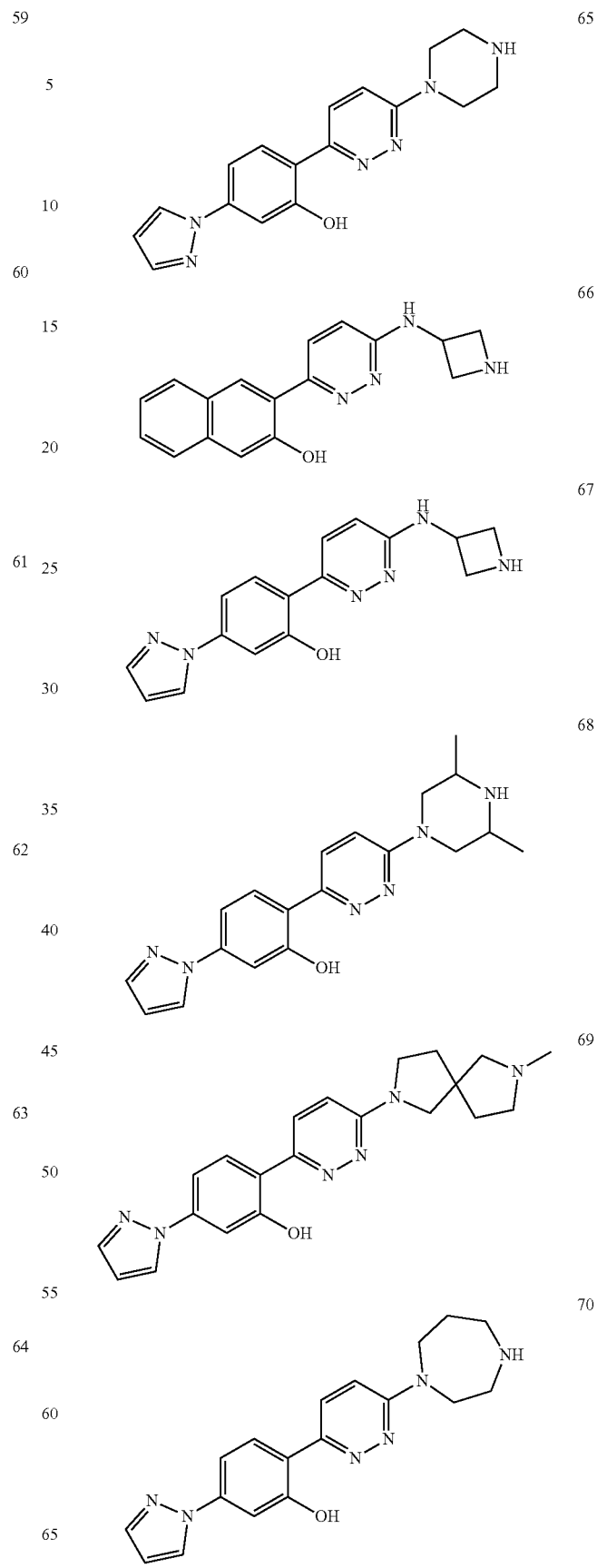

71
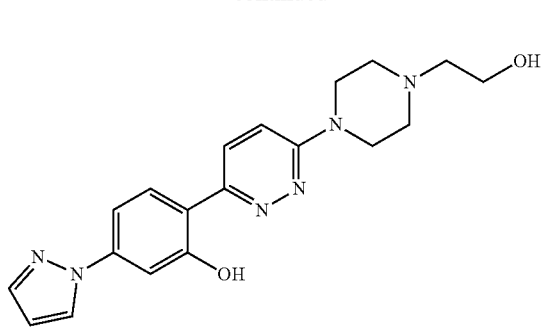
72
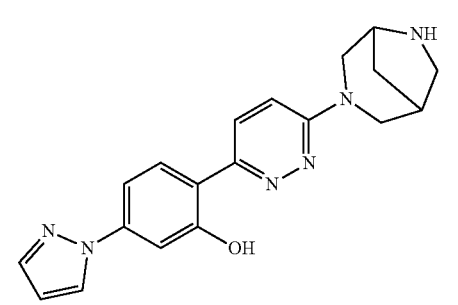
73
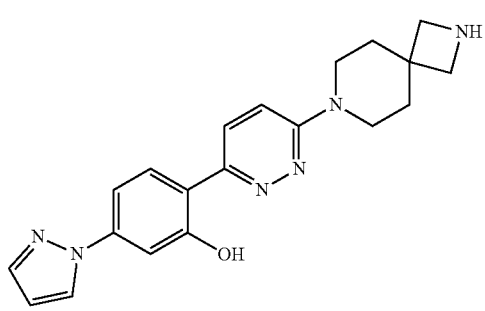
74
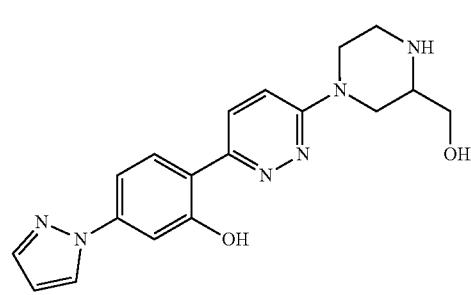
75
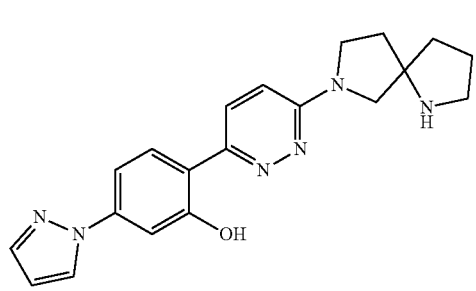
76
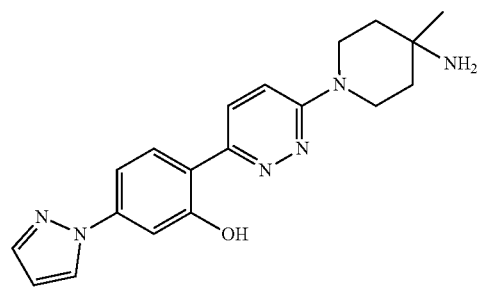
77
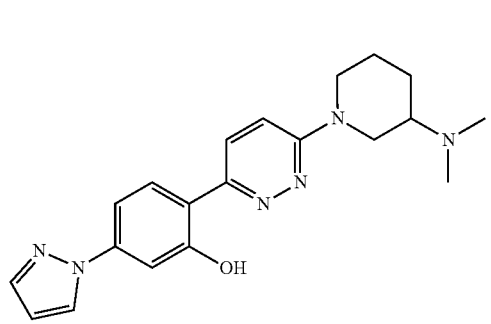
78
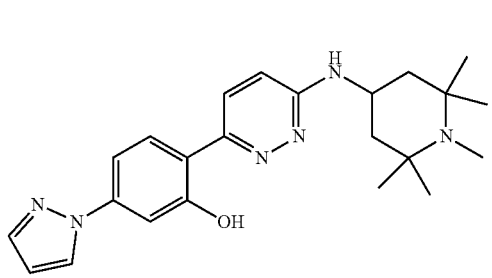
79
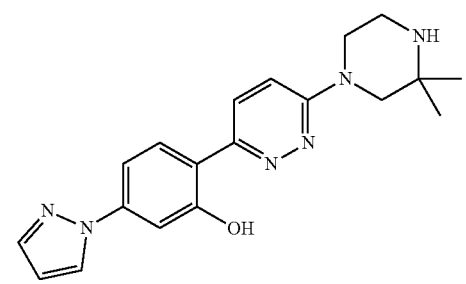
80
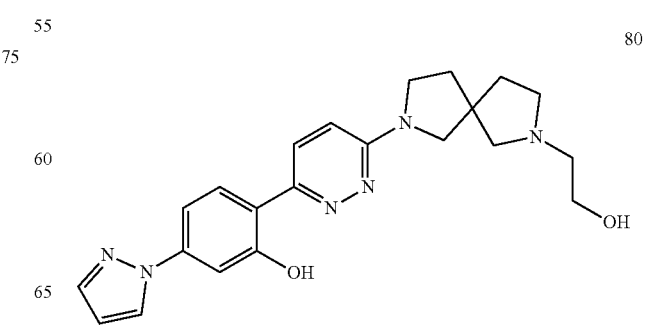

81
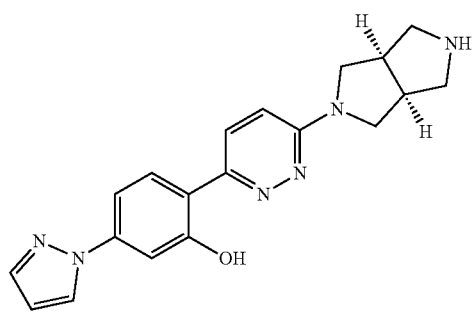
82
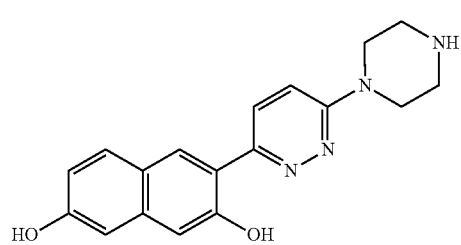
83
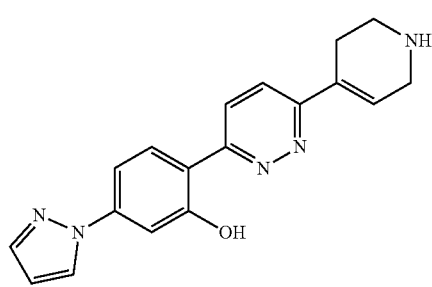
84
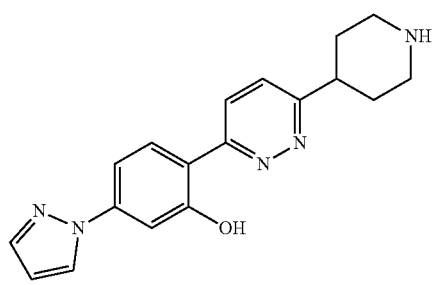
85
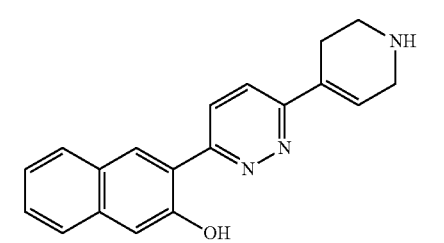
86
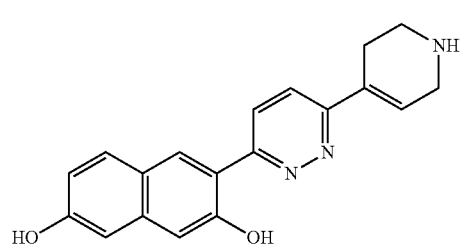
87
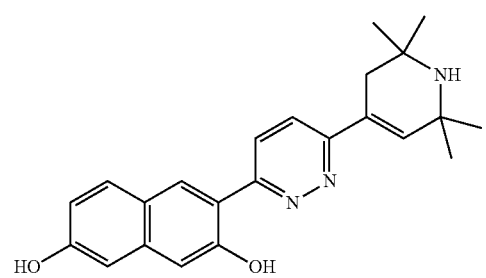
88
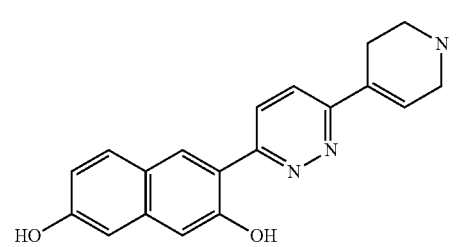
89
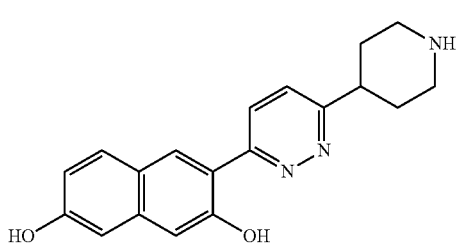
90
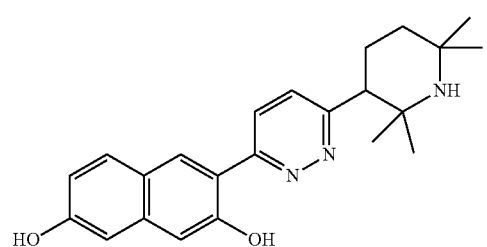
91
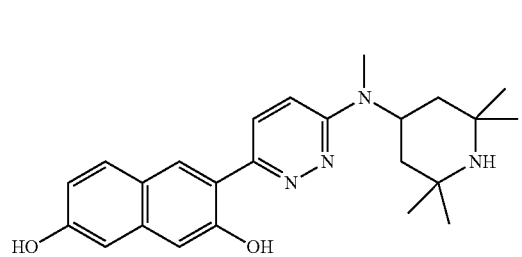
92
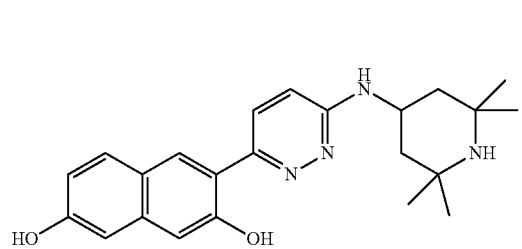

93
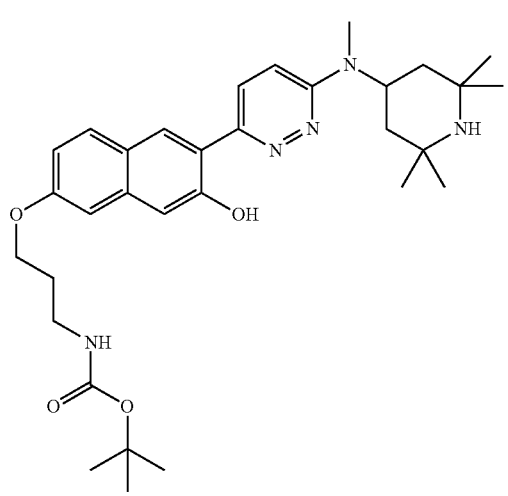
94
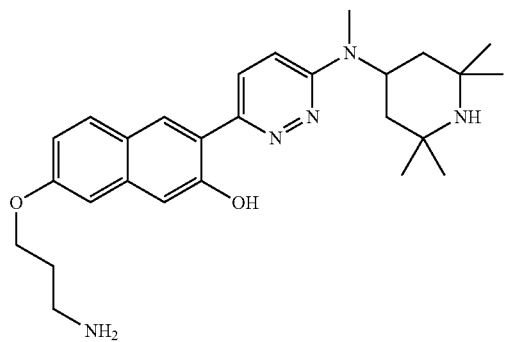
95
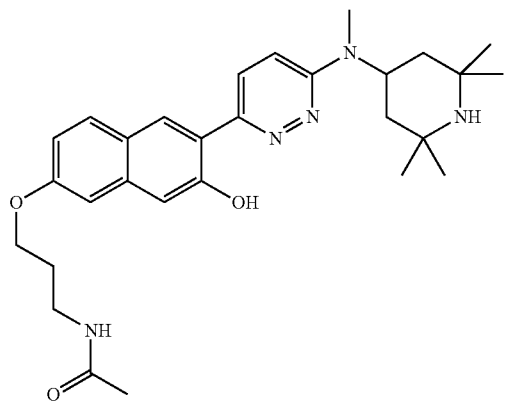
96
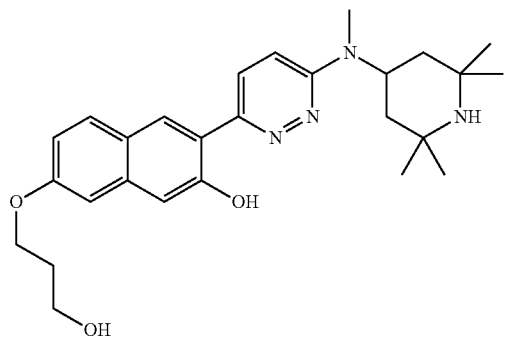
97
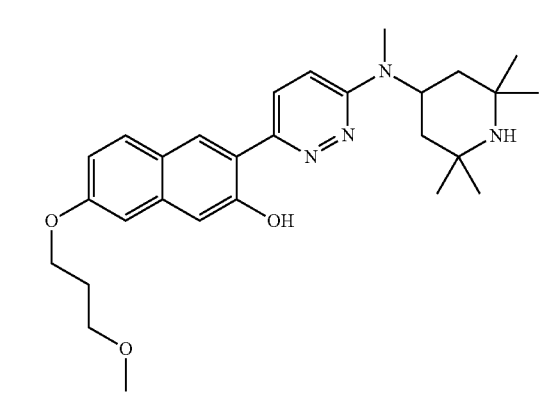
98
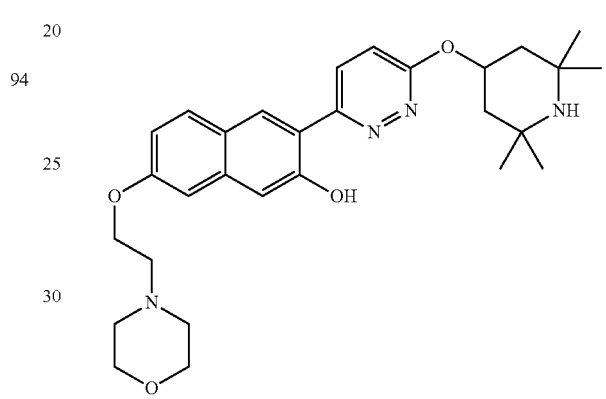
99
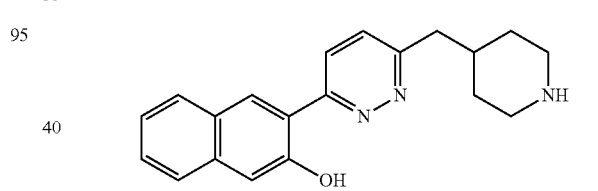
100
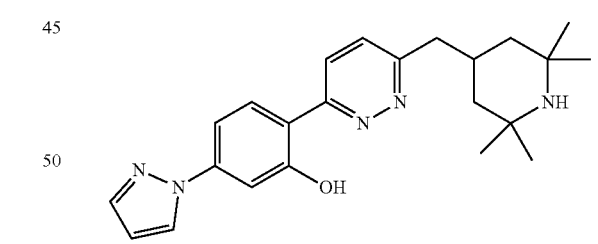
101
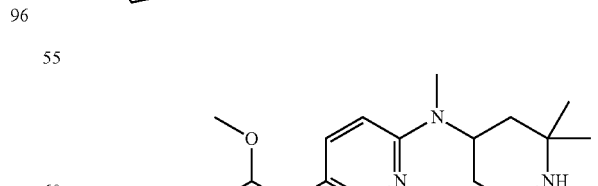
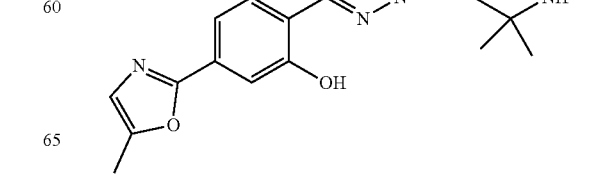

102 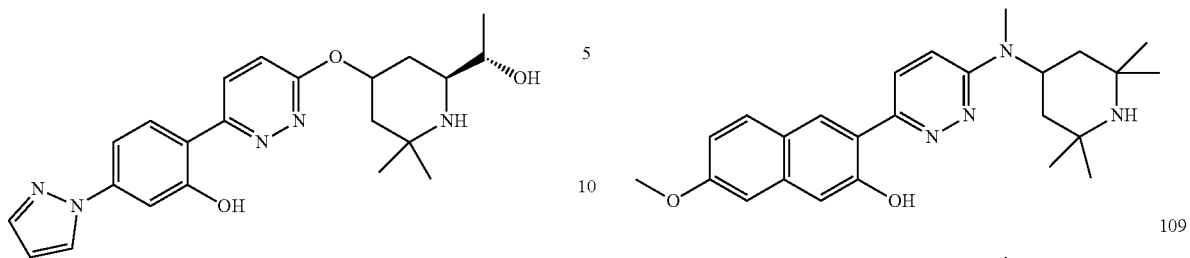
103 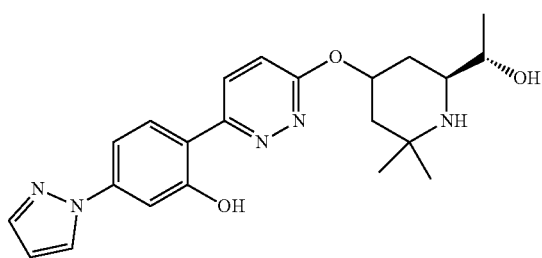
108 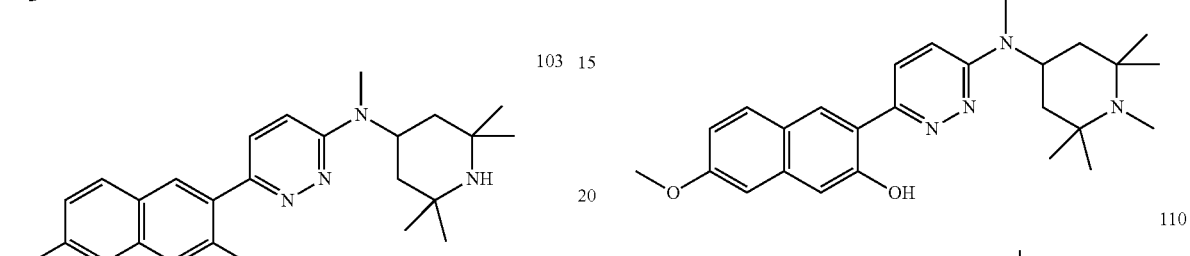
109 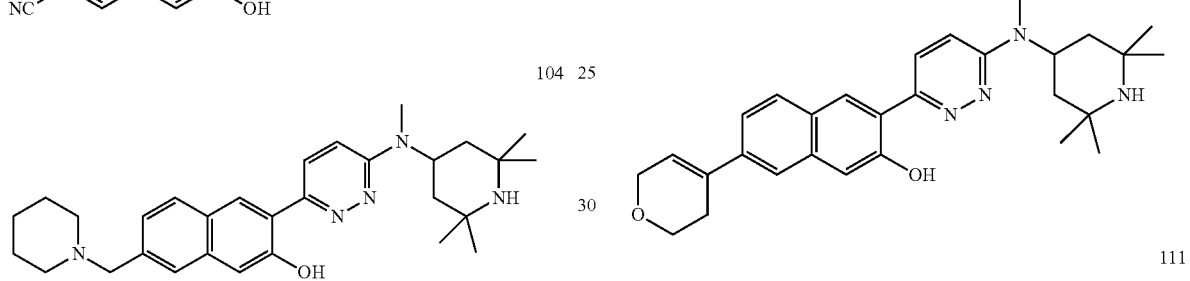
104 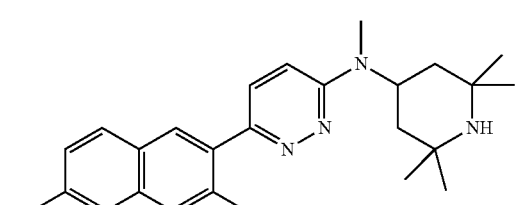
110 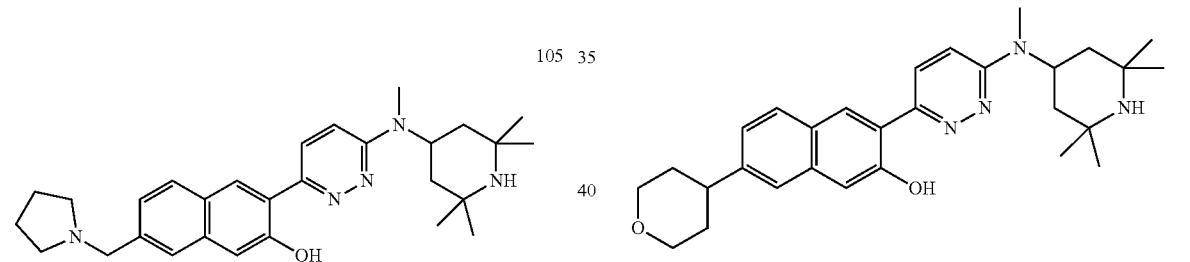
105 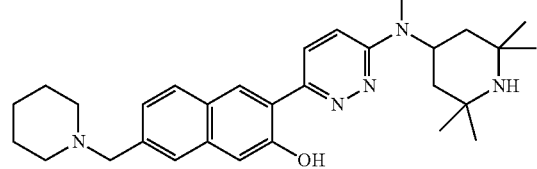
111 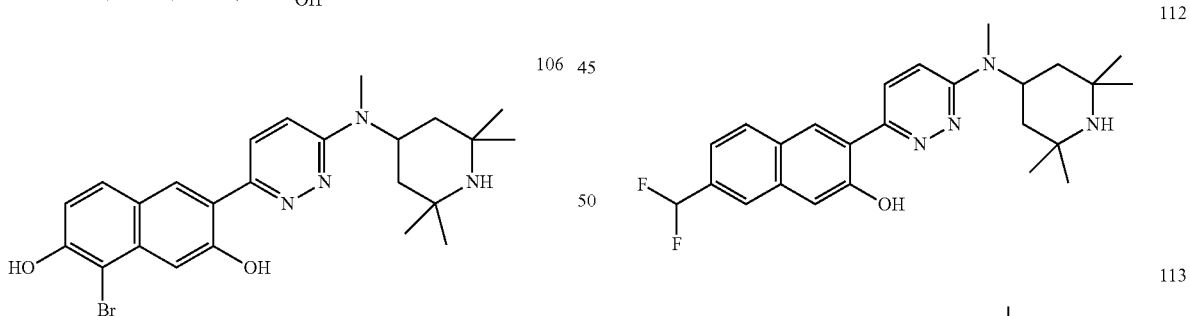
106 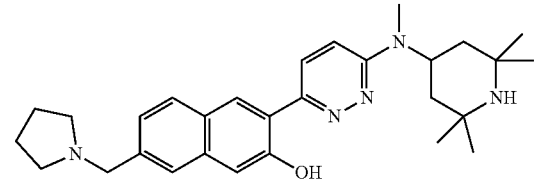
112 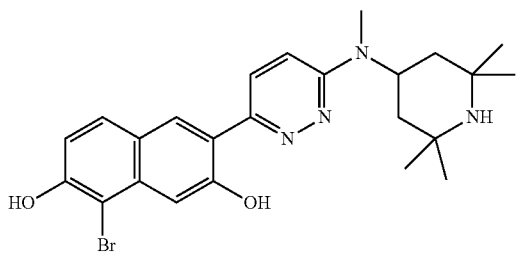
107 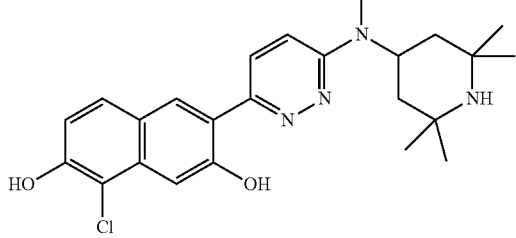
113 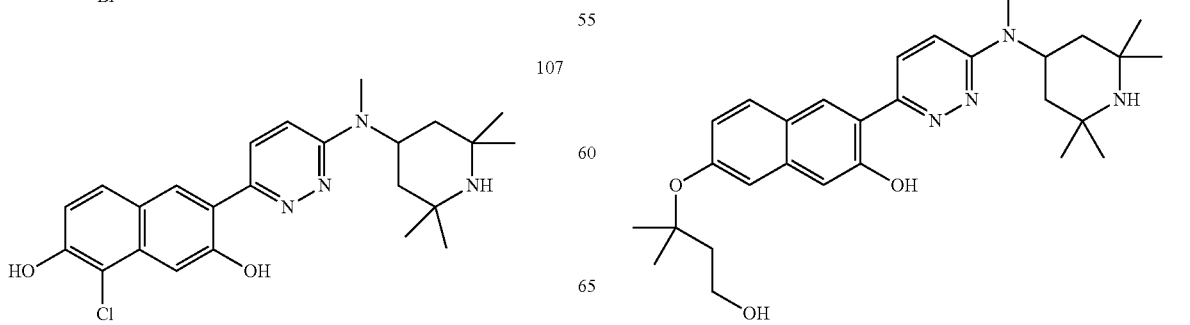

114 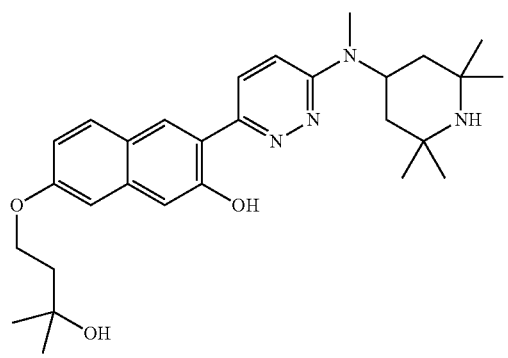
115 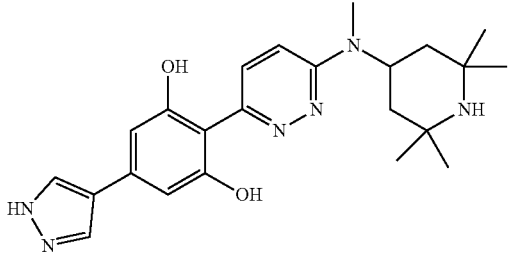
116 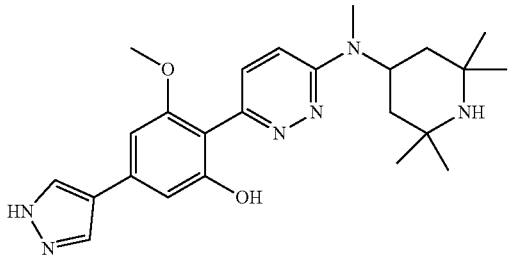
117 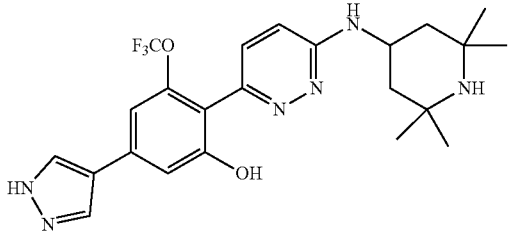
118 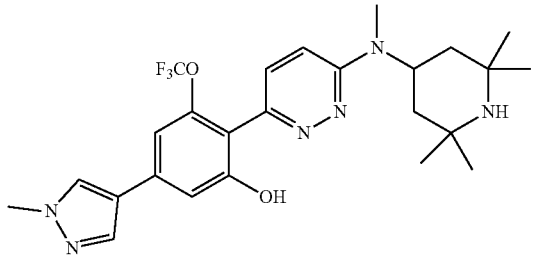
119 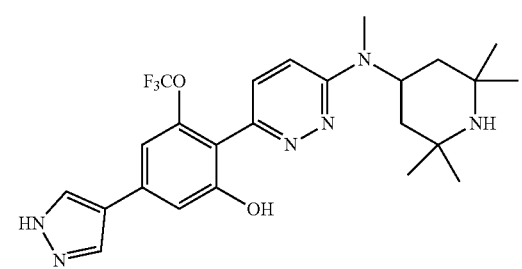
120 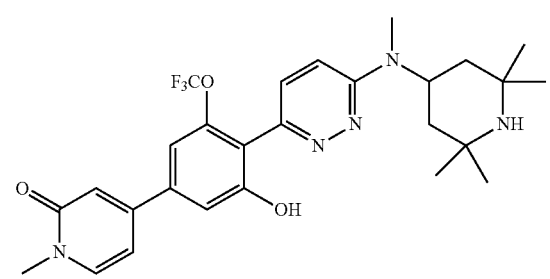
121 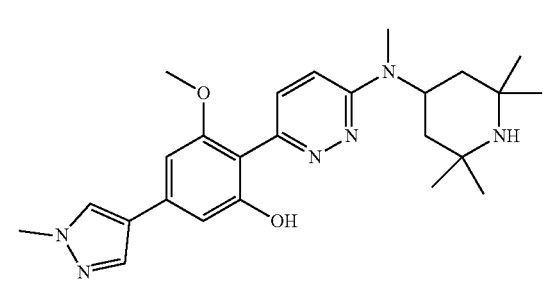
122 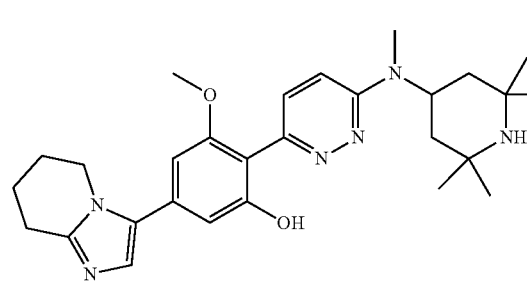
123 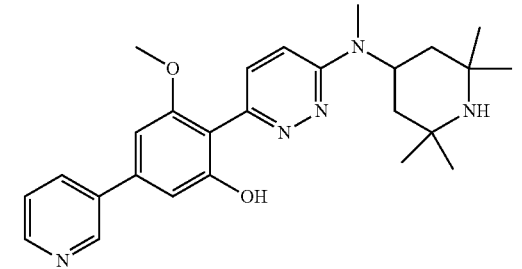

124
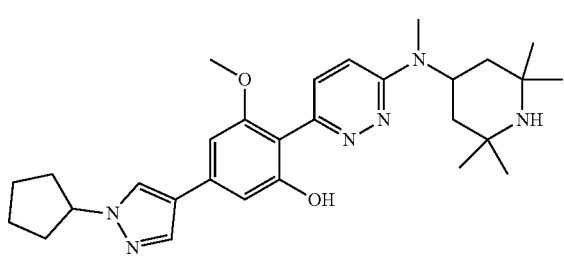
125
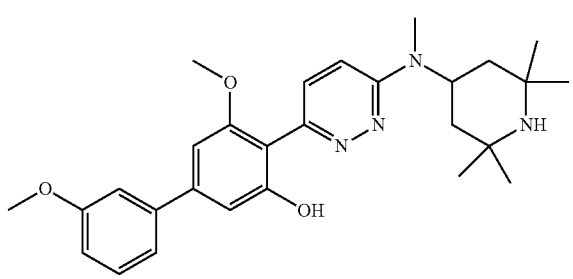
126
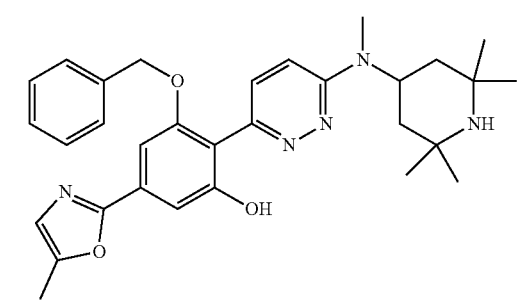
127
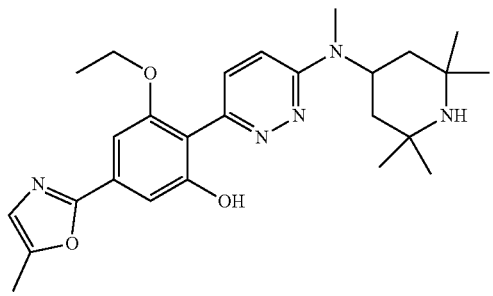
128
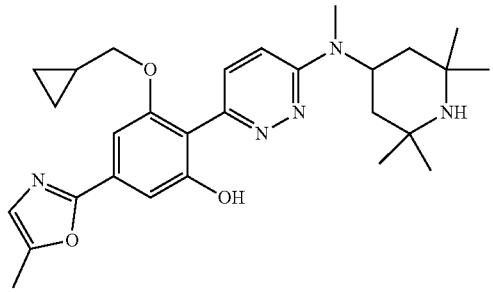
129
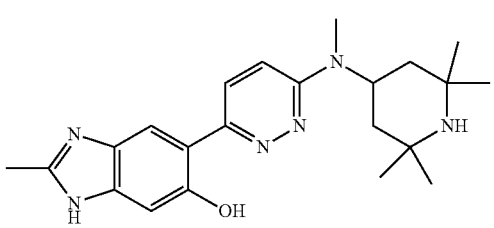
130
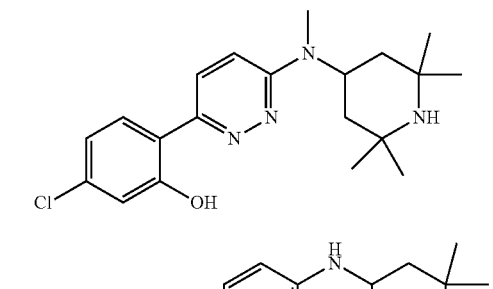
131
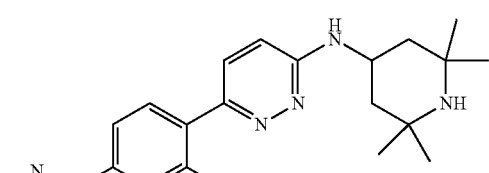
132
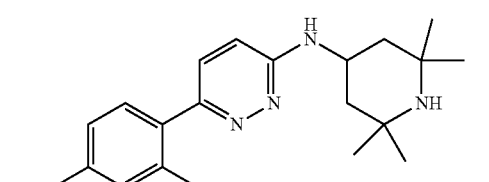
133
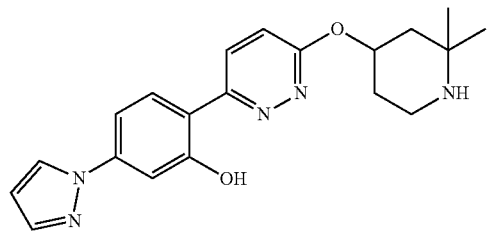
134
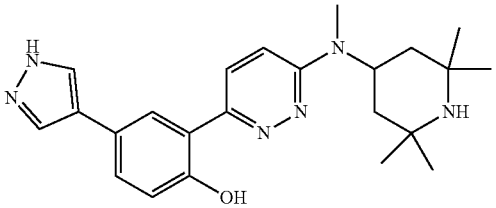
135
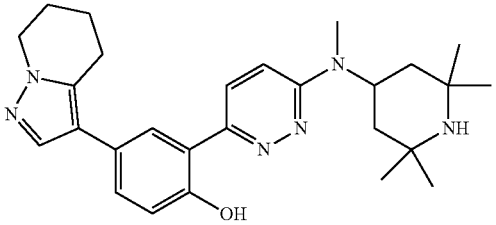

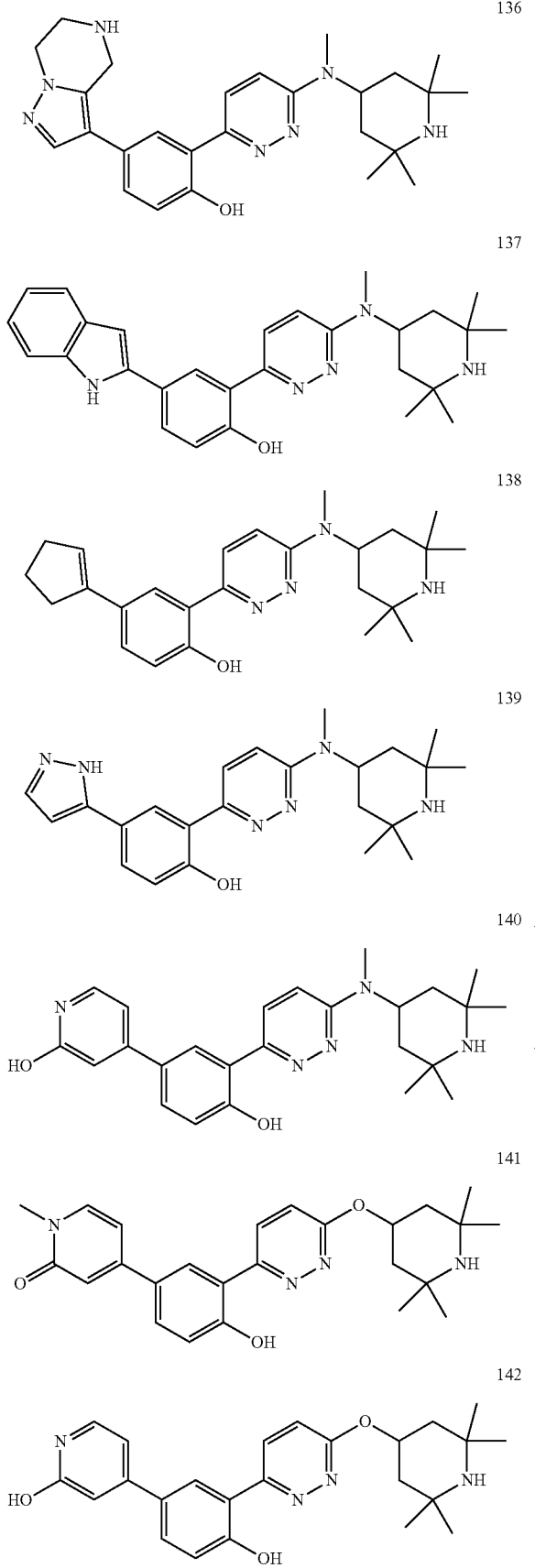

149
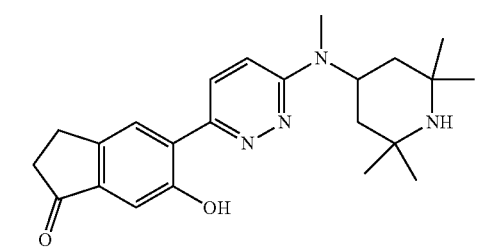
150
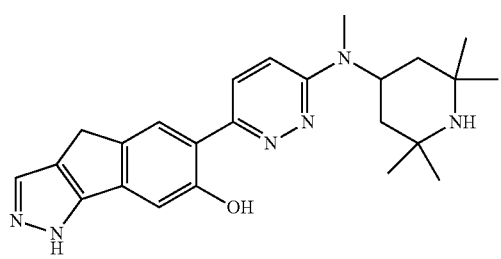
151
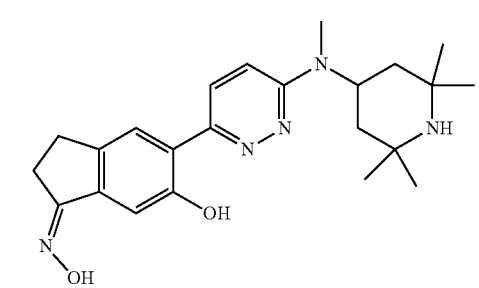
152
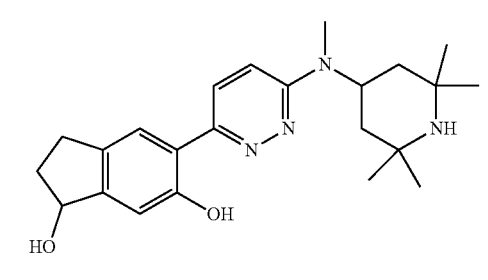
153
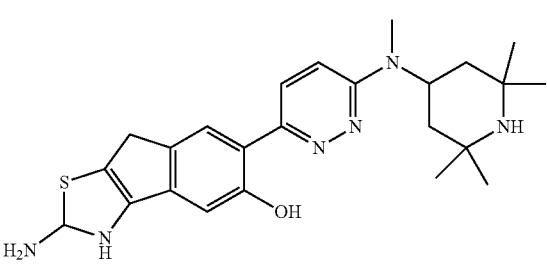
154
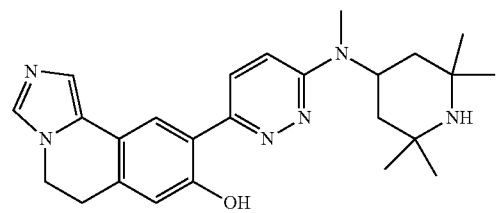
155
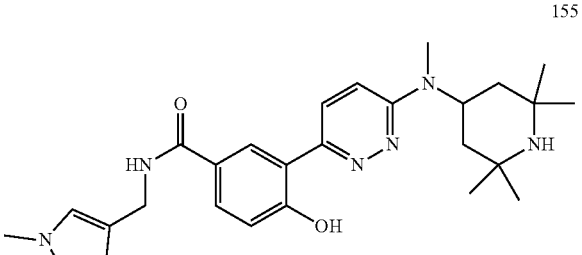
156
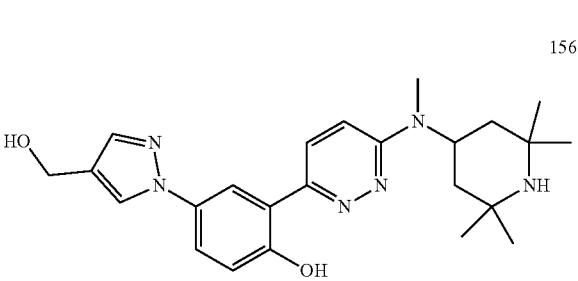
157
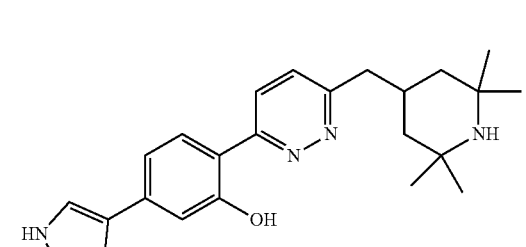
158
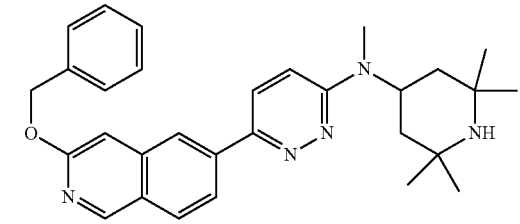
159
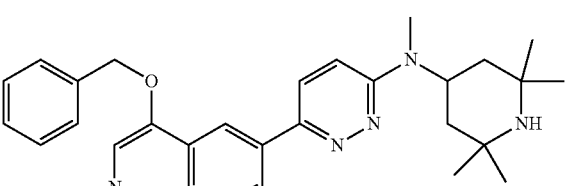
160
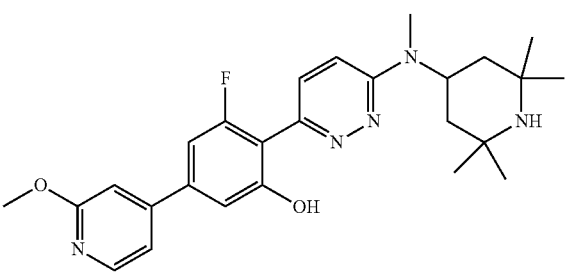

161
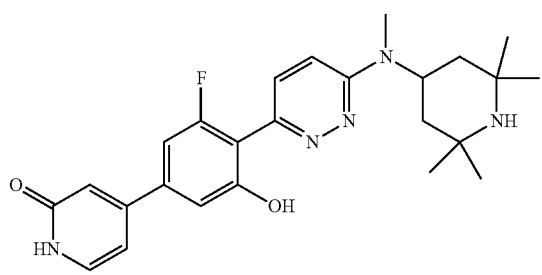
162
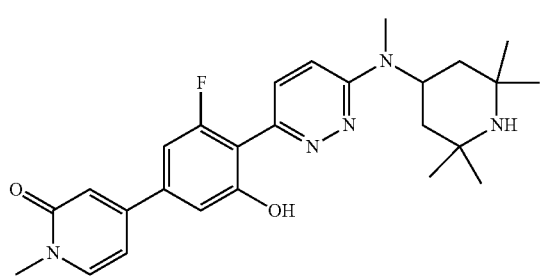
163
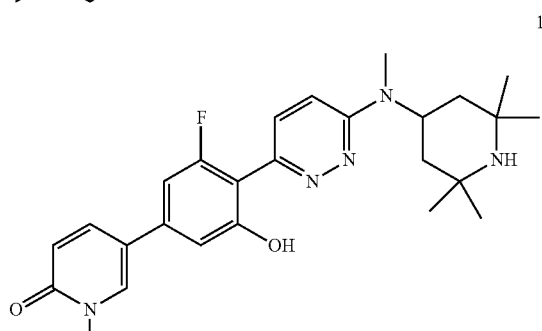
164
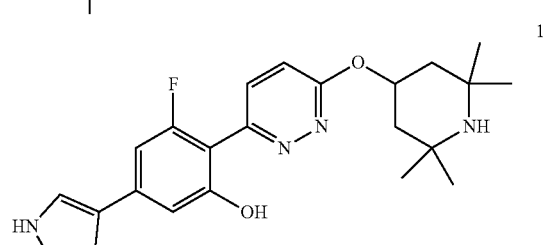
165
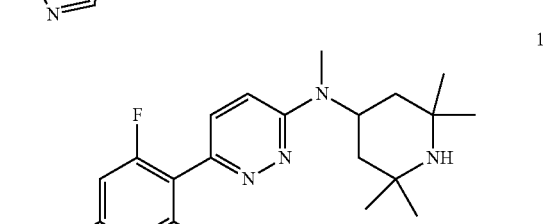
166
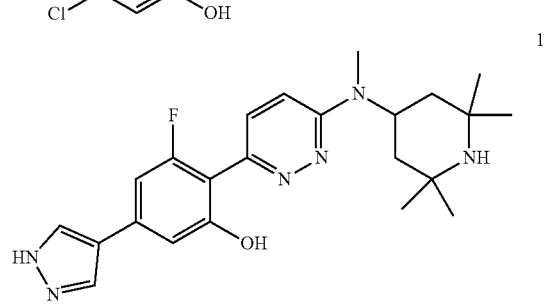
167
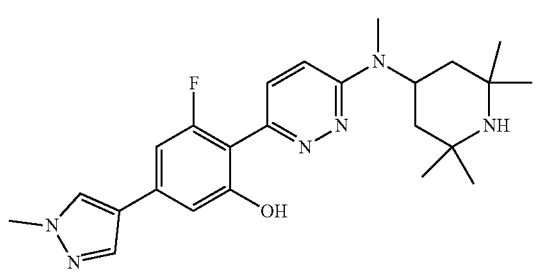
168
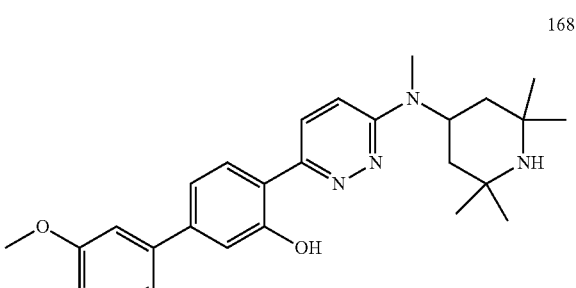
169
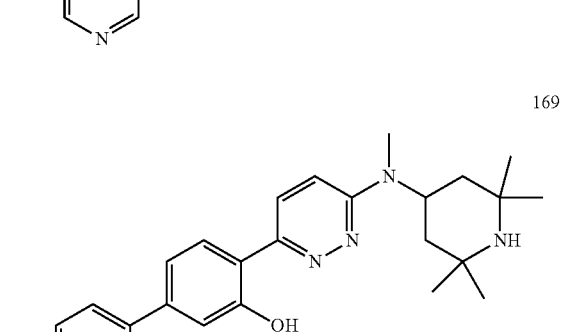
170
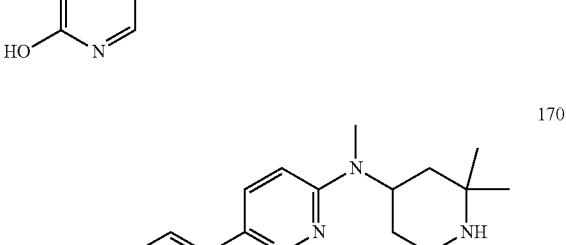
171
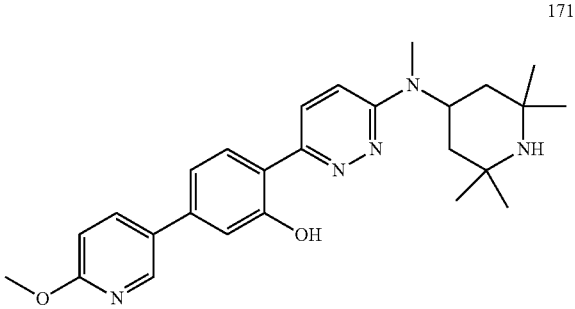

172
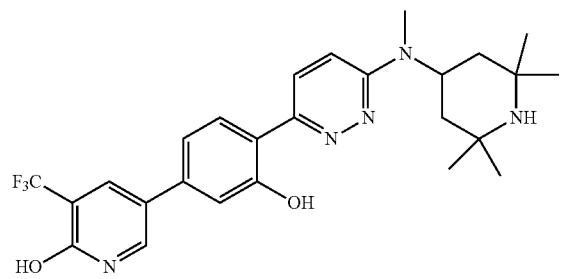
173
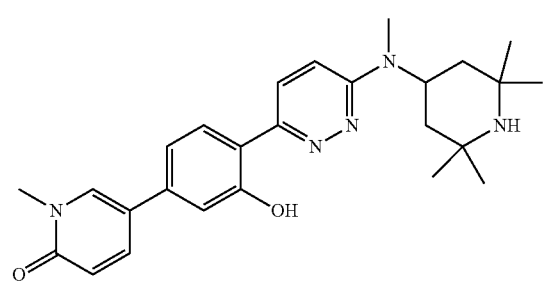
174
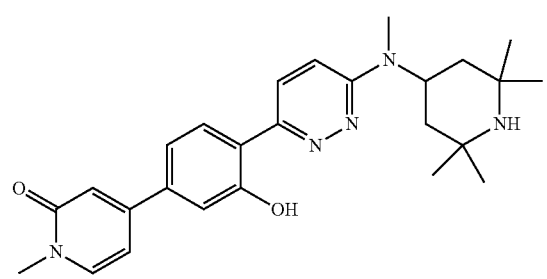
175
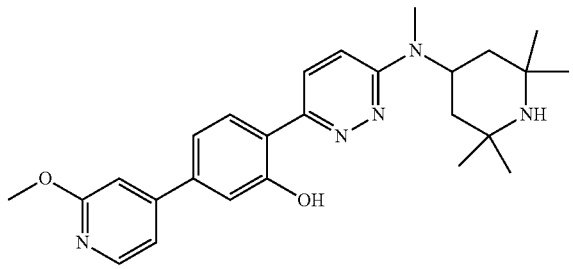
176
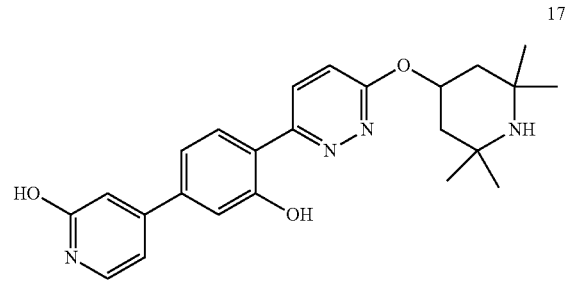
177
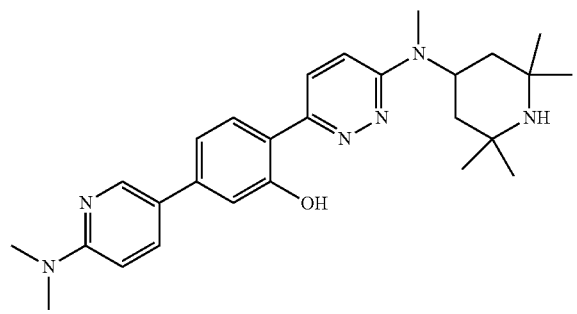
178
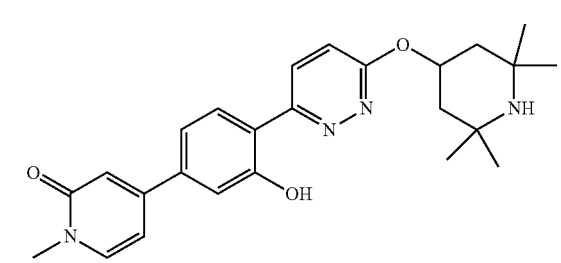
179
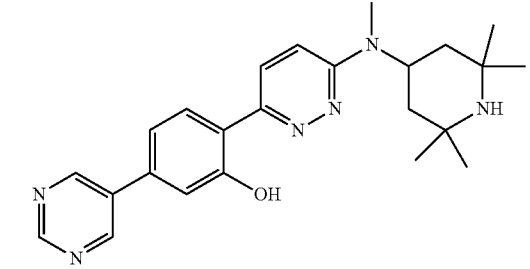
180
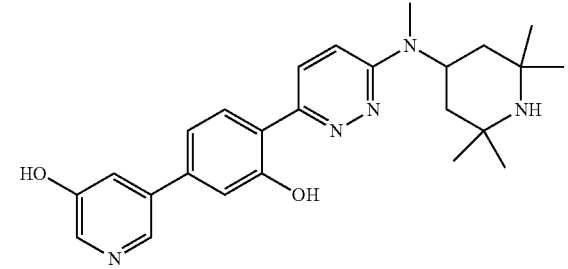
181
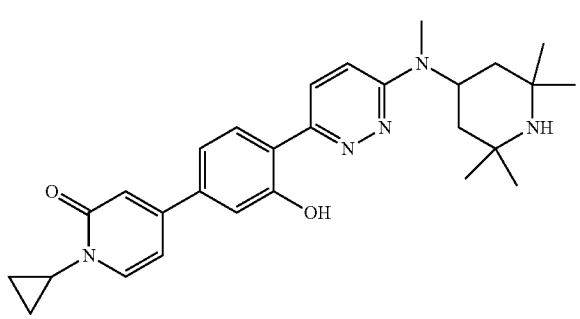

182
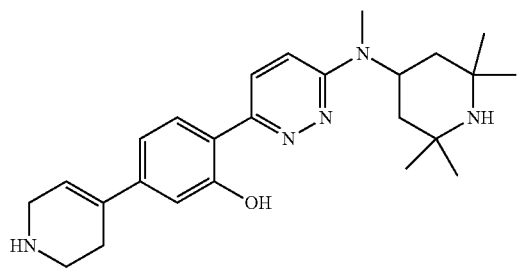
183
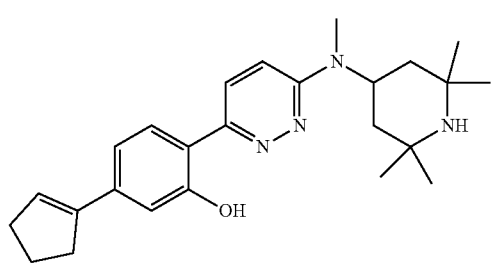
184
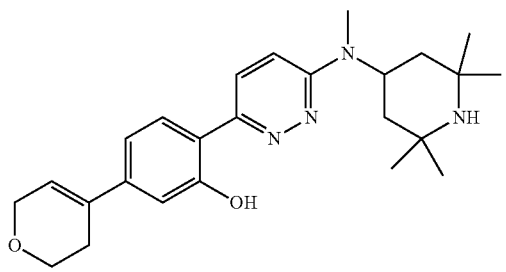
185
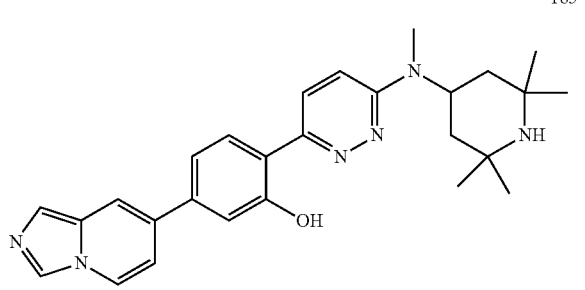
186
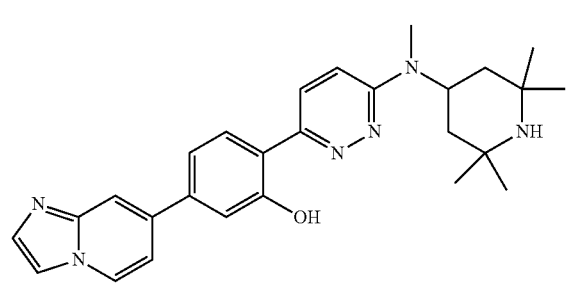
187
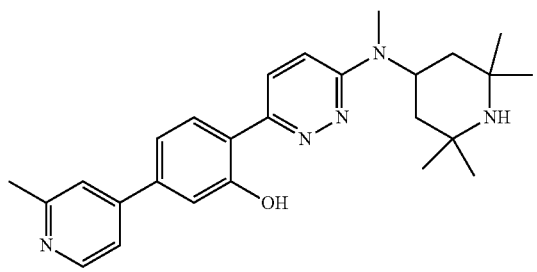
188
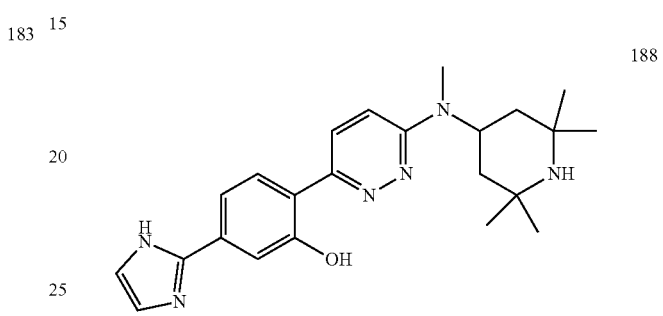
189
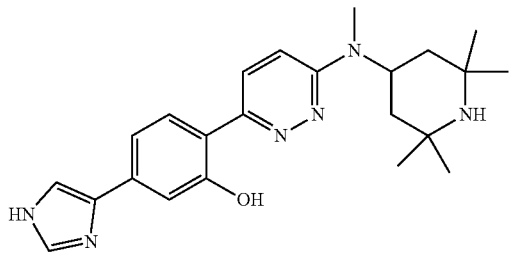
190
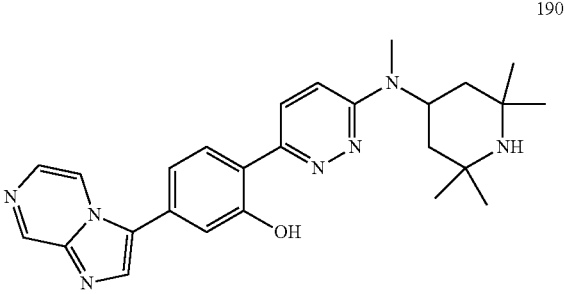
191
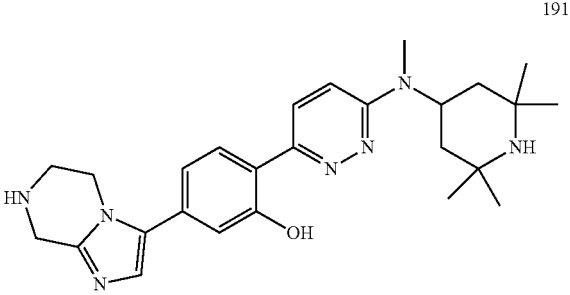

192 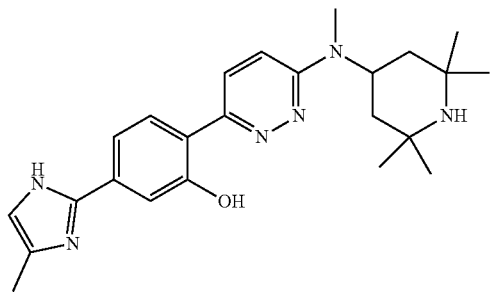
193 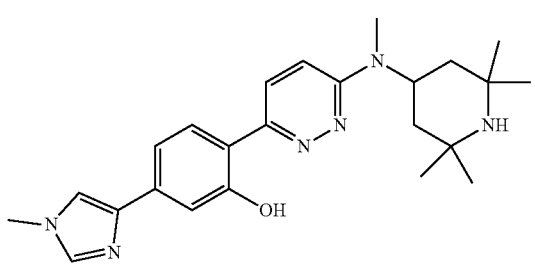
194 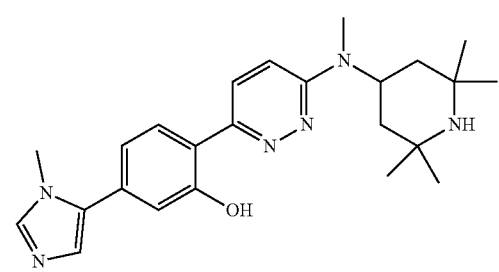
195 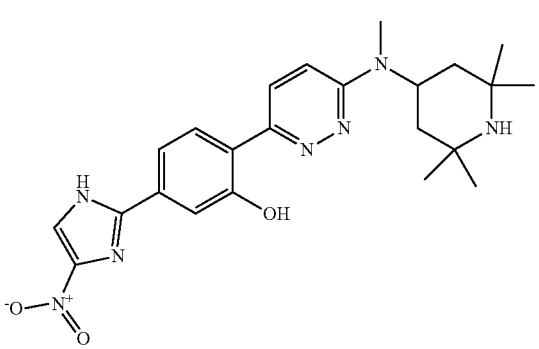
196 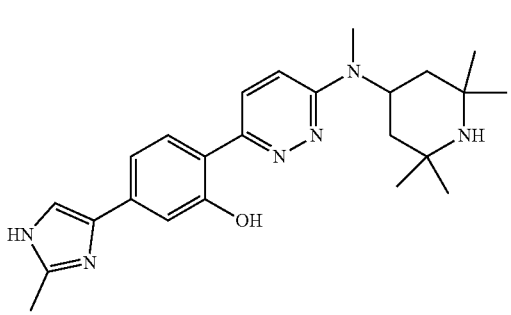
197 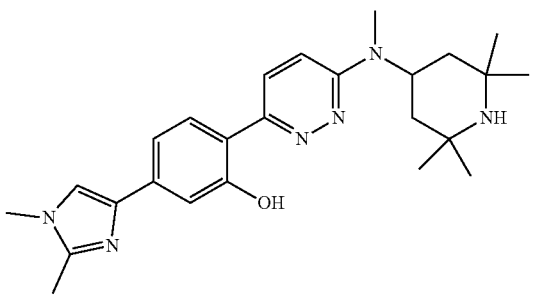
198 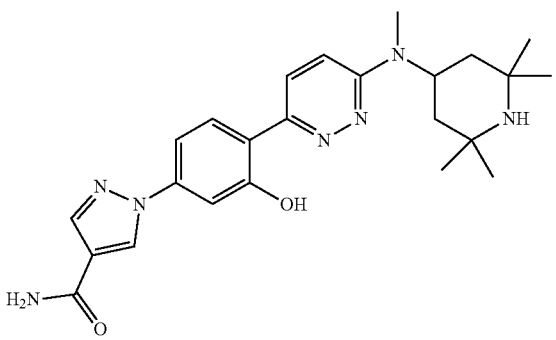
199
200
201
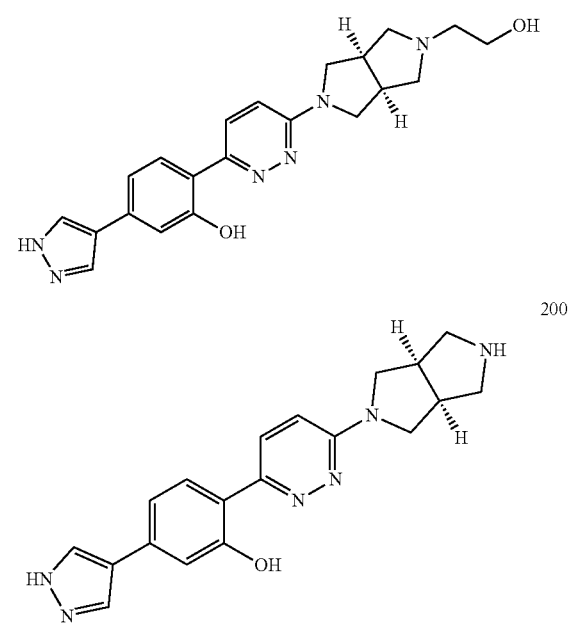

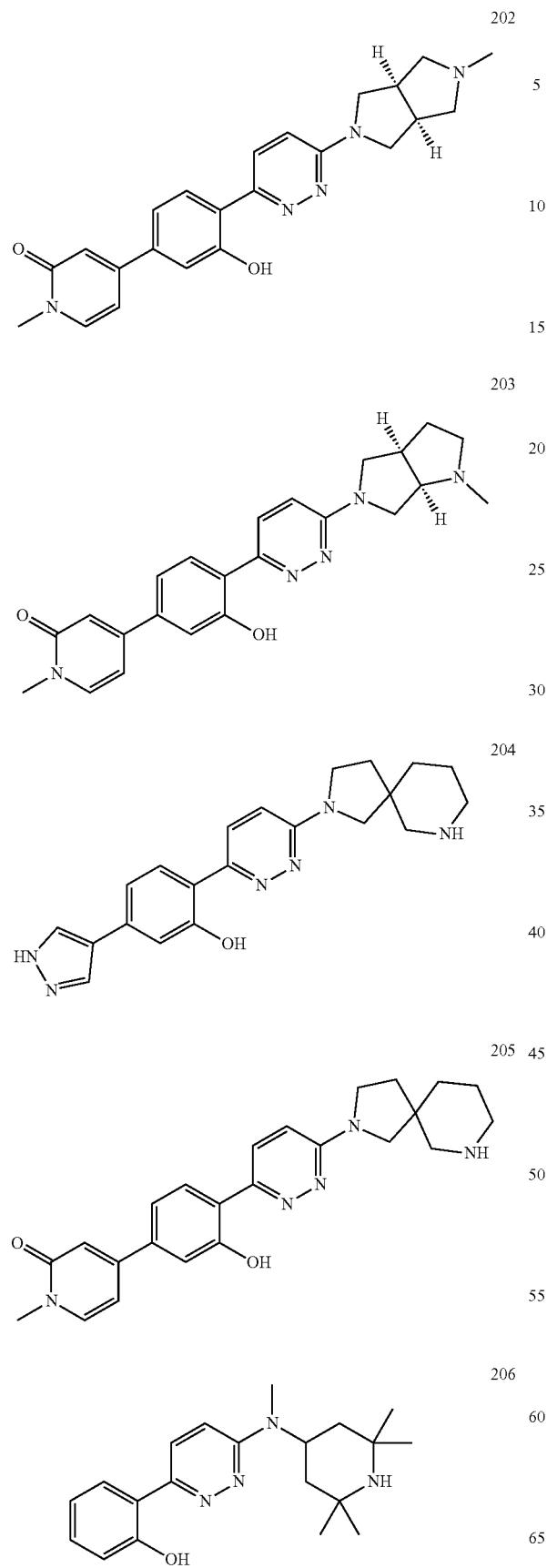
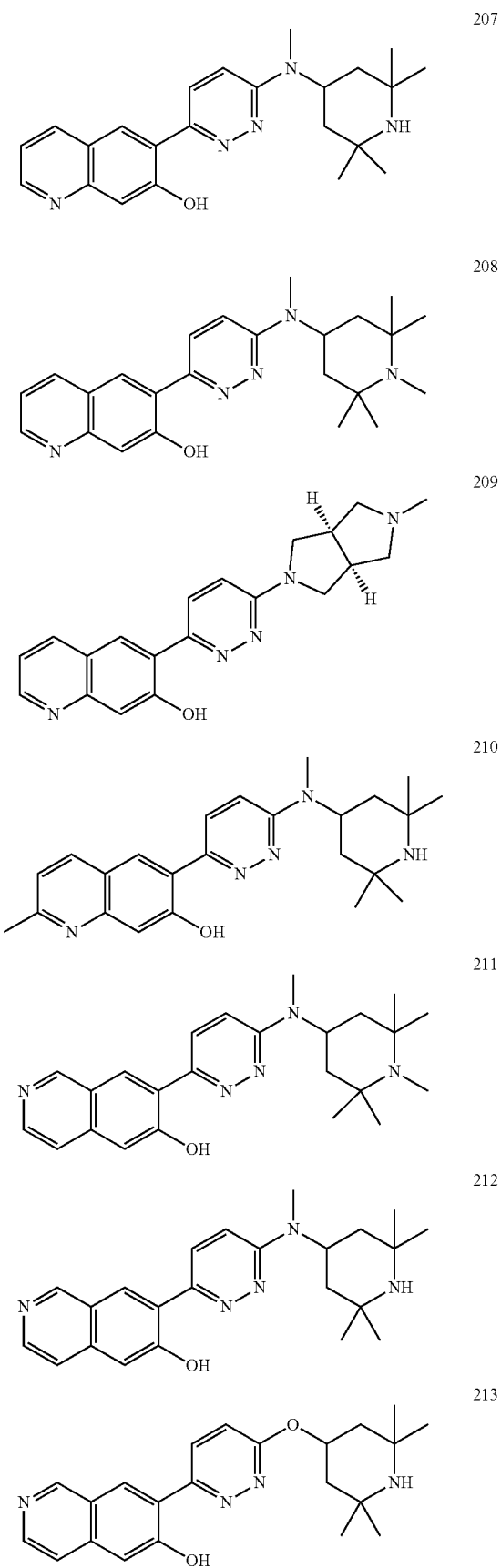

214
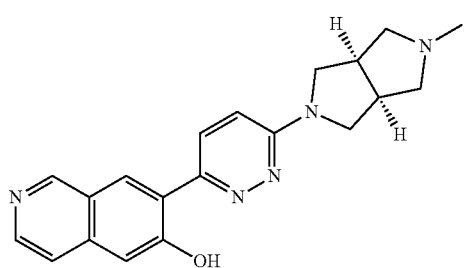
215
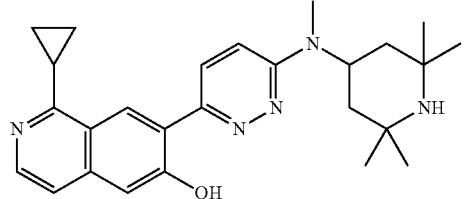
216
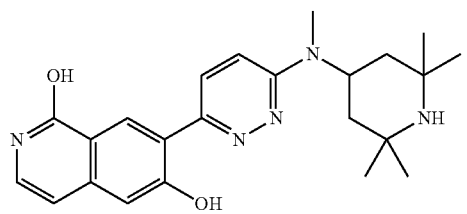
217
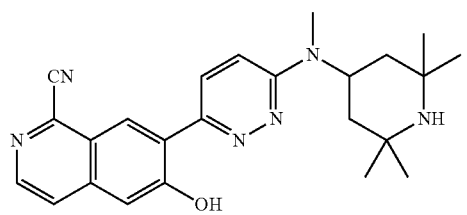
218
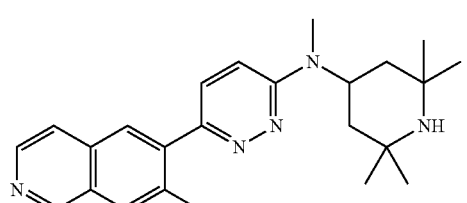
219
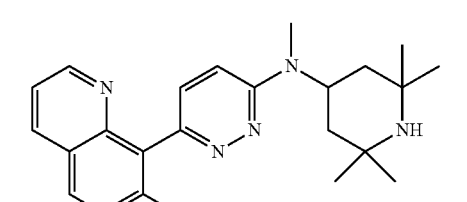
220
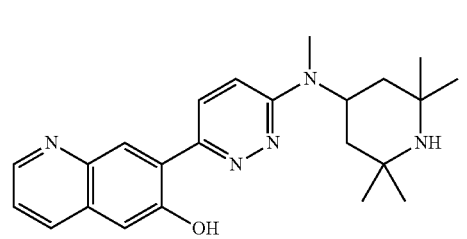
221
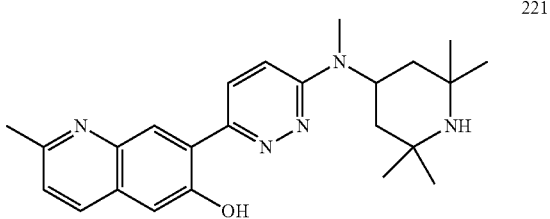
222
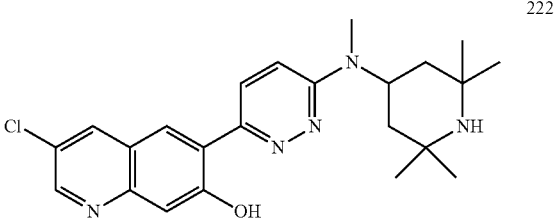
223
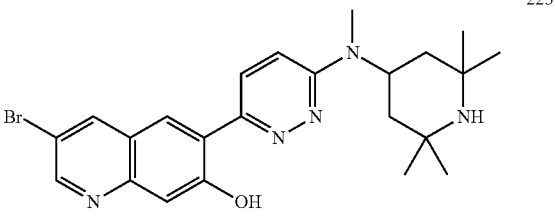
224
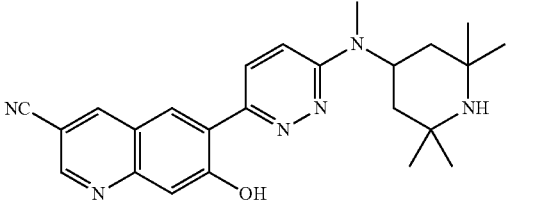
225
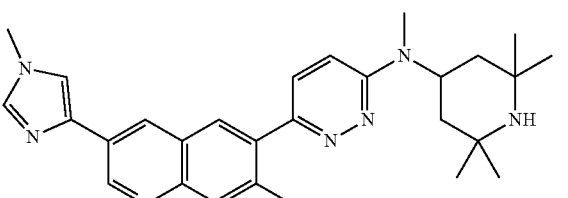
226
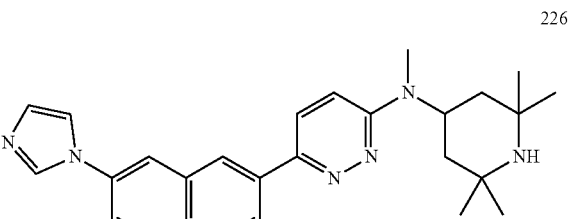
227
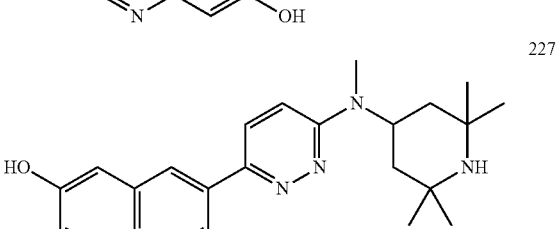

-continued
228
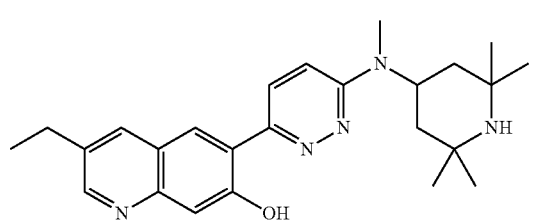
229
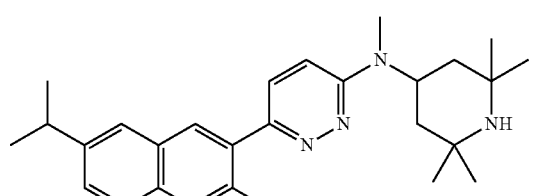
230
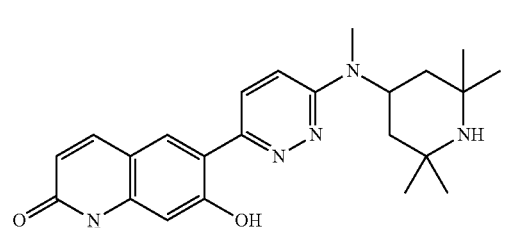
231
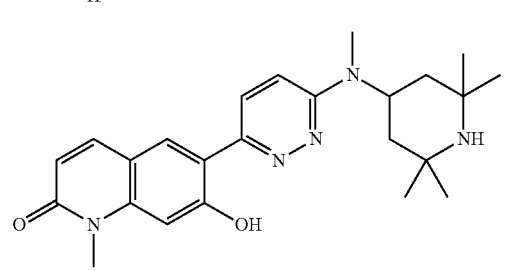
232
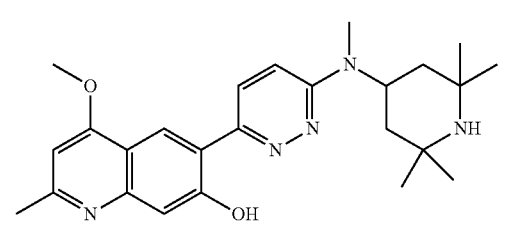
233
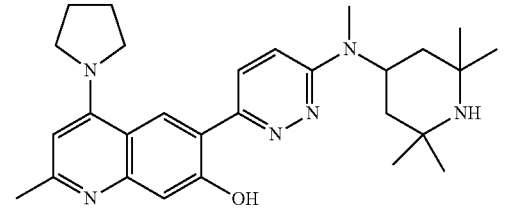
234
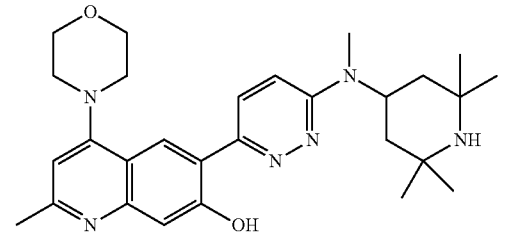
-continued
235
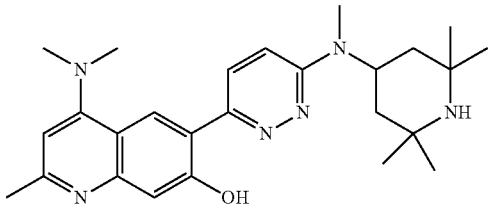
236
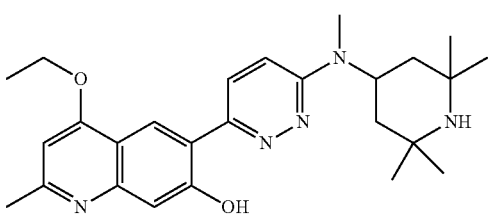
237
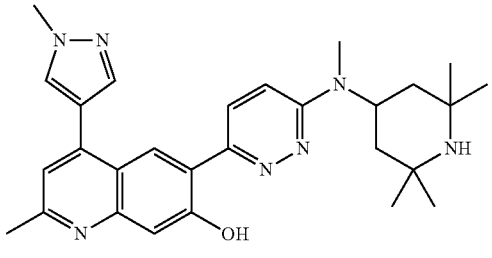
238
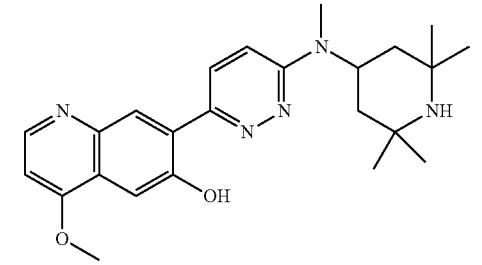
239
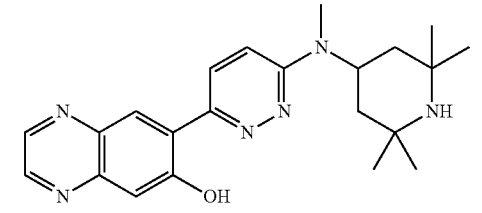
240
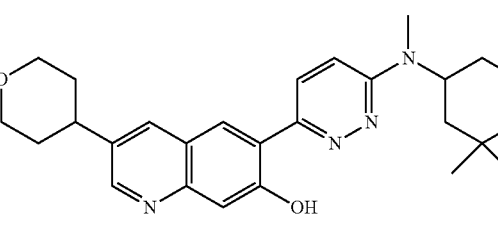
241
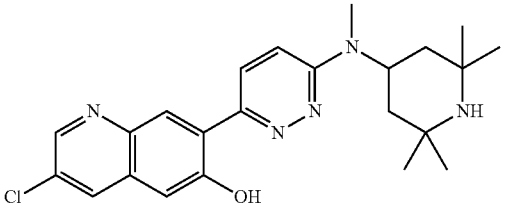

242 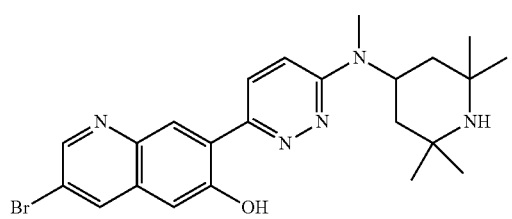
243 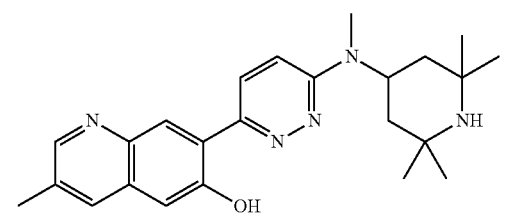
244 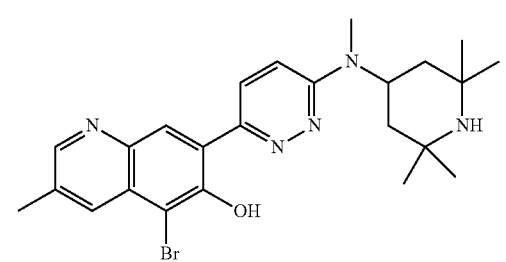
245 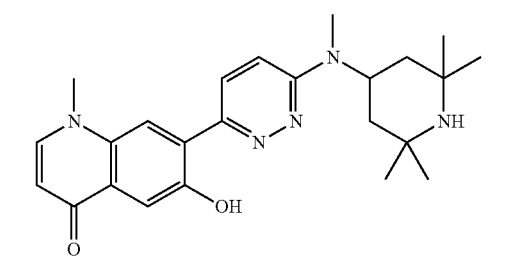
246 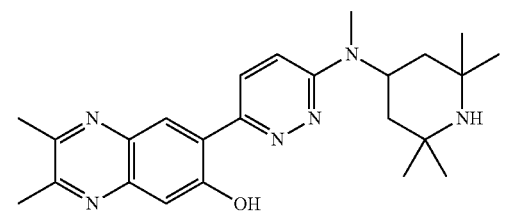
247 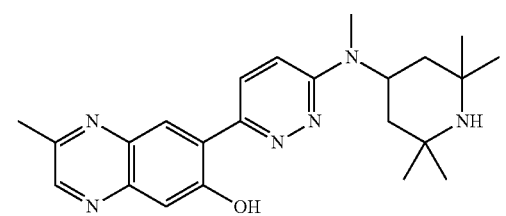
248 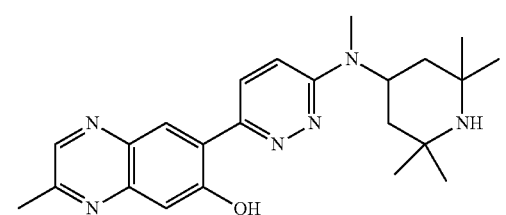
249 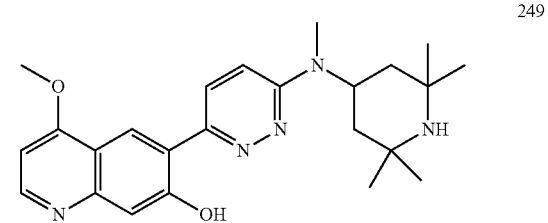
250 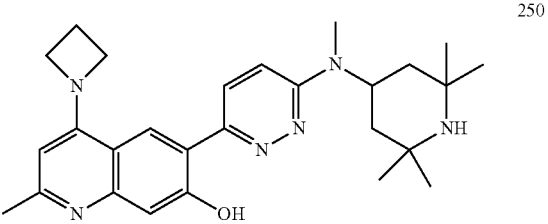
251 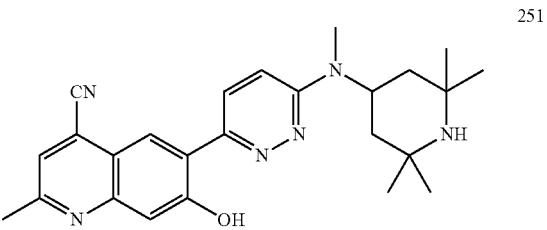
252 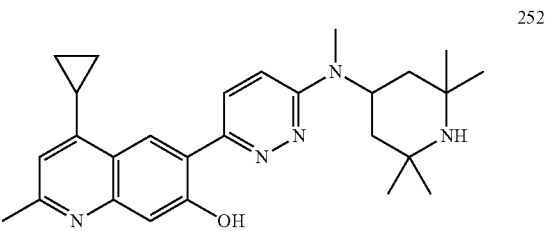
253 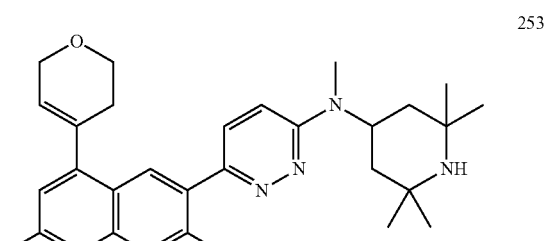
254 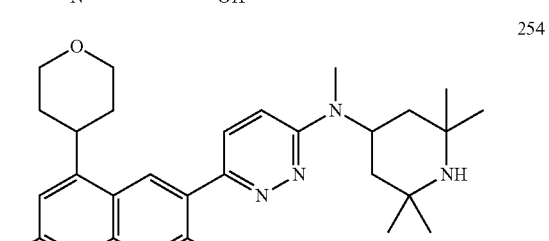
255 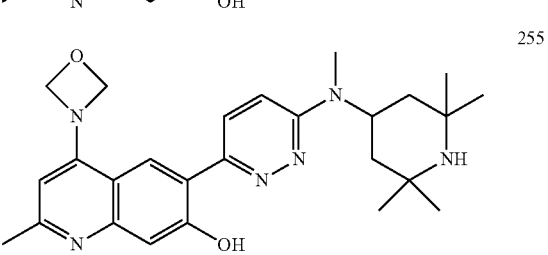

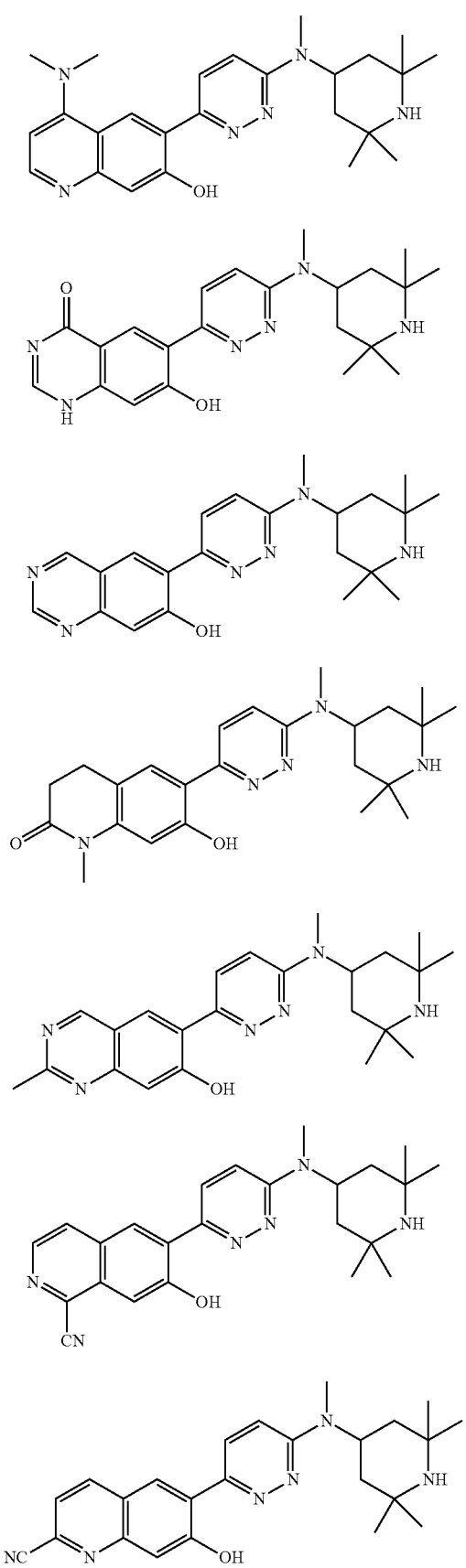
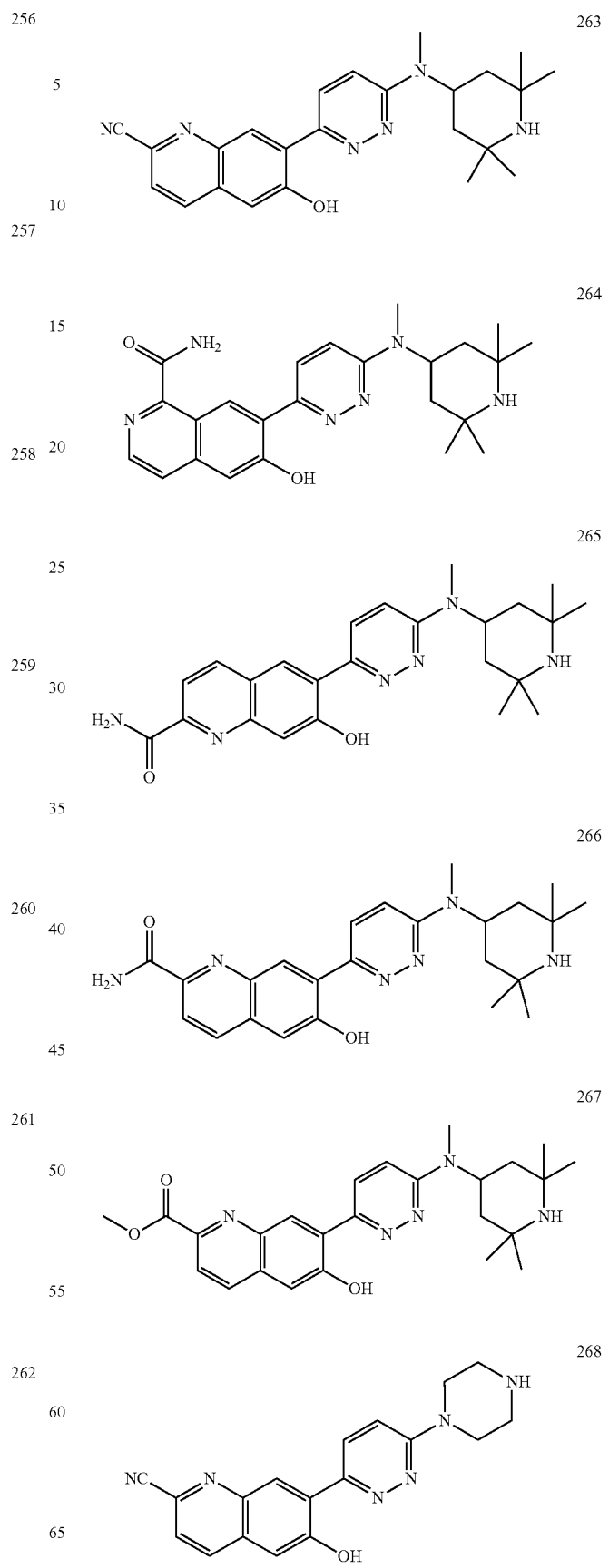

269 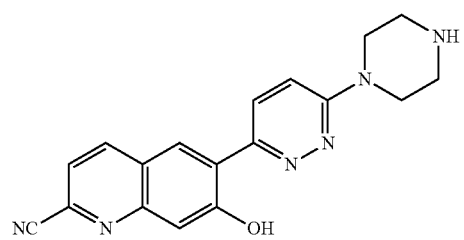
270 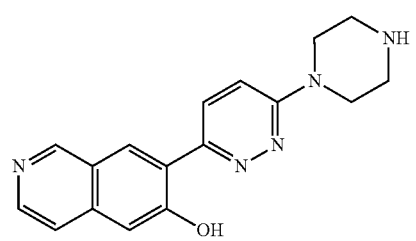
271 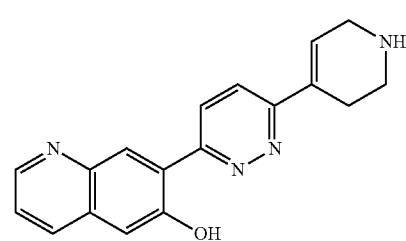
272 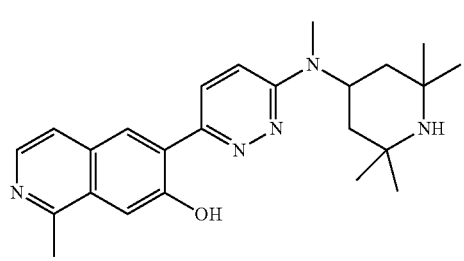
273 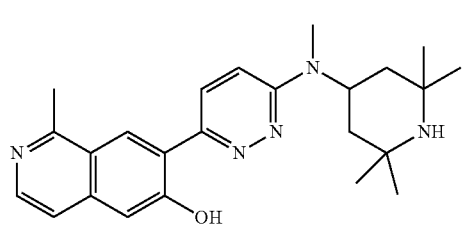
274 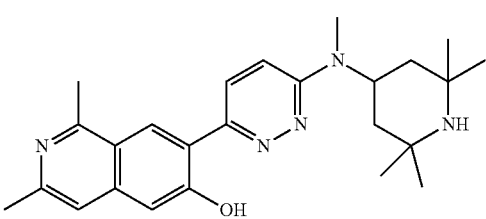
275 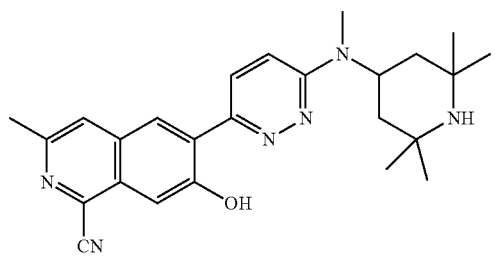
276 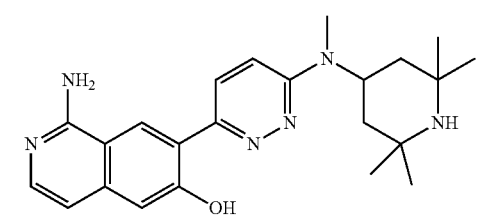
277 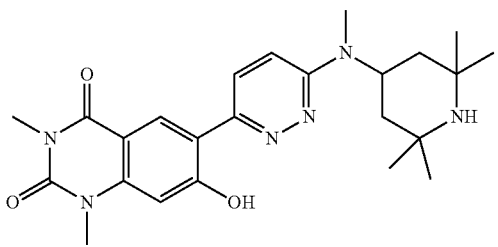
278 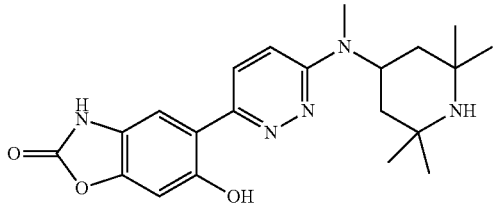
279 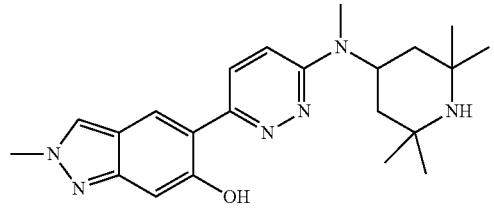
280 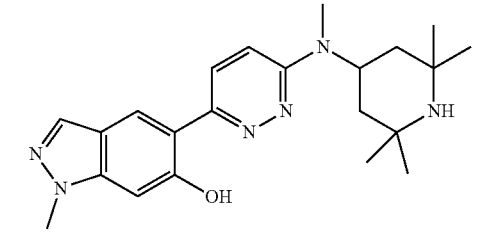
281 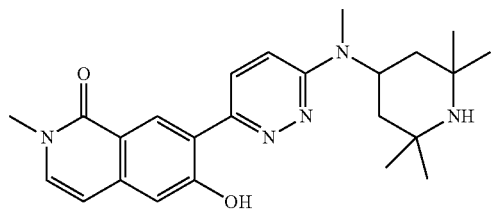

282
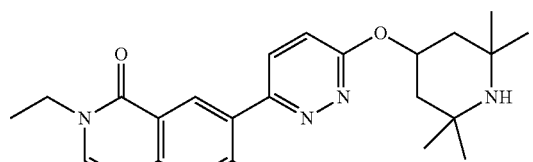
283
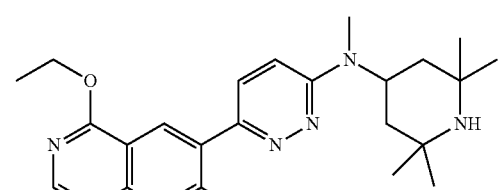
284
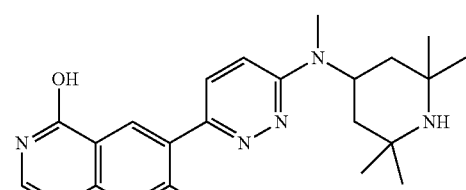
285
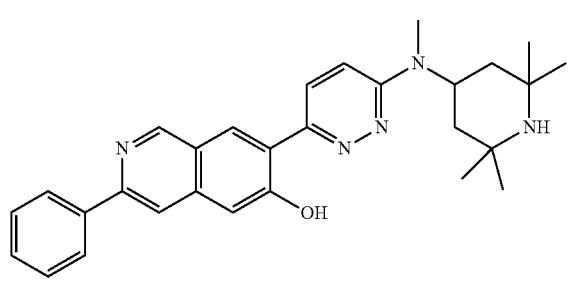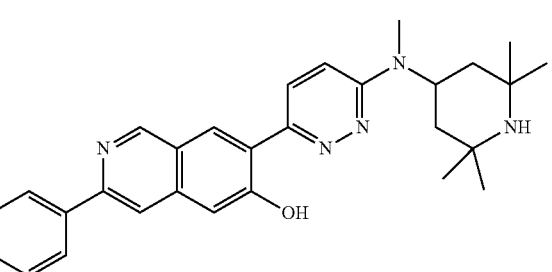
286
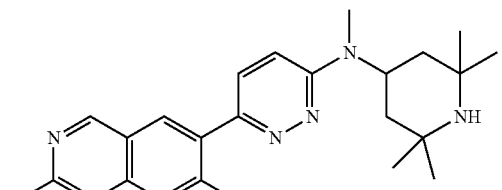
287
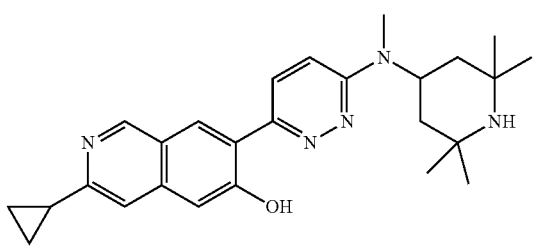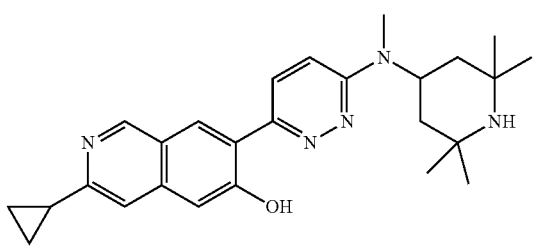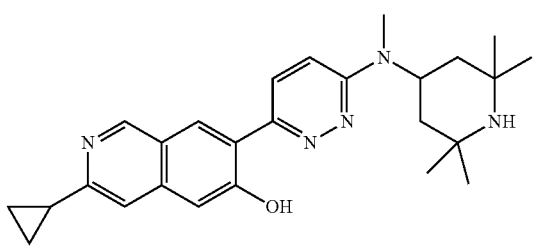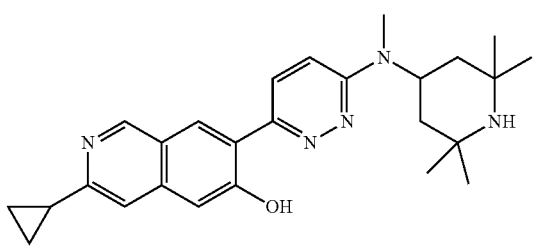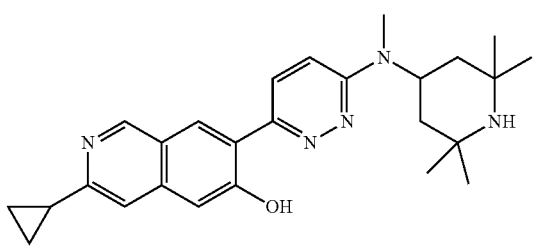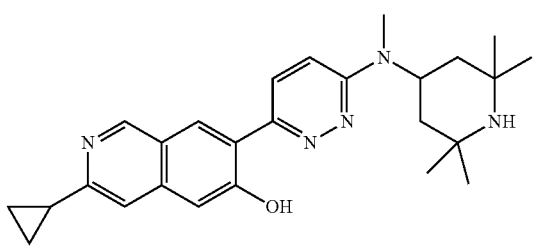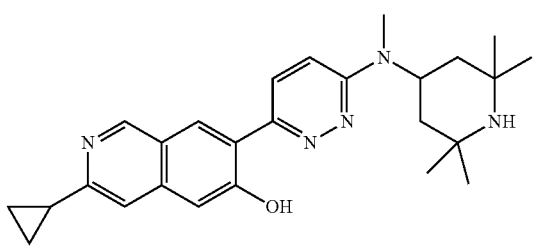
288
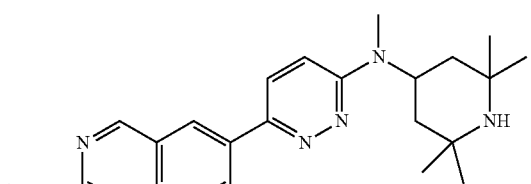
289
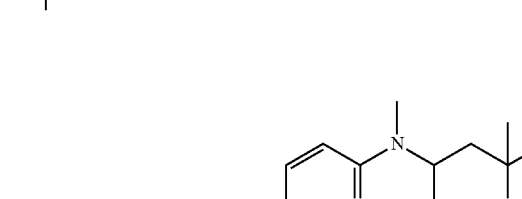
290
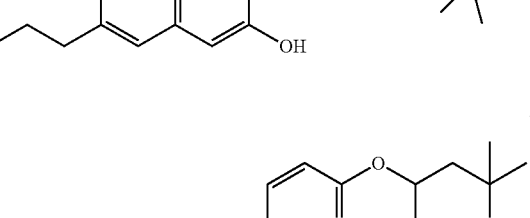
291
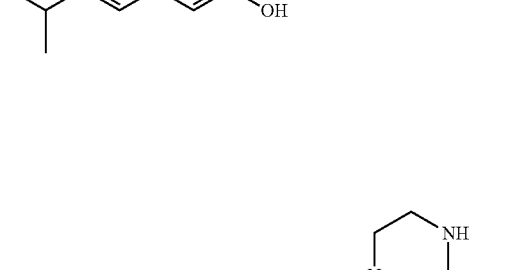
292
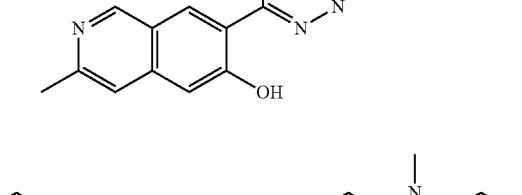
293
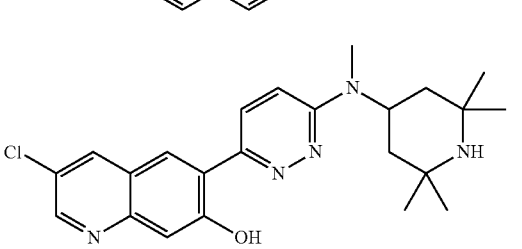

294
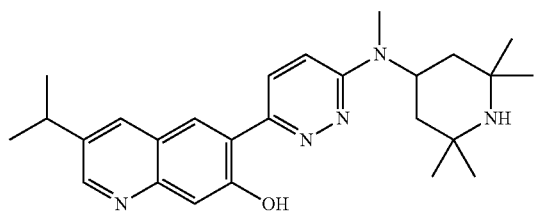
295
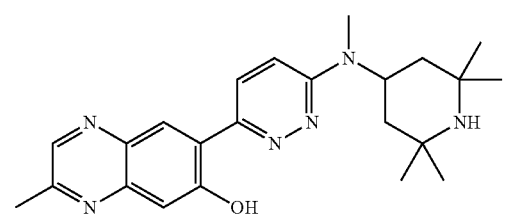
296
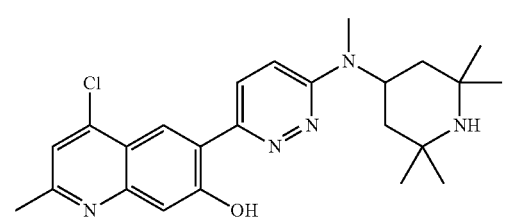
297
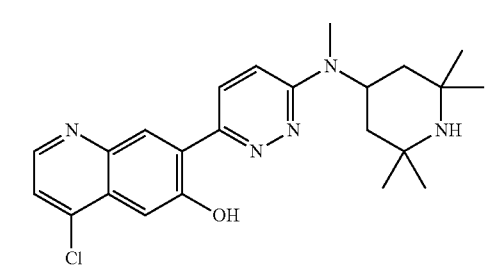
300
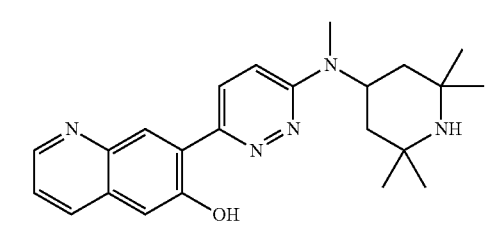
301
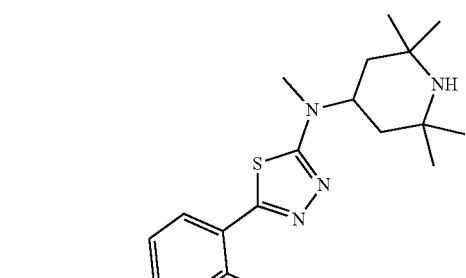
302
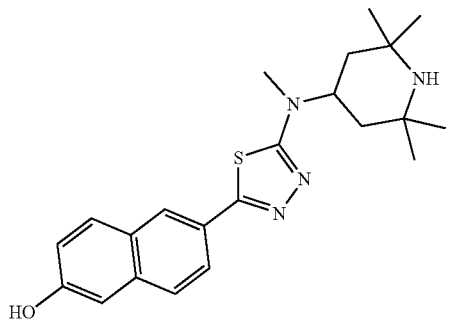
303
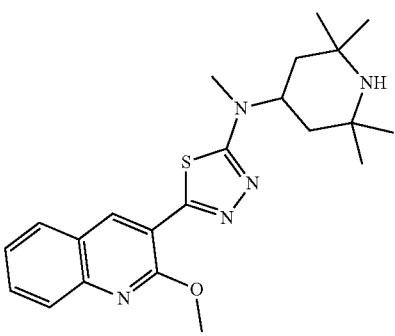
304
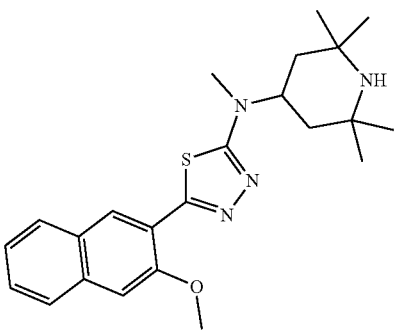
305
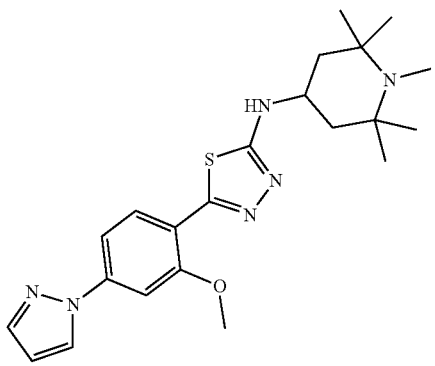

306
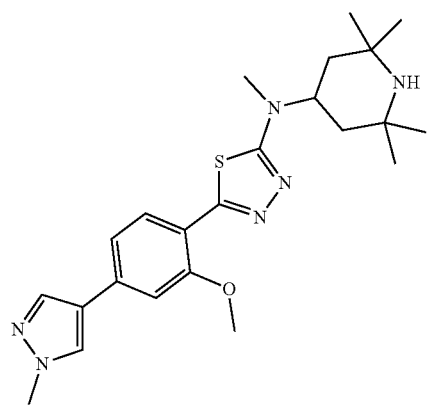
307
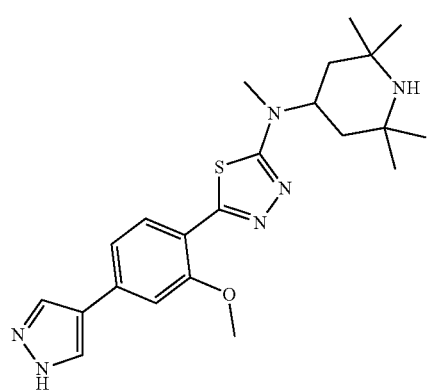
308
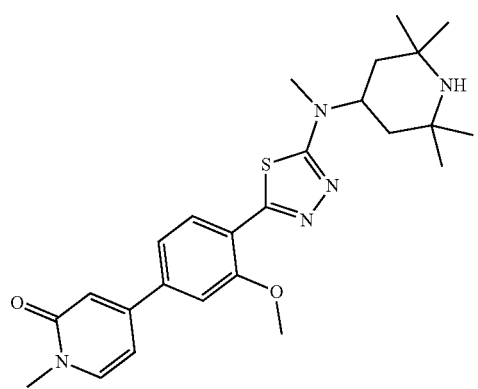
309
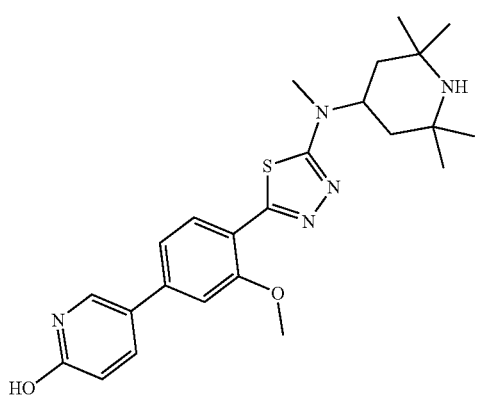
310
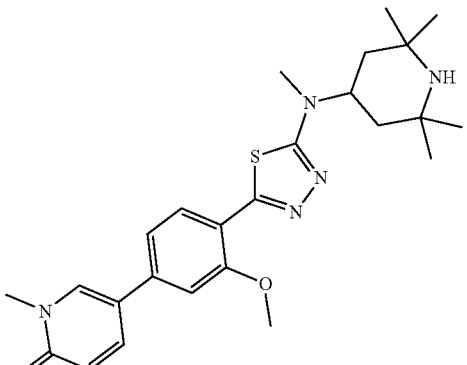
311
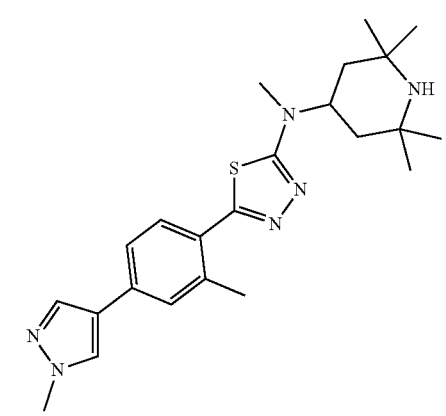
312
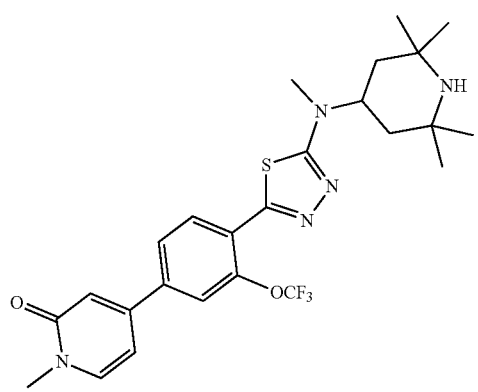
313
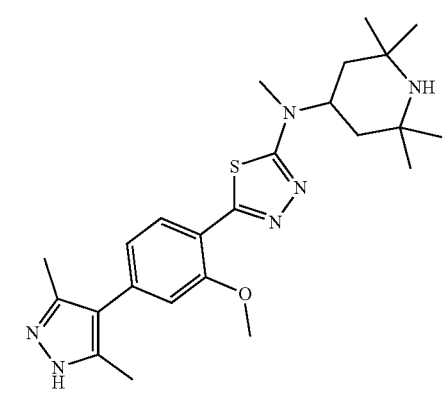

314
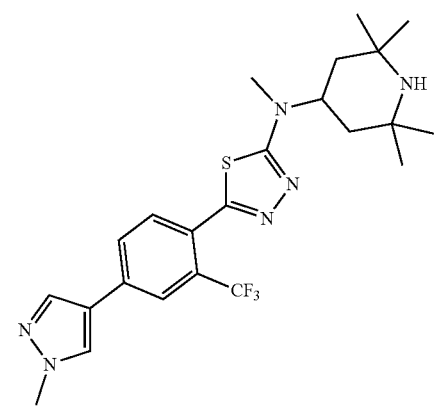
315
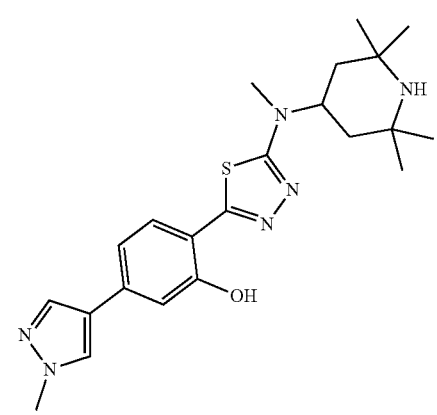
316
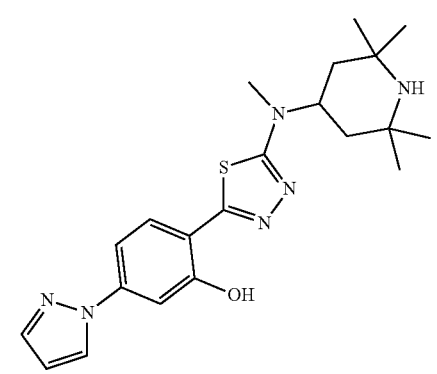
317
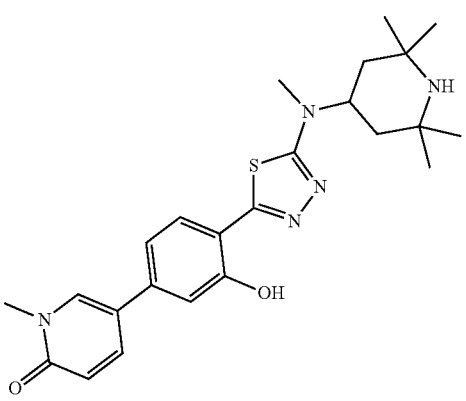
318
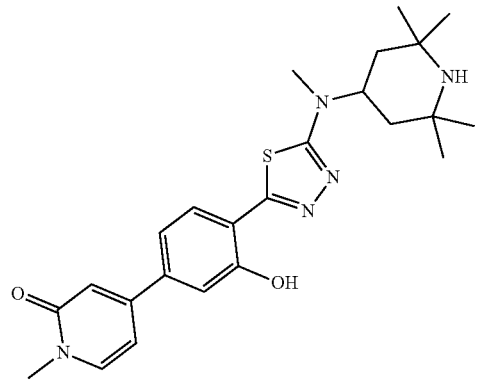
319
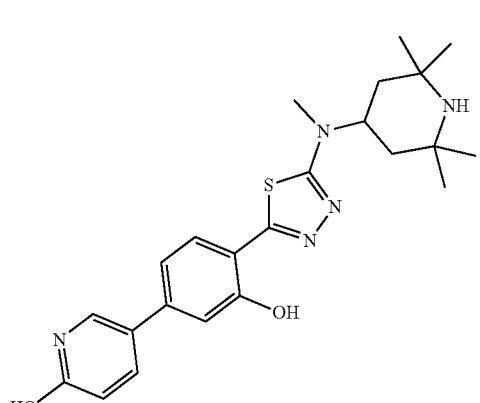
320
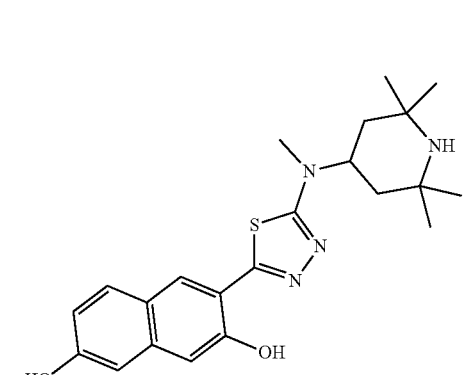
321
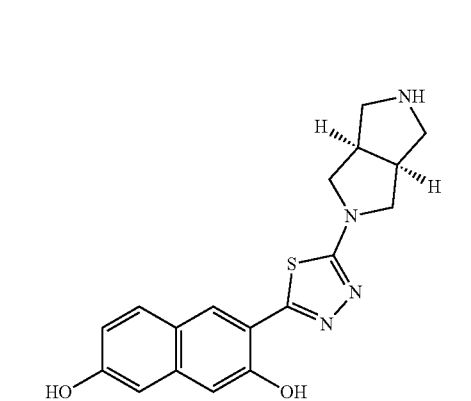

| | |
|---|---|
| 322 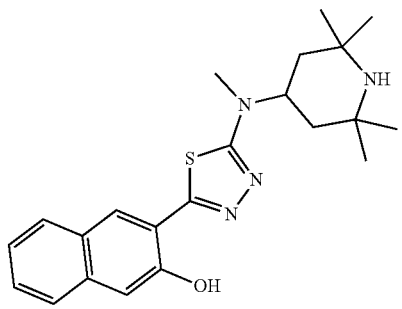 | 326 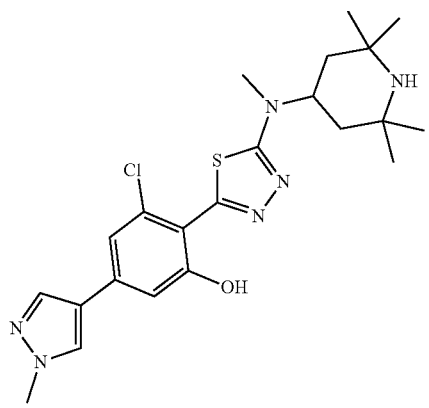 |
| 323 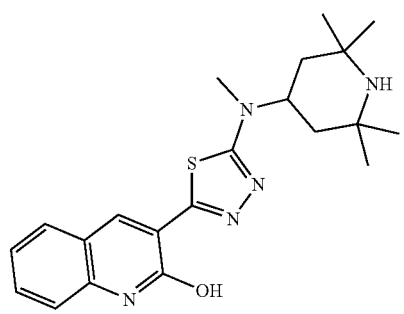 | 327 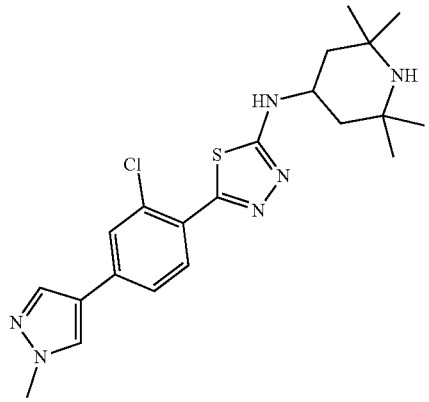 |
| 324 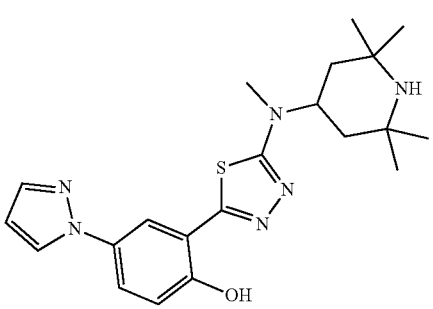 | 328 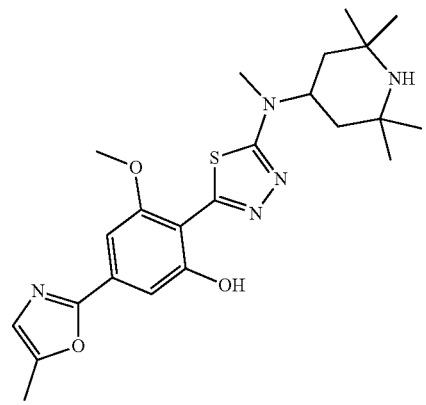 |
| 325 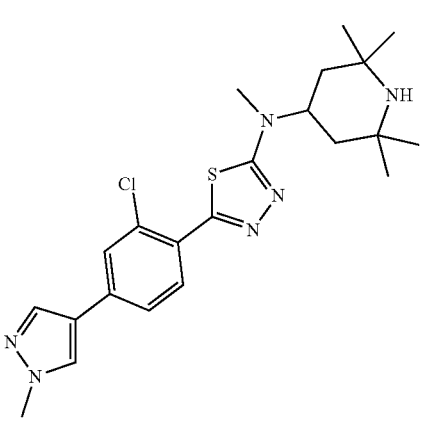 | 329 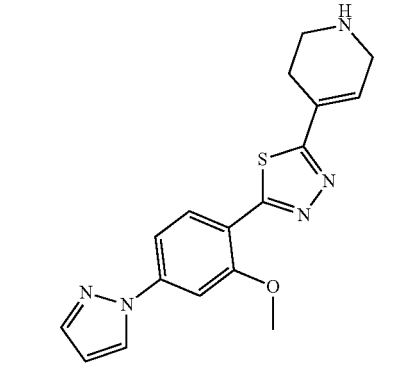 |

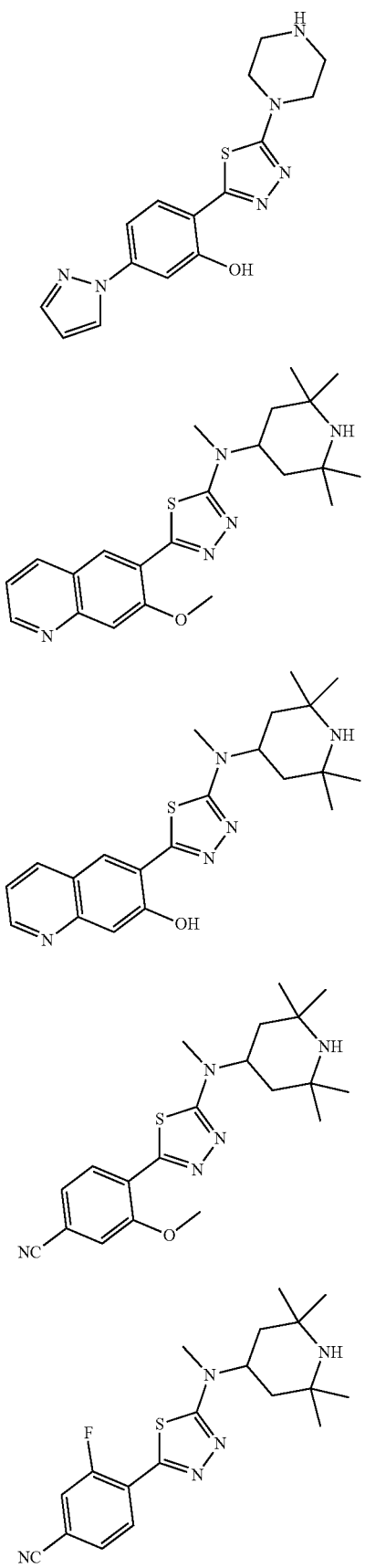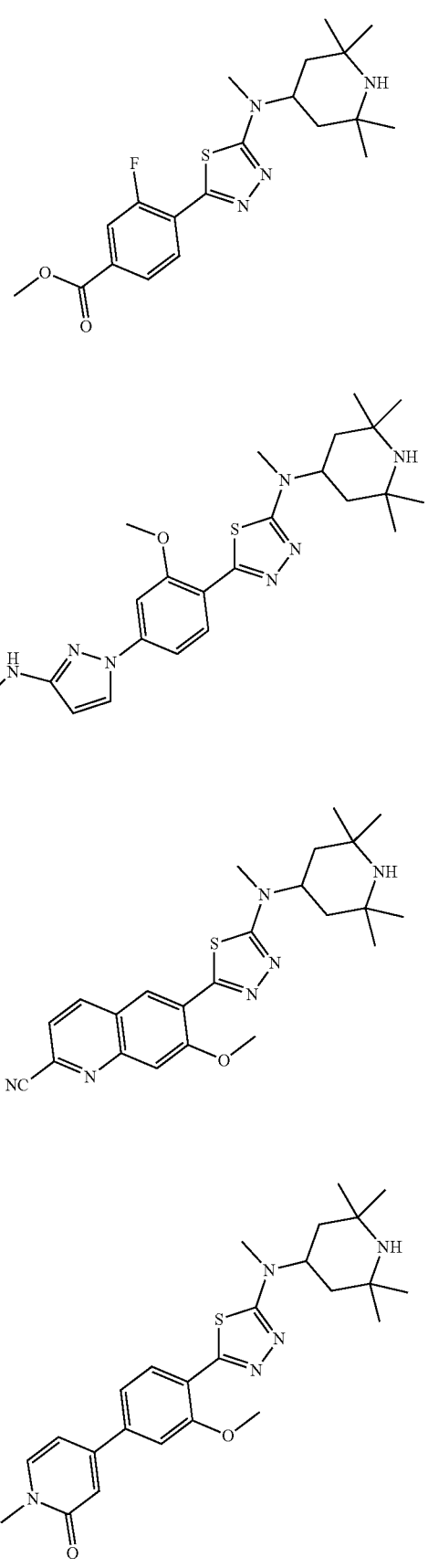

339
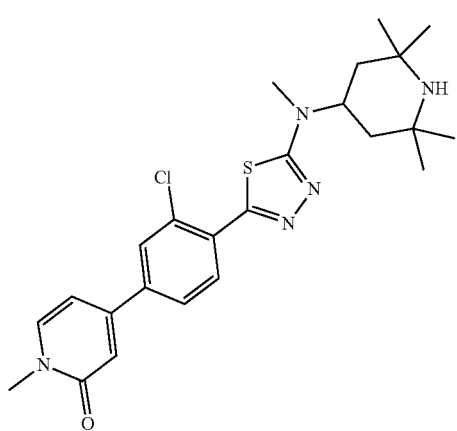
340
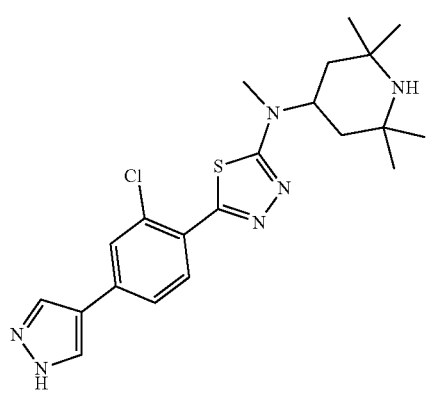
341
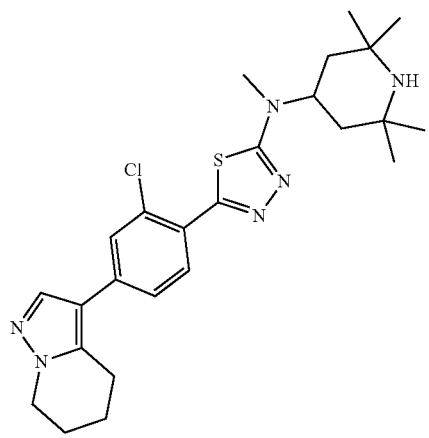
342
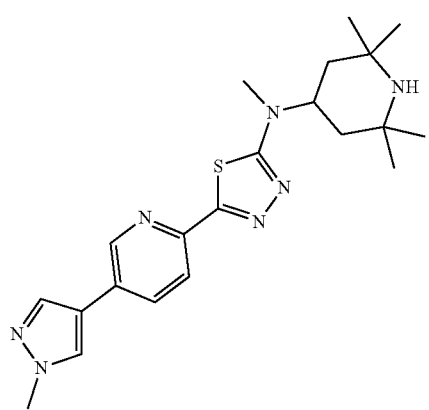
343
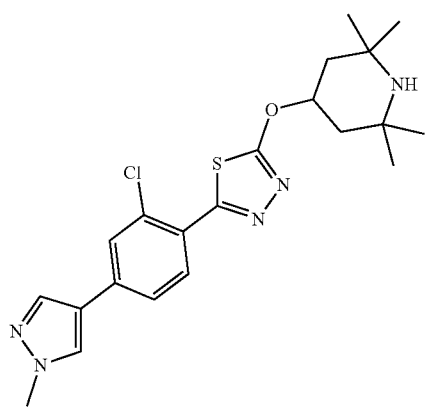
344
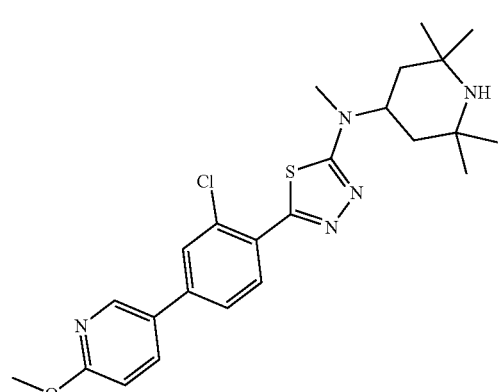
345
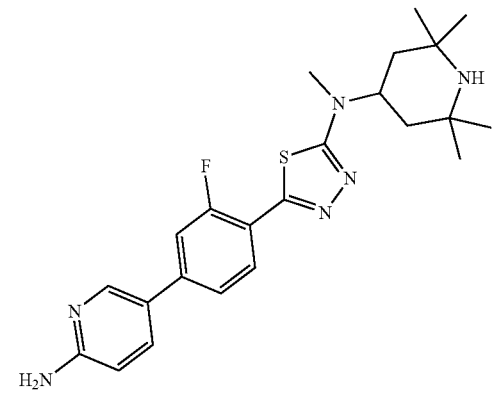
346
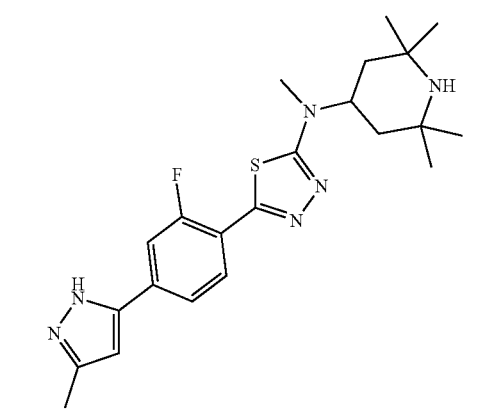

347 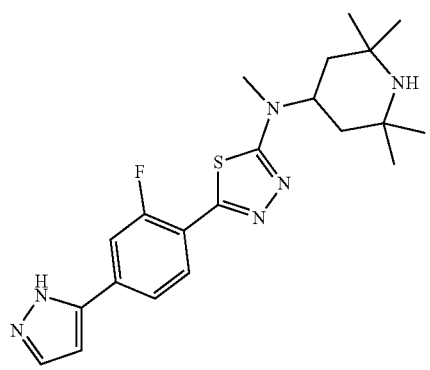
348 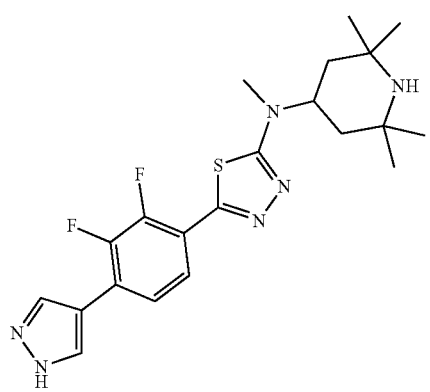
349 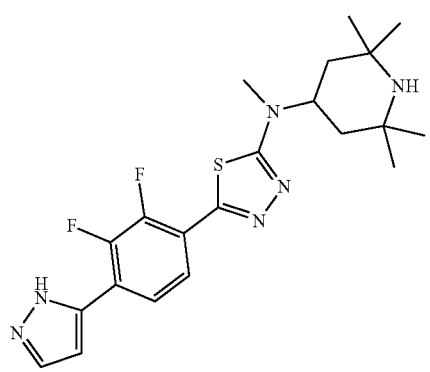
350 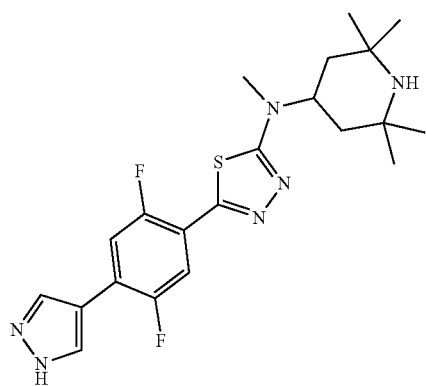
351 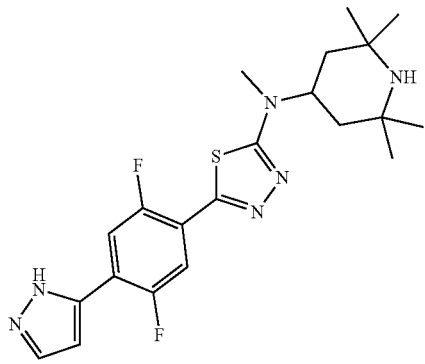
352 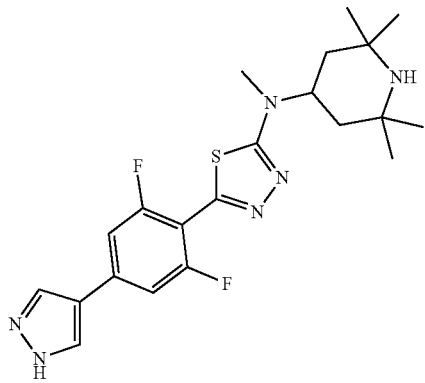
353 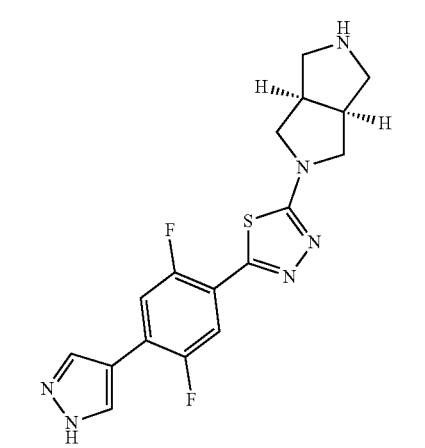
354 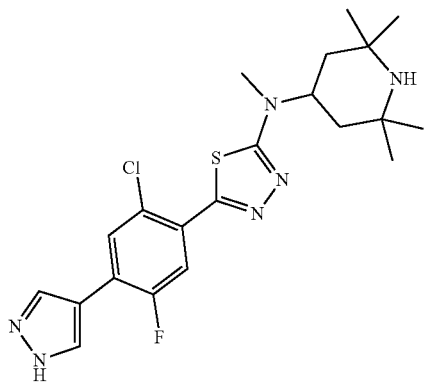

355
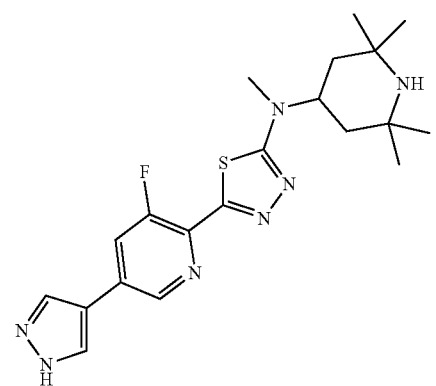
356
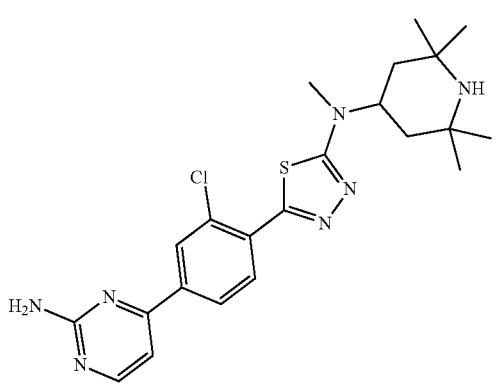
357
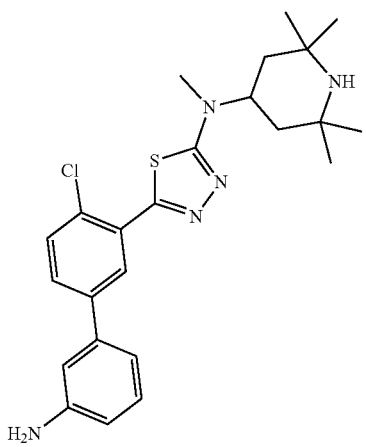
358
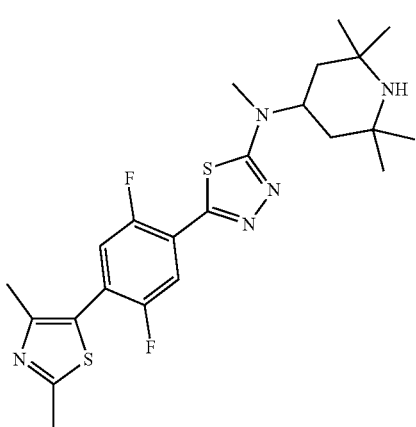
359
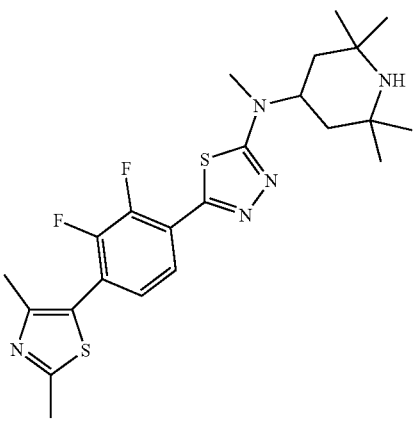
360
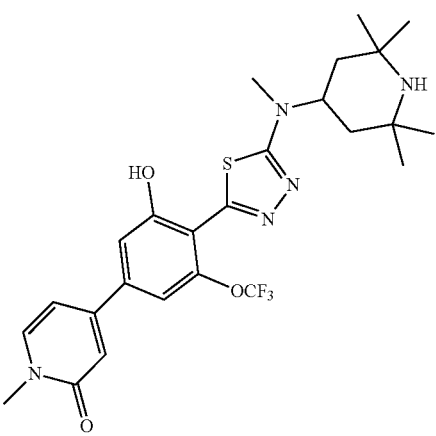
361
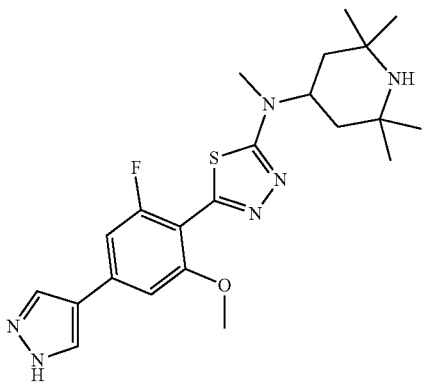

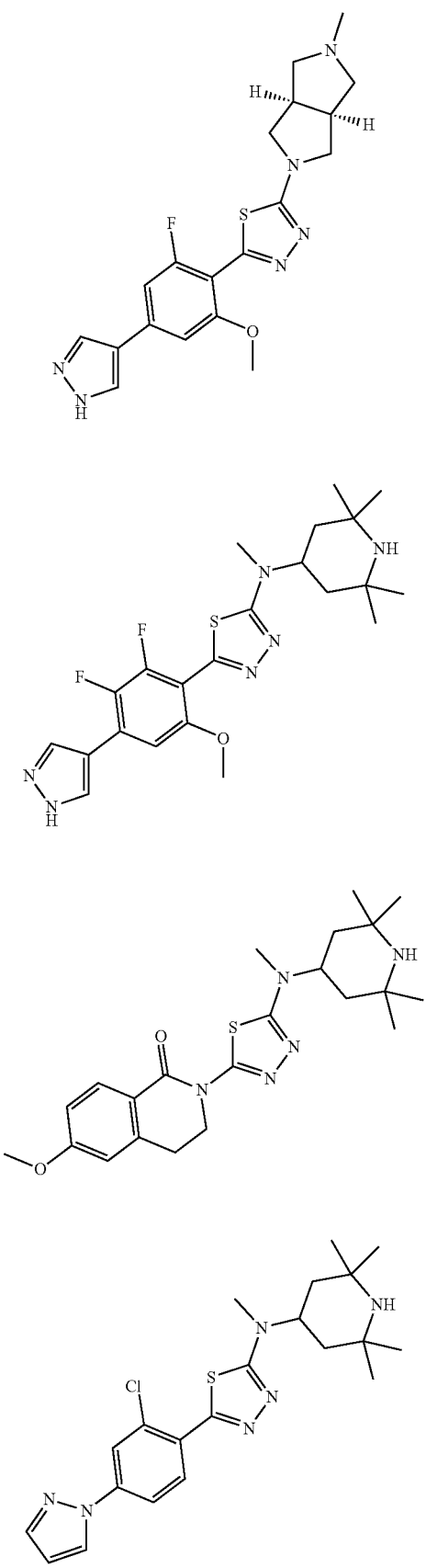
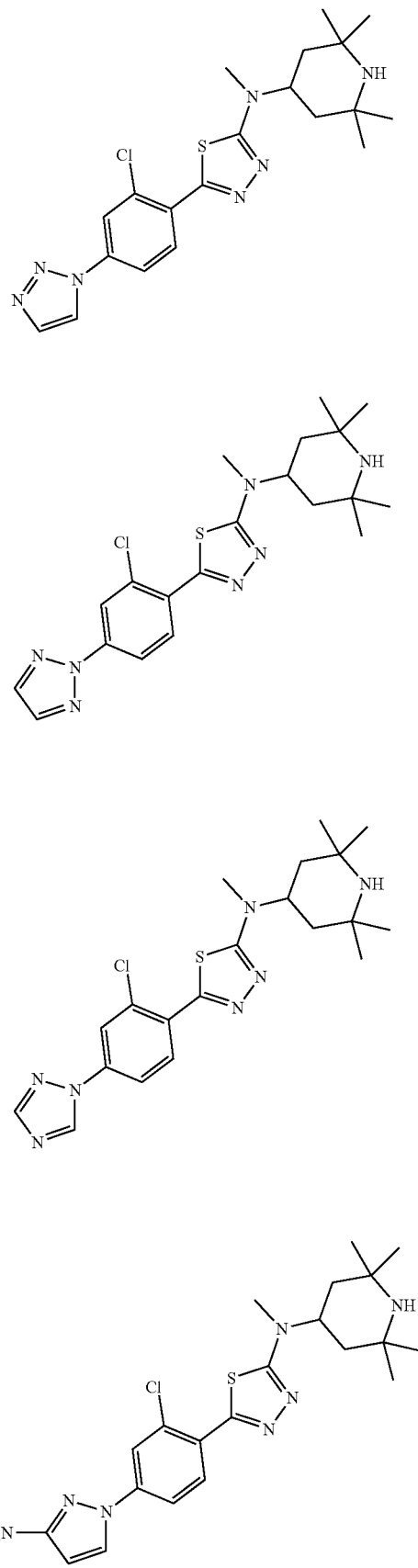

370 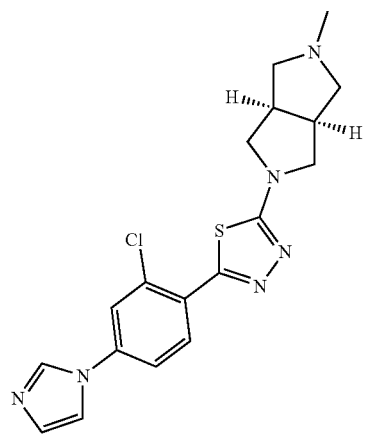
371 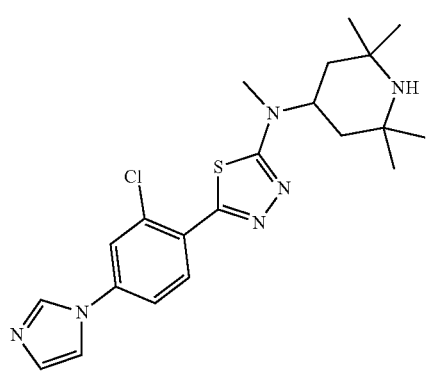
372 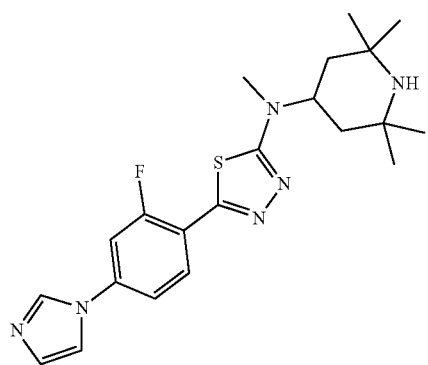
373 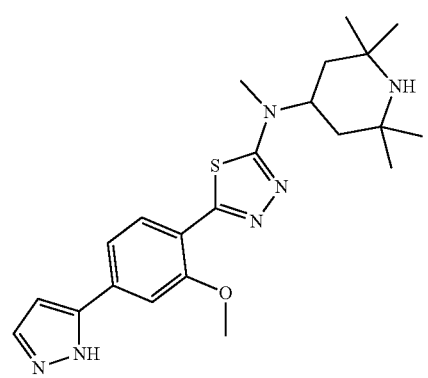
374 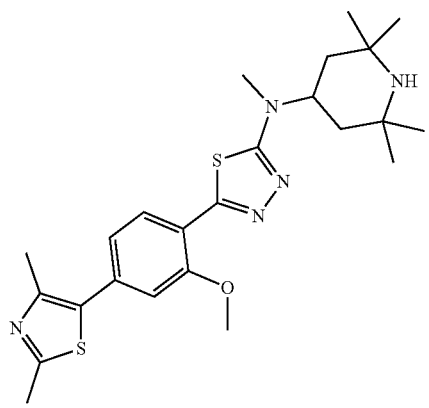
375 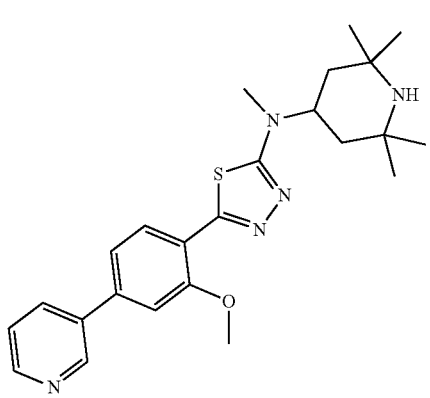
376 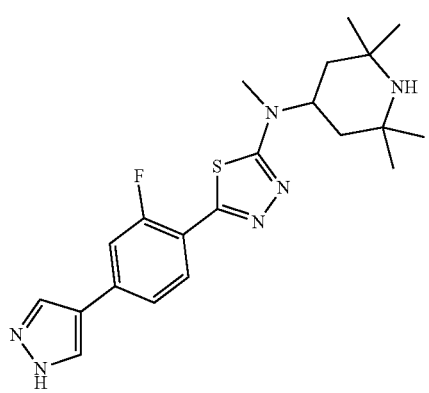
377 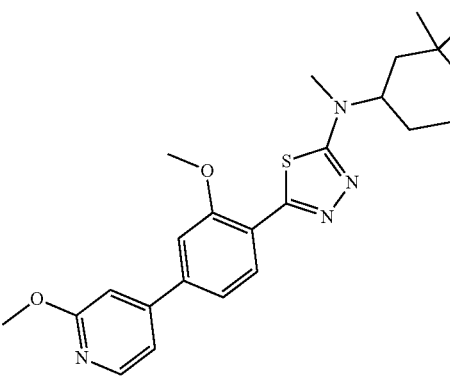

378 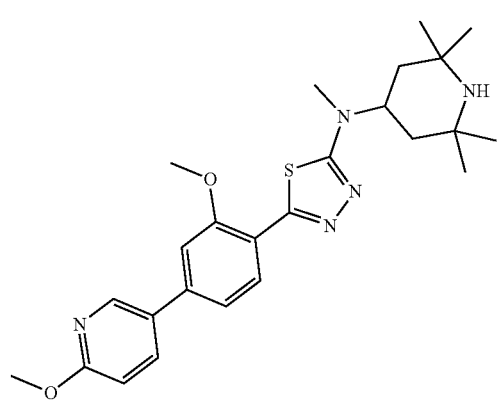
379 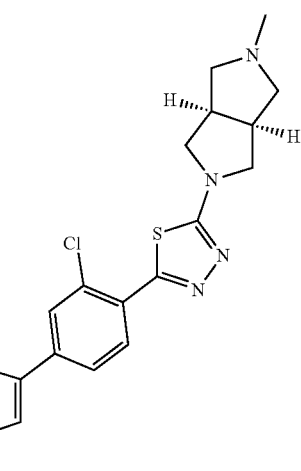
380 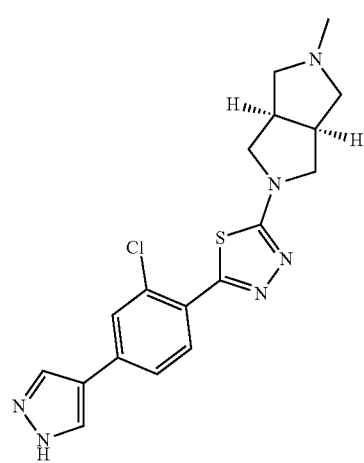
381 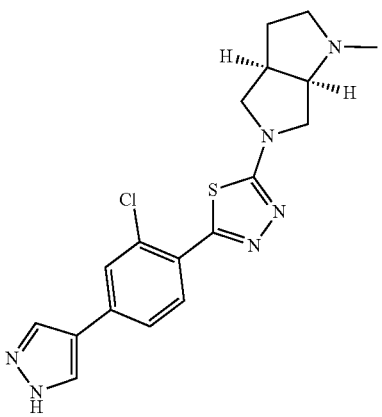
382 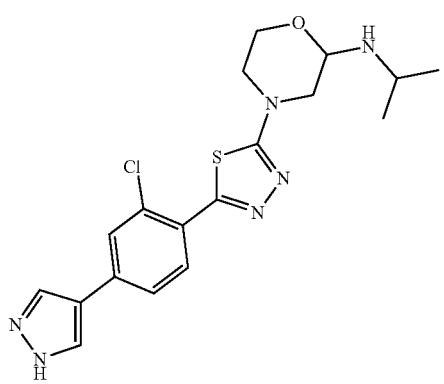
383 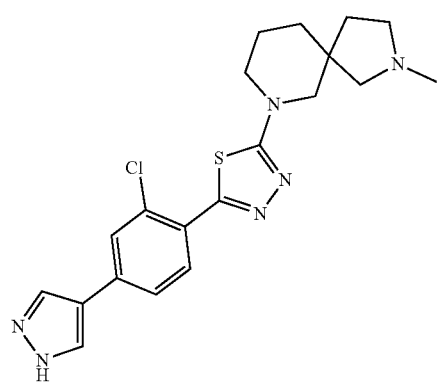
384 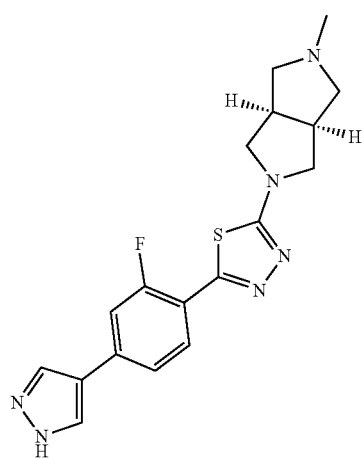

385
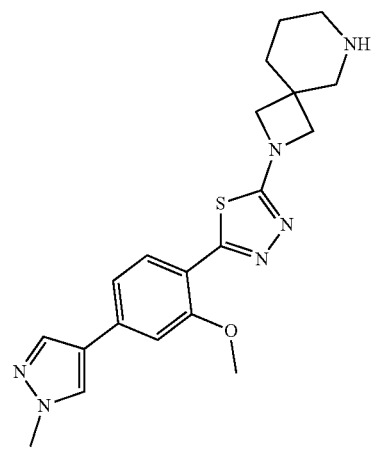
386
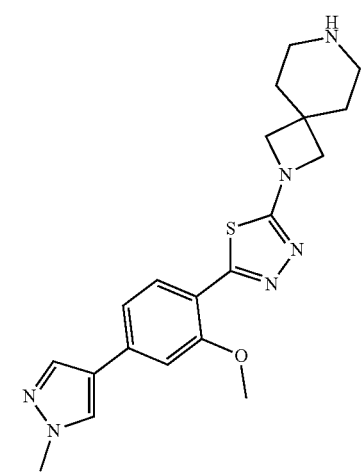
387
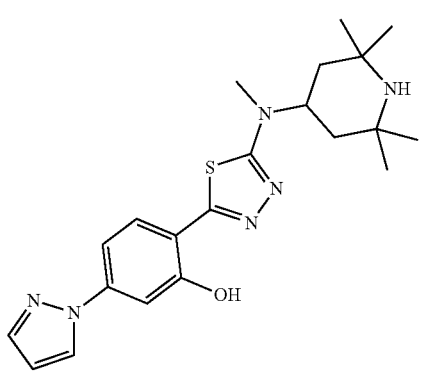
388
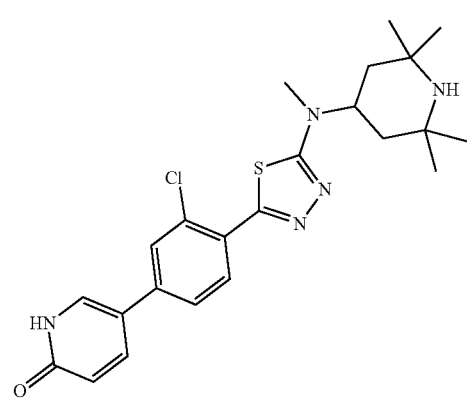
389
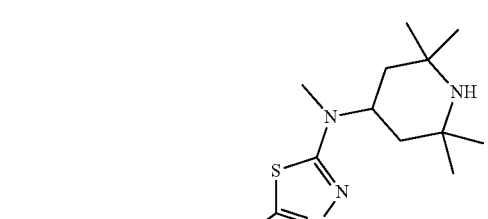
390
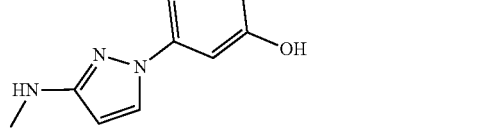
391
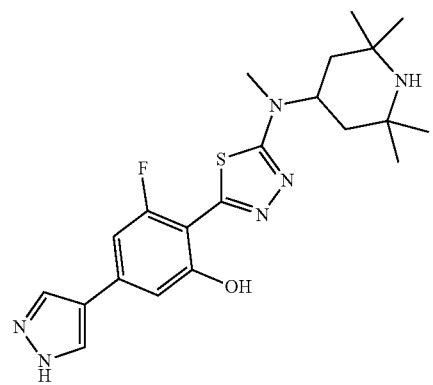

392 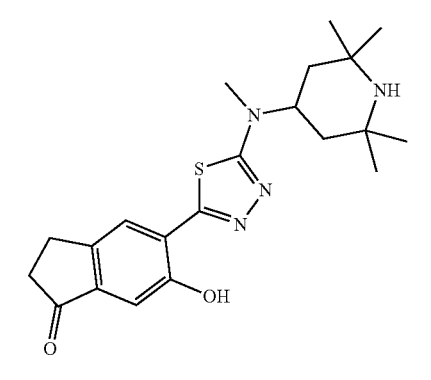
393 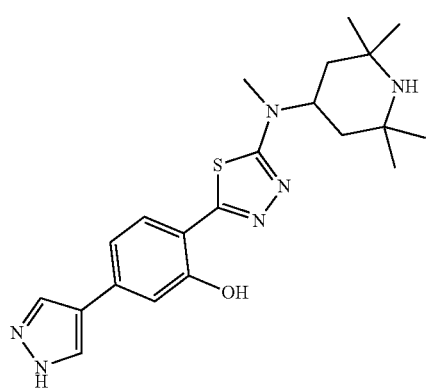
394 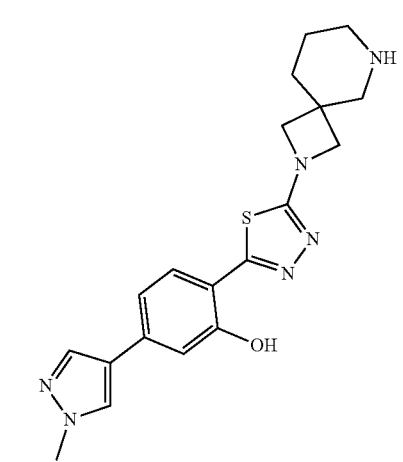
395 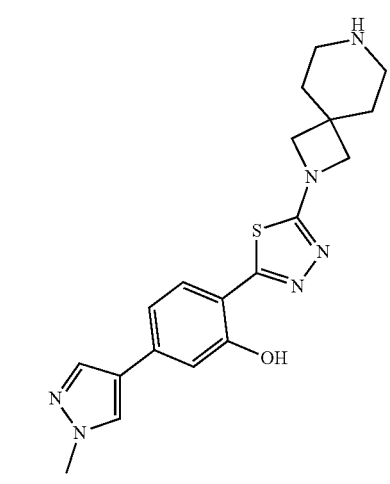
396 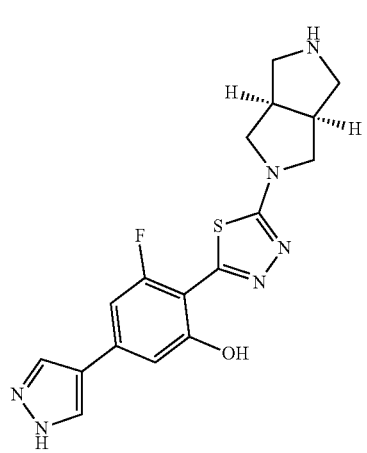
397 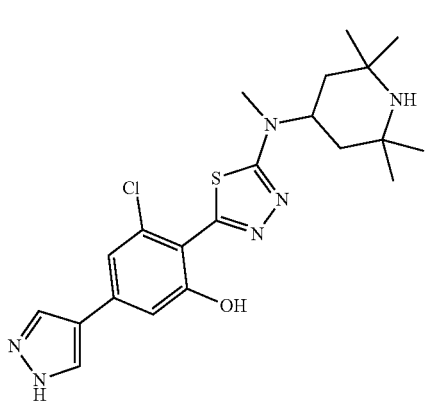
398 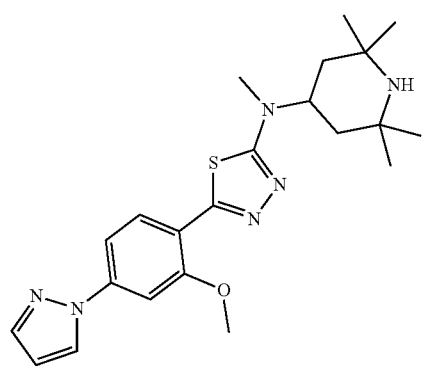
399 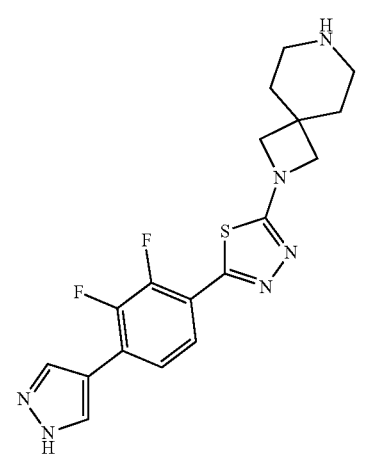

400 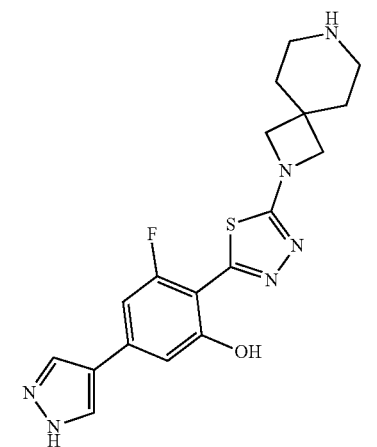
401 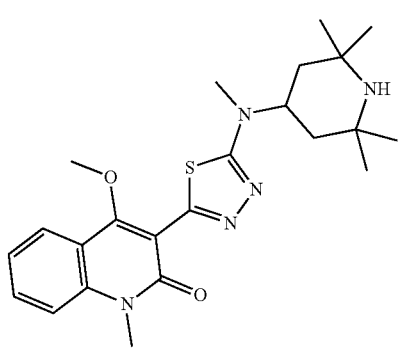
402 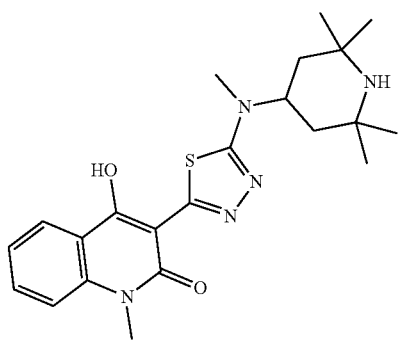
403 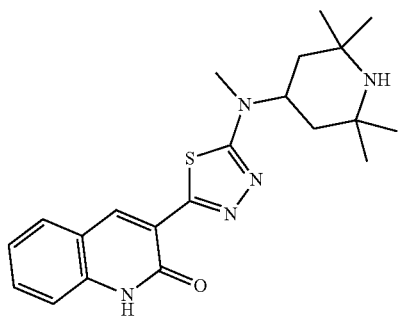
404 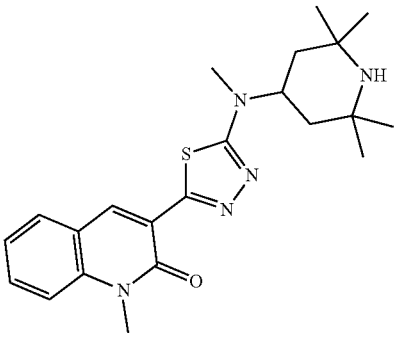
405 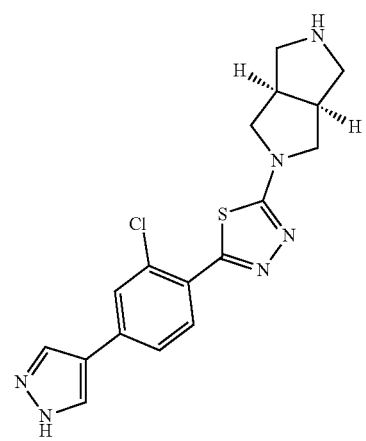
406 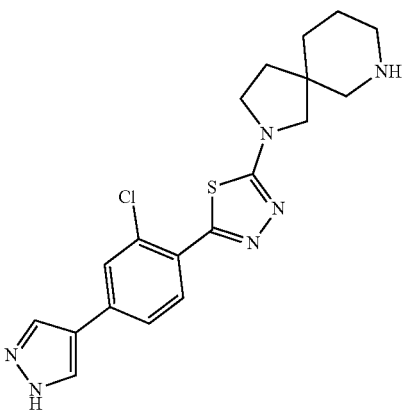
407 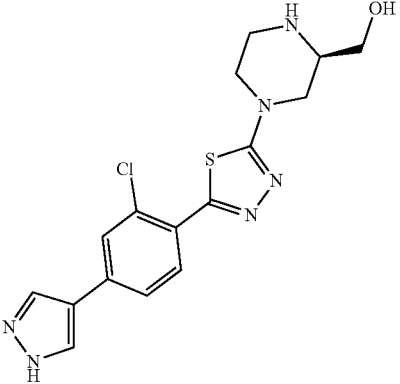

408
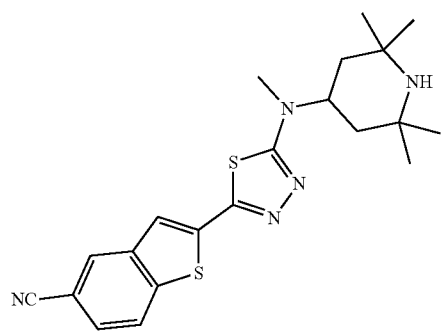
409
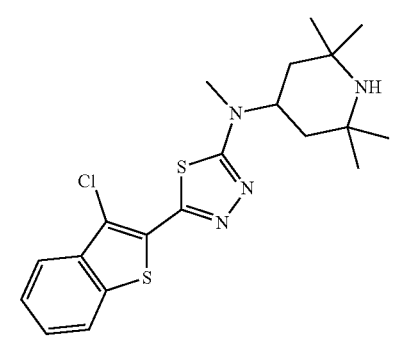
410
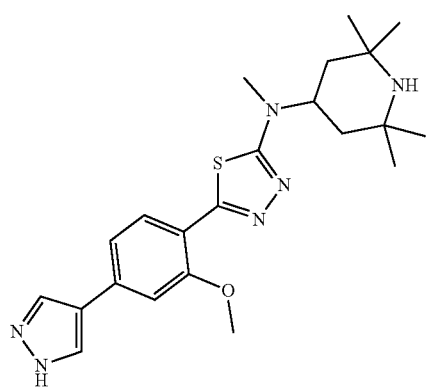
411
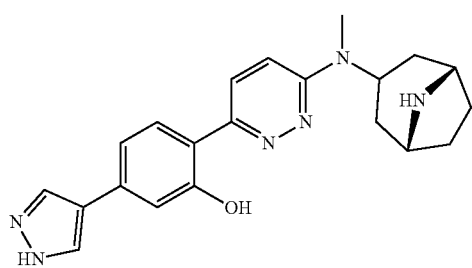
412
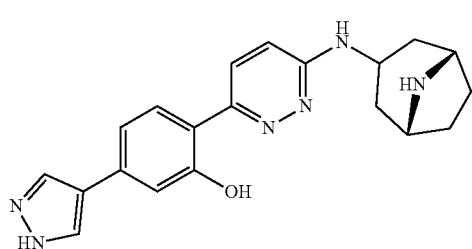
413
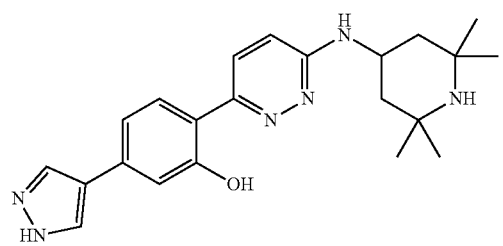
414
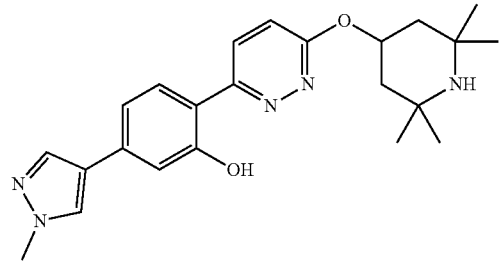
415
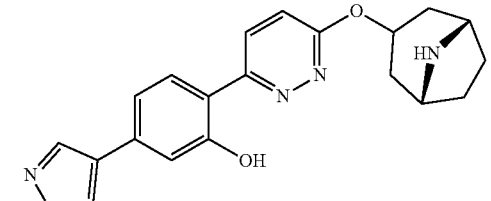
416
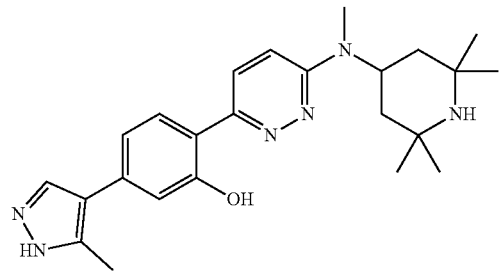
417
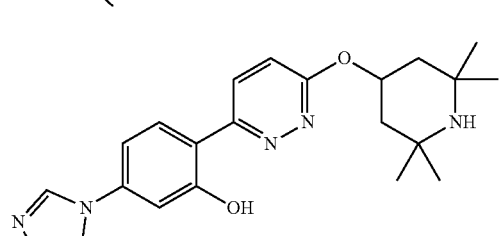
418
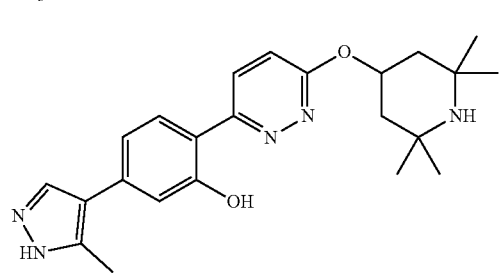

117
-continued

419

420

421

422

423

118
-continued

424

425

426

427

428

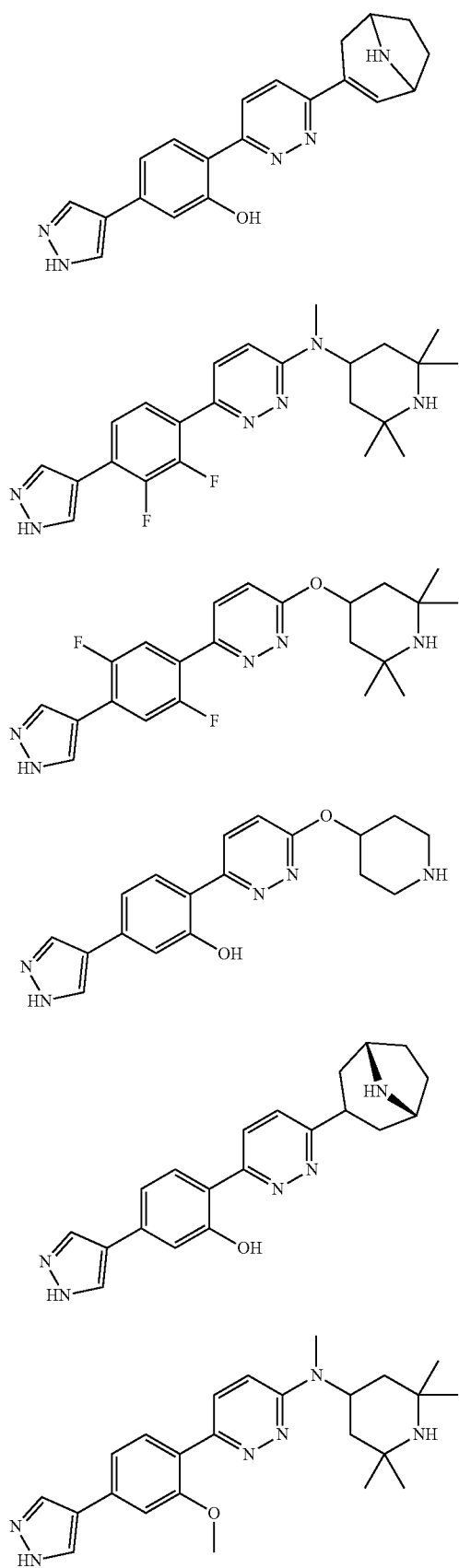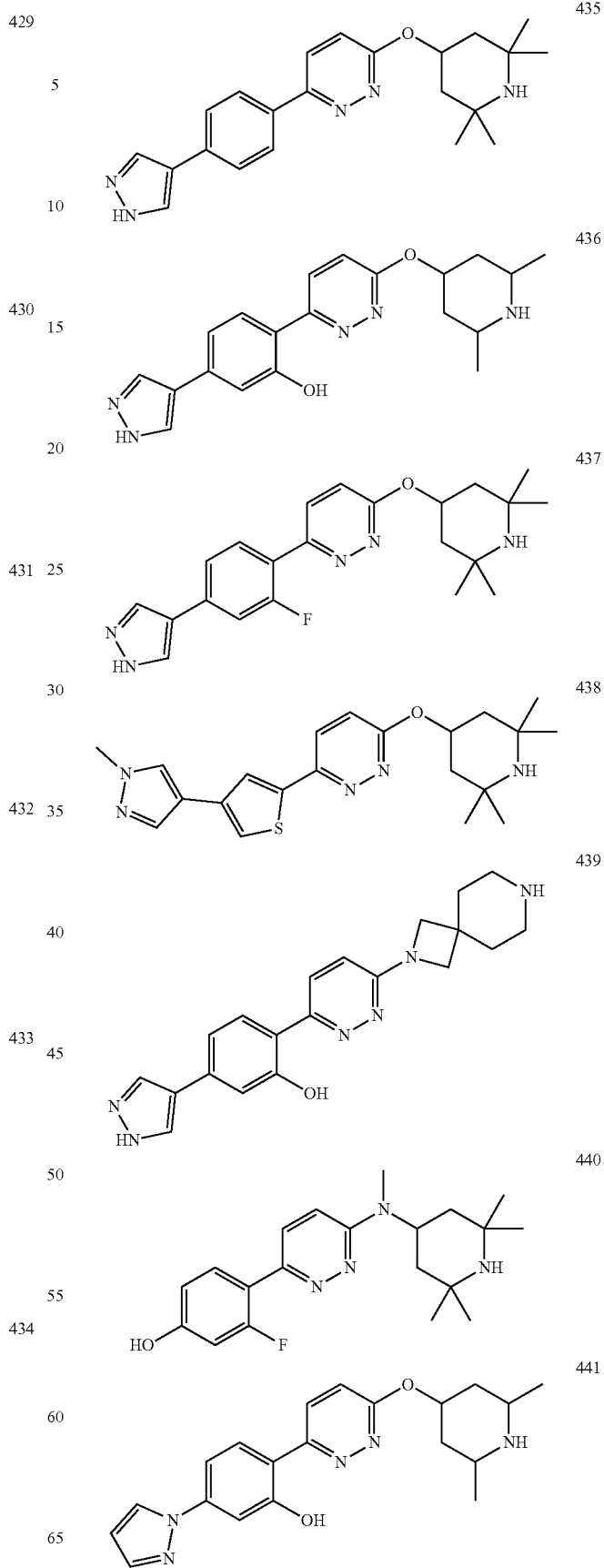

442 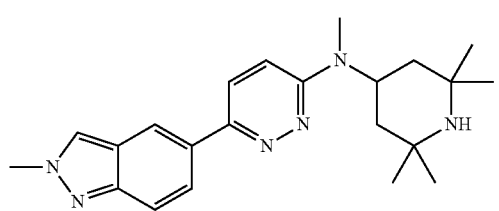
443 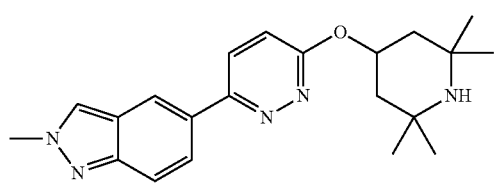
444 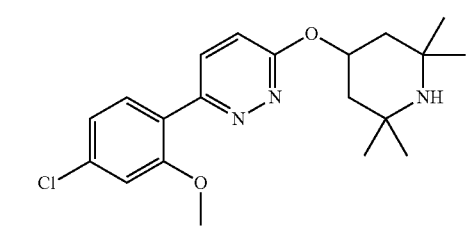
445 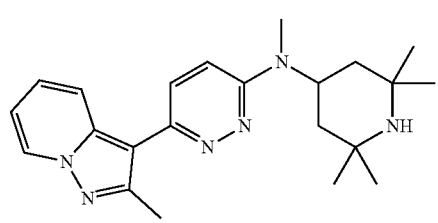
446 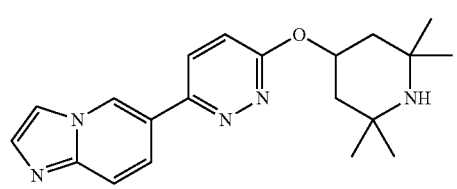
447 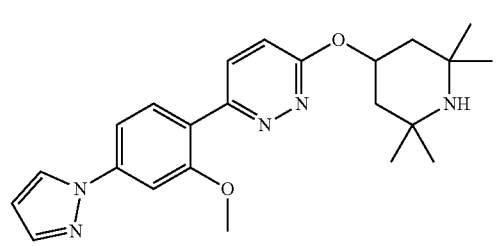
448 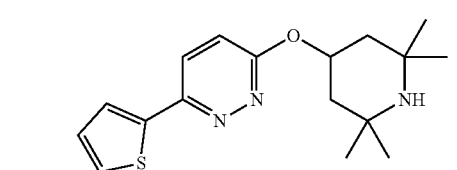
449 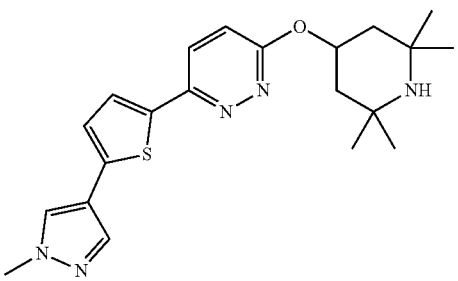
450 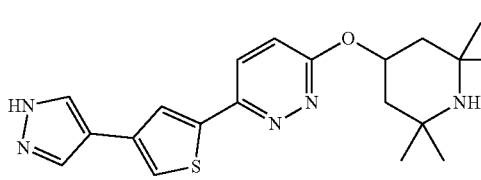
451 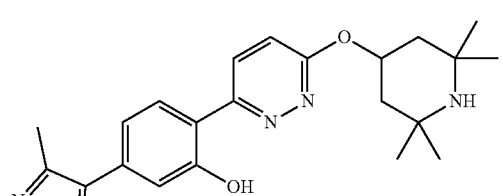
452 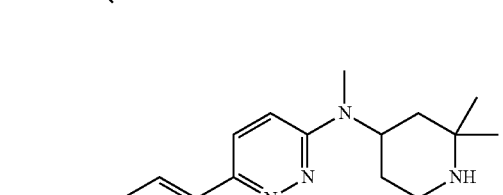
453 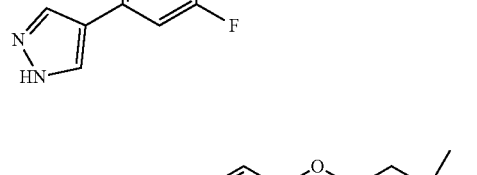
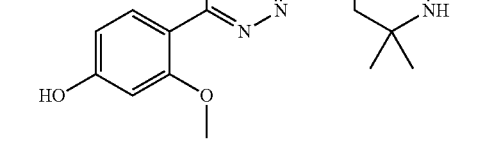
454 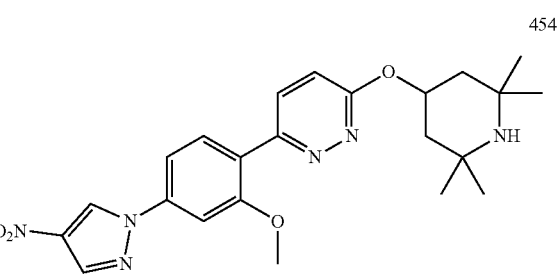

455
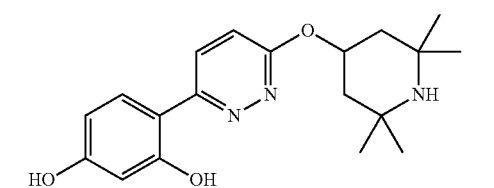
456
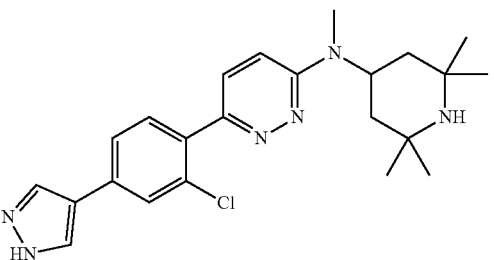
457
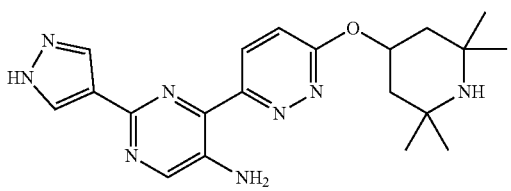
458
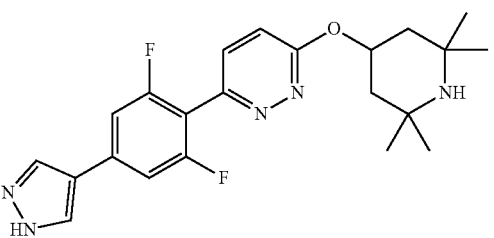
459
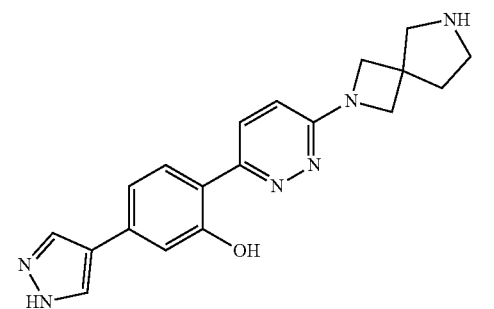
460
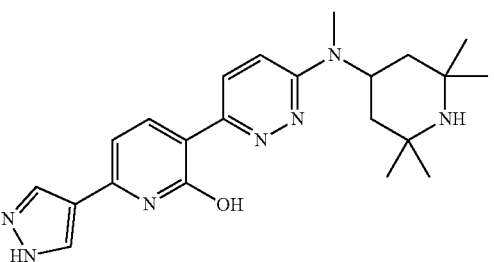
461
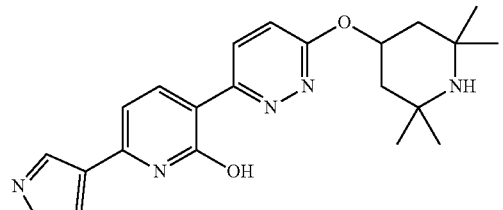
462
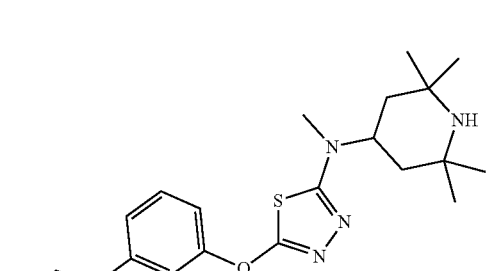
463
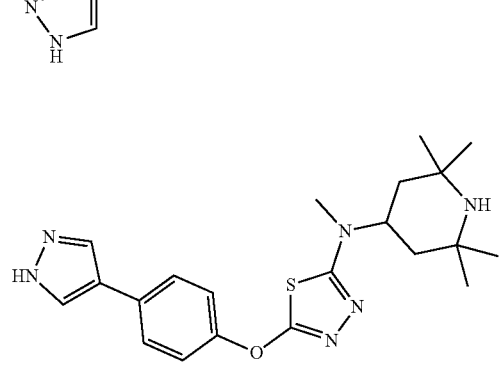
464
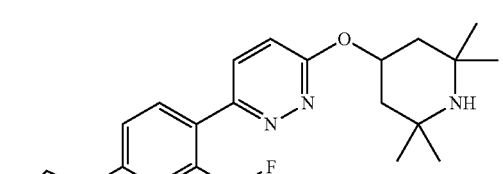
465
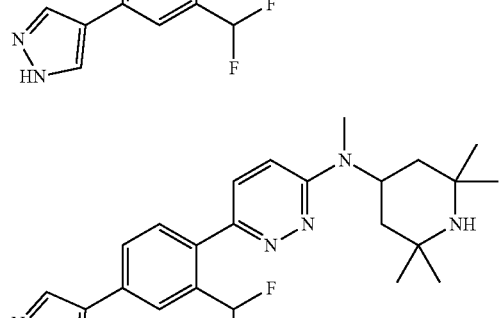
wherein a form of the compound is selected from the group consisting of a prodrug, salt, hydrate, solvate, clathrate, isotopologue, racemate, enantiomer, diastereomer, stereoisomer, polymorph and tautomer form thereof.
In another aspect, the compound of Formula (I) or a form thereof includes a compound selected from the group consisting of:

411 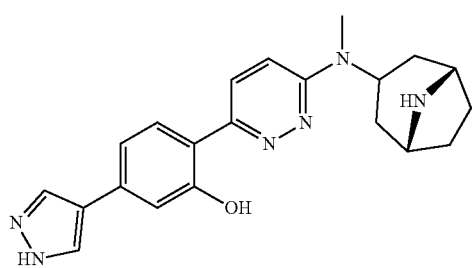
412 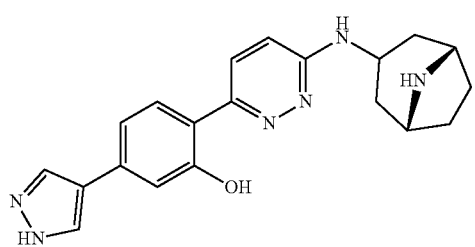
413 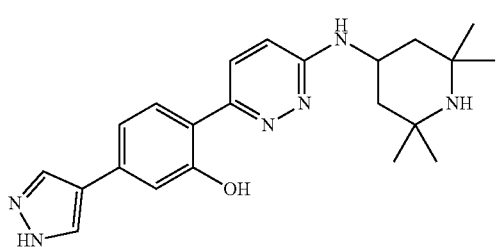
414 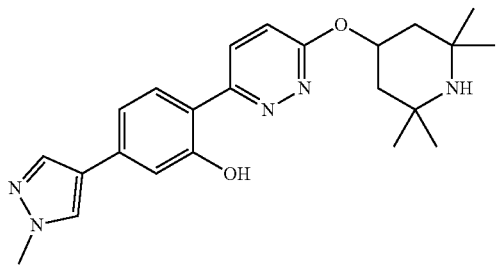
415 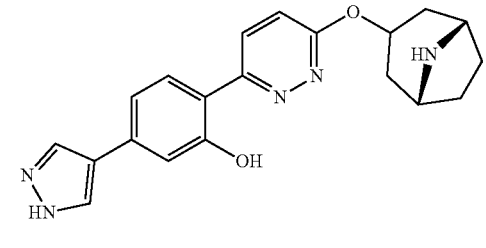
416 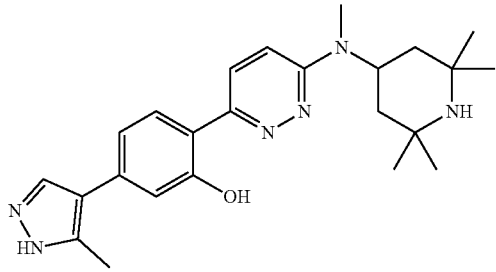
417 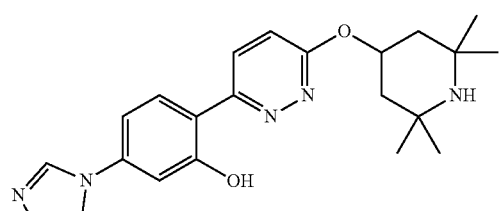
418 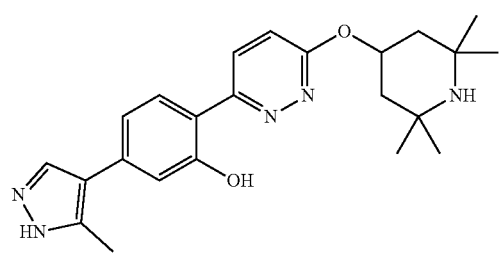
419 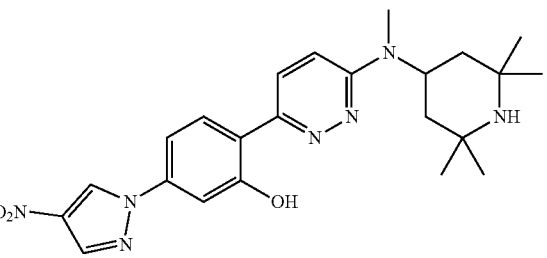
420 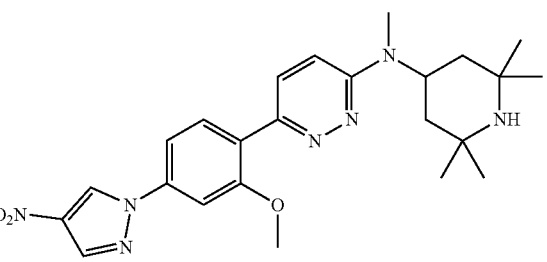
421 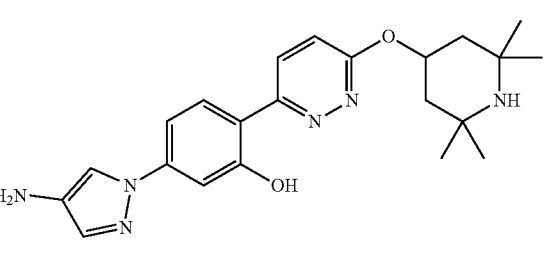
422 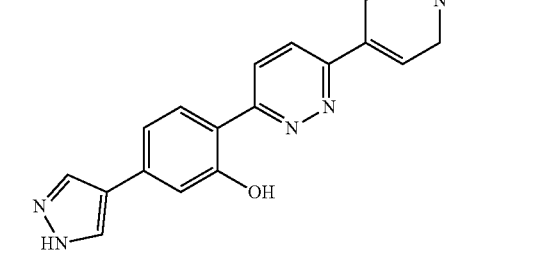

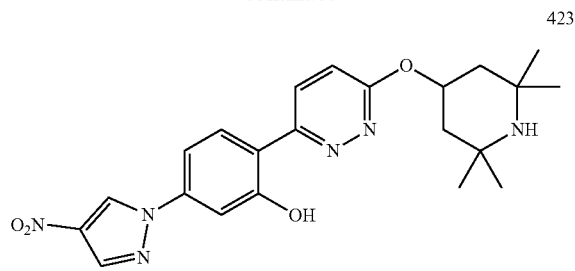
423
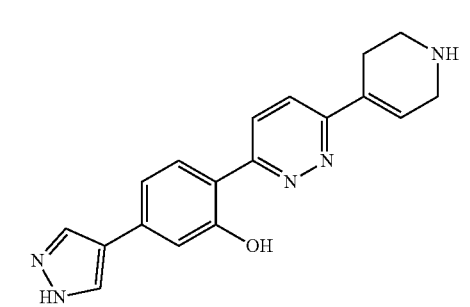
424
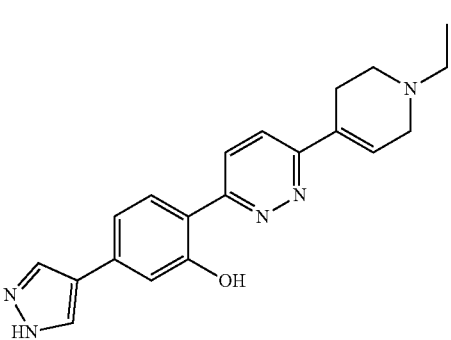
425
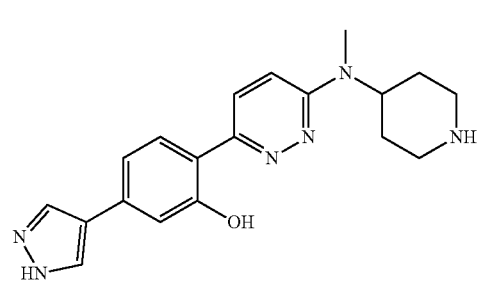
426
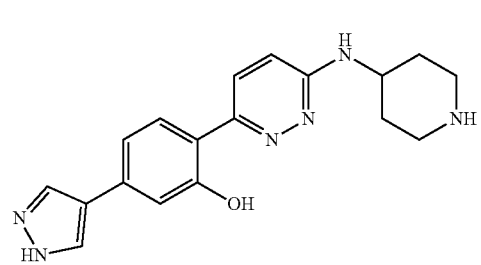
427
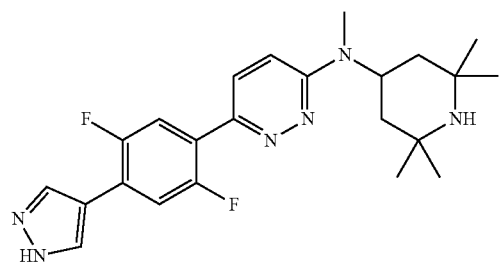
428
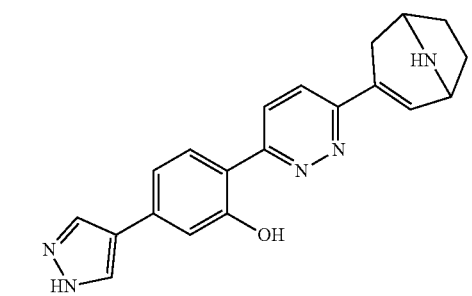
429
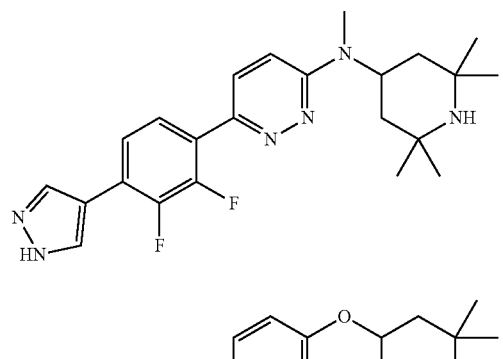
430
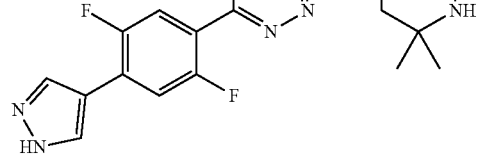
431
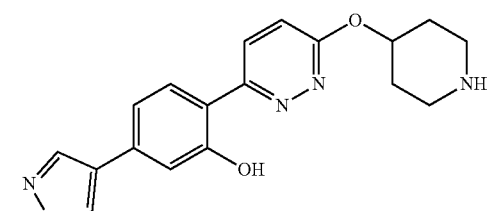
432
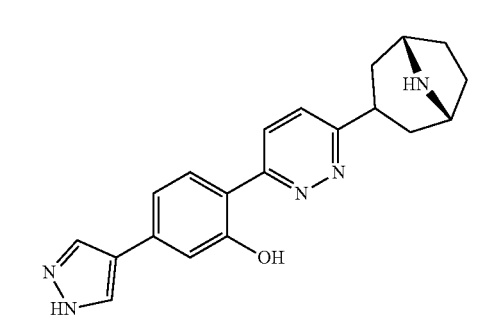
433

434 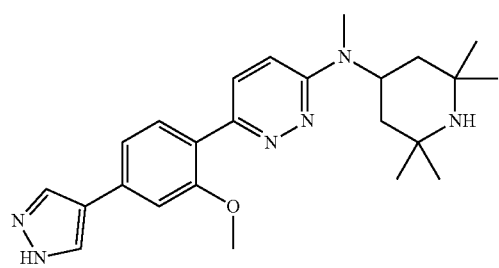
435 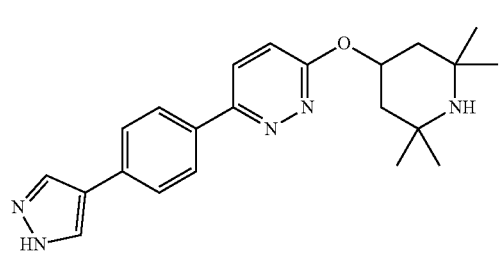
436 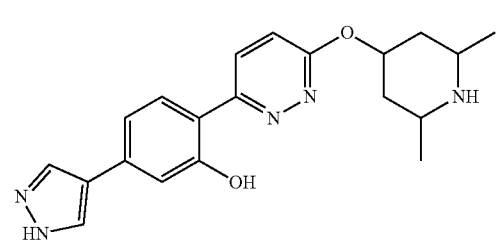
437 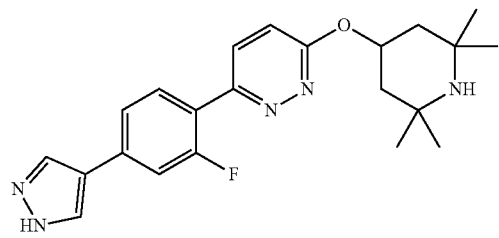
438 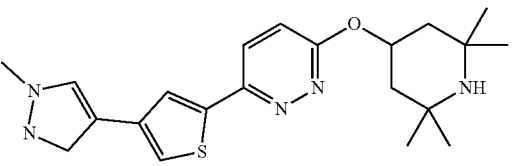
439 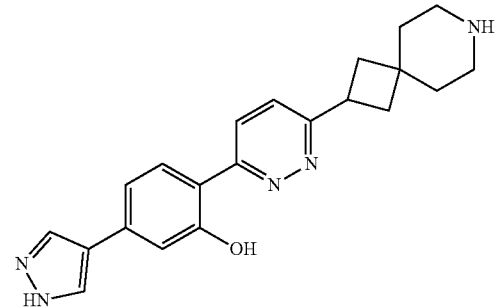
440 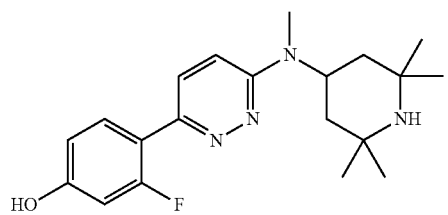
441 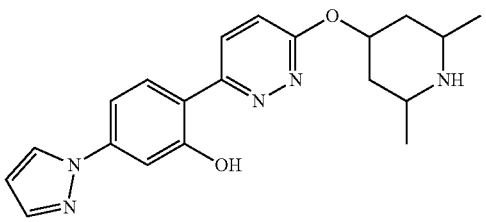
442 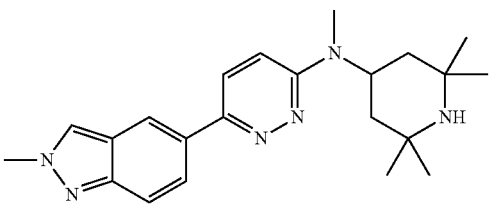
443 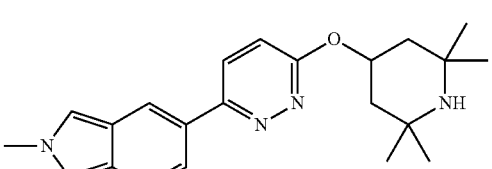
444 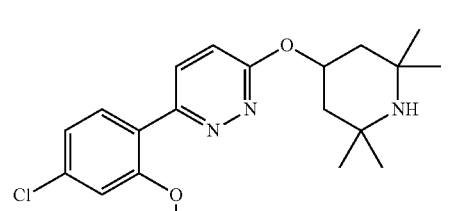
445 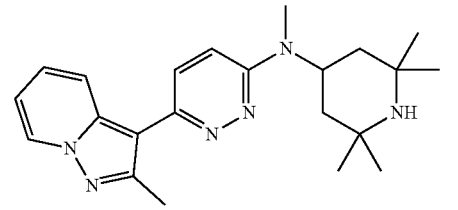
446 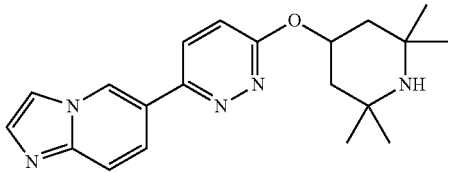

447 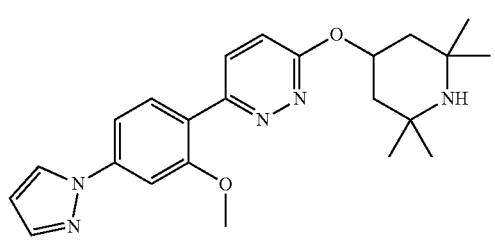
448 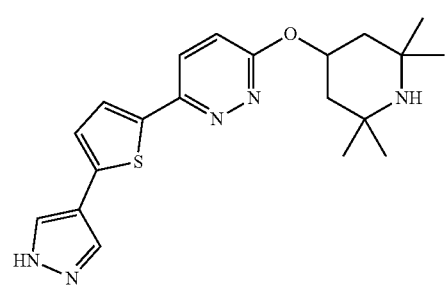
449 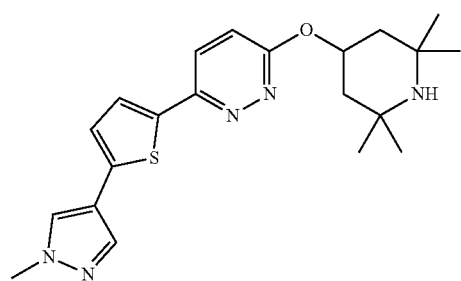
450 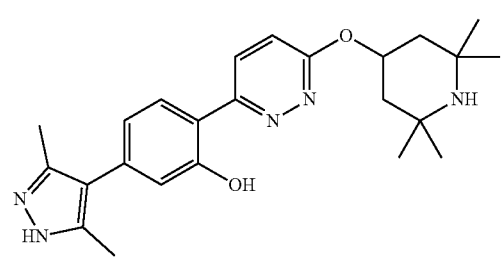
451 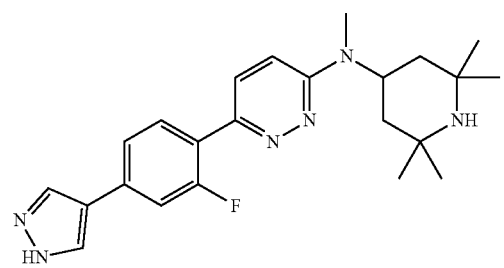
453 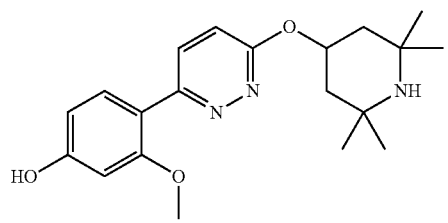
454 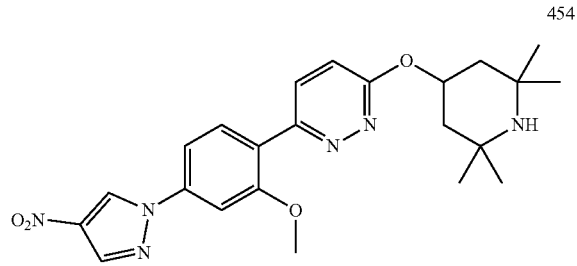
455 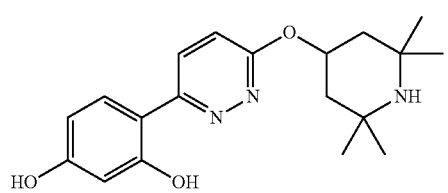
456 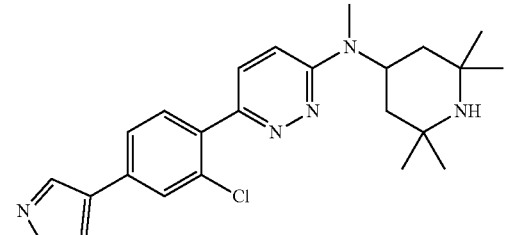
457 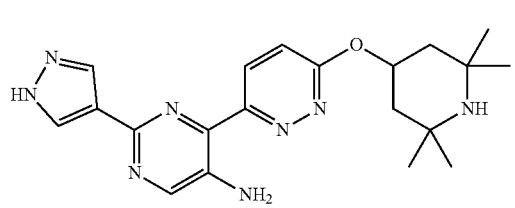
458 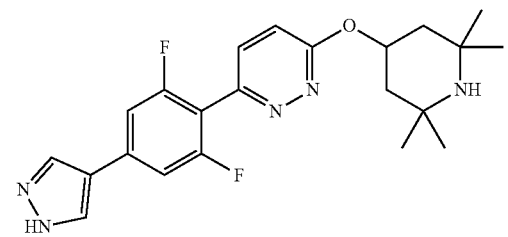

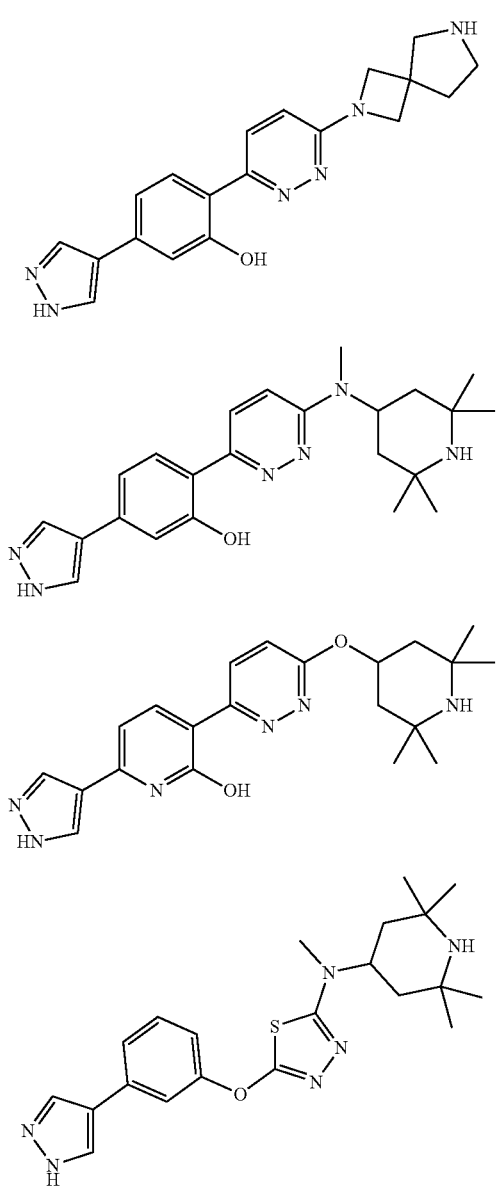
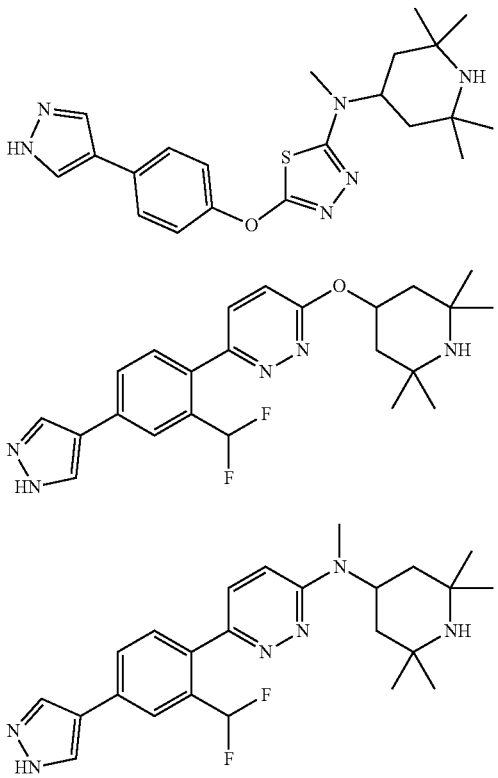

wherein a form of the compound is selected from the group consisting of a prodrug, salt, hydrate, solvate, clathrate, isotopologue, racemate, enantiomer, diastereomer, stereoisomer, polymorph and tautomer form thereof.

Another embodiment of the use of a compound of Formula (I) or a form thereof includes a method of use of a compound of Formula (I) or a form thereof for treating or ameliorating HD in a subject in need thereof, comprising administering an effective amount of the compound of Formula (I) or a form thereof (wherein compound number (#[1]) indicates that the salt form was isolated) to the subject, selected from the group consisting of:

| Cpd | Name |
|---|---|
| 1 | 6-(naphthalen-2-yl)-N-(2,2,6,6-tetramethylpiperidin-4-yl)pyridazin-3-amine |
| 2 | 6-(benzo[b]thiophen-2-yl)-N-methyl-N-(2,2,6,6-tetramethylpiperidin-4-yl)pyridazin-3-amine |
| 3 | 2-(6-(2,2,6,6-tetramethylpiperidin-4-yl-amino)-pyridazin-3-yl)phenol |
| 4 | 2-(6-(methyl-(2,2,6,6-tetramethylpiperidin-4-yl)amino)pyridazin-3-yl)benzo[b]-thiophene-5-carbonitrile |
| 5 | 6-(quinolin-3-yl)-N-(2,2,6,6-tetramethylpiperidin-4-yl)pyridazin-3-amine |
| 6 | 3-(benzo[b]-thiophen-2-yl)-6-(2,2,6,6-tetramethylpiperidin-4-yl-oxy)pyridazine |
| 7 | 2-(6-(methyl-(2,2,6,6-tetramethylpiperidin-4-yl)amino)-pyridazin-3-yl)phenol |
| 8 | 6-(6-(methyl-(2,2,6,6-tetramethylpiperidin-4-yl)amino)-pyridazin-3-yl)naphthalen-2-ol |
| 9 | 6-(benzo[b]-thiophen-2-yl)-N-(2,2,6,6-tetramethylpiperidin-4-yl)pyridazin-3-amine |
| 10 | 7-(6-((2,2,6,6-tetramethylpiperidin-4-yl)oxy)pyridazin-3-yl)isoquinoline |
| 11 | 6-(6-((2,2,6,6-tetramethylpiperidin-4-yl)oxy)pyridazin-3-yl)isoquinoline |
| 12 | N-methyl-6-(quinolin-7-yl)-N-(2,2,6,6-tetramethylpiperidin-4-yl)pyridazin-3-amine |
| 13 | N-methyl-6-(quinolin-6-yl)-N-(2,2,6,6-tetramethylpiperidin-4-yl)pyridazin-3-amine |
| 14 | 6-(isoquinolin-7-yl)-N-methyl-N-(2,2,6,6-tetramethylpiperidin-4-yl)pyridazin-3-amine |
| 15 | 6-(isoquinolin-6-yl)-N-methyl-N-(2,2,6,6-tetramethylpiperidin-4-yl)pyridazin-3-amine |
| 16 | 6-(imidazo[1,2-a]pyridin-6-yl)-N-methyl-N-(2,2,6,6-tetramethylpiperidin-4-yl)pyridazin-3-amine |

| Cpd | Name |
|---|---|
| 17 | N-methyl-6-(6-phenylpyridin-3-yl)-N-(2,2,6,6-tetramethylpiperidin-4-yl)pyridazin-3-amine |
| 18 | 6-(6-(1H-pyrrol-1-yl)pyridin-3-yl)-N-methyl-N-(2,2,6,6-tetramethylpiperidin-4-yl)pyridazin-3-amine |
| 19 | 6-(6-(1H-pyrazol-1-yl)pyridin-3-yl)-N-methyl-N-(2,2,6,6-tetramethylpiperidin-4-yl)pyridazin-3-amine |
| 20 | methyl-(6-quinoxalin-2-yl-pyridazin-3-yl)-(2,2,6,6-tetramethylpiperidin-4-yl)-amine |
| 21 | methyl-(6-quinolin-3-yl-pyridazin-3-yl)-(2,2,6,6-tetramethylpiperidin-4-yl)-amine |
| 22 | N-methyl-6-(phthalazin-6-yl)-N-(2,2,6,6-tetramethylpiperidin-4-yl)pyridazin-3-amine |
| 23 | 6-(benzo[c][1,2,5]oxa-diazol-5-yl)-N-(2,2,6,6-tetramethylpiperidin-4-yl)pyridazin-3-amine |
| 24 | 6-(benzo[d]thiazol-5-yl)-N-(2,2,6,6-tetramethylpiperidin-4-yl)pyridazin-3-amine |
| 25 | 6-(2-methylbenzo-[d]oxazol-6-yl)-N-(2,2,6,6-tetramethylpiperidin-4-yl)pyridazin-3-amine |
| 26 | 3-(6-(methyl(2,2,6,6-tetramethylpiperidin-4-yl)amino)pyridazin-3-yl)naphthalen-2-ol |
| 27 | 5-chloro-2-(6-(methyl(1,2,2,6,6-pentamethylpiperidin-4-yl)amino)pyridazin-3-yl)phenol |
| 28 | 3-(6-(2,2,6,6-tetramethylpiperidin-4-yl-amino)pyridazin-3-yl)naphthalen-2-ol |
| 29 | 5-chloro-2-(6-(1,2,2,6,6-pentamethylpiperidin-4-ylamino)pyridazin-3-yl)phenol |
| 30 | 4-hydroxy-3-(6-(methyl(2,2,6,6-tetramethylpiperidin-4-yl)amino)pyridazin-3-yl)benzonitrile |
| 31 | 3-(6-((2,2,6,6-tetramethylpiperidin-4-yl)oxy)pyridazin-3-yl)naphthalen-2-ol |
| 32[1] | 2-(6-(methyl(2,2,6,6-tetramethylpiperidin-4-yl)amino)pyridazin-3-yl)-4-(trifluoromethyl)phenol |
| 33 | 2-fluoro-6-(6-(methyl-(2,2,6,6-tetramethylpiperidin-4-yl)-amino)-pyridazin-3-yl)phenol |
| 34 | 3,5-dimethoxy-2-(6-(methyl(2,2,6,6-tetramethylpiperidin-4-yl)amino)pyridazin-3-yl)phenol |
| 35 | 4,5-dimethoxy-2-(6-(methyl(2,2,6,6-tetramethylpiperidin-4-yl)amino)pyridazin-3-yl)phenol |
| 36 | 5-methoxy-2-(6-(methyl(2,2,6,6-tetramethylpiperidin-4-yl)amino)pyridazin-3-yl)phenol |
| 37 | 4,5-difluoro-2-(6-(methyl(2,2,6,6-tetramethylpiperidin-4-yl)amino)pyridazin-3-yl)phenol |
| 38 | 5-fluoro-2-(6-(methyl(2,2,6,6-tetramethylpiperidin-4-yl)amino)pyridazin-3-yl)phenol |
| 39 | 3-hydroxy-4-(6-(methyl(2,2,6,6-tetramethylpiperidin-4-yl)amino)pyridazin-3-yl)benzonitrile |
| 40 | 1-allyl-6-(6-(methyl(2,2,6,6-tetramethylpiperidin-4-yl)amino)pyridazin-3-yl)naphthalen-2-ol |
| 41 | 6-(benzo[b]thiophen-2-yl)-N-(1,2,2,6,6-pentamethylpiperidin-4-yl)pyridazin-3-amine |
| 42 | N-allyl-3-hydroxy-4-(6-(methyl(2,2,6,6-tetramethylpiperidin-4-yl)amino)pyridazin-3-yl)benzamide |
| 43 | 2-(6-(methyl(2,2,6,6-tetramethylpiperidin-4-yl)amino)pyridazin-3-yl)-5-(1H-pyrazol-1-yl)phenol |
| 44 | 5-(5-methyl-oxazol-2-yl)-2-(6-(methyl-(2,2,6,6-tetramethylpiperidin-4-yl)-amino)-pyridazin-3-yl)phenol |
| 45 | 5-(4-(hydroxymethyl)-1H-pyrazole-1-yl)-2-(6-(methyl(2,2,6,6-tetramethylpiperidin-4-yl)amino)pyridazin-3-yl)phenol |
| 46 | 5-(1H-imidazol-1-yl)-2-(6-(methyl(2,2,6,6-tetramethylpiperidin-4-yl)amino)pyridazin-3-yl)phenol |
| 47 | 5-(4-amino-1H-pyrazole-1-yl)-2-(6-(methyl(2,2,6,6-tetramethylpiperidin-4-yl)amino)pyridazin-3-yl)phenol |
| 48 | 2-(6-(methyl(2,2,6,6-tetramethylpiperidin-4-yl)amino)pyridazin-3-yl)-5-(1H-pyrazol-4-yl)phenol |
| 49 | 5-(3-amino-1H-pyrazol-1-yl)-2-(6-(methyl(2,2,6,6-tetramethylpiperidin-4-yl)amino)pyridazin-3-yl)phenol |
| 50 | 2-(6-(methyl(2,2,6,6-tetramethylpiperidin-4-yl)amino)pyridazin-3-yl)-5-(1-(2-morpholino-ethyl)-1H-pyrazol-4-yl)phenol |
| 51 | 2-(6-(methyl(2,2,6,6-tetramethylpiperidin-4-yl)amino)pyridazin-3-yl)-5-(1-methyl-1H-pyrazol-4-yl)phenol |
| 52 | 5-(5-amino-1H-pyrazol-1-yl)-2-(6-(methyl-(2,2,6,6-tetramethylpiperidin-4-yl)amino)pyridazin-3-yl)phenol |
| 53[1] | 2-(6-(methyl(2,2,6,6-tetramethylpiperidin-4-yl)amino)pyridazin-3-yl)-4-(1H-pyrazol-1-yl)phenol |
| 54 | 2-((6-((2-hydroxy-ethyl)-(2,2,6,6-tetramethylpiperidin-4-yl)-amino)-pyridazin-3-yl)-5-pyrazol-1-yl)phenol |
| 55 | 2-(6-(piperidin-4-yloxy)pyridazin-3-yl)-5-(1H-pyrazol-1-yl)phenol |
| 56 | 2-(6-(((2S,4R,6R)-2,6-dimethylpiperidin-4-yl)oxy)pyridazin-3-yl)-5-(1H-pyrazol-1-yl)phenol |
| 57 | 2-(6-((-2,6-dimethylpiperidin-4-yl)oxy)pyridazin-3-yl)-5-(1H-pyrazol-1-yl)phenol |
| 58 | 5-(1H-pyrazol-1-yl)-2-(6-(pyrrolidin-3-yl-oxy)pyridazin-3-yl)phenol |
| 59 | 2-(6-(((2S,4S)-2-methylpiperidin-4-yl)oxy)pyridazin-3-yl)-5-(1H-pyrazol-1-yl)phenol |
| 60 | (5-(1H-pyrazol-1-yl)-2-(6-(pyrrolidin-3-ylmethoxy)pyridazin-3-yl)phenol |
| 61 | 2-(6-((3-fluoropiperidin-4-yl)oxy)pyridazin-3-yl)-5-(1H-pyrazol-1-yl)phenol |
| 62 | 2-(6-(1,2,2,6,6-pentamethyl-piperidin-4-yl-oxy)-pyridazin-3-yl)-5-(1H-pyrazol-1-yl)phenol |
| 63 | 5-1H-pyrazol-1-yl-2-(6-(2,2,6,6-tetramethylpiperidin-4-yl-oxy)-pyridazin-3-yl)phenol |
| 64 | 5-(1H-pyrazol-4-yl)-2-(6-((2,2,6,6-tetramethylpiperidin-4-yl)oxy)pyridazin-3-yl)phenol |
| 65[1] | 2-(6-piperazin-1-yl-pyridazin-3-yl)-5-(1H-pyrazol-1-yl)phenol |
| 66 | 3-(6-(azetidin-3-ylamino)-pyridazin-3-yl)naphthalen-2-ol |

-continued

| Cpd | Name |
|---|---|
| 67 | 2-(6-(azetidin-3-ylamino)pyridazin-3-yl)-5-(1H-pyrazol-1-yl)phenol |
| 68 | 2-(6-(3,5-dimethylpiperazin-1-yl)pyridazin-3-yl)-5-(1H-pyrazol-1-yl)phenol |
| 69 | 2-(6-(7-methyl-2,7-diazaspiro[4.4]nonan-2-yl)pyridazin-3-yl)-5-(1H-pyrazol-1-yl)phenol |
| 70 | 2-(6-(1,4-diazepan-1-yl)pyridazin-3-yl)-5-(1H-pyrazol-1-yl)phenol |
| 71 | 2-(6-(4-(2-hydroxyethyl)piperazin-1-yl)pyridazin-3-yl)-5-(1H-pyrazol-1-yl)phenol |
| 72 | 2-(6-(3,6-diazabicyclo[3.2.1]octan-3-yl)pyridazin-3-yl)-5-(1H-pyrazol-1-yl)phenol |
| 73 | 2-(6-(2,7-diazaspiro[3.5]nonan-7-yl)pyridazin-3-yl)-5-(1H-pyrazol-1-yl)phenol |
| 74 | 2-(6-(3-(hydroxymethyl)piperazin-1-yl)pyridazin-3-yl)-5-(1H-pyrazol-1-yl)phenol |
| 75 | 2-(6-(1,7-diazaspiro[4.4]nonan-7-yl)pyridazin-3-y1)-5-(1H-pyrazol-1-yl)phenol |
| 76 | 2-(6-(4-amino-4-methylpiperidin-1-yl)pyridazin-3-yl)-5-(1H-pyrazol-1-yl)phenol |
| 77 | 2-(6-(3-(dimethylamino)piperidin-1-yl)pyridazin-3-yl)-5-(1H-pyrazol-1-yl)phenol |
| 78 | 2-(6-(1,2,2,6,6-pentamethylpiperidin-4-ylamino)-pyridazin-3-yl)-5-1H-pyrazol-1-yl-phenol |
| 79 | 2-(6-(3,3-dimethylpiperazin-1-yl)pyridazin-3-yl)-5-(1H-pyrazol-1-yl)phenol |
| 80 | 2-(6-(7-(2-hydroxyethyl)-2,7-diazaspiro[4.4]-nonan-2-yl)pyridazin-3-yl)-5-(1H-pyrazol-1-yl)phenol |
| 81 | 2-(6-((3aR,6aS)-hexahydropyrrolo[3,4-c]pyrrol-2(1H)-yl)pyridazin-3-yl)-5-(1H-pyrazol-1-yl)phenol |
| 82[1] | 3-(6-(piperazin-1-yl)pyridazin-3-yl)naphthalene-2,7-diol |
| 83 | 5-(1H-pyrazol-1-yl)-2-(6-(1,2,3,6-tetrahydropyridin-4-yl)pyridazin-3-yl)phenol |
| 84 | 2-(6-piperidin-4-yl-pyridazin-3-yl)-5-1H-pyrazol-1-yl-phenol |
| 85 | 3-(6-(1,2,3,6-tetrahydropyridin-4-yl)pyridazin-3-yl)naphthalen-2-ol |
| 86[1] | 3-(6-(1,2,3,6-tetrahydropyridin-4-yl)pyridazin-3-yl)naphthalene-2,7-diol |
| 87 | 3-(6-(2,2,6,6-tetramethyl-1,2,3,6-tetrahydropyridin-4-yl)pyridazin-3-yl)naphthalene-2,7-diol |
| 88[1] | 3-(6-(1-methyl-1,2,3,6-tetrahydropyridin-4-yl)pyridazin-3-yl)naphthalene-2,7-diol |
| 89[1] | 3-(6-(piperidin-4-yl)pyridazin-3-yl)naphthalene-2,7-diol |
| 90 | 3-(6-((2,2,6,6-tetramethylpiperidin-4-yl)oxy)pyridazin-3-yl)naphthalene-2,7-diol |
| 91 | 3-(6-(methyl(2,2,6,6-tetramethylpiperidin-4-yl)amino)pyridazin-3-yl)naphthalene-2,7-diol |
| 92 | 3-(6-((2,2,6,6-tetramethylpiperidin-4-yl)amino)pyridazin-3-yl)naphthalene-2,7-diol |
| 93 | tert-butyl(3-((7-hydroxy-6-(6-(methyl(2,2,6,6-tetramethylpiperidin-4-yl)amino)pyridazin-3-yl)naphthalen-2-yl)oxy)propyl)carbamate |
| 94 | 7-(3-amino-propoxy)-3-(6-(methyl-(2,2,6,6-tetramethylpiperidin-4-yl)-amino)-pyridazin-3-yl)naphthalen-2-ol |
| 95 | N-(3-((7-hydroxy-6-(6-(methyl(2,2,6,6-tetramethylpiperidin-4-yl)amino)pyridazin-3-yl)naphthalen-2-yl)oxy)propyl)acetamide |
| 96 | 7-(3-hydroxypropoxy)-3-(6-(methyl(2,2,6,6-tetramethylpiperidin-4-yl)amino)pyridazin-3-yl)naphthalen-2-ol |
| 97 | 7-(3-methoxypropoxy)-3-(6-(methyl(2,2,6,6-tetramethylpiperidin-4-yl)amino)pyridazin-3-yl)naphthalen-2-ol |
| 98 | 7-(2-morpholinoethoxy)-3-(6-((2,2,6,6-tetramethylpiperidin-4-yl)oxy)pyridazin-3-yl)naphthalen-2-ol |
| 99 | 3-(6-(piperidin-4-ylmethyl)pyridazin-3-yl)naphthalen-2-ol |
| 100 | 5-(1H-pyrazol-1-yl)-2-(6-((2,2,6,6-tetramethylpiperidin-4-yl)methyl)pyridazin-3-yl)phenol |
| 101 | 3-methoxy-2-(6-(methyl(2,2,6-trimethylpiperidin-4-yl)amino)pyridazin-3-yl)-5-(5-methyloxazol-2-yl)phenol |
| 102 | 2-(6-(((6S)-6-((S)-1-hydroxyethyl)-2,2-dimethylpiperidin-4-yloxy)pyridazin-3-yl)-5-(1H-pyrazol-1-yl)phenol |
| 103 | 7-hydroxy-6-(6-(methyl(2,2,6,6-tetramethylpiperidin-4-yl)amino)pyridazin-3-yl)-2-naphthonitrile |
| 104 | 3-(6-(methyl(2,2,6,6-tetramethylpiperidin-4-yl)amino)pyridazin-3-yl)-7-(piperidinylmethyl)naphthalen-2-ol |
| 105 | 3-(6-(methyl(2,2,6,6-tetramethylpiperidin-4-yl)amino)pyridazin-3-yl)-7-(pyrrolidinylmethyl)naphthalen-2-ol |
| 106 | 1-bromo-6-(6-(methyl(2,2,6,6-tetramethylpiperidin-4-yl)amino)pyridazin-3-yl)naphthalene-2,7-diol |
| 107 | 1-chloro-6-(6-(methyl(2,2,6,6-tetramethylpiperidin-4-yl)amino)pyridazin-3-yl)naphthalene-2,7-diol |
| 108 | 7-methoxy-3-(6-(methyl(2,2,6,6-tetramethylpiperidin-4-yl)amino)pyridazin-3-yl)naphthalene-2-ol |
| 109 | 7-methoxy-3-(6-(methyl(1,2,2,6,6-pentamethylpiperidin-4-yl)amino)pyridazin-3-yl)naphthalen-2-ol |
| 110 | 7-(3,6-dihydro-2H-pyran-4-yl)-3-(6-(methyl(2,2,6,6-tetramethylpiperidin-4-yl)amino)pyridazin-3-yl)naphthalen-2-ol |
| 111 | 3-(6-(methyl(2,2,6,6-tetramethylpiperidin-4-yl)amino)pyridazin-3-yl)-7-(tetrahydro-2H-pyran-4-yl)naphthalene-2-ol |
| 112 | 7-(difluoromethyl)-3-(6-(methyl(2,2,6,6-tetramethylpiperidin-4-yl)amino)pyridazin-3-yl)naphthalen-2-ol |
| 113 | 7-((4-hydroxy-2-methylbutan-2-yl)oxy)-3-(6-(methyl(2,2,6,6-tetramethylpiperidin-4-yl)amino)pyridazin-3-yl)naphthalen-2-ol |
| 114 | 7-(3-hydroxy-3-methylbutoxy)-3-(6-(methyl(2,2,6,6-tetramethylpiperidin-4-yl)amino)pyridazin-3-yl)naphthalen-2-ol |
| 115 | 2-(6-(methyl(2,2,6,6-tetramethylpiperidin-4-yl)amino)pyridazin-3-yl)-5-(1H-pyrazol-4-yl)benzene-1,3-diol |

| Cpd | Name |
|---|---|
| 116 | 3-methoxy-2-(6-(methyl(2,2,6,6-tetramethylpiperidin-4-yl)amino)pyridazin-3-yl)-5-(1H-pyrazol-4-yl)phenol |
| 117 | 5-(1H-pyrazol-4-yl)-2-(6-((2,2,6,6-tetramethylpiperidin-4-yl)amino)pyridazin-3-yl)-3-(trifluoromethoxy)phenol |
| 118 | 2-(6-(methyl(2,2,6,6-tetramethylpiperidin-4-yl)amino)pyridazin-3-yl)-5-(1-methyl-1H-pyrazol-4-yl)-3-(trifluoromethoxy)phenol |
| 119 | 2-(6-(methyl(2,2,6,6-tetramethylpiperidin-4-yl)amino)pyridazin-3-yl)-5-(1H-pyrazol-4-yl)-3-(trifluoromethoxy)phenol |
| 120 | 4-(3-hydroxy-4-(6-(methyl(2,2,6,6-tetramethylpiperidin-4-yl)amino)pyridazin-3-yl)-5-(trifluoromethoxy)phenyl)-1-methylpyridin-2(1H)-one |
| 121 | 3-methoxy-2-(6-(methyl(2,2,6,6-tetramethylpiperidin-4-yl)amino)pyridazin-3-yl)-5-(1-methyl-1H-pyrazol-4-yl)phenol |
| 122 | 3-methoxy-2-(6-(methyl(2,2,6,6-tetramethylpiperidin-4-yl)amino)pyridazin-3-yl)-5-(5,6,7,8-tetrahydroimidazo[1,2-a]pyridin-3-yl)phenol |
| 123 | 3-methoxy-2-(6-(methyl(2,2,6,6-tetramethylpiperidin-4-yl)amino)pyridazin-3-yl)-5-(pyridine-3-yl)phenol |
| 124 | 5-(1-cyclopentyl-1H-pyrazol-4-yl)-3-methoxy-2-(6-(methyl(2,2,6,6-tetramethylpiperidin-4-yl)amino)pyridazin-3-yl)phenol |
| 125 | 3',5-dimethoxy-4-(6-(methyl(2,2,6,6-tetramethylpiperidin-4-yl)amino)pyridazin-3-yl)-(1,1'-biphenyl)-3-ol |
| 126 | 3-(benzyloxy)-2-(6-(methyl(2,2,6,6-tetramethylpiperidin-4-yl)amino)pyridazin-3-yl)-5-(5-methyloxazol-2-yl)phenol |
| 127 | 3-ethoxy-2-(6-(methyl(2,2,6,6-tetramethylpiperidin-4-yl)amino)pyridazin-3-yl)-5-(5-methyloxazol-2-yl)phenol |
| 128 | 3-(cyclopropylmethoxy)-2-(6-(methyl(2,2,6,6-tetramethylpiperidin-4-yl)amino)-pyridazin-3-yl)-5-(5-methyloxazol-2-yl)phenol |
| 129 | 2-methyl-5-(6-(methyl(2,2,6,6-tetramethylpiperidin-4-yl)amino)pyridazin-3-yl)-1H-benzo[d]imidazol-6-ol |
| 130 | 5-chloro-2-(6-(methyl(2,2,6,6-tetramethylpiperidin-4-yl)amino)pyridazin-3-yl)phenol |
| 131 | 5-(1H-pyrazol-1-yl)-2-(6-((2,2,6,6-tetramethylpiperidin-4-yl)amino)pyridazin-3-yl)phenol |
| 132 | 3-hydroxy-4-(6-((2,2,6,6-tetramethylpiperidin-4-yl)amino)pyridazin-3-yl)benzonitrile |
| 133 | 2-(6-((2,2-dimethylpiperidin-4-yl)oxy)pyridazin-3-yl)-5-(1H-pyrazol-1-yl)phenol |
| 134 | 2-(6-(methyl(2,2,6,6-tetramethylpiperidin-4-yl)amino)pyridazin-3-yl)-4-(1H-pyrazol-4-yl)phenol |
| 135 | 2-(6-(methyl(2,2,6,6-tetramethylpiperidin-4-yl)amino)pyridazin-3-yl)-4-(4,5,6,7-tetrahydropyrazolo[1,5-a]pyridin-3-yl)phenol |
| 136 | 2-(6-(methyl(2,2,6,6-tetramethylpiperidin-4-yl)amino)pyridazin-3-yl)-4-(4,5,6,7-tetrahydropyrazolo[1,5-a]pyrazin-3-yl)phenol |
| 137 | 4-(1H-indol-2-yl)-2-(6-(methyl(2,2,6,6-tetramethylpiperidin-4-yl)amino)pyridazin-3-yl)phenol |
| 138 | 4-(cyclopent-1-en-1-yl)-2-(6-(methyl(2,2,6,6-tetramethylpiperidin-4-yl)amino)pyridazin-3-yl)phenol |
| 139 | 2-(6-(methyl(2,2,6,6-tetramethylpiperidin-4-yl)amino)pyridazin-3-yl)-4-(1H-pyrazol-3-yl)phenol |
| 140 | 4-(4-hydroxy-3-(6-(methyl(2,2,6,6-tetramethylpiperidin-4-yl)amino)pyridazin-3-yl)phenyl)pyridin-2-ol |
| 141 | 4-(4-hydroxy-3-(6-((2,2,6,6-tetramethylpiperidin-4-yl)oxy)pyridazin-3-yl)phenyl)-1-methylpyridin-2(1H)-one |
| 142 | 4-(4-hydroxy-3-(6-((2,2,6,6-tetramethylpiperidin-4-yl)oxy)pyridazin-3-yl)phenyl)pyridin-2-ol |
| 143 | 5-(1H-indazol-7-yl)-2-(6-(methyl(2,2,6,6-tetramethylpiperidin-4-yl)amino)pyridazin-3-yl)phenol |
| 144 | 4-chloro-2-(6-(methyl(2,2,6,6-tetramethylpiperidin-4-yl)amino)pyridazin-3-yl)-5-(1H-pyrazol-4-yl)phenol |
| 145 | 4-fluoro-2-(6-(methyl(2,2,6,6-tetramethylpiperidin-4-yl)amino)pyridazin-3-yl)-5-(1H-pyrazol-4-yl)phenol |
| 146 | 5-fluoro-4-(1H-imidazol-4-yl)-2-(6-(methyl(2,2,6,6-tetramethylpiperidin-4-yl)amino)pyridazin-3-yl)phenol |
| 147 | 5-fluoro-2-(6-(methyl(2,2,6,6-tetramethylpiperidin-4-yl)amino)pyridazin-3-yl)-4-(1H-pyrazol-4-yl)phenol |
| 148 | 5-fluoro-2-(6-(methyl(2,2,6,6-tetramethylpiperidin-4-yl)amino)pyridazin-3-yl)-4-(1H-pyrazol-5-yl)phenol |
| 149 | 6-hydroxy-5-(6-(methyl(2,2,6,6-tetramethylpiperidin-4-yl)amino)pyridazin-3-yl)-2,3-dihydro-1H-inden-1-one |
| 150 | 6-(6-(methyl(2,2,6,6-tetramethylpiperidin-4-yl)amino)pyridazin-3-yl)-1,4-dihydroindeno[1,2-c]-1H-pyrazol-7-ol |
| 151[1] | 6-hydroxy-5-(6-(methyl(2,2,6,6-tetramethylpiperidin-4-yl)amino)pyridazin-3-yl)-2,3-dihydro-1H-inden-1-oneoxime |
| 152 | 5-(6-(methyl(2,2,6,6-tetramethylpiperidin-4-yl)amino)pyridazin-3-yl)-2,3-dihydro-1H-indene-1,6-diol |
| 153[1] | 2-amino-6-(6-(methyl(2,2,6,6-tetramethylpiperidin-4-yl)amino)pyridazin-3-yl)-8H-indeno[1,2-d]thiazol-5-ol |
| 154[1] | 9-(6-(methyl(2,2,6,6-tetramethylpiperidin-4-yl)amino)pyridazin-3-yl)-5,6-dihydroimidazo[5,1-a]isoquinolin-8-ol |
| 155 | 4-hydroxy-3-(6-(methyl(2,2,6,6-tetramethylpiperidin-4-yl)amino)pyridazin-3-yl)-N-((1-methyl-1H-pyrazol-4-yl)methyl)benzamide |

-continued

| Cpd | Name |
|---|---|
| 156 | 4-(4-(hydroxymethyl)-1H-pyrazol-1-yl)-2-(6-(methyl(2,2,6,6-tetramethylpiperidin-4-yl)amino)pyridazin-3-yl)phenol |
| 157 | 5-(1H-pyrazol-4-yl)-2-(6-((2,2,6,6-tetramethylpiperidin-4-yl)methyl)pyridazin-3-yl)phenol |
| 158 | 6-(3-(benzyloxy)isoquinolin-6-yl)-N-methyl-N-(2,2,6,6-tetramethylpiperidin-4-yl)pyridazin-3-amine |
| 159 | 6-(1-(benzyloxy)isoquinolin-7-yl)-N-methyl-N-(2,2,6,6-tetramethylpiperidin-4-yl)pyridazin-3-amine |
| 160[1] | 3-fluoro-5-(2-methoxypyridin-4-yl)-2-(6-(methyl(2,2,6,6-tetramethylpiperidin-4-yl)amino)pyridazin-3-yl)phenol |
| 161[1] | 4-(3-fluoro-5-hydroxy-4-(6-(methyl(2,2,6,6-tetramethylpiperidin-4-yl)amino)pyridazin-3-yl)phenyl)pyridin-2(1H)-one |
| 162[1] | 4-(3-fluoro-5-hydroxy-4-(6-(methyl(2,2,6,6-tetramethylpiperidin-4-yl)amino)pyridazin-3-yl)phenyl)-1-methyipyridin-2(1H)-one |
| 163[1] | 5-(3-fluoro-5-hydroxy-4-(6-(methyl(2,2,6,6-tetramethylpiperidin-4-yl)amino)pyridazin-3-yl)phenyl)-1-methyipyridin-2(1H)-one |
| 164[1] | 3-fluoro-5-(1H-pyrazol-4-yl)-2-(6-((2,2,6,6-tetramethylpiperidin-4-yl)oxy)pyridazin-3-yl)phenol |
| 165[1] | 5-chloro-3-fluoro-2-(6-(methyl(2,2,6,6-tetramethylpiperidin-4-yl)amino)pyridazin-3-yl)phenol |
| 166[1] | 3-fluoro-2-(6-(methyl(2,2,6,6-tetramethylpiperidin-4-yl)amino)pyridazin-3-yl)-5-(1H-pyrazol-4-yl)phenol |
| 167[1] | 3-fluoro-2-(6-(methyl(2,2,6,6-tetramethylpiperidin-4-yl)amino)pyridazin-3-yl)-5-(1-methyl-1H-pyrazol-4-yl)phenol |
| 168 | 5-(5-methoxypyridin-3-yl)-2-(6-(methyl(2,2,6,6-tetramethylpiperidin-4-yl)amino)pyridazin-3-yl)phenol |
| 169 | 5-(3-hydroxy-4-(6-(methyl(2,2,6,6-tetramethylpiperidin-4-yl)amino)pyridazin-3-yl)phenyl)pyridin-2-ol |
| 170 | 4-(3-hydroxy-4-(6-(methyl(2,2,6,6-tetramethylpiperidin-4-yl)amino)pyridazin-3-yl)phenyl)pyridin-2-ol |
| 171 | 5-(6-methoxypyridin-3-yl)-2-(6-(methyl(2,2,6,6-tetramethylpiperidin-4-yl)amino)pyridazin-3-yl)phenol |
| 172 | 5-(3-hydroxy-4-(6-(methyl(2,2,6,6-tetramethylpiperidin-4-yl)amino)pyridazin-3-yl)phenyl)-3-(trifluoromethyl)pyridin-2-ol |
| 173 | 5-(3-hydroxy-4-(6-(methyl(2,2,6,6-tetramethylpiperidin-4-yl)amino)pyridazin-3-yl)phenyl)-1-methyipyridin-2(1H)-one |
| 174 | 4-(3-hydroxy-4-(6-(methyl(2,2,6,6-tetramethylpiperidin-4-yl)amino)pyridazin-3-yl)phenyl)-1-methyipyridin-2(1H)-one |
| 175 | 5-(2-methoxypyridin-4-yl)-2-(6-(methyl(2,2,6,6-tetramethylpiperidin-4-yl)amino)pyridazin-3-yl)phenol |
| 176 | 4-(3-hydroxy-4-(6-((2,2,6,6-tetramethylpiperidin-4-yl)oxy)pyridazin-3-yl)phenyl)pyridin-2-ol |
| 177 | 5-(6-(dimethylamino)pyridin-3-yl)-2-(6-(methyl(2,2,6,6-tetramethylpiperidin-4-yl)amino)pyridazin-3-yl)phenol |
| 178 | 4-(3-hydroxy-4-(6-((2,2,6,6-tetramethylpiperidin-4-yl)oxy)pyridazin-3-yl)phenyl)-1-methylpyridin-2(1H)-one |
| 179 | 2-(6-(methyl(2,2,6,6-tetramethylpiperidin-4-yl)amino)pyridazin-3-yl)-5-(pyrimidin-5-yl)phenol |
| 180 | 5-(3-hydroxy-4-(6-(methyl(2,2,6,6-tetramethylpiperidin-4-yl)amino)pyridazin-3-yl)phenyl)pyridin-3-ol |
| 181 | 1-cyclopropyl-4-(3-hydroxy-4-(6-(methyl(2,2,6,6-tetramethylpiperidin-4-yl)amino)pyridazin-3-yl)phenyl)pyridin-2(1H)-one |
| 182 | 2-(6-(methyl(2,2,6,6-tetramethylpiperidin-4-yl)amino)pyridazin-3-yl)-5-(1,2,3,6-tetrahydropyridin-4-yl)phenol |
| 183 | 5-(cyclopent-1-en-1-yl)-2-(6-(methyl(2,2,6,6-tetramethylpiperidin-4-yl)amino)pyridazin-3-yl)phenol |
| 184 | 5-(3,6-dihydro-2H-pyran-4-yl)-2-(6-(methyl(2,2,6,6-tetramethylpiperidin-4-yl)amino)pyridazin-3-yl)phenol |
| 185 | 5-(imidazo[1,5-a]pyridin-7-yl)-2-(6-(methyl(2,2,6,6-tetramethylpiperidin-4-yl)amino)pyridazin-3-yl)phenol |
| 186 | 5-(imidazo[1,2-a]pyridin-7-yl)-2-(6-(methyl(2,2,6,6-tetramethylpiperidin-4-yl)amino)pyridazin-3-yl)phenol |
| 187 | 2-(6-(methyl(2,2,6,6-tetramethylpiperidin-4-yl)amino)pyridazin-3-yl)-5-(2-methylpyridin-4-yl)phenol |
| 188 | 5-(1H-imidazol-2-yl)-2-(6-(methyl(2,2,6,6-tetramethylpiperidin-4-yl)amino)pyridazin-3-yl)phenol |
| 189 | 5-(1H-imidazol-4-yl)-2-(6-(methyl(2,2,6,6-tetramethylpiperidin-4-yl)amino)pyridazin-3-yl)phenol |
| 190 | 5-(imidazo[1,2-a]pyrazin-3-yl)-2-(6-(methyl(2,2,6,6-tetramethylpiperidin-4-yl)amino)pyridazin-3-yl)phenol |
| 191 | 2-(6-(methyl(2,2,6,6-tetramethylpiperidin-4-yl)amino)pyridazin-3-yl)-5-(5,6,7,8-tetrahydroimidazo[1,2-a]pyrazin-3-yl)phenol |
| 192 | 2-(6-(methyl(2,2,6,6-tetramethylpiperidin-4-yl)amino)pyridazin-3-yl)-5-(4-methyl-1H-imidazol-2-yl)phenol |
| 193 | 2-(6-(methyl(2,2,6,6-tetramethylpiperidin-4-yl)amino)pyridazin-3-yl)-5-(1-methyl-1H-imidazol-4-yl)phenol |

-continued

| Cpd | Name |
|---|---|
| 194 | 2-(6-(methyl(2,2,6,6-tetramethylpiperidin-4-yl)amino)pyridazin-3-yl)-5-(1-methyl-1H-imidazol-5-yl)phenol |
| 195 | 2-(6-(methyl(2,2,6,6-tetramethylpiperidin-4-yl)amino)pyridazin-3-yl)-5-(4-nitro-1H-imidazol-2-yl)phenol |
| 196 | 2-(6-(methyl(2,2,6,6-tetramethylpiperidin-4-yl)amino)pyridazin-3-yl)-5-(2-methyl-1H-imidazol-4-yl)phenol |
| 197 | 5-(1,2-dimethyl-1H-imidazol-4-yl)-2-(6-(methyl(2,2,6,6-tetramethylpiperidin-4-yl)amino)pyridazin-3-yl)phenol |
| 198 | 1-(3-hydroxy-4-(6-(methyl(2,2,6,6-tetramethylpiperidin-4-yl)amino)pyridazin-3-yl)phenyl)-1H-pyrazole-4-carboxamide |
| 199 | 2-(6-((3aR,6aS)-5-(2-hydroxyethyl)hexahydropyrrolo[3,4-c]pyrrol-2(1H)-yl)pyridazin-3-yl)-5-(1H-pyrazol-4-yl)phenol |
| 200 | 2-(6-((3aR,6aS)-hexahydropyrrolo[3,4-c]pyrrol-2(1H)-yl)pyridazin-3-yl)-5-(1H-pyrazol-4-yl)phenol |
| 201 | 2-(6-((3aR,6aS)-5-methylHexahydropyrrolo[3,4-c]pyrrol-2(1H)-yl)pyridazin-3-yl)-5-(1H-pyrazol-4-yl)phenol |
| 202 | 4-(3-hydroxy-4-(6-(5-methylHexahydropyrrolo[3,4-c]pyrrol-2(1H)-yl)pyridazin-3-yl)phenyl)-1-methylpyridin-2(1H)-one |
| 203 | 4-(3-hydroxy-4-(6-((3aR,6aR)-1-methylHexahydropyrrolo[3,4-b]pyrrol-5(1H)-yl)pyridazin-3-yl)phenyl)-1-methylpyridin-2(1H)-one |
| 204 | 2-(6-(2,7-diazaspiro[4.5]decan-2-yl)pyridazin-3-yl)-5-(1H-pyrazol-4-yl)phenol |
| 205 | 4-(4-(6-(2,7-diazaspiro[4.5]decan-2-yl)pyridazin-3-yl)-3-hydroxyphenyl)-1-methylpyridin-2(1H)-one |
| 206 | 2-(6-(methyl-(2,2,6,6-tetramethylpiperidin-4-yl)-amino)-pyridazin-3-yl)phenol |
| 207 | 6-(6-(methyl(2,2,6,6-tetramethylpiperidin-4-yl)amino)pyridazin-3-yl)quinolin-7-ol |
| 208 | 6-(6-(methyl(1,2,2,6,6-pentamethylpiperidin-4-yl)amino)pyridazin-3-yl)quinolin-7-ol |
| 209 | 6-(6-((3aR,6aS)-5-methylHexahydropyrrolo[3,4-c]pyrrol-2(1H)-yl)pyridazin-3-yl)quinolin-7-ol |
| 210 | 2-methyl-6-(6-(methyl(2,2,6,6-tetramethylpiperidin-4-yl)amino)pyridazin-3-yl)quinolin-7-ol |
| 211 | 7-(6-(methyl(1,2,2,6,6-pentamethylpiperidin-4-yl)amino)pyridazin-3-yl)isoquinolin-6-ol |
| 212 | 7-(6-(methyl(2,2,6,6-tetramethylpiperidin-4-yl)amino)pyridazin-3-yl)isoquinolin-6-ol |
| 213 | 7-(6-((2,2,6,6-tetramethylpiperidin-4-yl)oxy)pyridazin-3-yl)isoquinoline-6-ol |
| 214 | 7-(6-((3aR,6aS)-5-methylHexahydropyrrolo[3,4-c]pyrrol-2(1H)-yl)pyridazin-3-yl)isoquinolin-6-ol |
| 215 | 1-cyclopropyl-7-(6-(methyl(2,2,6,6-tetramethylpiperidin-4-yl)amino)pyridazin-3-yl)isoquinolin-6-ol |
| 216 | 7-(6-(methyl(2,2,6,6-tetramethylpiperidin-4-yl)amino)pyridazin-3-yl)isoquinoline-1,6-diol |
| 217 | 6-hydroxy-7-(6-(methyl(2,2,6,6-tetramethylpiperidin-4-yl)amino)pyridazin-3-yl)isoquinoline-1-carbonitrile |
| 218 | 6-(6-(methyl(2,2,6,6-tetramethylpiperidin-4-yl)amino)pyridazin-3-yl)isoquinolin-7-ol |
| 219 | 8-(6-(methyl(2,2,6,6-tetramethylpiperidin-4-yl)amino)pyridazin-3-yl)quinolin-7-ol |
| 220 | 6-(6-(methyl(2,2,6,6-tetramethylpiperidin-4-yl)amino)pyridazin-3-yl)quinolin-6-ol |
| 221 | 2-methyl-7-(6-(methyl(2,2,6,6-tetramethylpiperidin-4-yl)amino)pyridazin-3-yl)quinolin-6-ol |
| 222 | 3-chloro-6-(6-(methyl(2,2,6,6-tetramethylpiperidin-4-yl)amino)pyridazin-3-yl)quinolin-7-ol |
| 223 | 3-bromo-6-(6-(methyl(2,2,6,6-tetramethylpiperidin-4-yl)amino)pyridazin-3-yl)quinolin-7-ol |
| 224 | 7-hydroxy-6-(6-(methyl(2,2,6,6-tetramethylpiperidin-4-yl)amino)pyridazin-3-yl)quinoline-3-carbonitrile |
| 225 | 6-(6-(methyl(2,2,6,6-tetramethylpiperidin-4-yl)amino)pyridazin-3-yl)-3-(1-methyl-1H-imidazol-4-yl)quinolin-7-ol |
| 226[1] | 3-(1H-imidazol-1-yl)-6-(6-(methyl(2,2,6,6-tetramethylpiperidin-4-yl)amino)pyridazin-3-yl)quinolin-7-ol |
| 227 | 6-(6-(methyl(2,2,6,6-tetramethylpiperidin-4-yl)amino)pyridazin-3-yl)quinoline-3,7-diol |
| 228 | 3-ethyl-6-(6-(methyl(2,2,6,6-tetramethylpiperidin-4-yl)amino)pyridazin-3-yl)quinolin-7-ol |
| 229 | 3-isopropyl-6-(6-(methyl(2,2,6,6-tetramethylpiperidin-4-yl)amino)pyridazin-3-yl)quinolin-7-ol |
| 230 | 7-hydroxy-6-(6-(methyl(2,2,6,6-tetramethylpiperidin-4-yl)amino)pyridazin-3-yl)quinolin-2(1H)-one |
| 231[1] | 7-hydroxy-1-methyl-6-(6-(methyl(2,2,6,6-tetramethylpiperidin-4-yl)amino)pyridazin-3-yl)quinolin-2(1H)-one |
| 232 | 4-methoxy-2-methyl-6-(6-(methyl(2,2,6,6-tetramethylpiperidin-4-yl)amino)pyridazin-3-yl)quinolin-7-ol |
| 233 | 2-methyl-6-(6-(methyl(2,2,6,6-tetramethylpiperidin-4-yl)amino)pyridazin-3-yl)-4-(pyrrolidin-1-yl)quinolin-7-ol |
| 234 | 2-methyl-6-(6-(methyl(2,2,6,6-tetramethylpiperidin-4-yl)amino)pyridazin-3-yl)-4-morpholinoquinolin-7-ol |
| 235 | 4-(dimethylamino)-2-methyl-6-(6-(methyl(2,2,6,6-tetramethylpiperidin-4-yl)amino)pyridazin-3-yl)quinolin-7-ol |
| 236 | 4-ethoxy-2-methyl-6-(6-(methyl(2,2,6,6-tetramethylpiperidin-4-yl)amino)pyridazin-3-yl)quinolin-7-ol |
| 237 | 2-methyl-6-(6-(methyl(2,2,6,6-tetramethylpiperidin-4-yl)amino)pyridazin-3-yl)-4-(1-methyl-1H-pyrazol-4-yl)quinolin-7-ol |

-continued

| Cpd | Name |
|---|---|
| 238[1] | 4-methoxy-7-(6-(methyl(2,2,6,6-tetramethylpiperidin-4-yl)amino)pyridazin-3-yl)quinolin-6-ol |
| 239[1] | 7-(6-(methyl(2,2,6,6-tetramethylpiperidin-4-yl)amino)pyridazin-3-yl)quinoxalin-6-ol |
| 240 | 6-(6-(methyl(2,2,6,6-tetramethylpiperidin-4-yl)amino)pyridazin-3-yl)-3-(tetrahydro-2H-pyran-4-yl)quinolin-7-ol |
| 241 | 3-chloro-7-(6-(methyl(2,2,6,6-tetramethylpiperidin-4-yl)amino)pyridazin-3-yl)quinolin-6-ol |
| 242 | 3-bromo-7-(6-(methyl(2,2,6,6-tetramethylpiperidin-4-yl)amino)pyridazin-3-yl)quinolin-6-ol |
| 243 | 3-methyl-7-(6-(methyl(2,2,6,6-tetramethylpiperidin-4-yl)amino)pyridazin-3-yl)quinolin-6-ol |
| 244 | 5-bromo-3-methyl-7-(6-(methyl(2,2,6,6-tetramethylpiperidin-4-yl)amino)pyridazin-3-yl)quinolin-6-ol |
| 245 | 6-hydroxy-1-methyl-7-(6-(methyl(2,2,6,6-tetramethylpiperidin-4-yl)amino)pyridazin-3-yl)quinolin-4(1H)-one |
| 246 | 2,3-dimethyl-7-(6-(methyl(2,2,6,6-tetramethylpiperidin-4-yl)amino)pyridazin-3-yl)quinolin-6-ol |
| 247 | 2-methyl-7-(6-(methyl(2,2,6,6-tetramethylpiperidin-4-yl)amino)pyridazin-3-yl)quinoxalin-6-ol |
| 248 | 3-methyl-7-(6-(methyl(2,2,6,6-tetramethylpiperidin-4-yl)amino)pyridazin-3-yl)quinoxalin-6-ol |
| 249 | 4-methoxy-6-(6-(methyl(2,2,6,6-tetramethylpiperidin-4-yl)amino)pyridazin-3-yl)quinolin-7-ol |
| 250 | 4-(azetidin-1-yl)-2-methyl-6-(6-(methyl(2,2,6,6-tetramethylpiperidin-4-yl)amino)pyridazin-3-yl)quinolin-7-ol |
| 251 | 7-hydroxy-2-methyl-6-(6-(methyl(2,2,6,6-tetramethylpiperidin-4-yl)amino)pyridazin-3-yl)quinolone-4-carbonitrile |
| 252 | 4-cyclopropyl-2-methyl-6-(6-(methyl(2,2,6,6-tetramethylpiperidin-4-yl)amino)pyridazin-3-yl)-quinolin-7-ol |
| 253 | 4-(3,6-dihydro-2H-pyran-4-yl)-2-methyl-6-(6-(methyl(2,2,6,6-tetramethylpiperidin-4-yl)amino)pyridazin-3-yl)quinolin-7-ol |
| 254[1] | 2-methyl-6-(6-(methyl(2,2,6,6-tetramethylpiperidin-4-yl)amino)pyridazin-3-yl)-4-(tetrahydro-2H-pyran-4-yl)quinolin-7-ol |
| 255 | 2-methyl-6-(6-(methyl(2,2,6,6-tetramethylpiperidin-4-yl)amino)pyridazin-3-yl)-4-(oxetan-3-yl)quinolin-7-ol |
| 256[1] | 4-(dimethylamino)-6-(6-(methyl(2,2,6,6-tetramethylpiperidin-4-yl)amino)pyridazin-3-yl)-quinolin-7-ol |
| 257 | 7-hydroxy-6-(6-(methyl(2,2,6,6-tetramethylpiperidin-4-yl)amino)pyridazin-3-yl)quinazolin-4(1H)-one |
| 258 | 6-(6-(methyl(2,2,6,6-tetramethylpiperidin-4-yl)amino)pyridazin-3-yl)quinazolin-7-ol |
| 259 | 7-hydroxy-1-methyl-6-(6-(methyl(2,2,6,6-tetramethylpiperidin-4-yl)amino)pyridazin-3-yl)-3,4-dihydroquinolin-2(1H)-one |
| 260 | 2-methyl-6-(6-(methyl(2,2,6,6-tetramethylpiperidin-4-yl)amino)pyridazin-3-yl)quinazolin-7-ol |
| 261 | 7-hydroxy-6-(6-(methyl(2,2,6,6-tetramethylpiperidin-4-yl)amino)pyridazin-3-yl)isoquinoline-1-carbonitrile |
| 262 | 7-hydroxy-6-(6-(methyl(2,2,6,6-tetramethylpiperidin-4-yl)amino)pyridazin-3-yl)quinoline-2-carbonitrile |
| 263 | 6-hydroxy-7-(6-(methyl(2,2,6,6-tetramethylpiperidin-4-yl)amino)pyridazin-3-yl)quinolin-2-carbonitrile |
| 264 | 6-hydroxy-7-(6-(methyl(2,2,6,6-tetramethylpiperidin-4-yl)amino)pyridazin-3-yl)isoquinoline-1-carboxamide |
| 265 | 7-hydroxy-6-(6-(methyl(2,2,6,6-tetramethylpiperidin-4-yl)amino)pyridazin-3-yl)quinolin-2-carboxamide |
| 266 | 6-hydroxy-7-(6-(methyl(2,2,6,6-tetramethylpiperidin-4-yl)amino)pyridazin-3-yl)quinoline-2-carboxamide |
| 267 | methyl 6-hydroxy-7-(6-(methyl(2,2,6,6-tetramethylpiperidin-4-yl)amino)pyridazin-3-yl)quinoline-2-carboxylate |
| 268 | 6-hydroxy-7-(6-(piperazin-1-yl)pyridazin-3-yl)quinoline-2-carbonitrile |
| 269 | 7-hydroxy-6-(6-(piperazin-1-yl)pyridazin-3-yl)quinoline-2-carbonitrile |
| 270 | 7-(6-(piperazin-1-yl)pyridazin-3-yl)isoquinolin-6-ol |
| 271 | 7-(6-(1,2,3,6-tetrahydropyridin-4-yl)pyridazin-3-yl)quinolin-6-ol |
| 272 | 1-methyl-6-(6-(methyl(2,2,6,6-tetramethylpiperidin-4-yl)amino)pyridazin-3-yl)isoquinolin-7-ol |
| 273 | 1-methyl-7-(6-(methyl(2,2,6,6-tetramethylpiperidin-4-yl)amino)pyridazin-3-yl)isoquinolin-6-ol |
| 274 | 1,3-dimethyl-7-(6-(methyl(2,2,6,6-tetramethylpiperidin-4-yl)amino)pyridazin-3-yl)isoquinolin-6-ol |
| 275 | 7-hydroxy-3-methyl-6-(6-(methyl(2,2,6,6-tetramethylpiperidin-4-yl)amino)pyridazin-3-yl)isoquinoline-1-carbonitrile |
| 276 | 1-amino-7-(6-(methyl(2,2,6,6-tetramethylpiperidin-4-yl)amino)pyridazin-3-yl)isoquinolin-6-ol |
| 277 | 7-hydroxy-1,3-dimethyl-6-(6-(methyl(2,2,6,6-tetramethylpiperidin-4-yl)amino)pyridazin-3-yl)quinazoline-2,4(1H,3H)-dione |
| 278 | 6-hydroxy-5-(6-(methyl(2,2,6,6-tetramethylpiperidin-4-yl)amino)pyridazin-3-yl)benzo[d]oxazol-2(3H)-one |

-continued

| Cpd | Name |
|---|---|
| 279 | 2-methyl-5-(6-(methyl(2,2,6,6-tetramethylpiperidin-4-yl)amino)pyridazin-3-yl)-2H-indazol-6-ol |
| 280 | 1-methyl-5-(6-(methyl(2,2,6,6-tetramethylpiperidin-4-yl)amino)pyridazin-3-yl)-1H-indazol-6-ol |
| 281[1] | 6-hydroxy-2-methyl-7-(6-(methyl(2,2,6,6-tetramethylpiperidin-4-yl)amino)pyridazin-3-yl)isoquinolin-1(2H)-one |
| 282 | 2-ethyl-6-hydroxy-7-(6-((2,2,6,6-tetramethylpiperidin-4-yl)oxy)pyridazin-3-yl)isoquinolin-1(2H)-one |
| 283 | 1-ethoxy-7-(6-(methyl(2,2,6,6-tetramethylpiperidin-4-yl)amino)pyridazin-3-yl)isoquinolin-6-ol |
| 284 | 7-(6-((2,2,6,6-tetramethylpiperidin-4-yl)oxy)pyridazin-3-yl)isoquinoline-1,6-diol |
| 285 | 7-(6-(methyl(2,2,6,6-tetramethylpiperidin-4-yl)amino)-pyridazin-3-yl)-3-phenylisoquinolin-6-ol |
| 286 | 3-methyl-7-(6-(methyl(2,2,6,6-tetramethylpiperidin-4-yl)amino)pyridazin-3-yl)isoquinolin-6-ol |
| 287 | 3-cyclopropyl-7-(6-(methyl(2,2,6,6-tetramethylpiperidin-4-yl)amino)pyridazin-3-yl)isoquinolin-6-ol |
| 288 | 3-isopropyl-7-(6-(methyl(2,2,6,6-tetramethylpiperidin-4-yl)amino)pyridazin-3-yl)isoquinolin-6-ol |
| 289 | 3-propyl-7-(6-((2,2,6,6-tetramethylpiperidin-4-yl)oxy)-pyridazin-3-yl)isoquinolin-6-ol |
| 290 | 3-isopropyl-7-(6-((2,2,6,6-tetramethylpiperidin-4-yl)oxy)-pyridazin-3-yl)isoquinolin-6-ol |
| 291 | 3-methyl-7-(6-(piperazin-1-yl)pyridazin-3-yl)isoquinolin-6-ol |
| 292 | 6-(3-(benzyloxy)isoquinolin-6-yl)-N-methyl-N-(2,2,6,6-tetramethylpiperidin-4-yl)pyridazin-3-amine |
| 293 | 3-chloro-6-(6-(methyl(2,2,6,6-tetramethylpiperidin-4-yl)amino)pyridazin-3-yl)quinolin-7-ol |
| 294 | 3-isopropyl-6-(6-(methyl(2,2,6,6-tetramethylpiperidin-4-yl)amino)pyridazin-3-yl)quinolin-7-ol |
| 295 | 3-methyl-7-(6-(methyl(2,2,6,6-tetramethylpiperidin-4-yl)amino)pyridazin-3-yl)quinoxalin-6-ol |
| 296 | 4-chloro-2-methyl-6-(6-(methyl(2,2,6,6-tetramethylpiperidin-4-yl)amino)pyridazin-3-yl)quinolin-7-ol |
| 297 | 4-chloro-7-(6-(methyl(2,2,6,6-tetramethylpiperidin-4-yl)amino)pyridazin-3-yl)quinolin-6-ol |
| 300 | 7-(6-(methyl(2,2,6,6-tetramethylpiperidin-4-yl)amino)pyridazin-3-yl)quinolin-6-ol |
| 301 | 5-(2-methoxy-4-(1H-pyrazol-1-yl)phenyl)-N-methyl-N-(2,2,6,6-tetramethylpiperidin-4-yl)-1,3,4-thiadiazol-2-amine |
| 302 | 6-(5-(methyl(2,2,6,6-tetramethylpiperidin-4-yl)amino)-1,3,4-thiadiazol-2-yl)naphthalen-2-ol |
| 303 | 5-(2-methoxyquinolin-3-yl)-N-methyl-N-(2,2,6,6-tetramethylpiperidin-4-yl)-1,3,4-thiadiazol-2-amine |
| 304 | 5-(3-methoxy-naphthalen-2-yl)-N-methyl-N-(2,2,6,6-tetramethylpiperidin-4-yl)-1,3,4-thiadiazol-2-amine |
| 305 | 5-(2-methoxy-4-(1H-pyrazol-lyl)phenyl)-N-(1,2,2,6,6-pentamethylpiperidin-4-yl)-1,3,4-thiadiazol-2-amine |
| 306 | 5-(2-methoxy-4-(1-methyl-1H-pyrazol-4-yl)phenyl)-N-methyl-N-(2,2,6,6-tetramethylpiperidin-4-yl)-1,3,4-thiadiazol-2-amine |
| 307 | 5-(2-methoxy-4-(1H-pyrazol-4-yl)phenyl)-N-methyl-N-(2,2,6,6-tetramethylpiperidin-4-yl)-1,3,4-thiadiazol-2-amine |
| 308 | 4-(3-methoxy-4-(5-(methyl(2,2,6,6-tetramethylpiperidin-4-yl)amino)-1,3,4-thiadiazol-2-yl)phenyl)-1-methylpyridin-2(1H)-one |
| 309 | 5-(3-methoxy-4-(5-(methyl(2,2,6,6-tetramethylpiperidin-4-yl)amino)-1,3,4-thiadiazol-2-yl)phenyl)pyridin-2-ol |
| 310 | 5-(3-methoxy-4-(5-(methyl(2,2,6,6-tetramethylpiperidin-4-yl)amino)-1,3,4-thiadiazol-2-yl)phenyl)-1-methylpyridin-2(1H)-one |
| 311 | N-methyl-5-(2-methyl-4-(1-methyl-1H-pyrazol-4-yl)phenyl)-N-(2,2,6,6-tetramethylpiperidin-4-yl)-1,3,4-thiadiazol-2-amine |
| 312 | 1-methyl-4-(4-(5-(methyl(2,2,6,6-tetramethylpiperidin-4-yl)amino)-1,3,4-thiadiazol-2-yl)-3-(trifluoromethoxy)phenyl)pyridin-2(1H)-one |
| 313 | 5-(4-(3,5-dimethyl-1H-pyrazol-4-yl)-2-methoxyphenyl)-N-methyl-N-(2,2,6,6-tetramethylpiperidin-4-yl)-1,3,4-thiadiazol-2-amine |
| 314 | N-methyl-5-(4-(1-methyl-1H-pyrazol-4-yl)-2-(trifluoromethyl)phenyl)-N-(2,2,6,6-tetramethylpiperidin-4-yl)-1,3,4-thiadiazol-2-amine |
| 315 | 2-(5-(methyl(2,2,6,6-tetramethylpiperidin-4-yl)amino)-1,3,4-thiadiazol-2-yl-5-(1-methyl-1H-pyrazol-4-yl)phenol |
| 316 | 2-(5-(methyl(2,2,6,6-tetramethylpiperidin-4-yl)amino)-1,3,4-thiadiazol-2-yl-5-(1H-pyrazol-1-yl)phenol |
| 317 | 5-(3-hydroxy-4-(5-(methyl(2,2,6,6-tetramethylpiperidin-4-yl)amino)-1,3,4-thiadiazol-2-yl)phenyl)-1-methylpyridin-2(1H)-one |
| 318 | 4-(3-hydroxy-4-(5-(methyl(2,2,6,6-tetramethylpiperidin-4-yl)amino)-1,3,4-thiadiazol-2-yl)phenyl)-1-methylpyridin-2(1H)-one |
| 319 | 5-(3-hydroxy-4-(5-(methyl(2,2,6,6-tetramethylpiperidin-4-yl)amino)-1,3,4-thiadiazol-2-yl)phenyl)pyridin-2-ol |
| 320 | 3-(5-(methyl(2,2,6,6-tetramethylpiperidin-4-yl)amino)-1,3,4-thiadiazol-2-yl)naphthalene-2,7-diol |

-continued

| Cpd | Name |
| --- | --- |
| 321 | 3-(5-((3aR,6aS)-hexahydropyrrolo[3,4-c]pyrrol-2(1H)-yl)-1,3,4-thiadiazol-2-yl)naphthalene-2,7-diol |
| 322[1] | 3-(5-(methyl(2,2,6,6-tetramethylpiperidin-4-yl)amino)-1,3,4-thiadiazol-2-yl)naphthalen-2-ol |
| 323 | 3-(5-(methyl(2,2,6,6-tetramethylpiperidin-4-yl)amino)-1,3,4-thiadiazol-2-yl)quinolin-2-ol |
| 324 | 2-(5-(methyl(2,2,6,6-tetramethylpiperidin-4-yl)amino)-1,3,4-thiadiazol-2-yl)-4-(1H-pyrazol-1-yl)phenol |
| 325 | 5-(2-chloro-4-(1-methyl-1H-pyrazol-4-yl)phenyl)-N-methyl-N-(2,2,6,6-tetramethylpiperidin-4-yl)-1,3,4-thiadiazol-2-amine |
| 326 | 3-chloro-2-(5-(methyl(2,2,6,6-tetramethylpiperidin-4-yl)amino)-1,3,4-thiadiazol-2-yl)-5-(1-methyl-1H-pyrazol-4-yl)phenol |
| 327 | 5-(2-chloro-4-(1-methyl-1H-pyrazol-4-yl)phenyl)-N-(2,2,6,6-tetramethylpiperidin-4-yl)-1,3,4-thiadiazol-2-amine |
| 328 | 3-methoxy-2-(5-(methyl(2,2,6,6-tetramethylpiperidin-4-yl)amino)-1,3,4-thiadiazol-2-yl)-5-methyloxazol-2-yl)phenol |
| 329 | 2-(2-methoxy-4-(1H-pyrazol-1-yl)phenyl)-5-(1,2,3,6-tetrahydropyridin-4-yl)-1,3,4-thiadiazole |
| 330 | 2-(5-(piperazin-1-yl)-1,3,4-thiadiazol-2-yl)-5-(1H-pyrazol-1-yl)phenol |
| 331 | 5-(7-methoxyquinolin-6-yl)-N-methyl-N-(2,2,6,6-tetramethylpiperidin-4-yl)-1,3,4-thiadiazole-2-amine |
| 332 | 6-(5-(methyl(2,2,6,6-tetramethylpiperidin-4-yl)amino)-1,3,4-thiadiazol-2-yl)quinolin-7-ol |
| 333 | 3-methoxy-4-(5-(methyl(2,2,6,6-tetramethylpiperidin-4-yl)amino)-1,3,4-thiadiazol-2-yl)benzonitrile |
| 334 | 3-fluoro-4-(5-(methyl(2,2,6,6-tetramethylpiperidin-4-yl)amino)-1,3,4-thiadiazol-2-yl)benzonitrile |
| 335 | methyl-3-fluoro-4-(5-(methyl(2,2,6,6-tetramethylpiperidin-4-yl)amino)-1,3,4-thiadiazol-2-yl)benzoate |
| 336 | 5-(2-methoxy-4-(3-(methylamino)-1H-pyrazol-1-yl)phenyl)-N-methyl-N-(2,2,6,6-tetramethylpiperidin-4-yl)-1,3,4-thiadiazol-2-amine |
| 337 | 7-methoxy-6-(5-(methyl(2,2,6,6-tetramethylpiperidin-4-yl)amino)-1,3,4-thiadiazol-2-yl)quinoline-2-carbonitrile |
| 338 | 4-(3-methoxy-4-(5-((2,2,6,6-tetramethylpiperidin-4-yl)oxy)-1,3,4-thiadiazol-2-yl)phenyl)-1-methylpyridin-2(1H)-one |
| 339 | 4-(3-chloro-4-(5-(methyl(2,2,6,6-tetramethylpiperidin-4-yl)amino)-1,3,4-thiadiazol-2-yl)phenyl)-1-methylpyridin-2(1H)-one |
| 340 | 5-(2-chloro-4-(1H-pyrazol-4-yl)phenyl)-N-methyl-N-(2,2,6,6-tetramethylpiperidin-4-yl)-1,3,4-thiadiazol-2-amine |
| 341 | 5-(2-chloro-4-(4,5,6,7-tetrahydropyrazolo[1,5-a]pyridin-3-yl)phenyl)-N-methyl-N-(2,2,6,6-tetramethylpiperidin-4-yl)-1,3,4-thiadiazol-2-amine |
| 342[1] | N-methyl-5-(5-(1-methyl-1H-pyrazol-4-yl)pyridin-2-yl)-N-(2,2,6,6-tetramethylpiperidin-4-yl)-1,3,4-thiadiazol-2-amine |
| 343 | 2-(2-chloro-4-(1-methyl-1H-pyrazol-4-yl)phenyl)-5-((2,2,6,6-tetramethylpiperidin-4-yl)oxy-1,3,4-thiadiazole |
| 344 | 5-(2-chloro-4-(6-methoxypyridin-3-yl)phenyl)-N-methyl-N-(2,2,6,6-tetramethylpiperidin-4-yl)-1,3,4-thiadiazol-2-amine |
| 345 | 5-(4-(6-aminopyridin-3-yl)-2-fluorophenyl)-N-methyl-N-(2,2,6,6-tetramethylpiperidin-4-yl)-1,3,4-thiadiazol-2-amine |
| 346 | 5-(2-fluoro-4-(3-methyl-1H-pyrazol-5-yl)phenyl)-N-methyl-N-(2,2,6,6-tetramethylpiperidin-4-yl)-1,3,4-thiadiazol-2-amine |
| 347 | 5-(2-fluoro-4-(1H-pyrazol-5-yl)phenyl)-N-methyl-N-(2,2,6,6-tetramethylpiperidin-4-yl)-1,3,4-thiadiazol-2-amine |
| 348 | 5-(2,3-difluoro-4-(1H-pyrazol-4-yl)phenyl)-N-methyl-N-(2,2,6,6-tetramethylpiperidin-4-yl)-1,3,4-thiadiazol-2-amine |
| 349 | 5-(2,3-difluoro-4-(1H-pyrazol-5-yl)phenyl)-N-methyl-N-(2,2,6,6-tetramethylpiperidin-4-yl)-1,3,4-thiadiazol-2-amine |
| 350 | 5-(2,5-difluoro-4-(1H-pyrazol-4-yl)phenyl)-N-methyl-N-(2,2,6,6-tetramethylpiperidin-4-yl)-1,3,4-thiadiazol-2-amine |
| 351 | 5-(2,5-difluoro-4-(1H-pyrazol-5-yl)phenyl)-N-methyl-N-(2,2,6,6-tetramethylpiperidin-4-yl)-1,3,4-thiadiazol-2-amine |
| 352 | 5-(2,6-difluoro-4-(1H-pyrazol-4-yl)phenyl)-N-methyl-N-(2,2,6,6-tetramethylpiperidin-4-yl)-1,3,4-thiadiazol-2-amine |
| 353 | 2-(2,5-difluoro-4-(1H-pyrazol-4-yl)phenyl)-5-((3aR,6aS)-hexahydropyrrolo[3,4-c]pyrrol-2(1H)-yl)-1,3,4-thiadiazole |
| 354 | 5-(2-chloro-5-fluoro-4-(1H-pyrazol-4-yl)phenyl)-N-methyl-N-(2,2,6,6-tetramethylpiperidin-4-yl)-1,3,4-thiadiazol-2-amine |
| 355 | 5-(3-fluoro-5-(1H-pyrazol-4-yl)pyridin-2-yl)-N-methyl-N-(2,2,6,6-tetramethylpiperidin-4-yl)-1,3,4-thiadiazol-2-amine |
| 356 | 5-(4-(2-aminopyrimidin-4-yl)-2-chlorophenyl)-N-methyl-N-(2,2,6,6-tetramethylpiperidin-4-yl)-1,3,4-thiadiazol-2-amine |
| 357 | 5-(5-(2-aminopyrimidin-4-yl)-2-chlorophenyl)-N-methyl-N-(2,2,6,6-tetramethylpiperidin-4-yl)-1,3,4-thiadiazol-2-amine |
| 358 | 5-(4-(2,4-dimethylthiazol-5-yl)-2,5-difluorophenyl)-N-methyl-N-(2,2,6,6-tetramethylpiperidin-4-yl)-1,3,4-thiadiazol-2-amine |
| 359 | 5-(4-(2,4-dimethylthiazol-5-yl)-2,3-difluorophenyl)-N-methyl-N-(2,2,6,6-tetramethylpiperidin-4-yl)-1,3,4-thiadiazol-2-amine |

| Cpd | Name |
|---|---|
| 360 | 4-(3-hydroxy-4-(5-(methyl(2,2,6,6-tetramethylpiperidin-4-yl)amino)-1,3,4-thiadiazol-2-yl)-5-(trifluoromethoxy)phenyl)-1-methylpyridin-2(1H)-one |
| 361 | 5-(2-fluoro-6-methoxy-4-(1H-pyrazol-4-yl)phenyl)-N-methyl-N-(2,2,6,6-tetramethylpiperidin-4-yl)-1,3,4-thiadiazol-2-amine |
| 362 | 2-(2-fluoro-6-methoxy-4-(1H-pyrazol-4-yl)phenyl)-5-((3aR,6aS)-5-methylhexahydropyrrolo[3,4-c]pyrrol-2(1H)-yl)-1,3,4-thiadiazole |
| 363 | 5-(2,3-difluoro-6-methoxy-4-(1H-pyrazol-4-yl)phenyl)-N-methyl-N-(2,2,6,6-tetramethylpiperidin-4-yl)-1,3,4-thiadiazol-2-amine |
| 364 | 6-methoxy-2-(5-(methyl(2,2,6,6-tetramethylpiperidin-4-yl)amino)-1,3,4-thiadiazol-2-yl)-3,4-dihydroisoquinolin-1-(2H)-one |
| 365 | 5-(2-chloro-4-(1H-pyrazol-1-yl)phenyl)-N-methyl-N-(2,2,6,6-tetramethylpiperidin-4-yl)-1,3,4-thiadiazol-2-amine |
| 366 | 5-(2-chloro-4-(1H-1,2,3-triazol-1-yl)phenyl)-N-methyl-N-(2,2,6,6-tetramethylpiperidin-4-yl)-1,3,4-thiadiazol-2-amine |
| 367 | 5-(2-chloro-4-(2H-1,2,3-triazol-2-yl)phenyl)-N-methyl-N-(2,2,6,6-tetramethylpiperidin-4-yl)-1,3,4-thiadiazol-2-amine |
| 368 | 5-(2-chloro-4-(1H-1,2,4-triazol-1-yl)phenyl)-N-methyl-N-(2,2,6,6-tetramethylpiperidin-4-yl)-1,3,4-thiadiazol-2-amine |
| 369 | 5-(4-(3-amino-1H-pyrazol-1-yl)-2-chlorophenyl)-N-methyl-N-(2,2,6,6-tetramethylpiperidin-4-yl)-1,3,4-thiadiazol-2-amine |
| 370 | 2-(2-chloro-4-(1H-imidazol-1-yl)phenyl)-5-((3aR,6aS)-5-methylhexahydropyrrolo[3,4c]pyrrol-2(1H)-yl)-1,3,4-thiadiazole |
| 371 | 5-(2-chloro-4-(1H-imidazol-1-yl)phenyl)-N-methyl-N-(2,2,6,6-tetramethylpiperidin-4-yl)-1,3,4-thiadiazol-2-amine |
| 372 | 5-(2-fluoro-4-(1H-imidazol-1-yl)phenyl)-N-methyl-N-(2,2,6,6-tetramethylpiperidin-4-yl)-1,3,4-thiadiazol-2-amine |
| 373 | 5-(2-methoxy-4-(1H-pyrazol-5-yl)phenyl)-N-methyl-N-(2,2,6,6-tetramethylpiperidin-4-yl)-1,3,4-thiadiazol-2-amine |
| 374 | 5-(4-(2,4-dimethylthiazol-5-yl)-2-methoxyphenyl)-N-methyl-N-(2,2,6,6-tetramethylpiperidin-4-yl)-1,3,4-thiadiazol-2-amine |
| 375 | 5-(2-methoxy-4-(pyridin-3-yl)phenyl)-N-methyl-N-(2,2,6,6-tetramethylpiperidin-4-yl)-1,3,4-thiadiazol-2-amine |
| 376 | 5-(2-fluoro-4-(1H-pyrazol-4-yl)phenyl)-N-methyl-N-(2,2,6,6-tetramethylpiperidin-4-yl)-1,3,4-thiadiazol-2-amine |
| 377 | 5-(2-methoxy-4-(2-methoxypyridin-4-yl)phenyl)-N-methyl-N-(2,2,6,6-tetramethylpiperidin-4-yl)-1,3,4-thiadiazol-2-amine |
| 378 | 5-(2-methoxy-4-(6-methoxypyridin-3-yl)phenyl)-N-methyl-N-(2,2,6,6-tetramethylpiperidin-4-yl)-1,3,4-thiadiazol-2-amine |
| 379 | 2-(2-chloro-4-(1-methyl-1H-pyrazol-4-yl)phenyl)-5-((3aR,6aS)-5-methylhexahydropyrrolo[3,4-c]pyrrol-2(1H)-yl)-1,3,4-thiadiazole |
| 380 | 2-(2-chloro-4-(1H-pyrazol-4-yl)phenyl)-5-((3aR,6aS)-5-methylhexahydropyrrolo[3,4-c]pyrrol-2(1H)-yl)-1,3,4-thiadiazole |
| 381 | 2-(2-chloro-4-(1H-pyrazol-4-yl)phenyl)-5-((3aR,6aR)-1-methy1Hexahydropyrrolo[3,4-b]pyrrol-5(1H)-yl)-1,3,4-thiadiazole |
| 382 | 1-(4-(5-(2-chloro-4-(1H-pyrazol-4-yl)phenyl)-1,3,4-thiadiazol-2-yl)morpholin-2-yl)-N,N-dimethylmethanamine |
| 383 | 2-(2-chloro-4-(1H-pyrazol-4-yl)phenyl)-5-(2-methyl-2,7-diazaspiro[4.5]decan-7-yl)-1,3,4-thiadiazole |
| 384 | 2-(2-fluoro-4-(1H-pyrazol-4-yl)phenyl)-5-((3aR,6aS)-5-methy1Hexahydropyrrolo[3,4-c]pyrrol-2(1H)-yl)-1,3,4-thiadiazole |
| 385 | 2-(2-methoxy-4-(1-methyl-1H-pyrazol-4-yl)phenyl)-5-(2,6-diazaspiro[3.5]nonan-2-yl)-1,3,4-thiadiazole |
| 386 | 2-(2-methoxy-4-(1-methyl-1H-pyrazol-4-yl)phenyl)-5-(2,7-diazaspiro[3.5]nonan-2-yl)-1,3,4-thiadiazole |
| 387 | 2-(5-(methyl(2,2,6,6-tetramethylpiperidin-4-yl)amino)-1,3,4-thiadiazol-2-yl)-5-(1H-pyrazol-1-yl)phenol |
| 388 | 5-(3-chloro-4-(5-(methyl(2,2,6,6-tetramethylpiperidin-4-yl)amino)-1,3,4-thiadiazol-2-yl)phenyl)pyridin-2(1H)-one |
| 389 | 2-(5-(methyl(2,2,6,6-tetramethylpiperidin-4-yl)amino)-1,3,4-thiadiazol-2-yl)-5-(3-(methylamino)-1H-pyrazol-1-yl)phenol |
| 390 | 3-fluoro-2-(5-(methyl(2,2,6,6-tetramethylpiperidin-4-yl)amino)-1,3,4-thiadiazol-2-yl)-5-(1H-pyrazol-4-yl)phenol |
| 391 | 3,4-difluoro-2-(5-(methyl(2,2,6,6-tetramethylpiperidin-4-yl)amino)-1,3,4-thiadiazol-2-yl)-5-(1H-pyrazol-4-yl)phenol |
| 392 | 6-hydroxy-5-(5-(methyl(2,2,6,6-tetramethylpiperidin-4-yl)amino)-1,3,4-thiadiazol-2-yl)-2,3-dihydro-1H-inden-1-one |
| 393 | 2-(5-(methyl(2,2,6,6-tetramethylpiperidin-4-yl)amino)-1,3,4-thiadiazol-2-yl)-5-(1H-pyrazol-4-yl)phenol |
| 394 | 2-(5-(2,6-diazaspiro[3.5]nonan-2-yl)-1,3,4-thiadiazol-2-yl)-5-(1-methyl-1H-pyrazol-4-yl)phenol |
| 395 | 2-(5-(2,7-diazaspiro[3.5]nonan-2-yl)-1,3,4-thiadiazol-2-yl)-5-(1-methyl-1H-pyrazol-4-yl)phenol |
| 396[1] | 3-fluoro-2-(5-((3aR,6aS)-hexahydropyrrolo[3,4-c]pyrrol-2(1H)-yl)-1,3,4-thiadiazol-2-yl)-5-(1H-pyrazol-4-yl)phenol |
| 397 | 3-chloro-2-(5-(methyl(2,2,6,6-tetramethylpiperidin-4-yl)amino)-1,3,4-thiadiazol-2-yl)-5-(1H-pyrazol-4-yl)phenol |

-continued

| Cpd | Name |
|---|---|
| 398 | 2-(2-methoxy-4-(1H-pyrazol-1-yl)phenyl)-5-((2,2,6,6-tetramethylpiperidin-4-yl)methyl)-1,3,4-thiadiazole |
| 399 | 2-(2,3-difluoro-4-(1H-pyrazol-4-yl)phenyl)-5-(2,7-diazaspiro[3.5]nonan-2-yl)-1,3,4-thiadiazole |
| 400 | 2-(5-(2,7-diazaspiro[3.5]nonan-2-yl)-1,3,4-thiadiazol-2-yl)-3-fluoro-5-(1H-pyrazol-4-yl)phenol |
| 401 | 4-methoxy-l-methyl-3-(5-(methyl(2,2,6,6-tetramethylpiperidin-4-yl)amino)-1,3,4-thiadiazol-2-yl)quinolin-2(1H)-one |
| 402 | 4-hydroxy-1-methyl-3-(5-(methyl(2,2,6,6-tetramethylpiperidin-4-yl)amino)-1,3,4-thiadiazol-2-yl)quinolin-2(1H)-one |
| 403 | 3-(5-(methyl(2,2,6,6-tetramethylpiperidin-4-yl)amino)-1,3,4-thiadiazol-2-yl)quinolin-2(1H)-one |
| 404 | 1-methyl-3-(5-(methyl(2,2,6,6-tetramethylpiperidin-4-yl)amino)-1,3,4-thiadiazol-2-yl)quinolin-2(1H)-one |
| 405[1] | 2-(2-chloro-4-(1H-pyrazol-4-yl)phenyl)-5-((3aR,6aS)-hexahydropyrrolo[3,4-c]pyrrol-2(1H)-yl)-1,3,4-thiadiazole |
| 406[1] | 2-(2-chloro-4-(1H-pyrazol-4-yl)phenyl)-5-(2,7-diazaspiro[4.5]decan-2-yl)-1,3,4-thiadiazole |
| 407[1] | (R)-(4-(5-(2-chloro-4-(1H-pyrazol-4-yl)phenyl)-1,3,4-thiadiazol-2-yl)piperazin-2-yl)methanol |
| 408 | 2-(5-(methyl(2,2,6,6-tetramethylpiperidin-4-yl)amino)-1,3,4-thiadiazol-2-yl)benzo[b]thiophene-5-carbonitrile |
| 409 | 5-(3-chlorobenzo[b]thiophen-2-yl)-N-methyl-N-(2,2,6,6-tetramethylpiperidin-4-yl)-1,3,4-thiadiazol-2-amine |
| 410 | 5-(2-methoxy-4-(1H-pyrazol-4-yl)phenyl)-N-methyl-N-(2,2,6,6-tetramethylpiperidin-4-yl)-1,3,4-thiadiazol-2-amine |
| 411[1] | 2-{6-[(1R,5S)-8-azabicyclo[3.2.1]oct-3-yl(methyl)amino]pyridazin-3-yl}-5-(1H-pyrazol-4-yl)phenol |
| 412[1] | 2-[6-((1R,5S)-8-azabicyclo[3.2.1]oct-3-ylamino)pyridazin-3-yl]-5-(1H-pyrazol-4-yl)phenol |
| 413[1] | 5-(1H-pyrazol-4-yl)-2-{6-[(2,2,6,6-tetramethylpiperidin-4-yl)amino]pyridazin-3-yl}phenol |
| 414 | 5-(1-methyl-1H-pyrazol-4-yl)-2-{6-[(2,2,6,6-tetramethylpiperidin-4-yl)oxy]pyridazin-3-yl}phenol |
| 415[1] | 2-[6-((1R,5S)-8-azabicyclo[3.2.1]oct-3-yloxy)pyridazin-3-yl]-5-(1H-pyrazol-4-yl)phenol |
| 416 | 5-(5-methyl-1H-pyrazol-4-yl)-2-{6-[methyl(2,2,6,6-tetramethylpiperidin-4-yl)amino]pyridazin-3-yl}phenol |
| 417 | 5-(1H-imidazol-1-yl)-2-{6-[(2,2,6,6-tetramethylpiperidin-4-yl)oxy]pyridazin-3-yl}phenol |
| 418 | 5-(5-methyl-1H-pyrazol-4-yl)-2-{6-[(2,2,6,6-tetramethylpiperidin-4-yl)oxy]pyridazin-3-yl}phenol |
| 419[1] | 2-{6-[methyl(2,2,6,6-tetramethylpiperidin-4-yl)amino]pyridazin-3-yl}-5-(4-nitro-1H-pyrazol-1-yl)phenol |
| 420 | 6-[2-methoxy-4-(4-nitro-1H-pyrazol-1-yl)phenyl]-N-methyl-N-(2,2,6,6-tetramethylpiperidin-4-yl)pyridazin-3-amine |
| 421 | 5-(4-amino-1H-pyrazol-1-yl)-2-{6-[(2,2,6,6-tetramethylpiperidin-4-yl)oxy]pyridazin-3-yl}phenol |
| 422[1] | 2-[6-(1-methyl-1,2,3,6-tetrahydropyridin-4-yl)pyridazin-3-yl]-5-(1H-pyrazol-4-yl)phenol |
| 423 | 5-(4-nitro-1H-pyrazol-1-yl)-2-{6-[(2,2,6,6-tetramethylpiperidin-4-yl)oxy]pyridazin-3-yl}phenol |
| 424[1] | 5-(1H-pyrazol-4-yl)-2-[6-(1,2,3,6-tetrahydropyridin-4-yl)pyridazin-3-yl]phenol |
| 425[1] | 2-[6-(1-ethyl-1,2,3,6-tetrahydropyridin-4-yl)pyridazin-3-yl]-5-(1H-pyrazol-4-yl)phenol |
| 426[1] | 2-{6-[methyl(piperidin-4-yl)amino]pyridazin-3-yl}-5-(1H-pyrazol-4-yl)phenol |
| 427[1] | 2-[6-(piperidin-4-ylamino)pyridazin-3-yl]-5-(1H-pyrazol-4-yl)phenol |
| 428[1] | 6-[2,5-difluoro-4-(1H-pyrazol-4-yl)phenyl]-N-methyl-N-(2,2,6,6-tetramethylpiperidin-4-yl)pyridazin-3-amine |
| 429[1] | 2-[6-(8-azabicyclo[3.2.1]oct-2-en-3-yl)pyridazin-3-yl]-5-(1H-pyrazol-4-yl)phenol |
| 430[1] | 6-[2,3-difluoro-4-(1H-pyrazol-4-yl)phenyl]-N-methyl-N-(2,2,6,6-tetramethylpiperidin-4-yl)pyridazin-3-amine |
| 431[1] | 3-[2,5-difluoro-4-(1H-pyrazol-4-yl)phenyl]-6-[(2,2,6,6-tetramethylpiperidin-4-yl)oxy]pyridazine |
| 432 | 2-[6-(piperidin-4-yloxy)pyridazin-3-yl]-5-(1H-pyrazol-4-yl)phenol |
| 433[1] | 2-{6-[(1R,5S)-8-azabicyclo[3.2.1]oct-3-ylamino]pyridazin-3-yl}-5-(1H-pyrazol-4-yl)phenol |
| 434[1] | 6-[2-methoxy-6-(1H-pyrazol-4-yl)pyridin-3-yl]-N-methyl-N-(2,2,6,6-tetramethylpiperidin-4-yl)pyridazin-3-amine |
| 435 | 3-[4-(1H-pyrazol-4-yl)phenyl]-6-[(2,2,6,6-tetramethylpiperidin-4-yl)oxy]pyridazine |
| 436[1] | 2-{6-[(2,6-dimethylpiperidin-4-yl)oxy]pyridazin-3-yl}-5-(1H-pyrazol-4-yl)phenol |
| 437[1] | 3-[2-fluoro-4-(1H-pyrazol-4-yl)phenyl]-6-[(2,2,6,6-tetramethylpiperidin-4-yl)oxy]pyridazine |
| 438 | 3-[4-(1-methyl-1H-pyrazol-4-yl)thiophen-2-yl]-6-[(2,2,6,6-tetramethylpiperidin-4-yl)oxy]pyridazine |
| 439[1] | 2-[6-(2,7-diazaspiro[3.5]non-2-yl)pyridazin-3-yl]-5-(1H-pyrazol-4-yl)phenol |
| 440 | 3-fluoro-4-{6-[methyl(2,2,6,6-tetramethylpiperidin-4-yl)amino]pyridazin-3-yl}phenol |
| 441 | 2-{6-[(2,6-dimethylpiperidin-4-yl)oxy]pyridazin-3-yl}-5-(1H-pyrazol-1-yl)phenol |

-continued

| Cpd | Name |
|---|---|
| 442 | N-methyl-6-(2-methyl-2H-indazol-5-yl)-N-(2,2,6,6-tetramethylpiperidin-4-yl)pyridazin-3-amine |
| 443 | 2-methyl-5-{6-[(2,2,6,6-tetramethylpiperidin-4-yl)oxy]pyridazin-3-yl}-2H-indazole |
| 444 | 3-(4-chloro-2-methoxyphenyl)-6-[(2,2,6,6-tetramethylpiperidin-4-yl)oxy]pyridazine |
| 445 | N-methyl-6-(2-methylpyrazolo[1,5-a]pyridin-3-yl)-N-(2,2,6,6-tetramethylpiperidin-4-yl)pyridazin-3-amine |
| 446 | 6-{6-[(2,2,6,6-tetramethylpiperidin-4-yl)oxy]pyridazin-3-yl}imidazo[1,2-a]pyridine |
| 447 | 3-[2-methoxy-4-(1H-pyrazol-1-yl)phenyl]-6-[(2,2,6,6-tetramethylpiperidin-4-yl)oxy]pyridazine |
| 448[1] | 3-[5-(1H-pyrazol-4-yl)thiophen-2-yl]-6-[(2,2,6,6-tetramethylpiperidin-4-yl)oxy]pyridazine |
| 449 | 3-[5-(1-methyl-1H-pyrazol-4-yl)thiophen-2-yl]-6-[(2,2,6,6-tetramethylpiperidin-4-yl)oxy]pyridazine |
| 450[1] | 3-[4-(1H-pyrazol-4-yl)thiophen-2-yl]-6-[(2,2,6,6-tetramethylpiperidin-4-yl)oxy]pyridazine |
| 451 | 5-(3,5-dimethyl-1H-pyrazol-4-yl)-2-{6-[(2,2,6,6-tetramethylpiperidin-4-yl)oxy]pyridazin-3-yl}phenol |
| 452 | 6-[2-fluoro-4-(1H-pyrazol-4-yl)phenyl]-N-methyl-N-(2,2,6,6-tetramethylpiperidin-4-yl)pyridazin-3-amine |
| 453 | 3-methoxy-4-{6-[(2,2,6,6-tetramethylpiperidin-4-yl)oxy]pyridazin-3-yl}phenol |
| 454 | 3-[2-methoxy-4-(4-nitro-1H-pyrazol-1-yl)phenyl]-6-[(2,2,6,6-tetramethylpiperidin-4-yl)oxy]pyridazine |
| 455 | 4-{6-[(2,2,6,6-tetramethylpiperidin-4-yl)oxy]pyridazin-3-yl}benzene-1,3-diol |
| 456[1] | 6-[2-chloro-4-(1H-pyrazol-4-yl)phenyl]-N-methyl-N-(2,2,6,6-tetramethylpiperidin-4-yl)pyridazin-3-amine |
| 457 | 2-(1H-pyrazol-4-yl)-4-{6-[(2,2,6,6-tetramethylpiperidin-4-yl)oxy]pyridazin-3-yl}pyrimidin-5-amine |
| 458[1] | 3-[2,6-difluoro-4-(1H-pyrazol-4-yl)phenyl]-6-[(2,2,6,6-tetramethylpiperidin-4-yl)oxy]pyridazine |
| 459 | 2-[6-(2,6-diazaspiro[3.4]oct-2-yl)pyridazin-3-yl]-5-(1H-pyrazol-4-yl)phenol |
| 460[1] | 3-{6-[methyl(2,2,6,6-tetramethylpiperidin-4-yl)amino]pyridazin-3-yl}-6-(1H-pyrazol-4-yl)pyridin-2-ol |
| 461 | 6-(1H-pyrazol-4-yl)-3-{6-[(2,2,6,6-tetramethylpiperidin-4-yl)oxy]pyridazin-3-yl}pyridin-2-ol |
| 462[1] | N,2,2,6,6-pentamethyl-N-{5-[3-(1H-pyrazol-4-y1)phenoxy]-1,3,4-thiadiazol-2-yl}piperidin-4-amine |
| 463[1] | N,2,2,6,6-pentamethyl-N-{5-[4-(1H-pyrazol-4-yl)phenoxy]-1,3,4-thiadiazol-2-yl}piperidin-4-amine |
| 464[1] | 3-[2-(difluoromethyl)-4-(1H-pyrazol-4-yl)phenyl]-6-[(2,2,6,6-tetramethylpiperidin-4-yl)oxy]pyridazine and |
| 465[1] | 6-[2-(difluoromethyl)-4-(1H-pyrazol-4-yl)phenyl]-N-methyl-N-(2,2,6,6-tetramethylpiperidin-4-yl')pyridazin-3-amine | wherein a form of the compound is selected from the group consisting of a prodrug, salt, hydrate, solvate, clathrate, isotopologue, racemate, enantiomer, diastereomer, stereoisomer, polymorph and tautomer form thereof.

In one aspect, the compound of Formula (I) or a form thereof includes a compound selected from the group consisting of:

| | |
|---|---|
| 411[1] | 2-{6-[(1R,5S)-8-azabicyclo[3.2.1]oct-3-yl(methyl)amino]pyridazin-3-yl}-5-(1H-pyrazol-4-yl)phenol |
| 412[1] | 2-[6-((1R,5S)-8-azabicyclo[3.2.1]oct-3-ylamino)pyridazin-3-yl]-5-(1H-pyrazol-4-yl)phenol |
| 413[1] | 5-(1H-pyrazol-4-yl)-2-{6-[(2,2,6,6-tetramethylpiperidin-4-yl)amino]pyridazin-3-yl}phenol |
| 414 | 5-(1-methyl-1H-pyrazol-4-yl)-2-{6-[(2,2,6,6-tetramethylpiperidin-4-yl)oxy]pyridazin-3-yl}phenol |
| 415[1] | 2-[6-((1R,5S)-8-azabicyclo[3.2.1]oct-3-yloxy)pyridazin-3-yl]-5-(1H-pyrazol-4-yl)phenol |
| 416 | 5-(5-methyl-1H-pyrazol-4-yl)-2-{6-[methyl(2,2,6,6-tetramethylpiperidin-4-yl)amino]pyridazin-3-yl}phenol |
| 417 | 5-(1H-imidazol-1-yl)-2-{6-[(2,2,6,6-tetramethylpiperidin-4-yl)oxy]pyridazin-3-yl}phenol |
| 418 | 5-(5-methyl-1H-pyrazol-4-yl)-2-{6-[(2,2,6,6-tetramethylpiperidin-4-yl)oxy]pyridazin-3-yl}phenol |
| 419[1] | 2-{6-[methyl(2,2,6,6-tetramethylpiperidin-4-yl)amino]pyridazin-3-yl}-5-(4-nitro-1H-pyrazol-1-yl)phenol |
| 420 | 6-[2-methoxy-4-(4-nitro-1H-pyrazol-1-yl)phenyl]-N-methyl-N-(2,2,6,6-tetramethylpiperidin-4-yl)pyridazin-3-amine |
| 421 | 5-(4-amino-1H-pyrazol-1-yl)-2-{6-[(2,2,6,6-tetramethylpiperidin-4-yl)oxy]pyridazin-3-yl}phenol |
| 422[1] | 2-[6-(1-methyl-1,2,3,6-tetrahydropyridin-4-yl)pyridazin-3-yl]-5-(1H-pyrazol-4-yl)phenol |
| 423 | 5-(4-nitro-1H-pyrazol-1-yl)-2-{6-[(2,2,6,6-tetramethylpiperidin-4-yl)oxy]pyridazin-3-yl}phenol |

-continued

| | |
|---|---|
| 424[1] | 5-(1H-pyrazol-4-yl)-2-[6-(1,2,3,6-tetrahydropyridin-4-yl)pyridazin-3-yl]phenol |
| 425[1] | 2-[6-(1-ethyl-1,2,3,6-tetrahydropyridin-4-yl)pyridazin-3-yl]-5-(1H-pyrazol-4-yl)phenol |
| 426[1] | 2-{6-[methyl(piperidin-4-yl)amino]pyridazin-3-yl}-5-(1H-pyrazol-4-yl)phenol |
| 427[1] | 2-[6-(piperidin-4-ylamino)pyridazin-3-yl]-5-(1H-pyrazol-4-yl)phenol |
| 428[1] | 6-[2,5-difluoro-4-(1H-pyrazol-4-yl)phenyl]-N-methyl-N-(2,2,6,6-tetramethylpiperidin-4-yl)pyridazin-3-amine |
| 429[1] | 2-[6-(8-azabicyclo[3.2.1]oct-2-en-3-yl)pyridazin-3-yl]-5-(1H-pyrazol-4-yl)phenol |
| 430[1] | 6-[2,3-difluoro-4-(1H-pyrazol-4-yl)phenyl]-N-methyl-N-(2,2,6,6-tetramethylpiperidin-4-yl)pyridazin-3-amine |
| 431[1] | 3-[2,5-difluoro-4-(1H-pyrazol-4-yl)phenyl]-6-[(2,2,6,6-tetramethylpiperidin-4-yl)oxy]pyridazine |
| 432 | 2-[6-(piperidin-4-yloxy)pyridazin-3-yl]-5-(1H-pyrazol-4-yl)phenol |
| 433[1] | 2-{6-[(1R,5S)-8-azabicyclo[3.2.1]oct-3-ylamino]pyridazin-3-yl}-5-(1H-pyrazol-4-yl)phenol |
| 434[1] | 6-[2-methoxy-6-(1H-pyrazol-4-yl)pyridin-3-yl]-N-methyl-N-(2,2,6,6-tetramethylpiperidin-4-yl)pyridazin-3-amine |
| 435 | 3-[4-(1H-pyrazol-4-yl)phenyl]-6-[(2,2,6,6-tetramethylpiperidin-4-yl)oxy]pyridazine |
| 436[1] | 2-{6-[(2,6-dimethylpiperidin-4-yl)oxy]pyridazin-3-yl}-5-(1H-pyrazol-4-yl)phenol |
| 437[1] | 3-[2-fluoro-4-(1H-pyrazol-4-yl)phenyl]-6-[(2,2,6,6-tetramethylpiperidin-4-yl)oxy]pyridazine |
| 438 | 3-[4-(1-methyl-1H-pyrazol-4-yl)thiophen-2-yl]-6-[(2,2,6,6-tetramethylpiperidin-4-yl)oxy]pyridazine |
| 439[1] | 2-[6-(2,7-diazaspiro[3.5]non-2-yl)pyridazin-3-yl]-5-(1H-pyrazol-4-yl)phenol |
| 440 | 3-fluoro-4-{6-[methyl(2,2,6,6-tetramethylpiperidin-4-yl)amino]pyridazin-3-yl}phenol |
| 441 | 2-{6-[(2,6-dimethylpiperidin-4-yl)oxy]pyridazin-3-yl}-5-(1H-pyrazol-1-yl)phenol |
| 442 | N-methyl-6-(2-methyl-2H-indazol-5-yl)-N-(2,2,6,6-tetramethylpiperidin-4-yl)pyridazin-3-amine |
| 443 | 2-methyl-5-{6-[(2,2,6,6-tetramethylpiperidin-4-yl)oxy]pyridazin-3-yl}-2H-indazole |
| 444 | 3-(4-chloro-2-methoxyphenyl)-6-[(2,2,6,6-tetramethylpiperidin-4-yl)oxy]pyridazine |
| 445 | N-methyl-6-(2-methylpyrazolo[1,5-a]pyridin-3-yl)-N-(2,2,6,6-tetramethylpiperidin-4-yl)pyridazin-3-amine |
| 446 | 6-{6-[(2,2,6,6-tetramethylpiperidin-4-yl)oxy]pyridazin-3-yl}imidazo[1,2-a]pyridine |
| 447 | 3-[2-methoxy-4-(1H-pyrazol-1-yl)phenyl]-6-[(2,2,6,6-tetramethylpiperidin-4-yl)oxy]pyridazine |
| 448[1] | 3-[5-(1H-pyrazol-4-yl)thiophen-2-yl]-6-[(2,2,6,6-tetramethylpiperidin-4-yl)oxy]pyridazine |
| 449 | 3-[5-(1-methyl-1H-pyrazol-4-yl)thiophen-2-yl]-6-[(2,2,6,6-tetramethylpiperidin-4-yl)oxy]pyridazine |
| 450[1] | 3-[4-(1H-pyrazol-4-yl)thiophen-2-yl]-6-[(2,2,6,6-tetramethylpiperidin-4-yl)oxy]pyridazine |
| 451 | 5-(3,5-dimethyl-1H-pyrazol-4-yl)-2-{6-[(2,2,6,6-tetramethylpiperidin-4-yl)oxy]pyridazin-3-yl}phenol |
| 452 | 6-[2-fluoro-4-(1H-pyrazol-4-yl)phenyl]-N-methyl-N-(2,2,6,6-tetramethylpiperidin-4-yl)pyridazin-3-amine |
| 453 | 3-methoxy-4-{6-[(2,2,6,6-tetramethylpiperidin-4-yl)oxy]pyridazin-3-yl}phenol |
| 454 | 3-[2-methoxy-4-(4-nitro-1H-pyrazol-1-yl)phenyl]-6-[(2,2,6,6-tetramethylpiperidin-4-yl)oxy]pyridazine |
| 455 | 4-{6-[(2,2,6,6-tetramethylpiperidin-4-yl)oxy]pyridazin-3-yl}benzene-1,3-diol |
| 456[1] | 6-[2-chloro-4-(1H-pyrazol-4-yl)phenyl]-N-methyl-N-(2,2,6,6-tetramethylpiperidin-4-yl)pyridazin-3-amine |
| 457 | 2-(1H-pyrazol-4-yl)-4-{6-[(2,2,6,6-tetramethylpiperidin-4-yl)oxy]pyridazin-3-yl}pyrimidin-5-amine |
| 458[1] | 3-[2,6-difluoro-4-(1H-pyrazol-4-yl)phenyl]-6-[(2,2,6,6-tetramethylpiperidin-4-yl)oxy]pyridazine |
| 459 | 2-[6-(2,6-diazaspiro[3.4]oct-2-yl)pyridazin-3-yl]-5-(1H-pyrazol-4-yl)phenol |
| 460[1] | 3-{6-[methyl(2,2,6,6-tetramethylpiperidin-4-yl)amino]pyridazin-3-yl}-6-(1H-pyrazol-4-yl)pyridin-2-ol |
| 461 | 6-(1H-pyrazol-4-yl)-3-{6-[(2,2,6,6-tetramethylpiperidin-4-yl)oxy]pyridazin-3-yl}pyridin-2-ol |
| 462[1] | N,2,2,6,6-pentamethyl-N-{5-[3-(1H-pyrazol-4-yl)phenoxy]-1,3,4-thiadiazol-2-yl}piperidin-4-amine |
| 463[1] | N,2,2,6,6-pentamethyl-N-{5-[4-(1H-pyrazol-4-yl)phenoxy]-1,3,4-thiadiazol-2-yl}piperidin-4-amine |
| 464[1] | 3-[2-(difluoromethyl)-4-(1H-pyrazol-4-yl)phenyl]-6-[(2,2,6,6-tetramethylpiperidin-4-yl)oxy]pyridazineand |
| 465[1] | 6-[2-(difluoromethyl)-4-(1H-pyrazol-4-yl)phenyl]-N-methyl-N-(2,2,6,6-tetramethylpiperidin-4-yl)pyridazin-3-amine | wherein a form of the compound is selected from the group consisting of a prodrug, salt, hydrate, solvate, clathrate, isotopologue, racemate, enantiomer, diastereomer, stereoisomer, polymorph and tautomer form thereof.

Another embodiment of the use of a compound salt of Formula (I) or a form thereof includes a method of use of a compound salt of Formula (I) or a form thereof for treating or ameliorating HD in a subject in need thereof, comprising administering an effective amount of the compound salt of Formula (I) or a form thereof to the subject, selected from the group consisting of:

| Cpd | Name |
|---|---|
| 32 | 2-(6-(methyl(2,2,6,6-tetramethylpiperidin-4-yl)amino)pyridazin-3-yl)-4-(trifluoromethyl)phenol hydrochloride |
| 53 | 2-(6-(methyl(2,2,6,6-tetramethylpiperidin-4-yl)amino)pyridazin-3-yl)-4-(1H-pyrazol-1-yl)phenol hydrochloride |
| 65 | 2-(6-piperazin-1-yl-pyridazin-3-yl)-5-1H-pyrazol-1-yl-phenol hydrochloride |
| 82 | 3-(6-(piperazin-1-yl)pyridazin-3-yl)naphthalene-2,7-diol trifluoroacetate |
| 86 | 3-(6-(1,2,3,6-tetrahydropyridin-4-yl)pyridazin-3-yl)naphthalene-2,7-diol trifluoroacetate |
| 88 | 3-(6-(1-methyl-1,2,3,6-tetrahydropyridin-4-yl)pyridazin-3-yl)naphthalene-2,7-diol trifluoroacetate |
| 89 | 3-(6-(piperidin-4-yl)pyridazin-3-yl)naphthalene-2,7-diol trifluoroacetate |
| 151 | 6-hydroxy-5-(6-(methyl(2,2,6,6-tetramethylpiperidin-4-yl)amino)pyridazin-3-yl)-2,3-dihydro-1H-inden-1-one oxime hydrochloride |
| 153 | 2-amino-6-(6-(methyl(2,2,6,6-tetramethylpiperidin-4-yl)amino)pyridazin-3-yl)-8H-indeno[1,2-d]thiazol-5-ol hydrochloride |
| 154 | 9-(6-(methyl(2,2,6,6-tetramethylpiperidin-4-yl)amino)pyridazin-3-yl)-5,6-dihydroimidazo[5,1-a] isoquinolin-8-ol hydrochloride |
| 160 | 3-fluoro-5-(2-methoxypyridin-4-yl)-2-(6-(methyl(2,2,6,6-tetramethylpiperidin-4-yl)amino)pyridazin-3-yl)phenol hydrochloride |
| 161 | 4-(3-fluoro-5-hydroxy-4-(6-(methyl(2,2,6,6-tetramethylpiperidin-4-yl)amino)pyridazin-3-yl)phenyl)pyridin-2(1H)-one hydrochloride |
| 162 | 4-(3-fluoro-5-hydroxy-4-(6-(methyl(2,2,6,6-tetramethylpiperidin-4-yl)amino)pyridazin-3-yl)phenyl)-1-methylpyridin-2(1H)-one hydrochloride |
| 163 | 5-(3-fluoro-5-hydroxy-4-(6-(methyl(2,2,6,6-tetramethylpiperidin-4-yl)amino)pyridazin-3-yl)phenyl)-1-methylpyridin-2(1H)-one hydrochloride |
| 164 | 3-fluoro-5-(1H-pyrazol-4-yl)-2-(6-((2,2,6,6-tetramethylpiperidin-4-yl)oxy)pyridazin-3-yl)phenol hydrochloride |
| 165 | 5-chloro-3-fluoro-2-(6-(methyl(2,2,6,6-tetramethylpiperidin-4-yl)amino)pyridazin-3-yl)phenol hydrochloride |
| 166 | 3-fluoro-2-(6-(methyl(2,2,6,6-tetramethylpiperidin-4-yl)amino)pyridazin-3-yl)-5-(1H-pyrazol-4-yl)phenol hydrochloride |
| 167 | 3-fluoro-2-(6-(methyl(2,2,6,6-tetramethylpiperidin-4-yl)amino)pyridazin-3-yl)-5-(1-methyl-1H-pyrazol-4-yl)phenol hydrochloride |
| 226 | 3-(1H-imidazol-1-yl)-6-(6-(methyl(2,2,6,6-tetramethylpiperidin-4-yl)amino)pyridazin-3-yl)quinolin-7-ol hydrochloride |
| 227 | 6-(6-(methyl(2,2,6,6-tetramethylpiperidin-4-yl)amino)pyridazin-3-yl)quinoline-3,7-diol formate |
| 231 | 7-hydroxy-1-methyl-6-(6-(methyl(2,2,6,6-tetramethylpiperidin-4-yl)amino)pyridazin-3-yl)quinolin-2(1H)-one hydrochloride |
| 238 | 4-methoxy-7-(6-(methyl(2,2,6,6-tetramethylpiperidin-4-yl)amino)pyridazin-3-yl)quinolin-6-ol formate |
| 239 | 7-(6-(methyl(2,2,6,6-tetramethylpiperidin-4-yl)amino)pyridazin-3-yl)quinoxalin-6-ol hydrochloride |
| 254 | 2-methyl-6-(6-(methyl(2,2,6,6-tetramethylpiperidin-4-yl)amino)pyridazin-3-yl)-4-(tetrahydro-2H-pyran-4-yl)quinolin-7-ol formate |
| 256 | 4-(dimethylamino)-6-(6-(methyl(2,2,6,6-tetramethylpiperidin-4-yl)amino)pyridazin-3-yl)-quinolin-7-ol formate |
| 281 | 6-hydroxy-2-methyl-7-(6-(methyl(2,2,6,6-tetramethylpiperidin-4-yl)amino)pyridazin-3-yl)isoquinolin-1(2H)-one hydrochloride |
| 322 | 3-(5-(methyl(2,2,6,6-tetramethylpiperidin-4-yl)amino)-1,3,4-thiadiazol-2-yl)naphthalen-2-ol hydrobromide |
| 342 | N-methyl-5-(5-(1-methyl-1H-pyrazol-4-yl)pyridin-2-yl)-N-(2,2,6,6-tetramethylpiperidin-4-yl)-1,3,4-thiadiazol-2-amine hydrochloride |
| 396 | 3-fluoro-2-(5-((3aR,6aS)-hexahydropyrrolo[3,4-c]pyrrol-2(1H)-yl)-1,3,4-thiadiazol-2-yl)-5-(1H-pyrazol-4-yl)phenol dihydrochloride |
| 405 | 2-(2-chloro-4-(1H-pyrazol-4-yl)phenyl)-5-((3aR,6aS)-hexahydropyrrolo[3,4-c]pyrrol-2(1H)-yl)-1,3,4-thiadiazole hydrochloride |
| 406 | 2-(2-chloro-4-(1H-pyrazol-4-yl)phenyl)-5-(2,7-diazaspiro[4.5]decan-2-yl)-1,3,4-thiadiazole hydrochloride |
| 407 | (R)-(4-(5-(2-chloro-4-(1H-pyrazol-4-yl)phenyl)-1,3,4-thiadiazol-2-yl)piperazin-2-yl)methanol hydrochloride |
| 411 | 2-{6-[8-azabicyclo[3.2.1]oct-3-yl(methyl)amino]pyridazin-3-yl}-5-(1H-pyrazol-4-yl)phenol hydrochloride |
| 412 | 2-[6-(8-azabicyclo[3.2.1]oct-3-ylamino)pyridazin-3-yl]-5-(1H-pyrazol-4-yl)phenol hydrochloride |
| 413 | 5-(1H-pyrazol-4-yl)-2-{6-[(2,2,6,6-tetramethylpiperidin-4-yl)amino]pyridazin-3-yl}phenol hydrochloride |
| 415 | 2-[6-(8-azabicyclo[3.2.1]oct-3-yloxy)pyridazin-3-yl]-5-(1H-pyrazol-4-yl)phenol hydrochloride |
| 419 | 2-{6-[methyl(2,2,6,6-tetramethylpiperidin-4-yl)amino]pyridazin-3-yl}-5-(4-nitro-1H-pyrazol-1-yl)phenol dihydrochloride |
| 422 | 2-[6-(1-methyl-1,2,3,6-tetrahydropyridin-4-yl)pyridazin-3-yl]-5-(1H-pyrazol-4-yl)phenol trihydrochloride |
| 424 | 5-(1H-pyrazol-4-yl)-2-[6-(1,2,3,6-tetrahydropyridin-4-yl)pyridazin-3-yl]phenol trihydrochloride |
| 425 | 2-[6-(1-ethyl-1,2,3,6-tetrahydropyridin-4-yl)pyridazin-3-yl]-5-(1H-pyrazol-4-yl)phenol trihydrochloride |
| 426 | 2-{6-[methyl(piperidin-4-yl)amino]pyridazin-3-yl}-5-(1H-pyrazol-4-yl)phenol tetrahydrochloride |
| 427 | 2-[6-(piperidin-4-ylamino)pyridazin-3-yl]-5-(1H-pyrazol-4-yl)phenol tetrahydrochloride |

| Cpd | Name |
|---|---|
| 428 | 6-[2,5-difluoro-4-(1H-pyrazol-4-yl)phenyl]-N-methyl-N-(2,2,6,6-tetramethylpiperidin-4-yl)pyridazin-3-amine tetrahydrochloride |
| 429 | 2-[6-(8-azabicyclo[3.2.1]oct-2-en-3-yl)pyridazin-3-yl]-5-(1H-pyrazol-4-yl)phenol hydrochloride |
| 430 | 6-[2,3-difluoro-4-(1H-pyrazol-4-yl)phenyl]-N-methyl-N-(2,2,6,6-tetramethylpiperidin-4-yl)pyridazin-3-amine hydrochloride |
| 431 | 3-[2,5-difluoro-4-(1H-pyrazol-4-yl)phenyl]-6-[(2,2,6,6-tetramethylpiperidin-4-yl)oxy]pyridazine trihydrochloride |
| 433 | 2-{6-[(1R,5S)-8-azabicyclo[3.2.1]oct-3-ylamino]pyridazin-3-yl}-5-(1H-pyrazol-4-yl)phenol hydrochloride |
| 434 | 6-[2-methoxy-6-(1H-pyrazol-4-yl)pyridin-3-yl]-N-methyl-N-(2,2,6,6-tetramethylpiperidin-4-yl)pyridazin-3-amine hydrochloride |
| 436 | 2-{6-[(2,6-dimethylpiperidin-4-yl)oxy]pyridazin-3-yl}-5-(1H-pyrazol-4-yl)phenol trihydrochloride |
| 437 | 3-[2-fluoro-4-(1H-pyrazol-4-yl)phenyl]-6-[(2,2,6,6-tetramethylpiperidin-4-yl)oxy]pyridazine hydrochloride |
| 439 | 2-[6-(2,7-diazaspiro[3.5]non-2-yl)pyridazin-3-yl]-5-(1H-pyrazol-4-yl)phenol tetrahydrochloride |
| 448 | 3-[5-(1H-pyrazol-4-yl)thiophen-2-yl]-6-[(2,2,6,6-tetramethylpiperidin-4-yl)oxy]pyridazine hydrochloride |
| 450 | 3-[4-(1H-pyrazol-4-yl)thiophen-2-yl]-6-[(2,2,6,6-tetramethylpiperidin-4-yl)oxy]pyridazine hydrochloride |
| 456 | 6-[2-chloro-4-(1H-pyrazol-4-yl)phenyl]-N-methyl-N-(2,2,6,6-tetramethylpiperidin-4-yl)pyridazin-3-amine trihydrochloride |
| 458 | 3-[2,6-difluoro-4-(1H-pyrazol-4-yl)phenyl]-6-[(2,2,6,6-tetramethylpiperidin-4-yl)oxy]pyridazine trihydrochloride |
| 460 | 3-{6-[methyl(2,2,6,6-tetramethylpiperidin-4-yl)amino]pyridazin-3-yl}-6-(1H-pyrazol-4-yl)pyridin-2-ol hydrochloride |
| 462 | N,2,2,6,6-pentamethyl-N-{5-[3-(1H-pyrazol-4-yl)phenoxy]-1,3,4-thiadiazol-2-yl}piperidin-4-amine hydrochloride |
| 463 | N,2,2,6,6-pentamethyl-N-{5-[4-(1H-pyrazol-4-yl)phenoxy]-1,3,4-thiadiazol-2-yl}piperidin-4-amine hydrochloride |
| 464 | 3-[2-(difluoromethyl)-4-(1H-pyrazol-4-yl)phenyl]-6-[(2,2,6,6-tetramethylpiperidin-4-yl)oxy]pyridazine hydrochloride and |
| 465 | 6-[2-(difluoromethyl)-4-(1H-pyrazol-4-yl)phenyl]-N-methyl-N-(2,2,6,6-tetramethylpiperidin-4-yl)pyridazin-3-amine hydrochloride | wherein a form of the compound salt is selected from the group consisting of a prodrug, hydrate, solvate, clathrate, isotopologue, racemate, enantiomer, diastereomer, stereoisomer, polymorph and tautomer form thereof.

In one aspect, the compound salt of Formula (I) or a form thereof includes a compound salt selected from the group consisting of:

| | |
|---|---|
| 411 | 2-{6-[8-azabicyclo[3.2.1]oct-3-yl(methyl)amino]pyridazin-3-yl}-5-(1H-pyrazol-4-yl)phenol hydrochloride |
| 412 | 2-[6-(8-azabicyclo[3.2.1]oct-3-ylamino)pyridazin-3-yl]-5-(1H-pyrazol-4-yl)phenol hydrochloride |
| 413 | 5-(1H-pyrazol-4-yl)-2-{6-[(2,2,6,6-tetramethylpiperidin-4-yl)amino]pyridazin-3-yl}phenol hydrochloride |
| 415 | 2-[6-(8-azabicyclo[3.2.1]oct-3-yloxy)pyridazin-3-yl]-5-(1H-pyrazol-4-yl)phenol hydrochloride |
| 419 | 2-{6-[methyl(2,2,6,6-tetramethylpiperidin-4-yl)amino]pyridazin-3-yl}-5-(4-nitro-1H-pyrazol-1-yl)phenol dihydrochloride |
| 422 | 2-[6-(1-methyl-1,2,3,6-tetrahydropyridin-4-yl)pyridazin-3-yl]-5-(1H-pyrazol-4-yl)phenol trihydrochloride |
| 424 | 5-(1H-pyrazol-4-yl)-2-[6-(1,2,3,6-tetrahydropyridin-4-yl)pyridazin-3-yl]phenol trihydrochloride |
| 425 | 2-[6-(1-ethyl-1,2,3,6-tetrahydropyridin-4-yl)pyridazin-3-yl]-5-(1H-pyrazol-4-yl)phenol trihydrochloride |
| 426 | 2-{6-[methyl(piperidin-4-yl)amino]pyridazin-3-yl}-5-(1H-pyrazol-4-yl)phenol tetrahydrochloride |
| 427 | 2-[6-(piperidin-4-ylamino)pyridazin-3-yl]-5-(1H-pyrazol-4-yl)phenol tetrahydrochloride |
| 428 | 6-[2,5-difluoro-4-(1H-pyrazol-4-yl)phenyl]-N-methyl-N-(2,2,6,6-tetramethylpiperidin-4-yl)pyridazin-3-amine tetrahydrochloride |
| 429 | 2-[6-(8-azabicyclo[3.2.1]oct-2-en-3-yl)pyridazin-3-yl]-5-(1H-pyrazol-4-yl)phenol hydrochloride |
| 430 | 6-[2,3-difluoro-4-(1H-pyrazol-4-yl)phenyl]-N-methyl-N-(2,2,6,6-tetramethylpiperidin-4-yl)pyridazin-3-amine hydrochloride |
| 431 | 3-[2,5-difluoro-4-(1H-pyrazol-4-yl)phenyl]-6-[(2,2,6,6-tetramethylpiperidin-4-yl)oxy]pyridazine trihydrochloride |
| 433 | 2-{6-[(1R,5S)-8-azabicyclo[3.2.1]oct-3-ylamino]pyridazin-3-yl}-5-(1H-pyrazol-4-yl)phenol hydrochloride |
| 434 | 6-[2-methoxy-6-(1H-pyrazol-4-yl)pyridin-3-yl]-N-methyl-N-(2,2,6,6-tetramethylpiperidin-4-yl)pyridazin-3-amine hydrochloride |

-continued

| | |
|---|---|
| 436 | 2-{6-[(2,6-dimethylpiperidin-4-yl)oxy]pyridazin-3-yl}-5-(1H-pyrazol-4-yl)phenol trihydrochloride |
| 437 | 3-[2-fluoro-4-(1H-pyrazol-4-yl)phenyl]-6-[(2,2,6,6-tetramethylpiperidin-4-yl)oxy]pyridazine hydrochloride |
| 439 | 2-[6-(2,7-diazaspiro[3.5]non-2-yl)pyridazin-3-yl]-5-(1H-pyrazol-4-yl)phenol tetrahydrochloride |
| 448 | 3-[5-(1H-pyrazol-4-yl)thiophen-2-yl]-6-[(2,2,6,6-tetramethylpiperidin-4-yl)oxy]pyridazine hydrochloride |
| 450 | 3-[4-(1H-pyrazol-4-yl)thiophen-2-yl]-6-[(2,2,6,6-tetramethylpiperidin-4-yl)oxy]pyridazine hydrochloride |
| 456 | 6-[2-chloro-4-(1H-pyrazol-4-yl)phenyl]-N-methyl-N-(2,2,6,6-tetramethylpiperidin-4-yl)pyridazin-3-amine trihydrochloride |
| 458 | 3-[2,6-difluoro-4-(1H-pyrazol-4-yl)phenyl]-6-[(2,2,6,6-tetramethylpiperidin-4-yl)oxy]pyridazine trihydrochloride |
| 460 | 3-{6-[methyl(2,2,6,6-tetramethylpiperidin-4-yl)amino]pyridazin-3-yl}-6-(1H-pyrazol-4-yl)pyridin-2-ol hydrochloride |
| 462 | N,2,2,6,6-pentamethyl-N-{5-[3-(1H-pyrazol-4-yl)phenoxy]-1,3,4-thiadiazol-2-yl}piperidin-4-amine hydrochloride |
| 463 | N,2,2,6,6-pentamethyl-N-{5-[4-(1H-pyrazol-4-yl)phenoxy]-1,3,4-thiadiazol-2-yl}piperidin-4-amine hydrochloride |
| 464 | 3-[2-(difluoromethyl)-4-(1H-pyrazol-4-yl)phenyl]-6-[(2,2,6,6-tetramethylpiperidin-4-yl)oxy]pyridazine hydrochloride and |
| 465 | 6-[2-(difluoromethyl)-4-(1H-pyrazol-4-yl)phenyl]-N-methyl-N-(2,2,6,6-tetramethylpiperidin-4-yl)pyridazin-3-amine hydrochloride | wherein a form of the compound salt is selected from the group consisting of a prodrug, hydrate, solvate, clathrate, isotopologue, racemate, enantiomer, diastereomer, stereoisomer, polymorph and tautomer form thereof.

Another embodiment of the present description includes a method of use of a compound of Formula (I) or a form thereof for treating or ameliorating HD in a subject in need thereof, comprising administering an effective amount of the compound of Formula (I) or a form thereof to the subject.

Another embodiment of the present description includes a method of use of a compound of Formula (I) or a form thereof for treating or ameliorating HD in a subject in need thereof, comprising administering an effective amount of the compound salt of Formula (I) or a form thereof to the subject.

Another embodiment of the present description includes a use of the compound of Formula (I) or a form thereof for treating or ameliorating HD in a subject in need thereof, comprising administering an effective amount of the compound of Formula (I) or a form thereof to the subject.

Another embodiment of the present description includes a use of the compound salt of Formula (I) or a form thereof for treating or ameliorating HD in a subject in need thereof, comprising administering an effective amount of the compound salt of Formula (I) or a form thereof to the subject.

Chemical Definitions

As used herein, the term "$C_{1-4}$alkyl" generally refers to saturated hydrocarbon radicals having from one to four carbon atoms in a straight or branched chain configuration, including, without limitation, methyl, ethyl, n-propyl, isopropyl, n-butyl, isobutyl, sec-butyl, tert-butyl, and the like. In some embodiments, $C_{1-4}$alkyl includes $C_{1-3}$alkyl, $C_{1-2}$alkyl, and the like. A $C_{1-4}$alkyl radical may be optionally substituted where allowed by available valences.

As used herein, the term "$C_{2-6}$alkenyl" generally refers to partially unsaturated hydrocarbon radicals having from two to five carbon atoms in a straight or branched chain configuration and one or more carbon-carbon double bonds therein, including, without limitation, ethenyl, allyl, propenyl and the like. In some embodiments, $C_{2-6}$alkenyl includes $C_{2-4}$alkenyl, $C_{2-3}$alkenyl, and the like. A $C_{2-6}$alkenyl radical may be optionally substituted where allowed by available valences.

As used herein, the term "$C_{1-4}$alkoxy" generally refers to saturated hydrocarbon radicals having from one to four carbon atoms in a straight or branched chain configuration of the formula: —O—$C_{1-4}$alkyl, including, without limitation, methoxy, ethoxy, n-propoxy, isopropoxy, n-butoxy, isobutoxy, sec-butoxy, tert-butoxy, and the like. In some embodiments, $C_{1-4}$alkoxy includes $C_{1-3}$alkoxy, $C_{1-2}$alkoxy and the like. A $C_{1-4}$alkoxy radical may be optionally substituted where allowed by available valences.

As used herein, the term "$C_{3-14}$cycloalkyl" generally refers to a saturated monocyclic, bicyclic or polycyclic hydrocarbon radical, including, without limitation, cyclopropyl, cyclobutyl, cyclopentyl, cyclohexyl, cycloheptyl, cyclooctyl, 1H-indanyl, indenyl, tetrahydro-naphthalenyl and the like. In some embodiments, $C_{3-14}$cycloalkyl includes $C_{3-10}$cycloalkyl, $C_{3-8}$cycloalkyl, $C_{3-7}$cycloalkyl, $C_{5-8}$cycloalkyl, $C_{9-10}$cycloalkyl and the like. A $C_{3-14}$cycloalkyl radical may be optionally substituted where allowed by available valences.

As used herein, the term "$C_{3-14}$cycloalkenyl" generally refers to a partially unsaturated monocyclic, bicyclic or polycyclic hydrocarbon radical having one or more chemically stable carbon-carbon double bonds therein, including, without limitation, cyclopropenyl, cyclobutenyl, cyclopentenyl, cyclohexenyl, cycloheptenyl, cyclooctenyl and the like. In some embodiments, $C_{3-14}$cycloalkenyl includes $C_{3-7}$cycloalkenyl, $C_{3-8}$cycloalkenyl, $C_{5-8}$cycloalkenyl, $C_{3-10}$cycloalkenyl and the like. A $C_{3-14}$cycloalkenyl radical may be optionally substituted where allowed by available valences.

As used herein, the term "aryl" generally refers to a monocyclic, bicyclic or polycyclic aromatic carbon atom ring structure radical, including, without limitation, phenyl, naphthyl, anthracenyl, fluorenyl, azulenyl, phenanthrenyl and the like. An aryl radical may be optionally substituted where allowed by available valences.

As used herein, the term "heteroaryl" generally refers to a monocyclic, bicyclic or polycyclic aromatic carbon atom ring structure radical in which one or more carbon atom ring members have been replaced, where allowed by structural stability, with one or more heteroatoms, such as an O, S or N atom, including, without limitation, furanyl, thienyl (also referred to as thiophenyl), pyrrolyl, pyrazolyl, imidazolyl, isoxazolyl, isothiazolyl, oxazolyl, thiazolyl, triazolyl, oxadiazolyl, thiadiazolyl, tetrazolyl, pyranyl, thiopyranyl, pyridinyl, pyrimidinyl, pyrazinyl, pyridazinyl, triazinyl, indolyl, indazolyl, indolizinyl, benzofuranyl, benzothienyl, benzimidazolyl, benzothiazolyl, benzooxazolyl, 9H-purinyl, quinoxalinyl, isoindolyl, quinolinyl, isoquinolinyl, quinazolinyl, acridinyl, phthalazinyl, imidazo[1,2-a]pyridinyl, imidazo[1,5-a]pyridinyl, imidazo[5,1-a]isoquinolinyl, 1,4-dihydroindeno[1,2-c]-1H-pyrazolyl, 2,3-dihydro-1H-inden-1-one, 2,3-dihydro-1H-indenyl, 3,4-dihydroquinolin-2(1H)-one, 5,6-dihydroimidazo[5,1-a]isoquinolinyl, 8H-indeno[1,2-d]thiazolyl, benzo[c][1,2,5]oxadiazolyl, benzo[d]oxazol-2(3H)-one, quinolin-2(1H)-one, quinazolin-4-(1H)-one, quinazoline-2,4(1H,3H)-dione, benzo-[d]oxazolyl, pyrazolo[1,5-a]pyridinyl, and the like. A heteroaryl radical may be optionally substituted on a carbon or nitrogen atom ring member where allowed by available valences.

As used herein, the term "heterocyclyl" generally refers to a saturated or partially unsaturated monocyclic, bicyclic or polycyclic carbon atom ring structure radical in which one or more carbon atom ring members have been replaced, where allowed by structural stability, with a heteroatom, such as an O, S or N atom, including, without limitation, oxiranyl, oxetanyl, azetidinyl, dihydrofuranyl, tetrahydrofuranyl, dihydrothienyl, tetrahydrothienyl, pyrrolinyl, pyrrolidinyl, dihydropyrazolyl, pyrazolinyl, pyrazolidinyl, dihydroimidazolyl, imidazolinyl, imidazolidinyl, isoxazolinyl, isoxazolidinyl, isothiazolinyl, isothiazolidinyl, oxazolinyl, oxazolidinyl, thiazolinyl, thiazolidinyl, triazolinyl, triazolidinyl, oxadiazolinyl, oxadiazolidinyl, thiadiazolinyl, thiadiazolidinyl, tetrazolinyl, tetrazolidinyl, dihydro-2H-pyranyl, dihydro-pyridinyl, tetrahydro-pyridinyl, 1,2,3,6-tetrahydropyridinyl, hexahydro-pyridinyl, dihydro-pyrimidinyl, tetrahydro-pyrimidinyl, 1,4,5,6-tetrahydropyrimidinyl, dihydro-pyrazinyl, tetrahydro-pyrazinyl, dihydro-pyridazinyl, tetrahydro-pyridazinyl, piperazinyl, piperidinyl, morpholinyl, thiomorpholinyl, dihydro-triazinyl, tetrahydro-triazinyl, hexahydro-triazinyl, 1,4-diazepanyl, dihydro-indolyl, indolinyl, tetrahydro-indolyl, dihydro-indazolyl, tetrahydro-indazolyl, dihydro-isoindolyl, dihydro-benzofuranyl, tetrahydro-benzofuranyl, dihydro-benzothienyl, tetrahydro-benzothienyl, dihydro-benzimidazolyl, tetrahydro-benzimidazolyl, dihydro-benzooxazolyl, 2,3-dihydrobenzo[d]oxazolyl, tetrahydro-benzooxazolyl, dihydro-benzooxazinyl, 3,4-dihydro-2H-benzo[b][1,4]oxazinyl, tetrahydro-benzooxazinyl, benzo[1,3]dioxolyl, benzo[1,4]dioxanyl, dihydro-purinyl, tetrahydro-purinyl, dihydro-quinolinyl, tetrahydro-quinolinyl, 1,2,3,4-tetrahydroquinolinyl, dihydro-isoquinolinyl, 3,4-dihydroisoquinolin-(1H)-yl, tetrahydro-isoquinolinyl, 1,2,3,4-tetrahydroisoquinolinyl, dihydro-quinazolinyl, tetrahydro-quinazolinyl, dihydro-quinoxalinyl, tetrahydro-quinoxalinyl, 1,2,3,4-tetrahydroquinoxalinyl, 1,3-dioxolanyl, 2,5-dihydro-1H-pyrrolyl, 4,5-dihydro-1H-imidazolyl, tetrahydro-2H-pyranyl, hexahydropyrrolo[3,4-b][1,4]oxazin-(2H)-yl, (4aR,7aS)-hexahydropyrrolo[3,4-b][1,4]oxazin-(4aH)-yl, 3,4-dihydro-2H-pyrido[3,2-b][1,4]oxazinyl, (cis)-octahydrocyclopenta[c]pyrrolyl, hexahydropyrrolo[3,4-b]pyrrol-(1H)-yl, (3aR,6aR)-hexahydropyrrolo[3,4-b]pyrrol-(1H)-yl, (3aR,6aS)-hexahydropyrrolo[3,4-c]pyrrol-(1H)-yl, 5H-pyrrolo[3,4-b]pyridin-(7H)-yl, 5,7-dihydro-6H-pyrrolo[3,4-b]pyridinyl, tetrahydro-1H-pyrrolo[3,4-b]pyridin-(2H,7H,7aH)-yl, hexahydro-1H-pyrrolo[3,4-b]pyridin-(2H)-yl, (4aR,7aR)-hexahydro-1H-pyrrolo[3,4-b]pyridin-(2H)-yl, octahydro-6H-pyrrolo[3,4-b]pyridinyl, 2,3,4,9-tetrahydro-1H-carbazolyl, 1,2,3,4-tetrahydropyrazino[1,2-a]indolyl, 2,3-dihydro-1H-pyrrolo[1,2-a]indolyl, (3aR,6aR)-hexahydrocyclopenta[c]pyrrol-(1H)-yl, (3aR,4R,6aS)-hexahydrocyclopenta[c]pyrrol-(1H)-yl, (3aR,4S,6aS)-hexahydrocyclopenta[c]pyrrol-(1H)-yl, (3aR,5r,6aS)-hexahydrocyclopenta[c]pyrrol-(1H)-yl, 1,3-dihydro-2H-isoindolyl, octahydro-2H-isoindolyl, (3aS)-1,3,3a,4,5,6-hexahydro-2H-isoindolyl, (3aR,4R,7aS)-1H-isoindol-(3H,3aH,4H,5H,6H,7H,7aH)-yl, (3aR,7aS)-octahydro-2H-isoindolyl, (3aR,4R,7aS)-octahydro-2H-isoindolyl, (3aR,4S,7aS)-octahydro-2H-isoindolyl, 2,5-diazabicyclo[2.2.1]heptanyl, 2-azabicyclo[2.2.1]heptenyl, 3-azabicyclo[3.1.0]hexanyl, 3,6-diazabicyclo[3.1.0]hexanyl, (1R,5S)-3-azabicyclo[3.1.0]hexanyl, (1S,5R)-3-azabicyclo[3.2.0]heptanyl, 5-azaspiro[2.4]heptanyl, 2,6-diazaspiro[3.3]heptanyl, 2,5-diazaspiro[3.4]octanyl, 2,6-diazaspiro[3.4]octanyl, 2,7-diazaspiro[3.5]nonanyl, 2,7-diazaspiro[4.4]nonanyl, 2-azaspiro[4.5]decanyl, 2,8-diazaspiro[4.5]decanyl, 3,6-diazabicyclo[3.2.1]octyl, 1,4-dihydroindeno[1,2-c]pyrazolyl, dihydropyranyl, dihydropyridinyl, dihydroquinolinyl, 8H-indeno[1,2-d]thiazolyl, tetrahydroimidazo[1,2-a]pyridinyl, pyridin-2(1H)-one, (1R,5S)-8-azabicyclo[3.2.1]octyl, 8-azabicyclo[3.2.1]oct-2-enyl and the like. A heterocyclyl radical may be optionally substituted on a carbon or nitrogen atom ring member where allowed by available valences.

As used herein, the term "$C_{2-4}$alkenyl-amino-carbonyl" refers to a radical of the formula: —C(=O)—NH—$C_{2-4}$alkenyl.

As used herein, the term "$C_{1-4}$alkoxy-$C_{1-4}$alkoxy" refers to a radical of the formula: —O—$C_{1-4}$alkyl-O—$C_{1-4}$alkyl.

As used herein, the term "$C_{1-4}$alkoxy-carbonyl" refers to a radical of the formula: —C(=O)—O—$C_{1-4}$alkyl.

As used herein, the term "$C_{1-4}$alkoxy-carbonyl-amino" refers to a radical of the formula: —NH—C(=O)—O—$C_{1-4}$alkyl.

As used herein, the term "$C_{1-4}$alkoxy-carbonyl-amino-$C_{1-4}$alkoxy" refers to a radical of the formula: —O—$C_{1-4}$alkyl-NH—C(=O)—O—$C_{1-4}$alkyl.

As used herein, the term "$C_{1-4}$alkyl-$C_{1-4}$alkoxy" refers to a radical of the formula: —O—$C_{1-4}$alkyl-$C_{1-4}$alkyl.

As used herein, the term "$C_{1-4}$alkyl-amino" refers to a radical of the formula: —NH—$C_{1-4}$alkyl.

As used herein, the term "($C_{1-4}$alkyl)$_2$-amino" refers to a radical of the formula: —N($C_{1-4}$alkyl)$_2$.

As used herein, the term "$C_{1-4}$alkyl-amino-$C_{1-4}$alkoxy" refers to a radical of the formula: —O—$C_{1-4}$alkyl-NH—$C_{1-4}$alkyl.

As used herein, the term "($C_{1-4}$alkyl)$_2$-amino-$C_{1-4}$alkoxy" refers to a radical of the formula: —O—$C_{1-4}$alkyl-N($C_{1-4}$alkyl)$_2$.

As used herein, the term "$C_{1-4}$alkyl-amino-$C_{1-4}$alkyl" refers to a radical of the formula: —$C_{1-4}$alkyl-NH—$C_{1-4}$alkyl.

As used herein, the term "($C_{1-4}$alkyl)$_2$-amino-$C_{1-4}$alkyl" refers to a radical of the formula: —$C_{1-4}$alkyl-N($C_{1-4}$alkyl)$_2$.

As used herein, the term "$C_{1-4}$alkyl-amino-carbonyl" refers to a radical of the formula: —C(=O)—NH—$C_{1-4}$alkyl.

As used herein, the term "($C_{1-4}$alkyl)$_2$-amino-carbonyl" refers to a radical of the formula: —C(=O)—N($C_{1-4}$alkyl)$_2$.

As used herein, the term "$C_{1-4}$alkyl-amino-carbonyl-$C_{1-4}$alkyl" refers to a radical of the formula: —$C_{1-4}$alkyl-C(=O)—NH—$C_{1-4}$alkyl.

As used herein, the term "$(C_{1-4}alkyl)_2$-amino-carbonyl-$C_{1-4}$alkyl" refers to a radical of the formula: —$C_{1-4}$alkyl-C(=O)—N($C_{1-4}$alkyl)$_2$.

As used herein, the term "$C_{1-4}$alkyl-carbonyl" refers to a radical of the formula: —C(=O)—$C_{1-4}$alkyl.

As used herein, the term "$C_{1-4}$alkyl-carbonyl-amino" refers to a radical of the formula: —NH—C(=O)—$C_{1-4}$alkyl.

As used herein, the term "$C_{1-4}$alkyl-carbonyl-amino-$C_{1-4}$alkoxy" refers to a radical of the formula: —O—$C_{1-4}$alkyl-NH—C(=O)—$C_{1-4}$alkyl.

As used herein, the term "$C_{1-4}$alkyl-carbonyl-amino-$C_{1-4}$alkyl" refers to a radical of the formula: —$C_{1-4}$alkyl-NH—C(=O)—$C_{1-4}$alkyl.

As used herein, the term "amino" refers to a radical of the formula: —$NH_2$. As used herein, the term "amino-$C_{1-4}$alkoxy" refers to a radical of the formula: —O—$C_{1-4}$alkyl-$NH_2$.

As used herein, the term "amino-$C_{1-4}$alkyl" refers to a radical of the formula: —$C_{1-4}$alkyl-$NH_2$.

As used herein, the term "amino-carbonyl" refers to a radical of the formula: —C(=O)—$NH_2$.

As used herein, the term "cyano" refers to a radical of the formula: —CN.

As used herein, the term "$C_{3-7}$cycloalkyl-$C_{1-4}$alkoxy" refers to a radical of the formula: —O—$C_{1-4}$alkyl-$C_{3-7}$cycloalkyl.

As used herein, the term "halo-$C_{1-4}$alkoxy" refers to a radical of the formula: —O—$C_{1-4}$alkyl-halo, wherein $C_{1-4}$alkyl may be partially or completely substituted where allowed by available valences with one or more halogen atoms. In some embodiments, halo-$C_{1-4}$alkoxy includes halo-$C_{1-6}$alkoxy, halo-$C_{1-4}$alkoxy and the like.

As used herein, the term "halo-$C_{1-4}$alkyl" refers to a radical of the formula: —$C_{1-4}$alkyl-halo, wherein $C_{1-4}$alkyl may be partially or completely substituted where allowed by available valences with one or more halogen atoms. In some embodiments, halo-$C_{1-4}$alkyl includes halo-$C_{1-6}$alkyl, halo-$C_{1-4}$alkyl and the like.

As used herein, the term "heteroaryl-$C_{1-4}$alkyl" refers to a radical of the formula: —$C_{1-4}$alkyl-heteroaryl.

As used herein, the term "heteroaryl-$C_{1-4}$alkyl-amino" refers to a radical of the formula: —NH—$C_{1-4}$alkyl-heteroaryl.

As used herein, the term "heteroaryl-$C_{1-4}$alkyl-amino-carbonyl" refers to a radical of the formula: —C(=O)—NH—$C_{1-4}$alkyl-heteroaryl.

As used herein, the term "heteroaryl-$C_{1-4}$alkyl-amino-carbonyl-$C_{1-4}$alkyl" refers to a radical of the formula: —$C_{1-4}$alkyl-C(=O)—NH—$C_{1-4}$alkyl-heteroaryl.

As used herein, the term "heteroaryl-$C_{1-4}$alkyl-carbonyl-amino" refers to a radical of the formula: —NH—C(=O)—$C_{1-4}$alkyl-heteroaryl.

As used herein, the term "heteroaryl-$C_{1-4}$alkyl-carbonyl-amino-$C_{1-4}$alkyl" refers to a radical of the formula: —$C_{1-4}$alkyl-NH—C(=O)—$C_{1-4}$alkyl-heteroaryl.

As used herein, the term "heterocyclyl-$C_{1-4}$alkoxy" refers to a radical of the formula: —$C_{1-4}$alkoxy-heterocyclyl.

As used herein, the term "heterocyclyl-$C_{1-4}$alkyl" refers to a radical of the formula: —$C_{1-4}$alkyl-heterocyclyl.

As used herein, the term "hydroxyl" refers to a radical of the formula: —OH.

As used herein, the term "hydroxyl-$C_{1-4}$alkoxy" refers to a radical of the formula: —O—$C_{1-4}$alkyl-OH, wherein $C_{1-4}$alkyl may be partially or completely substituted where allowed by available valences with one or more hydroxy radicals.

As used herein, the term "hydroxyl-$C_{1-4}$alkyl" refers to a radical of the formula: —$C_{1-4}$alkyl-OH, wherein $C_{1-4}$alkyl may be partially or completely substituted where allowed by available valences with one or more hydroxy radicals.

As used herein, the term "hydroxyl-$C_{1-4}$alkyl-amino" refers to a radical of the formula: —NH—$C_{1-4}$alkyl-OH, wherein $C_{1-4}$alkyl may be partially or completely substituted where allowed by available valences with one or more hydroxyl radicals.

As used herein, the term "hydroxyl-imino" refers to the =NOH radical of the formula: C(=NOH).

As used herein, the term "oxo" refers to the radical of the formula: C=O.

As used herein, the term "phenyl-$C_{1-4}$alkoxy" refers to a radical of the formula: —$C_{1-4}$alkoxy-phenyl.

As used herein, the term "substituent" means positional variables on the atoms of a core molecule that are substituted at a designated atom position, replacing one or more hydrogens on the designated atom, provided that the designated atom's normal valency is not exceeded, and that the substitution results in a stable compound. Combinations of substituents and/or variables are permissible only if such combinations result in stable compounds. A person of ordinary skill in the art should note that any carbon as well as heteroatom with valences that appear to be unsatisfied as described or shown herein is assumed to have a sufficient number of hydrogen atom(s) to satisfy the valences described or shown. In certain instances one or more substituents having a double bond (e.g., "oxo" or "=O") as the point of attachment may be described, shown or listed herein within a substituent group, wherein the structure may only show a single bond as the point of attachment to the core structure of Formula (I). A person of ordinary skill in the art would understand that, while only a single bond is shown, a double bond is intended for those substituents.

As used herein, the term "and the like," with reference to the definitions of chemical terms provided herein, means that variations in chemical structures that could be expected by one skilled in the art include, without limitation, isomers (including chain, branching or positional structural isomers), hydration of ring systems (including saturation or partial unsaturation of monocyclic, bicyclic or polycyclic ring structures) and all other variations where allowed by available valences which result in a stable compound.

For the purposes of this description, where one or more substituent variables for a compound of Formula (I) or a form thereof encompass functionalities incorporated into a compound of Formula (I), each functionality appearing at any location within the disclosed compound may be independently selected, and as appropriate, independently and/or optionally substituted.

As used herein, the terms "independently selected," or "each selected" refer to functional variables in a substituent list that may occur more than once on the structure of Formula (I), the pattern of substitution at each occurrence is independent of the pattern at any other occurrence. Further, the use of a generic substituent variable on any formula or structure for a compound described herein is understood to include the replacement of the generic substituent with species substituents that are included within the particular genus, e.g., aryl may be replaced with phenyl or naphthalenyl and the like, and that the resulting compound is to be included within the scope of the compounds described herein.

As used herein, the terms "each instance of" or "in each instance, when present," when used preceding a phrase such as " . . . $C_{3-14}$cycloalkyl, $C_{3-14}$cycloalkyl-$C_{1-4}$alkyl, aryl, aryl-$C_{1-4}$alkyl, heteroaryl, heteroaryl-$C_{1-4}$alkyl, heterocyclyl and heterocyclyl-$C_{1-4}$alkyl," are intended to refer to the $C_{3-14}$cycloalkyl, aryl, heteroaryl and heterocyclyl ring systems when each are present either alone or as a substituent.

As used herein, the term "optionally substituted" means optional substitution with the specified substituent variables, groups, radicals or moieties.

Compound Forms

As used herein, the term "form" means a compound of Formula (I) having a form selected from the group consisting of a free acid, free base, prodrug, salt, hydrate, solvate, clathrate, isotopologue, racemate, enantiomer, diastereomer, stereoisomer, polymorph and tautomer form thereof.

In certain embodiments described herein, the form of the compound of Formula (I) is a free acid, free base or salt thereof.

In certain embodiments described herein, the form of the compound of Formula (I) is a salt thereof.

In certain embodiments described herein, the form of the compound of Formula (I) is an isotopologue thereof.

In certain embodiments described herein, the form of the compound of Formula (I) is a stereoisomer, racemate, enantiomer or diastereomer thereof.

In certain embodiments described herein, the form of the compound of Formula (I) is a tautomer thereof.

In certain embodiments described herein, the form of the compound of Formula (I) is a pharmaceutically acceptable form.

In certain embodiments described herein, the compound of Formula (I) or a form thereof is isolated for use.

As used herein, the term "isolated" means the physical state of a compound of Formula (I) or a form thereof after being isolated and/or purified from a synthetic process (e.g., from a reaction mixture) or natural source or combination thereof according to an isolation or purification process or processes described herein or which are well known to the skilled artisan (e.g., chromatography, recrystallization and the like) in sufficient purity to be characterized by standard analytical techniques described herein or well known to the skilled artisan.

As used herein, the term "protected" means that a functional group in a compound of Formula (I) or a form thereof is in a form modified to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York. Such functional groups include hydroxy, phenol, amino and carboxylic acid. Suitable protecting groups for hydroxy or phenol include trialkylsilyl or diarylalkylsilyl (e.g., t-butyldimethylsilyl, t-butyldiphenylsilyl or trimethylsilyl), tetrahydropyranyl, benzyl, substituted benzyl, methyl, methoxymethanol, and the like. Suitable protecting groups for amino, amidino and guanidino include t-butoxycarbonyl, benzyloxycarbonyl, and the like. Suitable protecting groups for carboxylic acid include alkyl, aryl or arylalkyl esters. In certain instances, the protecting group may also be a polymer resin, such as a Wang resin or a 2-chlorotrityl-chloride resin. Protecting groups may be added or removed in accordance with standard techniques, which are well-known to those skilled in the art and as described herein. It will also be appreciated by those skilled in the art, although such protected derivatives of compounds described herein may not possess pharmacological activity as such, they may be administered to a subject and thereafter metabolized in the body to form compounds described herein which are pharmacologically active. Such derivatives may therefore be described as "prodrugs". All prodrugs of compounds described herein are included within the scope of the use described herein.

As used herein, the term "prodrug" means a form of an instant compound (e.g., a drug precursor) that is transformed in vivo to yield an active compound of Formula (I) or a form thereof. The transformation may occur by various mechanisms (e.g., by metabolic and/or non-metabolic chemical processes), such as, for example, by hydrolysis and/or metabolism in blood, liver and/or other organs and tissues. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

In one example, when a compound of Formula (I) or a form thereof contains a carboxylic acid functional group, a prodrug can comprise an ester formed by the replacement of the hydrogen atom of the acid group with a functional group such as alkyl and the like. In another example, when a compound of Formula (I) or a form thereof contains a hydroxyl functional group, a prodrug form can be prepared by replacing the hydrogen atom of the hydroxyl with another functional group such as alkyl, alkylcarbonyl or a phosphonate ester and the like. In another example, when a compound of Formula (I) or a form thereof contains an amine functional group, a prodrug form can be prepared by replacing one or more amine hydrogen atoms with a functional group such as alkyl or substituted carbonyl. Pharmaceutically acceptable prodrugs of compounds of Formula (I) or a form thereof include those compounds substituted with one or more of the following groups: carboxylic acid esters, sulfonate esters, amino acid esters, phosphonate esters and mono-, di- or triphosphate esters or alkyl substituents, where appropriate. As described herein, it is understood by a person of ordinary skill in the art that one or more of such substituents may be used to provide a compound of Formula (I) or a form thereof as a prodrug.

One or more compounds described herein may exist in unsolvated as well as solvated forms with pharmaceutically acceptable solvents such as water, ethanol, and the like, and the description herein is intended to embrace both solvated and unsolvated forms.

As used herein, the term "solvate" means a physical association of a compound described herein with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. As used herein, "solvate" encompasses both solution-phase and isolatable solvates. Non-limiting examples of suitable solvates include ethanolates, methanolates, and the like.

As used herein, the term "hydrate" means a solvate wherein the solvent molecule is water.

The compounds of Formula (I) can form salts, which are intended to be included within the scope of this description. Reference to a compound of Formula (I) or a form thereof herein is understood to include reference to salt forms thereof, unless otherwise indicated. The term "salt(s)", as employed herein, denotes acidic salts formed with inorganic and/or organic acids, as well as basic salts formed with inorganic and/or organic bases. In addition, when a compound of Formula (I) or a form thereof contains both a basic moiety, such as, without limitation an amine moiety, and an acidic moiety, such as, but not limited to a carboxylic acid, zwitterions ("inner salts") may be formed and are included within the term "salt(s)" as used herein.

The term "pharmaceutically acceptable salt(s)", as used herein, means those salts of compounds described herein that are safe and effective (i.e., non-toxic, physiologically acceptable) for use in mammals and that possess biological activity, although other salts are also useful. Salts of the compounds of the Formula (I) may be formed, for example, by reacting a compound of Formula (I) or a form thereof with an amount of acid or base, such as an equivalent amount, in a medium such as one in which the salt precipitates or in an aqueous medium followed by lyophilization.

Pharmaceutically acceptable salts include one or more salts of acidic or basic groups present in compounds described herein. Embodiments of acid addition salts include, and are not limited to, acetate, ascorbate, benzoate, benzenesulfonate, bisulfate, bitartrate, borate, bromide, butyrate, chloride, citrate, camphorate, camphorsulfonate, ethanesulfonate, formate, fumarate, gentisinate, gluconate, glucaronate, glutamate, iodide, isonicotinate, lactate, maleate, methanesulfonate, naphthalenesulfonate, nitrate, oxalate, pamoate, pantothenate, phosphate, propionate, saccharate, salicylate, succinate, sulfate, tartrate, thiocyanate, toluenesulfonate (also known as tosylate), trifluoroacetate salts and the like. Certain embodiments of acid addition salts include chloride, dichloride, trichloride, bromide, acetate, formate or trifluoroacetate salts.

Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33, 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Suitable basic salts include, but are not limited to, aluminum, ammonium, calcium, lithium, magnesium, potassium, sodium and zinc salts.

All such acid salts and base salts are intended to be included within the scope of pharmaceutically acceptable salts as described herein. In addition, all such acid and base salts are considered equivalent to the free forms of the corresponding compounds for purposes of this description.

Compounds of Formula (I) and forms thereof, may further exist in a tautomeric form. All such tautomeric forms are contemplated and intended to be included within the scope of the compounds of Formula (I) or a form thereof as described herein.

The compounds of Formula (I) or a form thereof may contain asymmetric or chiral centers, and, therefore, exist in different stereoisomeric forms. The present description is intended to include all stereoisomeric forms of the compounds of Formula (I) as well as mixtures thereof, including racemic mixtures.

The compounds described herein may include one or more chiral centers, and as such may exist as racemic mixtures (R/S) or as substantially pure enantiomers and diastereomers. The compounds may also exist as substantially pure (R) or (S) enantiomers (when one chiral center is present). In one embodiment, the compounds described herein are (S) isomers and may exist as enantiomerically pure compositions substantially comprising only the (S) isomer. In another embodiment, the compounds described herein are (R) isomers and may exist as enantiomerically pure compositions substantially comprising only the (R) isomer. As one of skill in the art will recognize, when more than one chiral center is present, the compounds described herein may also exist as a (R,R), (R,S), (S,R) or (S,S) isomer, as defined by IUPAC Nomenclature Recommendations.

As used herein, the term "substantially pure" refers to compounds consisting substantially of a single isomer in an amount greater than or equal to 90%, in an amount greater than or equal to 92%, in an amount greater than or equal to 95%, in an amount greater than or equal to 98%, in an amount greater than or equal to 99%, or in an amount equal to 100% of the single isomer.

In one aspect of the description, a compound of Formula (I) or a form thereof is a substantially pure (S) enantiomer form present in an amount greater than or equal to 90%, in an amount greater than or equal to 92%, in an amount greater than or equal to 95%, in an amount greater than or equal to 98%, in an amount greater than or equal to 99%, or in an amount equal to 100%.

In one aspect of the description, a compound of Formula (I) or a form thereof is a substantially pure (R) enantiomer form present in an amount greater than or equal to 90%, in an amount greater than or equal to 92%, in an amount greater than or equal to 95%, in an amount greater than or equal to 98%, in an amount greater than or equal to 99%, or in an amount equal to 100%.

As used herein, a "racemate" is any mixture of isometric forms that are not "enantiomerically pure", including mixtures such as, without limitation, in a ratio of about 50/50, about 60/40, about 70/30, or about 80/20.

In addition, the present description embraces all geometric and positional isomers. For example, if a compound of Formula (I) or a form thereof incorporates a double bond or a fused ring, both the cis- and trans-forms, as well as mixtures, are embraced within the scope of the description. Diastereomeric mixtures can be separated into their individual diastereomers on the basis of their physical chemical differences by methods well known to those skilled in the art, such as, for example, by chromatography and/or fractional crystallization. Enantiomers can be separated by use of chiral HPLC column or other chromatographic methods known to those skilled in the art. Enantiomers can also be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this description.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this description, as are positional isomers (such as, for example, 4-pyridyl and 3-pyridyl). Individual stereoisomers of the compounds described herein may, for example, be substantially free of other isomers, or may be present in a racemic mixture, as described supra.

The use of the terms "salt", "solvate", "ester", "prodrug" and the like, is intended to equally apply to the salt, solvate, ester and prodrug of enantiomers, stereoisomers, rotamers, tautomers, positional isomers, racemates or isotopologues of the instant compounds.

The term "isotopologue" refers to isotopically-enriched compounds described herein which are identical to those recited herein, but for the fact that one or more atoms are replaced by an atom having an atomic mass or mass number different from the atomic mass or mass number usually found in nature. Examples of isotopes that can be incorporated into compounds described herein include isotopes of hydrogen, carbon, nitrogen, oxygen, phosphorus, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, $^{35}$Cl and $^{36}$Cl, respectively, each of which are also within the scope of this description.

Certain isotopically-enriched compounds described herein (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances.

Polymorphic crystalline and amorphous forms of the compounds of Formula (I) and of the salts, solvates, hydrates, esters and prodrugs of the compounds of Formula (I) are further intended to be included in the present description.

Compound Uses

The present description relates to a method of use of a compound of Formula (I) or a form thereof for treating or ameliorating HD in a subject in need thereof, comprising administering an effective amount of the compound or a form thereof to the subject.

The present description further relates to use of the compound of Formula (I) or a form thereof for treating or ameliorating HD in a subject in need thereof.

The present description further relates to use of the compound of Formula (I) or a form thereof having activity toward HD.

The present description further relates to use of the compound of Formula (I) or a form thereof in a combination therapy to provide additive or synergistic activity, thus enabling the development of a combination product for treating or ameliorating HD.

In addition to monotherapeutic use, the instant compounds are useful in a combination therapy with current standard of agents, having additive or synergistic activity with one or more known agents.

A combination therapy comprising compounds described herein in combination with one or more known drugs may be used to treat HD regardless of whether HD is responsive to the known drug.

Embodiments of the present description include the use of a compound of Formula (I) or a form thereof in a combination therapy for treating or ameliorating HD in a subject in need thereof, comprising administering an effective amount of the compound of Formula (I) or a form thereof and an effective amount of one or more agent(s).

Embodiments of the present description include the use of a compound of Formula (I) or a form thereof in a combination therapy for treating or ameliorating HD in a subject in need thereof, comprising administering an effective amount of the compound of Formula (I) or a form thereof and an effective amount of one or more agent(s).

In an embodiment of a use or method provided herein, compounds of Formula (I) or a form thereof used in combination with one or more additional agents can be administered to a subject or contacted with a subject or patient cell(s) prior to, concurrently with, or subsequent to administering to the subject or patient or contacting the cell with an additional agent(s). A compound(s) of Formula (I) or a form thereof and an additional agent(s) can be administered to a subject or contacted with a cell in single composition or different compositions. In a specific embodiments, a compound(s) of Formula (I) or a form thereof is used in combination with gene therapy to inhibit HTT expression (using, e.g., viral delivery vectors) or the administration of another small molecule HTT inhibitor. In another specific embodiment, a compound(s) of Formula (I) or a form thereof are used in combination with cell replacement using differentiated non-mutant HTT stem cells. In another specific embodiment, a compound(s) of Formula (I) or a form thereof are used in combination with cell replacement using differentiated HTT stem cells.

In one embodiment, provided herein is the use of compounds of Formula (I) or a form thereof in combination with supportive standard of care therapies, including palliative care.

An embodiment of the present description includes the use of a compound of Formula (I) or a form thereof in the preparation of a kit comprising the compound of Formula (I) or a form thereof and instructions for administering an effective amount of the compound of Formula (I) or a form thereof and an effective amount of one or more agent(s) in a combination therapy for treating or ameliorating HD in a subject in need thereof.

Accordingly, the present description relates to use of a compound of Formula (I) or a form thereof for treating or ameliorating HD. In accordance with the use of the present description, compounds that are useful in selectively treating or ameliorating HD, have been identified and use of these compounds for treating or ameliorating HD has been provided.

One embodiment of the use of the present description relates to use of a compound of Formula (I) or a form thereof for treating or ameliorating HD in a subject in need thereof, comprising administering an effective amount of the compound of Formula (I) or a form thereof to the subject.

One embodiment of the use of the present description relates to a method of use of a compound of Formula (I) or a form thereof for treating or ameliorating HD in a subject in need thereof, comprising administering an effective amount of the compound to the subject.

An embodiment of the use of the present description relates to a method of use of a compound of Formula (I) or a form thereof for treating or ameliorating HD in a subject in need thereof, comprising administering an effective amount of the compound to the subject.

An embodiment of the use of the present description relates to use of a compound of Formula (I) or a form thereof in the manufacture of a medicament for treating or ameliorating HD in a subject in need thereof, comprising administering an effective amount of the medicament to the subject.

An embodiment of the use of the present description relates to use of a compound of Formula (I) or a form thereof in the preparation of a kit comprising the compound of Formula (I) or a form thereof and instructions for administering the compound for treating or ameliorating HD in a subject in need thereof.

In one respect, for each of such embodiments, the subject is treatment naive. In another respect, for each of such embodiments, the subject is not treatment naive.

As used herein, the term "treating" refers to: (i) preventing a disease, disorder or condition from occurring in a subject that may be predisposed to the disease, disorder and/or condition but has not yet been diagnosed as having the disease, disorder and/or condition; (ii) inhibiting a disease, disorder or condition, i.e., arresting the development thereof; and/or (iii) relieving a disease, disorder or condition, i.e., causing regression of the disease, disorder and/or condition.

As used herein, the term "subject" refers to an animal or any living organism having sensation and the power of voluntary movement, and which requires oxygen and organic food. Nonlimiting examples include members of the human, primate, equine, porcine, bovine, murine, rattus, canine and feline specie. In some embodiments, the subject is a mammal or a warm-blooded vertebrate animal. In other embodiments, the subject is a human. As used herein, the term "patient" may be used interchangeably with "subject" and "human".

As used herein, the terms "effective amount" or "therapeutically effective amount" mean an amount of compound of Formula (I) or a form, composition or medicament thereof effective in inhibiting the above-noted diseases and thus producing the desired therapeutic, ameliorative, inhibitory or preventative effect in a subject in need thereof.

The dose administered to achieve an effective target plasma concentration may also be administered based upon the weight of the subject or patient. Doses administered on a weight basis may be in the range of about 0.001 mg/kg/day to about 3500 mg/kg/day, or about 0.001 mg/kg/day to about 3000 mg/kg/day, or about 0.001 mg/kg/day to about 2500 mg/kg/day, or about 0.001 mg/kg/day to about 2000 mg/kg/day, or about 0.001 mg/kg/day to about 1500 mg/kg/day, or about 0.001 mg/kg/day to about 1000 mg/kg/day, or about 0.001 mg/kg/day to about 500 mg/kg/day, or about 0.001 mg/kg/day to about 250 mg/kg/day, or about 0.001 mg/kg/day to about 100 mg/kg/day, or about 0.001 mg/kg/day to about 75 mg/kg/day, or about 0.001 mg/kg/day to about 50 mg/kg/day, or about 0.001 mg/kg/day to about 40 mg/kg/day, or about 0.001 mg/kg/day to about 30 mg/kg/day, or about 0.001 mg/kg/day to about 20 mg/kg/day, or about 0.001 mg/kg/day to about 10 mg/kg/day, or about 0.01 mg/kg/day to about 2000 mg/kg/day, or about 0.01 mg/kg/day to about 1500 mg/kg/day, or about 0.01 mg/kg/day to about 1000 mg/kg/day, or about 0.01 mg/kg/day to about 600 mg/kg/day, or about 0.01 mg/kg/day to about 500 mg/kg/day, or about 0.01 mg/kg/day to about 300 mg/kg/day, or about 0.015 mg/kg/day to about 200 mg/kg/day, or about 0.02 mg/kg/day to about 100 mg/kg/day, or about 0.025 mg/kg/day to about 100 mg/kg/day, or about 0.03 mg/kg/day to about 100 mg/kg/day, wherein said amount is orally administered once (once in approximately a 24 hour period), twice (once in approximately a 12 hour period) or thrice (once in approximately an 8 hour period) daily according to subject weight.

In certain embodiments, the effective amount will be in a range of from about 0.001 mg/kg/day to about 500 mg/kg/day, or about 0.01 mg/kg/day to about 500 mg/kg/day, or about 0.1 mg to about 500 mg/kg/day, or about 1.0 mg/day to about 500 mg/kg/day, in single, divided, or a continuous dose for a patient or subject having a weight in a range of between about 40 to about 200 kg (which dose may be adjusted for patients or subjects above or below this range, particularly children under 40 kg). The typical adult subject is expected to have a median weight in a range of about 70 kg.

In another embodiment, where daily doses are adjusted based upon the weight of the subject or patient, compounds described herein may be formulated for delivery at about 0.02, 0.025, 0.03, 0.05, 0.06, 0.075, 0.08, 0.09, 0.10, 0.20, 0.25, 0.30, 0.50, 0.60, 0.75, 0.80, 0.90, 1.0, 1.10, 1.20, 1.25, 1.50, 1.75, 2.0, 3.0, 5.0, 10, 20, 30, 40, 50, 100, 150, 200, 250, 300, 400 or 500 mg/kg/day. Daily doses adjusted based upon the weight of the subject or patient may be administered as a single, divided, or continuous dose. In embodiments where a dose of compound is given more than once per day, the dose may be administered twice, thrice, or more times per day.

Within the scope of the present description, the "effective amount" of a compound of Formula (I) or a form thereof for use in the manufacture of a medicament, for use in the preparation of a pharmaceutical kit or in a method of use for treating or ameliorating HD in a subject in need thereof is intended to include an amount in a range of from about 0.001 mg/kg/day to about 3500 mg/kg/day, or about 0.001 mg/kg/day to about 3000 mg/kg/day, or about 0.001 mg/kg/day to about 2500 mg/kg/day, or about 0.001 mg/kg/day to about 2000 mg/kg/day, or about 0.001 mg/kg/day to about 1500 mg/kg/day, or about 0.001 mg/kg/day to about 1000 mg/kg/day, or about 0.001 mg/kg/day to about 500 mg/kg/day, or about 0.001 mg/kg/day to about 250 mg/kg/day, or about 0.001 mg/kg/day to about 100 mg/kg/day, or about 0.001 mg/kg/day to about 75 mg/kg/day, or about 0.001 mg/kg/day to about 50 mg/kg/day, or about 0.001 mg/kg/day to about 40 mg/kg/day, or about 0.001 mg/kg/day to about 30 mg/kg/day, or about 0.001 mg/kg/day to about 20 mg/kg/day, or about 0.001 mg/kg/day to about 10 mg/kg/day, or about 0.01 mg/kg/day to about 2000 mg/kg/day, or about 0.01 mg/kg/day to about 1500 mg/kg/day, or about 0.01 mg/kg/day to about 1000 mg/kg/day, or about 0.01 mg/kg/day to about 600 mg/kg/day, or about 0.01 mg/kg/day to about 500 mg/kg/day, or about 0.01 mg/kg/day to about 300 mg/kg/day, or about 0.015 mg/kg/day to about 200 mg/kg/day, or about 0.02 mg/kg/day to about 100 mg/kg/day, or about 0.025 mg/kg/day to about 100 mg/kg/day, or about 0.03 mg/kg/day to about 100 mg/kg/day, wherein said amount is administered once (once in approximately a 24 hour period; i.e., "q.d."), twice (once in approximately a 12 hour period; i.e., "b.i.d." or "q.12 h"), thrice (once in approximately an 8 hour period; i.e., "t.i.d." or "q.8 h"), or four times (once in approximately a 6 hour period; i.e., "q.d.s.", "q.i.d." or "q.6 h") daily according to subject weight.

Such amounts may further include an amount in a range of from about 0.001 mg to about 3500 mg administered daily; 0.001 mg to about 3000 mg administered daily; 0.001 mg to about 2500 mg administered daily; 0.001 mg to about 2000 mg administered daily; 0.001 mg to about 1500 mg administered daily; 0.001 mg to about 1000 mg administered daily; 0.001 mg to about 500 mg administered daily; 0.001 mg to about 250 mg administered daily; 1.0 mg to about 3500 mg administered daily; 1.0 mg to about 1500 mg administered daily; 1.0 mg to about 1000 mg administered daily; 10.0 mg to about 600 mg administered daily; 0.5 mg to about 2000 mg administered daily; or, an amount in a range of from about 5.0 mg to about 300 mg administered daily.

For example, the effective amount may be the amount required to treat HD in a subject or, more specifically, in a human. The effective amount for a subject will depend upon various factors, including the subject's body weight, size and health. Effective amounts for a given patient can be determined by routine experimentation that is within the skill and judgment of the clinician.

For any compound, the effective amount can be estimated initially either in cell culture assays or in relevant animal models, such as a mouse, chimpanzee, marmoset or tamarin animal model. Relevant animal models may also be used to determine the appropriate concentration range and route of administration. Such information can then be used to determine useful doses and routes for administration in humans. Therapeutic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is therapeutic index, and can be expressed as the ratio, $LD_{50}/ED_{50}$. In some embodiments, the effective amount is such that a large therapeutic index is achieved. In further embodiments, the dosage is within a range of circulating concentrations that include an $ED_{50}$ with little or no toxicity. The dosage may vary within this range depending upon the dosage form employed, sensitivity of the patient, and the route of administration.

More specifically, the concentration-biological effect relationships observed with regard to a compound of Formula (I) or a form thereof indicate a target plasma concentration ranging from approximately 0.001 µg/mL to approximately 50 µg/mL, from approximately 0.01 µg/mL to approximately 20 µg/mL, from approximately 0.05 µg/mL to approximately 10 µg/mL, or from approximately 0.1 µg/mL to approximately 5 µg/mL. To achieve such plasma concentrations, the compounds described herein may be administered at doses that vary, such as, for example, without limitation, from 0.1 ng to 10,000 mg, depending upon the route of administration in single, divided, or continuous doses for a patient weighing between about 10 to about 100 kg (which dose may be adjusted for patients within this weight range, particularly for children under 40 kg).

The exact dosage will be determined by the practitioner, in light of factors related to the subject. Dosage and administration may be adjusted to provide sufficient levels of the active agent(s) or to maintain the desired effect. Factors which may be taken into account include the severity of the disease state, general health of the subject, ethnicity, age, weight, gender, diet, time of day and frequency of administration, drug combination(s), reaction sensitivities, experience with other therapies, and tolerance/response to therapy. Long-acting pharmaceutical compositions may be administered every 2, 3 or 4 days, once every week, or once every two weeks depending on half-life and clearance rate of the particular formulation.

The compounds and compositions described herein may be administered to the subject via any drug delivery route known in the art. Nonlimiting examples include oral, ocular, rectal, buccal, topical, nasal, sublingual, transdermal, subcutaneous, intramuscular, intravenous (bolus and infusion), intracerebral, and pulmonary routes of administration.

In one aspect, provided herein are methods for modulating the amount of HTT (huntingtin protein), comprising contacting a human cell with a compound of Formula (I) or a form thereof. In a specific embodiment, provided herein are methods for modulating the amount of HTT, comprising contacting a human cell with a compound of Formula (I) or a form thereof that modulates the expression of HTT. The human cell can be contacted with a compound of Formula (I) or a form thereof in vitro, or in vivo, e.g., in a non-human animal or in a human. In a specific embodiment, the human cell is from or in a human. In another specific embodiment, the human cell is from or in a human with HD. In another specific embodiment, the human cell is from or in a human with HD, caused by a CAG repeat in the Htt gene, resulting in a loss of HTT expression and/or function. In another embodiment, the human cell is from a human with HD. In another embodiment, the human cell is in a human with HD. In one embodiment, the compound is a form of the compound of Formula (I).

In a specific embodiment, provided herein is a method for enhancing the inhibition of mutant HTT transcribed from the Htt gene, comprising contacting a human cell with a compound of Formula (I) or a form thereof. The human cell can be contacted with a compound of Formula (I) or a form thereof in vitro, or in vivo, e.g., in a non-human animal or in a human. In a specific embodiment, the human cell is from or in a human. In another specific embodiment, the human cell is from or in a human with HD. In another specific embodiment, the human cell is from or in a human with HD, caused by a CAG repeat in the Htt gene, resulting in a loss of wild-type "normal" HTT expression and/or function. In another embodiment, the human cell is from a human with HD. In another embodiment, the human cell is in a human with HD. In one embodiment, the compound is a form of the compound of Formula (I).

In another aspect, provided herein is a method for modulating the inhibition of mutant HTT transcribed from the Htt gene, comprising administering to a non-human animal model for HD a compound of Formula (I) or a form thereof. In a specific embodiment, provided herein is a method for modulating the inhibition of mutant HTT transcribed from the Htt gene, comprising administering to a non-human animal model for HD a compound of Formula (I) or a form thereof. In a specific embodiment, the compound is a form of the compound of Formula (I).

In another aspect, provided herein is a method for decreasing the amount of mutant HTT, comprising contacting a human cell with a compound of Formula (I) or a form thereof. In a specific embodiment, provided herein is a method for decreasing the amount of mutant HTT, comprising contacting a human cell with a compound of Formula (I) that inhibits the transcription of mutant HTT (huntingtin mRNA) from the Htt gene. In another specific embodiment, provided herein is a method for decreasing the amount of HTT, comprising contacting a human cell with a compound of Formula (I) that inhibits the expression of mutant HTT transcribed from the Htt gene. The human cell can be contacted with a compound of Formula (I) or a form thereof in vitro, or in vivo, e.g., in a non-human animal or in a human. In a specific embodiment, the human cell is from or in a human. In another specific embodiment, the human cell is from or in a human with HD. In another specific embodiment, the human cell is from or in a human with HD, caused by a CAG repeat in the Htt gene, resulting in a loss of HTT expression and/or function. In another embodiment, the human cell is from a human with HD. In another embodiment, the human cell is in a human with HD. In one embodiment, the compound is a form of the compound of Formula (I).

In certain embodiments, treating or ameliorating HD with a compound of Formula (I) or a form thereof (alone or in combination with an additional agent) has a therapeutic effect and/or beneficial effect. In a specific embodiment, treating HD with a compound of Formula (I) or a form thereof (alone or in combination with an additional agent)

results in one, two or more of the following effects: (i) reduces or ameliorates the severity of HD; (ii) delays onset of HD; (iii) inhibits the progression of HD; (iv) reduces hospitalization of a subject; (v) reduces hospitalization length for a subject; (vi) increases the survival of a subject; (vii) improves the quality of life for a subject; (viii) reduces the number of symptoms associated with HD; (ix) reduces or ameliorates the severity of a symptom(s) associated with HD; (x) reduces the duration of a symptom associated with HD; (xi) prevents the recurrence of a symptom associated with HD; (xii) inhibits the development or onset of a symptom of HD; and/or (xiii) inhibits of the progression of a symptom associated with HD.

Metabolites of the Compounds

Also included within the scope of the present description are the use of in vivo metabolic products of the compounds described herein. Such products may result, for example, from the oxidation, reduction, hydrolysis, amidation, esterification and the like of the administered compound, primarily due to enzymatic processes. Accordingly, the description includes the use of compounds produced by a process comprising contacting a compound described herein with a mammalian tissue or a mammal for a period of time sufficient to yield a metabolic product thereof.

Such products typically are identified by preparing a radio-labeled isotopologue (e.g., $^{14}C$ or $^3H$) of a compound described herein, administering the radio-labeled compound in a detectable dose (e.g., greater than about 0.5 mg/kg) to a mammal such as a rat, mouse, guinea pig, dog, monkey or human, allowing sufficient time for metabolism to occur (typically about 30 seconds to about 30 hours), and identifying the metabolic conversion products from urine, bile, blood or other biological samples. The conversion products are easily isolated since they are "radiolabeled" by virtue of being isotopically-enriched (others are isolated by the use of antibodies capable of binding epitopes surviving in the metabolite). The metabolite structures are determined in conventional fashion, e.g., by MS or NMR analysis. In general, analysis of metabolites may be done in the same way as conventional drug metabolism studies well-known to those skilled in the art. The conversion products, so long as they are not otherwise found in vivo, are useful in diagnostic assays for therapeutic dosing of the compounds described herein even if they possess no biological activity of their own.

Pharmaceutical Compositions

Embodiments of the present description include the use of a compound of Formula (I) or a form thereof in a pharmaceutical composition for treating or ameliorating HD in a subject in need thereof, comprising administering an effective amount of the compound of Formula (I) or a form thereof in admixture with one or more pharmaceutically acceptable excipient(s).

An embodiment of the present description includes the use of a pharmaceutical composition of the compound of Formula (I) or a form thereof in the preparation of a kit comprising the pharmaceutical composition of the compound of Formula (I) or a form thereof and instructions for administering the compound for treating or ameliorating HD in a subject in need thereof.

As used herein, the term "composition" means a product comprising the specified ingredients in the specified amounts, as well as any product which results, directly or indirectly, from combination of the specified ingredients in the specified amounts.

The pharmaceutical composition may be formulated to achieve a physiologically compatible pH, ranging from about pH 3 to about pH 11. In some embodiments, the pharmaceutical composition is formulated to achieve a pH of from about pH 3 to about pH 7. In other embodiments, the pharmaceutical composition is formulated to achieve a pH of from about pH 5 to about pH 8.

The term "pharmaceutically acceptable excipient" refers to an excipient for administration of a pharmaceutical agent, such as the compounds described herein. The term refers to any pharmaceutical excipient that may be administered without undue toxicity. Pharmaceutically acceptable excipients may be determined in part by the particular composition being administered, as well as by the particular mode of administration and/or dosage form. Nonlimiting examples of pharmaceutically acceptable excipients include carriers, solvents, stabilizers, adjuvants, diluents, etc. Accordingly, there exists a wide variety of suitable formulations of pharmaceutical compositions for the instant compounds described herein (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive antibodies. Other exemplary excipients include antioxidants such as ascorbic acid; chelating agents such as EDTA; carbohydrates such as dextrin, hydroxyalkylcellulose, hydroxyalkylmethylcellulose (e.g., hydroxypropylmethylcellulose, also known as HPMC), stearic acid; liquids such as oils, water, saline, glycerol and ethanol; wetting or emulsifying agents; pH buffering substances; and the like. Liposomes are also included within the definition of pharmaceutically acceptable excipients.

The pharmaceutical compositions described herein may be formulated in any form suitable for the intended use described herein. Suitable formulations for oral administration include solids, liquid solutions, emulsions and suspensions, while suitable inhalable formulations for pulmonary administration include liquids and powders. Alternative formulations include syrups, creams, ointments, tablets, and lyophilized solids which can be reconstituted with a physiologically compatible solvent prior to administration.

When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents, and preserving agents, in order to provide a palatable preparation.

Pharmaceutically acceptable excipients suitable for use in conjunction with tablets include, for example, inert diluents, such as celluloses, calcium or sodium carbonate, lactose, calcium or sodium phosphate; disintegrating agents, such as croscarmellose sodium, cross-linked povidone, maize starch, or alginic acid; binding agents, such as povidone, starch, gelatin or acacia; and lubricating agents, such as magnesium stearate, stearic acid, or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example celluloses, lactose, calcium phosphate, or kaolin, or as soft gelatin capsules wherein the active ingredient is mixed with non-aqueous or oil medium, such as glycerin, propylene glycol, polyethylene glycol, peanut oil, liquid paraffin, or olive oil.

In other embodiments, pharmaceutical compositions described herein may be formulated as suspensions comprising a compound of Formula (I) or a form thereof in admixture with one or more pharmaceutically acceptable excipient(s) suitable for the manufacture of a suspension. In yet other embodiments, pharmaceutical compositions described herein may be formulated as dispersible powders and granules suitable for preparation of a suspension by the addition of one or more excipient(s).

Excipients suitable for use in connection with suspensions include suspending agents, such as sodium carboxymethylcellulose, methylcellulose, hydroxypropyl methylcelluose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); and thickening agents, such as carbomer, beeswax, hard paraffin, or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

The pharmaceutical compositions described herein may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions described herein may be in the form of a sterile injectable preparation, such as a sterile injectable aqueous emulsion or oleaginous suspension. Such emulsion or suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,2-propanediol. The sterile injectable preparation may also be prepared as a lyophilized powder. Among the acceptable vehicles and solvents that may be employed are water, Ringer's solution and isotonic sodium chloride solution. In addition, sterile fixed oils may be employed as a solvent or suspending medium. For this purpose any bland fixed oil may be employed including synthetic mono- or di-glycerides. In addition, fatty acids such as oleic acid may likewise be used in the preparation of injectables.

The compounds described herein may be substantially insoluble in water and sparingly soluble in most pharmaceutically acceptable protic solvents and vegetable oils, but generally soluble in medium-chain fatty acids (e.g., caprylic and capric acids) or triglycerides and in propylene glycol esters of medium-chain fatty acids. Thus, contemplated in the description are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In some embodiments, the compound described herein is formulated for oral administration in a lipid-based composition suitable for low solubility compounds. Lipid-based formulations can generally enhance the oral bioavailability of such compounds. As such, pharmaceutical compositions described herein may comprise a effective amount of a compound of Formula (I) or a form thereof, together with at least one pharmaceutically acceptable excipient selected from medium chain fatty acids or propylene glycol esters thereof (e.g., propylene glycol esters of edible fatty acids such as caprylic and capric fatty acids) and pharmaceutically acceptable surfactants, such as polysorbate 20 or 80 (also referred to as Tween® 20 or Tween®80, respectively) or polyoxyl 40 hydrogenated castor oil.

In other embodiments, the bioavailability of low solubility compounds may be enhanced using particle size optimization techniques including the preparation of nanoparticles or nanosuspensions using techniques known to those skilled in the art. The compound forms present in such preparations include amorphous, partially amorphous, partially crystalline or crystalline forms.

In alternative embodiments, the pharmaceutical composition may further comprise one or more aqueous solubility enhancer(s), such as a cyclodextrin. Nonlimiting examples of cyclodextrin include hydroxypropyl, hydroxyethyl, glucosyl, maltosyl and maltotriosyl derivatives of α-, β-, and γ-cyclodextrin, and hydroxypropyl-β-cyclodextrin (HPBC). In some embodiments, the pharmaceutical composition further comprises HPBC in a range of from about 0.1% to about 20%, from about 1% to about 15%, or from about 2.5% to about 10%. The amount of solubility enhancer employed may depend on the amount of the compound in the composition.

Preparation of Compounds

Compounds provided herein can be prepared by those skilled in the art, such as, by the synthetic methods set forth in International Application Publication Number WO2014/028459 A1, published Feb. 20, 2014, International Application Publication Number WO2014/116845 A1, published Jul. 31, 2014, and International Application Publication Number WO2015/017589 A1, published Feb. 5, 2015, each of which are herein incorporated by reference.

General Schemes

The following reaction schemes illustrate methods to make compounds described herein. It is understood that one skilled in the art would be able to make these compounds by similar methods or by methods known to one skilled in the art.

In general, starting components and reagents may be commercially obtained from various sources such as commercial vendors, synthesized according to methodology known to those skilled in the art, or prepared as described herein. It is understood that in the following description, combinations of substituents and/or variables of the depicted formulae are permissible only if such contributions result in stable compounds.

In general, compounds of Formula (I) described herein can be synthesized following the general procedure for Scheme 1.

Scheme 1

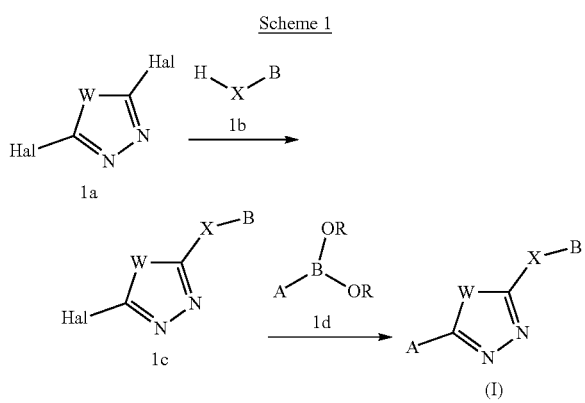

(I)

General Procedure for Scheme 1

The starting materials for the above reaction scheme are commercially available or can be prepared according to methods known to one skilled in the art or by methods disclosed herein. In general, the compounds described herein are prepared in the above reaction Scheme 1 as follows: a halogenated Compound 1a (wherein Hal is a halogen selected from bromine or chlorine) is reacted with a Compound 1b (wherein H is a reactive hydrogen atom in an amine or alcohol X functional group, wherein X and B for a compound of Formula (I) are as described herein) using a displacement or a metal-mediated cross coupling reaction, such as a Buchwald reaction, to provide an intermediate Compound 1c. Compound 1c is carried forward and reacted with a boronate acid or boronate ester Compound 1d (where B represents a boron atom, R represents a an acid or ester functional group or, when taken together with boron, form a ring system and A for a compound of Formula (I) is as described herein) using a transition metal-mediated cross coupling reaction, such as a Suzuki reaction, to provide a Compound of Formula (I).

In a complementary manner, compounds of Formula (I) may also be synthesized in reverse order wherein the boronate Compound 1d is reacted first with Compound 1a followed by reaction of the intermediate with amine Compound 1b. Other variations representing different combinations for substituting either or both boronate Compound 1d and amine Compound 1b on Compound 1a are intended to be included within the scope of the synthetic methodologies described herein.

SPECIFIC EXAMPLES

To assist in understanding the present description, the following specific examples are included. The experiments relating to this description should not, of course, be construed as specifically limiting the description and such variations of the description, now known or later developed, which would be within the purview of one skilled in the art are considered to fall within the scope of the description as described herein and hereinafter claimed.

Other than in the working examples, unless indicated to the contrary, all numbers expressing quantities of materials, reagents, reaction conditions, experimental data, and so forth used in the specification and claims are to be understood as being modified by the term "about". Accordingly, all such numbers represent approximations that may vary depending upon the desired properties sought to be obtained by a reaction or as a result of variable experimental conditions. Therefore, within an expected range of experimental reproducibility, the term "about" in the context of the resulting data, refers to a range for data provided that may vary according to a standard deviation from the mean. As well, for experimental results provided, the resulting data may be rounded up or down to present data consistently, without loss of significant figures. At the very least, and not as an attempt to limit the application of the doctrine of equivalents to the scope of the claims, each numerical parameter should be construed in light of the number of significant digits and ordinary rounding techniques.

While the numerical ranges and parameters setting forth the broad scope of the description are approximations, the numerical values set forth in the working examples are reported as precisely as possible. Any numerical value, however, inherently contains certain errors necessarily resulting from the standard deviation found in their respective testing measurements.

The column chromatography system used for product purification was an ISCO CombiFlash™ brand chromatography system (manufactured by Teledyne Isco).

SYNTHETIC EXAMPLES

Greater details of the present description are provided with reference to the following non-limiting examples, which are offered to more fully illustrate the description, but are not to be construed as limiting the scope thereof. The examples illustrate the preparation of certain compounds described herein, and the testing of these compounds in vitro and/or in vivo. Those of skill in the art will understand that the techniques described in these examples represent techniques described by the inventors to function well in the practice of the description, and as such constitute preferred modes for the practice thereof. However, those of skill in the art should appreciate in light of the present disclosure that many changes can be made to the specific methods that are disclosed and still obtain a like or similar result without departing from the spirit and scope of the description.

As used above, and throughout this description, the following abbreviations, unless otherwise indicated, shall be understood to have the following meanings:

| Abbreviation | Meaning |
| --- | --- |
| AcOH or HOAc | acetic acid |
| ACN or MeCN | acetonitrile |
| Bn | benzyl |
| BnBr | benzyl bromide |
| BnO or OBn | benzyloxy |
| Boc | tert-butoxycarbonyl |
| Boc$_2$O or (Boc)$_2$O | di-tert-butyl dicarbonate |

| Abbreviation | Meaning |
|---|---|
| tBuXPhos-Pd-G3 | [(2-di-tert-butylphosphino-2',4',6'-triisopropyl-1,1'-biphenyl)-2-(2'-amino-1,1'-biphenyl)] palladium(II) methanesulfonate |
| Cbz | benzyloxycarbonyl |
| DCE | dichloroethane |
| DCM | dichloromethane ($CH_2Cl_2$) |
| DIBAL-H | diisobutylaluminium hydride |
| DIPEA | N,N-diisopropylethylamine |
| DMF | dimethyl formamide |
| DMA | dimethylacetamide |
| DMAP | 4-dimethylaminopyridine |
| DMB | 2,4-dimethoxybenzyl |
| DMSO | dimethylsulfoxide |
| EA or EtOAc | ethyl acetate |
| EtOH | ethanol |
| $Et_2O$ | diethyl ether |
| HCl | hydrochloric acid |
| HPLC | high performance liquid chromatography |
| h/hr/hrs/min/s | hour(s)(h, hr or hrs)/minute(s)(min/mins)/second(s) |
| $K_2CO_3$ | potassium carbonate |
| KOAc | potassium acetate |
| $K_3PO_4$ | potassium phosphate |
| LAH | lithium aluminium hydride |
| LC/MS, LCMS or LC-MS | liquid chromatographic mass spectroscopy |
| LDA | lithium diisopropylamide |
| LiHMDS | lithium bis(trimethylsilyl)amide |
| $Me_4tBu$-XPhos | di-tert-butyl(2',4',6'-triisopropyl-3,4,5,6-tetramethyl-[1,1'-biphenyl]-2-yl)phosphine |
| MeI | methyl iodide |
| MeOH | methanol |
| $Me_2NH$ or $NHMe_2$ | dimethyl amine |
| MS | mass spectroscopy |
| $N_2$ | nitrogen |
| $Na_2SO_4$ | sodium sulfate |
| $NaBH(OAc)_3$ | sodium triacetoxyborohydride |
| NaHMDS | sodium bis(trimethylsilyl)amide |
| NBS | N-bromosuccinimide |
| $NH_4OH$ | ammonium hydroxide |
| NMO | N-methylmorpholine-N-oxide |
| NMP | N-methyl-2-pyrrolidone |
| n-BuLi | n-butyl lithium |
| NMR | nuclear magnetic resonance |
| Pd/C | palladium on carbon |
| $Pd_2(dba)_3$ | tris(dibenzylideneacetone)dipalladium(0) |
| $Pd(dppf)Cl_2$ | [1,1'-bis(diphenylphosphino)ferrocene] dichloropalladium(II) |
| $Pd(PPh_3)_4$ | tetrakis(triphenylphosphine)palladium |
| Pin | pinacol |
| psi | pounds per square inch pressure |
| S-Phos | 2-dicyclohexylphosphino-2',6'-dimethoxybiphenyl |
| TBDPSCl | tert-butyldiphenylchlorosilane |
| TBS | tert-butyldimethylsilyl |
| TBSCl | tert-butyldimethylsilyl chloride |
| t-BuOK | potassium tert-butoxide |
| TEA or $NEt_3$ | triethylamine |
| TFA | trifluoroacetic acid |
| THF | tetrahydrofuran |
| THP | tetrahydro-2H-pyranyl |
| THPO or OTHP | tetrahydro-2H-pyran-2-yl-oxy |
| TIPS-H or TIPSH | triisopropyl silane |
| TLC | thin layer chromatography |
| TMP | 2,2,6,6-tetramethylpiperidinyl |
| TMPMgCl—LiCl | 2,2,6,6-tetramethylpiperidinylmagnesium chloride lithium chloride |
| TMSI | trimethylsilyl iodide |
| TMSOK | potassium trimethylsilanolate |

Example 1 (Compound 411)

2-{6-[8-Azabicyclo[3.2.1]oct-3-yl(methyl)amino]pyridazin-3-yl}-5-(1H-pyrazol-4-yl)phenol hydrochloride Step 1: 3,6-Dibromopyridazine (133.7 mg, 0.56 mmol), tert-butyl (1R,5S)-3-(methylamino)-8-azabicyclo[3.2.1]octane-8-carboxylate (85 mg, 0.28 mmol) and DIPEA (0.15 mL, 0.84 mmol) were mixed in 1 mL of ACN and heated to 100° C. for 1 h until LC-MS showed complete consumption of the starting material. The reaction mixture was concentrated and purified via column chromatography: eluting with gradient $CH_2Cl_2$/MeOH (0% to 30% MeOH), column: silica 4 g to afford tert-butyl (1S,5R)-3-[(6-bromopyridazin-3-yl)-methyl-amino]-8-azabicyclo[3.2.1]octane-8-carboxylate (55 mg, 49.25% yield).

Step 2: tert-Butyl 3-[(6-bromopyridazin-3-yl)-methyl-amino]-8-azabicyclo[3.2.1]octane-8-carboxylate (55 mg, 0.14 mmol), 4-[3-(methoxymethoxy)-4-(4,4,5,5-tetramethyl-1,3,2-dioxaborolan-2-yl)phenyl]-1-tetrahydropyran-2-yl-pyrazole (68.82 mg, 0.17 mmol), Pd(dppf)Cl$_2$ (10.34 mg, 0.01 mmol), K$_2$CO$_3$ (57.98 mg, 0.42 mmol) were mixed in a Schlenk tube. The reaction was degassed with N$_2$ for 15 min and dioxane (2 mL) and water (0.5 mL) were added and the reaction was heated to 90° C. for 16 h. The reaction was cooled to room temperature, partitioned between EtOAc and water. The organic layers were dried over Na$_2$SO$_4$, concentrated under vacuum, purified via column chromatography: eluting with gradient CH$_2$Cl$_2$/EtOAc (0% to 80%), column: silica 4 g, to provide tert-butyl (1S,5R)-3-[[6-[2-(methoxymethoxy)-4-(1-tetrahydropyran-2-ylpyrazol-4-yl)phenyl]pyridazin-3-yl]-methyl-amino]-8-azabicyclo[3.2.1]octane-8-carboxylate (52 mg, 62%) as a tan solid.

Step 3: To a solution of tert-butyl (1S,5R)-3-[[6-[2-(methoxymethoxy)-4-(1-tetrahydropyran-2-ylpyrazol-4-yl)phenyl]pyridazin-3-yl]-methyl-amino]-8-azabicyclo[3.2.1]octane-8-carboxylate (52 mg, 0.086 mmol) in a 1 mL mixture of CH$_2$Cl$_2$ and 0.5 mL of MeOH was added HCl (4 mol/L) in 1,4-dioxane (0.06 mL). The reaction was stirred overnight. The precipitate was filtered, then dried under vacuum to provide 2-[6-[8-azabicyclo[3.2.1]octan-3-yl(methyl)amino]pyridazin-3-yl]-5-(1H-pyrazol-4-yl)phenol; hydrochloride (15 mg, 42.25% yield) as a yellow solid.

LC-MS: 377 [M+H]$^+$. $^1$H NMR (500 MHz, DMSO-d$_6$) δ: 9.37-9.51 (m, 1H), 8.87-8.96 (m, 1H), 8.31 (d, J=9.8 Hz, 1H), 8.12 (s, 2H), 7.74 (d, J=8.2 Hz, 2H), 7.19-7.27 (m, 2H), 4.80-4.92 (m, 1H), 4.08-4.14 (m, 3H), 3.07 (s, 3H), 2.30 (td, J=12.6, 2.8 Hz, 2H), 1.99-2.15 (m, 4H), 1.74-1.87 (m, 2H)

Using the procedure described for Example 1 above, additional compounds described herein may be prepared by substituting the appropriate starting materials reagents, and reaction conditions, obtaining compounds such as those selected from:

sulfonate (80 mg, 0.16 mmol), (tert-butyl 3-methyl-4-(4,4,5,5-tetramethyl-1,3,2-dioxaborolan-2-yl)-1H-pyrazole-1-carboxylate (59 mg, 0.19 mmol), Pd(dppf)Cl$_2$ (7 mg, 0.01 mmol), K$_2$CO$_3$ (66 mg, 0.48 mmol) were mixed in a Schlenk tube. The reaction was degassed with N$_2$ for 15 min and dioxane (2 mL) and water (0.5 mL) were added and the reaction was heated to 90° C. for 16 h. The reaction was cooled to room temperature, partitioned between EtOAc and water. The organic layers were dried over Na$_2$SO$_4$, concentrated under vacuum, then purified via column chromatography: eluting with gradient CH$_2$Cl$_2$/MeOH (0% to 30% MeOH), column: silica 4 g to provide tert-butyl 4-(3-methoxy-4-(6-(methyl(2,2,6,6-tetramethylpiperidin-4-yl)amino)pyridazin-3-yl)phenyl)-3-methyl-1H-pyrazole-1-carboxylate (46 mg, 54%) as light brown solid.

Step 2: A solution of tert-butyl 4-(3-methoxy-4-(6-(methyl(2,2,6,6-tetramethylpiperidin-4-yl)amino)pyridazin-3-yl)phenyl)-3-methyl-1H-pyrazole-1-carboxylate (46 mg, 0.09 mmol) in 2 mL of dry CH$_2$Cl$_2$ was cooled in ice-water bath. Boron tribromide 1.0 M in CH$_2$Cl$_2$ (0.45 mL, 0.45 mmol) was added and the reaction mixture was stirred at room temperature for 16 hours. The reaction was quenched with 2 mL of MeOH, stirred for 30 min, then concentrated and purified via column chromatography: eluting with gradient CH$_2$Cl$_2$/MeOH (2.5% NH$_4$OH) (0% to 30% MeOH/NH$_4$OH), column: silica 4 g, to provide tert-butyl 2-(6-(methyl(2,2,6,6-tetramethylpiperidin-4-yl)amino)pyridazin-3-yl)-5-(3-methyl-1H-pyrazol-4-yl)phenol (20 mg, 55%) as a yellow solid.

LC-MS: 421 [M+H]$^+$. $^1$H NMR (500 MHz, DMSO-d$_6$) δ: 13.74 (s, 1H), 12.63-12.71 (m, 1H), 8.20 (d, J=9.5 Hz, 1H), 8.03-8.04 (m, 1H), 7.86 (d, J=8.0 Hz, 1H), 7.73-7.75 (m, 1H), 7.36 (d, J=9.5 Hz, 1H), 7.03-7.06 (m, 2H), 4.90-5.05

| Cpd | Data |
|---|---|
| 412 | LC-MS: 363 [M + H]$^+$. $^1$H NMR (500 MHz, DMSO-d$_6$) δ: 9.24-9.34 (m, 1H), 9.09-9.21 (m, 1H), 8.30 (d, J = 9.8 Hz, 1H), 8.09 (s, 2H), 7.64-7.67 (m, 1H), 7.63 (d, J = 8.2 Hz, 1H), 7.25-7.27 (m, 1H), 7.24 (s, 1H), 5.42 (br s, 2H), 4.23-4.31 (m, 1H), 4.00-4.13 (m, 2H), 2.17 (s, 4H), 1.97-2.02 (m, 2H), 1.94 (td, J = 12.6, 2.5 Hz, 2H) |
| 413 | LC-MS: 393 [M + H]$^+$. $^1$H NMR (500 MHz, DMSO-d$_6$) δ: 9.34-9.49 (m, 1H), 8.43-8.56 (m, 1H), 8.30 (d, J = 9.8 Hz, 1H), 8.10 (s, 2H), 7.63 (s, 2H), 7.19-7.30 (m, 2H), 5.77 (br s, 2H), 4.41-4.62 (m, 1H), 2.08 (dd, J = 11.7, 2.8 Hz, 2H), 1.72 (td, J = 12.1, 2.8 Hz, 2H), 1.53 (s, 6H), 1.49 (s, 6H) |
| 415 | LC-MS: 364 [M + H]$^+$. $^1$H NMR (500 MHz, methanol-d$_4$) δ: 8.61 (d, J = 9.5 Hz, 1H), 8.24 (s, 2H), 7.85 (d, J = 8.2 Hz, 1H), 7.72 (d, J = 9.5 Hz, 1H), 7.38 (dd, J = 8.2, 1.6 Hz, 1H), 7.32 (d, J = 1.6 Hz, 1H), 5.65 (spt, J = 5.7 Hz, 1H), 4.25 (dd, J = 3.6, 2.8 Hz, 2H), 4.17-4.32 (m, 2H), 2.24 (s, 4H), 2.11 (tt, J = 11.2, 2.8 Hz, 2H) (3 hydrogens corresponding to OH and NH unobserved) |
| 433 | LC-MS: 363 [M + H]$^+$. $^1$H NMR (500 MHz, methanol-d$_4$) δ: 8.42 (d, J = 9.5 Hz, 1H), 8.34 (s, 2H), 7.80 (d, J = 9.8 Hz, 1H), 7.74 (d, J = 8.5 Hz, 1H), 7.40 (dd, J = 8.2, 2.5 Hz, 1H), 7.32 (d, J = 1.6 Hz, 1H), 4.18 (td, J = 6.9, 0.9 Hz, 1H), 4.11-4.16 (m, 2H), 2.42-2.52 (m, 4H), 2.32-2.35 (m, 1H), 2.28-2.32 (m, 1H), 2.15-2.25 (m, 2H), (4 hydrogens corresponding to OH and NH unobserved) |

Example 2 (Compound 416)

5-(5-Methyl-1H-pyrazol-4-yl)-2-{6-[methyl(2,2,6,6-tetramethylpiperidin-4-yl)amino]pyridazin-3-yl}phenol Step 1: 3-Methoxy-4-(6-(methyl(2,2,6,6-tetramethylpiperidin-4-yl)amino)pyridazin-3-yl)phenyl trifluoromethanesulfonate (m, 1H), 2.92 (s, 3H), 2.43 (s, 3H), 1.43-1.54 (m, 2H), 1.15-1.43 (m, 2H), 1.14 (s, 6H), 1.09 (s, 6H)

Using the procedure described for Example 2 above, additional compounds described herein may be prepared by substituting the appropriate starting materials reagents, and reaction conditions, obtaining compounds such as those selected from:

| Cpd | Data |
|---|---|
| 414 | LC-MS: 408 [M + H]$^+$. $^1$H NMR (500 MHz, DMSO-d$_6$) δ: 13.84 (s, 1H), 8.10-8.29 (m, 2H), 7.92 (s, 1H), 7.84 (d, J = 8.2 Hz, 1H), 7.36 (d, J = 9.8 Hz, 1H), 7.08-7.19 (m, 2H), 4.87-5.03 (m, 1H), 3.87 (s, 3H), 2.96 (s, 3H), 1.48-1.59 (m, 2H), 1.38-1.48 (m, 2H), 1.26 (s, 6H), 1.09 (s, 6H) |
| 418 | LC-MS: 422 [M + H]$^+$. $^1$H NMR (500 MHz, DMSO-d$_6$) δ: 12.89 (s, 1H), 12.29-12.48 (m, 1H), 8.41 (dd, J = 8.8, 0.9 Hz, 1H), 7.95 (dd, J = 7.9, 0.9 Hz, 1H), 7.37 (dd, J = 9.1, 1.3 Hz, 1H), 6.85-6.94 (m, 2H), 5.61-5.70 (m, 1H), 2.25 (br s., 6H), 2.09 (dd, J = 11.8, 3.9 Hz, 2H), 1.25-1.33 (m, 2H), 1.24 (s, 6H), 1.11 (s, 6H), (1 hydrogen corresponding to OH or NH unobserved) |
| 451 | LC-MS: 408 [M + H]$^+$. $^1$H NMR (500 MHz, DMSO-d$_6$) δ: 13.00 (s, 1H), 12.59-12.80 (m, 1H), 8.42 (d, J = 9.5 Hz, 1H), 7.94 (d, J = 8.8 Hz, 1H), 7.38 (d, J = 9.5 Hz, 1H), 7.03-7.18 (m, 2H), 5.55-5.78 (m, 1H), 2.39 (br s., 3H), 2.03-2.13 (m, 2H), 1.26-1.41 (m, 2H), 1.24 (s, 6H), 1.11 (s, 6H), (1 hydrogen corresponding to OH or NH unobserved) |

Example 3 (Compound 419)

2-{6-[Methyl(2,2,6,6-tetramethylpiperidin-4-yl)amino]pyridazin-3-yl}-5-(4-nitro-1H-pyrazol-1-yl)phenol dihydrochloride Step 1: 3-Methoxy-4-(6-(methyl(2,2,6,6-tetramethylpiperidin-4-yl)amino)pyridazin-3-yl)phenyl trifluoromethanesulfonate (335 mg, 0.67 mmol), 4-nitro-1H-pyrazole (340 mg, 4.5 mmol), Pd$_2$(dba)$_3$ (67 mg, 0.07 mmol), Me$_4$tBuXPhos (35 mg, 0.07 mmol), K$_3$PO$_4$ (368 mg, 1.73 mmol) were mixed in a Schlenk tube. The reaction was degassed with N$_2$ for 15 min and dioxane (8 mL) was added and the reaction was heated to 90° C. for 16 h. The reaction was cooled to room temperature, filtered through celite, concentrated, purified via column chromatography: eluting with gradient CH$_2$Cl$_2$/MeOH (0% to 30% MeOH), column: silica 12 g, to provide 6-(2-methoxy-4-(4-nitro-1H-pyrazol-1-yl)phenyl)-N-methyl-N-(2,2,6,6-tetramethylpiperidin-4-yl)pyridazin-3-amine (202 mg, 65%).

LC-MS: 466 [M+H]$^+$. $^1$H NMR (500 MHz, DMSO-d$_6$) δ: 9.81-9.85 (m, 1H), 8.61 (d, J=0.6 Hz, 1H), 7.91 (d, J=8.5 Hz, 1H), 7.81 (d, J=9.8 Hz, 1H), 7.73 (d, J=1.9 Hz, 1H), 7.68 (dd, J=8.2, 2.2 Hz, 1H), 7.10-7.21 (m, 1H), 5.08-5.26 (m, 1H), 3.96 (s, 3H), 2.95 (s, 3H), 1.59-1.75 (m, 4H), 1.40 (s, 6H), 1.33, (s, 6H), (1 hydrogen corresponding to OH or NH unobserved)

Step 2: 6-(2-Methoxy-4-(4-nitro-1H-pyrazol-1-yl)phenyl)-N-methyl-N-(2,2,6,6-tetramethylpiperidin-4-yl)pyridazin-3-amine (150 mg, 0.32 mmol), benzenethiol (33 μL, 0.32 mmol) and K$_2$CO$_3$ (44 mg, 0.32 mmol) were mixed in a microwave tube. The reaction was degassed with N$_2$ for 15 min and dry NMP (1.5 mL) was added. The reaction was heated in a Biotage microwave at 190° C. for 20 min, then diluted with 10 mL EtOAc, and washed with water and brine. The product was dried over Na$_2$SO$_4$, concentrated under vacuum, then purified via column chromatography: eluting with gradient CH$_2$Cl$_2$/MeOH (0% to 30% MeOH), column: silica 4 g, to provide 2-(6-(methyl(2,2,6,6-tetramethylpiperidin-4-yl)amino)pyridazin-3-yl)-5-(4-nitro-1H-pyrazol-1-yl)phenol (60 mg, 42%) as a brown solid.

LC-MS: 452 [M+H]$^+$. $^1$H NMR (500 MHz, DMSO-d$_6$) δ: 9.77 (s, 1H), 8.68 (d, J=9.8 Hz, 1H), 8.62 (s, 1H), 8.27 (d, J=8.8 Hz, 1H), 7.87-7.94 (m, 1H), 7.66 (dd, J=8.5, 2.6 Hz, 1H), 7.64 (d, J=2.6 Hz, 1H), 5.03-5.22 (m, 1H), 3.01 (s, 3H), 1.84-1.94 (m, 2H), 1.70-1.77 (m, 2H), 1.53 (s, 6H), 1.43 (s, 6H), (2 hydrogens corresponding to OH and NH unobserved)

Using the procedure described for Example 3 above, additional compounds described herein may be prepared by substituting the appropriate starting materials reagents, and reaction conditions, obtaining compounds such as those selected from:

| Cpd | Data |
|---|---|
| 417 | LC-MS: 394 [M + H]$^+$. $^1$H NMR (500 MHz, DMSO-d$_6$) δ: 13.49 (br s, 1H), 8.49 (d, J = 9.8 Hz, 1H), 8.39 (s, 1H), 8.10 (d, J = 8.8 Hz, 1H), 7.79-7.92 (m, 1H), 7.43 (d, J = 9.5 Hz, 1H), 7.34 (d, J = 2.5 Hz, 1H), 7.30 (dd, J = 8.5, 2.5 Hz, 1H), 7.12 (s, 1H), 5.61-5.71 (m, 1H), 2.09 (dd, J = 12.0, 3.8 Hz, 2H), 1.25-1.32 (m, 2H), 1.24 (s, 6H), 1.11 (s, 6H), (1 hydrogen corresponding to OH or NH unobserved) |
| 421 | LC-MS: 409 [M + H]$^+$. $^1$H NMR (500 MHz, methanol-d$_4$) δ: 8.31 (d, J = 9.5 Hz, 1H), 7.92 (d, J = 9.1 Hz, 1H), 7.79 (d, J = 0.6 Hz, 1H), 7.44 (d, J = 0.9 Hz, 1H), 7.24-7.33 (m, 3H), 5.77 (tt, J = 11.2, 4.1 Hz, 1H), 2.28 (dd, J = 12.3, 4.2 Hz, 2H), 1.49 (t, J = 12.3 Hz, 2H), 1.42 (s, 6H), 1.30 (s, 6H), (4 hydrogens corresponding to OH and NH unobserved) |
| 423 | LC-MS: 439 [M + H]$^+$. $^1$H NMR (500 MHz, DMSO-d$_6$) δ: 9.71 (d, J = 0.6 Hz, 1H), 8.58 (d, J = 0.6 Hz, 1H), 8.47 (d, J = 9.5 Hz, 1H), 8.14 (d, J = 8.5 Hz, 1H), 7.59-7.64 (m, 2H), 7.44 (d, J = 9.5 Hz, 1H), 5.67-5.73 (m, 1H), 2.18-2.28 (m, 2H), 1.45-1.56 (m, 2H), 1.37 (s, 6H), 1.27 (s, 6H),), (2 hydrogens corresponding to OH and NH unobserved) |

Example 4 (Compound 424)

5-(1H-Pyrazol-4-yl)-2-[6-(1,2,3,6-tetrahydropyridin-4-yl)pyridazin-3-yl]phenol trihydrochloride Step 1: 3-Bromo-6-(2-methoxy-4-(1-(tetrahydro-2H-pyran-2-yl)-1H-pyrazol-4-yl)phenyl)pyridazine (100 mg, 0.24 mmol), (1-(tert-butoxycarbonyl)-1,2,3,6-tetrahydropyridin-4-yl)boronic acid (66 mg, 0.29 mmol), PddppfCl$_2$ (8 mg, 0.012 mmol), K$_2$CO$_3$ (99 mg, 0.72 mmol) were mixed in a Schlenk tube. The reaction was degassed with N$_2$ for 15 min and dioxane (2 mL) and water (0.5 mL) were added and the reaction was heated to 90° C. for 16 h. The reaction was cooled to room temperature, and partitioned between EtOAc and water. The organic layers were dried over $Na_2SO_4$, then concentrated under vacuum, and purified via column chromatography: eluting with gradient $CH_2Cl_2$/MeOH (0% to 20% MeOH), column: silica 4 g, to provide 5-(1H-pyrazol-4-yl)-2-(6-(1,2,3,6-tetrahydropyridin-4-yl)pyridazin-3-yl)phenol (102 mg, 82%) as an off-white solid.

Step 2: A solution of 5-(1H-pyrazol-4-yl)-2-(6-(1,2,3,6-tetrahydropyridin-4-yl)pyridazin-3-yl)phenol (102 mg, 0.196 mmol) in 2 mL of dry $CH_2Cl_2$ was cooled in ice-water bath. Boron tribromide 1.0 M in $CH_2Cl_2$ (0.98 mL, 0.98 mmol) was added and the reaction mixture was stirred at room temperature for 16 hours. The reaction was quenched with 2 mL of MeOH, stirred for 30 min, then concentrated and purified using preparative HPLC to provide 5-(1H-pyrazol-4-yl)-2-(6-(1,2,3,6-tetrahydropyridin-4-yl)pyridazin-3-yl)phenol (41 mg, 66%) as an off-white solid.

LC-MS: 320 [M+H]$^+$. $^1$H NMR (500 MHz, DMSO-d$_6$) δ: 9.19 (br S, 2H), 8.54 (d, J=9.6 Hz, 1H), 8.22, (d, J=9.6 Hz, 1H), 8.18 (s, 1H), 8.05 (d, J=8.8 Hz, 1H), 7.25-7.29 (m, 2H), 6.92 (s, 1H), 3.85-3.92 (m, 2H), 3.38-3.41 (m, 2H), 2.88-2.98 (m, 2H), (1 hydrogen corresponding to OH or NH unobserved)

Using the procedure described for Example 4 above, additional compounds described herein may be prepared by substituting the appropriate starting materials reagents, and reaction conditions, obtaining compounds such as those selected from:

mL) and water (1 mL) were added and the reaction was heated to 90° C. for 16 h. The reaction was cooled to room temperature, partitioned between EtOAc and water. The organic layers were dried over $Na_2SO_4$, concentrated under vacuum, purified via column chromatography: eluting with gradient hexanes/EtOAc (0% to 40% EtOAc), column: silica 4 g, to provide 3-bromo-6-(2-methoxy-4-(1-(tetrahydro-2H-pyran-2-yl)-1H-pyrazol-4-yl)phenyl)pyridazine (690 mg, 79%) as an off-white fluffy solid.

Step 2: 3-Bromo-6-(2-methoxy-4-(1-(tetrahydro-2H-pyran-2-yl)-1H-pyrazol-4-yl)phenyl)pyridazine (50 mg, 0.12 mmol), tert-butyl 4-aminopiperidine-1-carboxylate (36 mg, 0.18 mmol), potassium t-butoxide (41 mg, 0.36 mmol), tBuXPhos-Pd-G3 (10 mg, 0.012 mmol) were mixed in a Schlenk tube. The reaction was degassed with Ar then dry THF (2 mL) was added and the reaction was heated to 80° C. for 12 h. The reaction was cooled to room temperature, then partitioned between EtOAc and water. The organic layers were dried over $Na_2SO_4$, concentrated under vacuum, and purified via column chromatography: eluting with gradient $CH_2Cl_2$/MeOH (0% to 15% MeOH), column: silica 4 g, to provide tert-butyl 4-((6-(2-methoxy-4-(1-(tetrahydro-2H-pyran-2-yl)-1H-pyrazol-4-yl)phenyl)pyridazin-3-yl)amino)piperidine-1-carboxylate (45 mg, 70%) as a tan solid.

Step 3: A solution of 4-((6-(2-methoxy-4-(1-(tetrahydro-2H-pyran-2-yl)-1H-pyrazol-4-yl)phenyl)pyridazin-3-yl)amino)piperidine-1-carboxylate (45 mg, 0.084 mmol) in 2 mL of dry $CH_2Cl_2$ was cooled in an ice-water bath. Boron tribromide 1.0 M in $CH_2Cl_2$ (0.42 mL, 0.42 mmol) was added and the reaction mixture was stirred at room temperature for 16 hours. The reaction was quenched with 2 mL of MeOH, stirred for 30 min, then concentrated and purified using preparative HPLC to provide 2-(6-(piperidin-4-ylamino)pyridazin-3-yl)-5-(1H-pyrazol-4-yl)phenol (21 mg, 73%) as a yellowish solid.

| Cpd | Data |
|---|---|
| 422 | LC-MS: 334 [M + H]$^+$. $^1$H NMR (500 MHz, DMSO-d$_6$) δ: 11.06 (br s, 1H), 8.56 (d, J = 9.2 Hz, 1H), 8.25 (d, J = 9.2 Hz, 1H), 8.20 (s, 2H), 8.05 (d, J = 8.8 Hz, 1H), 7.22-7.31 (m, 2H), 6.92 (s, 1H), 4.06-4.12 (m, 1H), 3.87-3.94 (m, 1H), 3.62-3.70 (m, 1H), 3.21-3.30 (m, 1H), 3.07-3.12 (m, 2H), 3.03 (s, 3H), (1 hydrogen corresponding to OH or NH unobserved) |
| 425 | LC-MS: 348 [M + H]$^+$. $^1$H NMR (500 MHz, DMSO-d$_6$) δ: 10.94 (br S, 1H), 8.56 (d, J = 9.6 Hz, 1H), 8.26 (d, J = 9.6 Hz, 1H), 8.19-8.23 (m, 2H), 8.05 (d, J = 8.4 Hz, 1H), 7.26-7.31 (m, 2H), 6.93 (s, 1H), 4.07-4.13 (m, 1H), 3.85-3.91 (m, 1H), 3.70-3.74 (m, 1H), 3.22-3.30 (m, 3H), 3.08-3.14 (m, 2H), 1.33 (t, J = 7.2Hz, 3H), (1 hydrogen corresponding to OH or NH unobserved) |
| 429 | LC-MS: 346 [M + H]$^+$. $^1$H NMR (500 MHz, methanol-d$_4$) δ: 1.79-1.89 (m, 1H) 1.98-2.11 (m, 1H) 2.11-2.33 (m, 2H) 2.65-2.80 (m, 1H) 3.09-3.21 (m, 1H) 4.02-4.16 (m, 2H) 7.02-7.14 (m, 1H) 7.24 (s, 2 H) 7.85-7.97 (m, 1H) 8.04 (d, J = 9.46 Hz, 3H) 8.33 (d, J = 9.46 Hz, 1H) |

Example 5 (Compound 427)

2-[6-(Piperidin-4-ylamino)pyridazin-3-yl]-5-(1H-pyrazol-4-yl)phenol tetrahydrochloride Step 1: 3,6-Dibromopyridazine (500 mg, 2.1 mmol), 4-(3-methoxy-4-(4,4,5,5-tetramethyl-1,3,2-dioxaborolan-2-yl)phenyl)-1-(tetrahydro-2H-pyran-2-yl)-1H-pyrazole (970 mg, 2.52 mmol), Pd(dppf)Cl$_2$ (77 mg, 0.11 mmol), $K_2CO_3$ (870 mg, 6.3 mmol) were mixed in a Schlenk tube. The reaction was degassed with $N_2$ for 15 min and dioxane (8

LC-MS: 377 [M+H]$^+$. $^1$H NMR (500 MHz, DMSO-d$_6$) δ: 8.95 (s, 2H), 8.25 (d, J=9.6 Hz, 1H), 8.09 (s, 2H), 7.69 (d, J=8.8 Hz, 1H), 7.49-7.41 (m, 1H), 7.21-7.24 (m, 2H), 4.11-4.15 (m, 1H), 3.34-3.39 (m, 4H), 3.01-3.08 (m, 2H), 2.11-2.17 (m, 2H), 1.79 (q, J=9.2 Hz, 2H)

Using the procedure described for Example 5 above, additional compounds described herein may be prepared by substituting the appropriate starting materials reagents, and reaction conditions, obtaining compounds such as those selected from:

| Cpd | Data |
|---|---|
| 426 | LC-MS: 351 [M + H]⁺. ¹H NMR (500 MHz, DMSO-d₆) δ: 9-22-9.28 (m, 2H), 8.34 (d, J = 9.6 Hz, 1H), 8.06-8.11 (m, 2H), 78.5-7.89 (m, 1H), 7.74 (d, J = 8.2 Hz, 1H), 7.20-7.27 (m, 2H), 4.67-4.75 (m, 2H), 3.35-3.39 (m, 2H), 3.07-3.09 (m, 2H), 3.05 (s, 3H), 2.21 (q, J = 10.2 Hz, 2H), 1.83-1.88 (m, 2H) |
| 432 | LC-MS: 338 [M + H]⁺. ¹H NMR (500 MHz, methanol-d₄) δ: 8.72 (d, J = 9.6 Hz, 1H), 8.41-8.54 (m, 2H), 7.91-8.08 (m, 1H), 7.82 (d, J = 8.0 Hz, 1H), 7.49 (d, J = 8.2 Hz, 1H), 7.38 (s, 1H), 5.51 (quint, J = 2.8 Hz, 1H), 3.30-3.46 (m, 2H), 3.28-3.31 (m, 2H), 2.33-2.38 (m, 2H), 2.25-2.32 (m, 2H), (3 hydrogens corresponding to OH and NH unobserved) |
| 436 | LC-MS: 366 [M + H]⁺. ¹H NMR (500 MHz, DMSO-d₆) δ: 9.17-9.30 (m, 1H), 8.81-8.95 (m, 1H), 8.49 (d, J = 9.8 Hz, 1H), 8.17 (s, 2H), 7.94 (d, J = 8.8 Hz, 1H), 7.46 (d, J = 9.8 Hz, 1H), 7.18-7.29 (m, 2H), 5.47 (spt, J = 5.7 Hz, 1H), 3.31-3.52 (m, 2H), 2.41 (dd, J = 12.9, 5.7 Hz, 2H), 1.68 (q, J = 12.0 Hz, 2H), 1.34 (d, J = 6.3 Hz, 6H), (1 hydrogen corresponding to OH or NH unobserved) |
| 439 | LC-MS: 363 [M + H]⁺. ¹H NMR (500 MHz, DMSO-d₆) δ: 9.07 (s, 2H), 8.28 (d, J = 10 Hz, 1H), 1.7 (s, 2H), 7.81 (d, J = 8.8 Hz, 1H), 7.73 (d, J = 9.6 Hz, 1H), 7.19-7.22 (m, 2H), 3.75-3.81 (m, 4H), 3.58-3.69 (m, 4H), 1.85-1.89 (m, 4H), (1 hydrogen corresponding to OH or NH unobserved) |
| 459 | LC-MS: 349 [M + H]⁺. ¹H NMR (500 MHz, DMSO-d₆) δ: 10.53 (s, 1H), 10.40 (s, 1H), 9.79 (br s, 1H), 9.67 (br s, 1H), 8.28 (d, J = 9.6 Hz, 1H), 8.06 (s, 2H), 7.65 (d, J = 9.6 Hz, 1H), 7.58 (d, J = 8.4 Hz, 1H), 7.21-7.25 (m, 1H), 4.53 (q, J = 14 Hz, 2H), 3.64 (d, J = 12.8 Hz, 1H), 3.52 (d, J = 12.8 Hz, 1H), 3.37-3.40 (m, 2H), 3.15-3.24 (m, 2H), 1.92-2.02 (m, 2H) |

Example 6 (Compound 430)

6-[2,3-Difluoro-4-(1H-pyrazol-4-yl)phenyl]-N-methyl-N-(2,2,6,6-tetramethylpiperidin-4-yl)pyridazin-3-amine hydrochloride Step 1: To a RBF, equipped with a N₂ inlet, were added: 6-bromo-N-methyl-N-(2,2,6,6-tetramethyl-4-piperidyl)pyridazin-3-amine (90 mg, 0.28 mmol), 4-[2,3-difluoro-4-(4,4,5,5-tetramethyl-1,3,2-dioxaborolan-2-yl)phenyl]-1-tetrahydropyran-2-yl-pyrazole (128.8 mg, 0.33 mmol), Pd(PPh₃)₄ (31.8 mg, 0.03 mmol), Na₂CO₃ (87.43 mg, 0.83 mmol). The reaction was degassed with N₂ for 15 min then dioxane (8 mL) and water (2 mL) were added. The reaction was heated to 90° C. for 16 h, then cooled to room temperature, and partitioned between EtOAc and water. The organic layers were dried over Na₂SO₄, concentrated on a rotavap, and purified via column chromatography: eluting with gradient CH₂Cl₂/MeOH (0% to 30%), column: silica 4 g to provide 6-(2,3-Difluoro-4-(1-(tetrahydro-2H-pyran-2-yl)-1H-pyrazol-4-yl)phenyl)-N-methyl-N-(2,2,6,6-tetramethylpiperidin-4-yl)pyridazin-3-amine (88 mg, 63%) as a grey solid.

Step 2: 6-[2,3-Difluoro-4-(1-tetrahydropyran-2-ylpyrazol-4-yl)phenyl]-N-methyl-N-(2,2,6,6-tetramethyl-4-piperidyl)pyridazin-3-amine (88 mg, 0.17 mmol) was dissolved in MeOH (2 mL) and 4M HCl in dioxane (90 μL, 0.34 mmol) was added dropwise. The reaction mixture was stirred at room temperature for 30 min until LC-MS showed complete consumption of starting material. The reaction mixture was concentrated under reduced pressure to provide 6-(2,3-difluoro-4-(1H-pyrazol-4-yl)phenyl)-N-methyl-N-(2,2,6,6-tetramethylpiperidin-4-yl)pyridazin-3-amine hydrochloride salt.

LC-MS: 427 [M+H]⁺. ¹H NMR (500 MHz, DMSO-d₆) δ: 9.21-9.33 (m, 1H), 8.27-8.43 (m, 1H), 8.20 (s, 2H), 8.01 (d, J=9.8 Hz, 1H), 7.60-7.79 (m, 3H), 5.01-5.14 (m, 1H), 3.05 (s, 3H), 2.10 (td, J=13.2, 1.6 Hz, 2H), 1.79 (dd, J=12.9, 4.1 Hz, 2H), 1.55 (s, 6H), 1.50 (s, 6H)

Using the procedure described for Example 6 above, additional compounds described herein may be prepared by substituting the appropriate starting materials reagents, and reaction conditions, obtaining compounds such as those selected from:

| Cpd | Data |
|---|---|
| 426 | LC-MS: 427 [M + H]⁺. ¹H NMR (500 MHz, DMSO-d₆) δ: 9.22-9.38 (m, 1H), 8.33-8.45 (m, 1H), 8.21 (d, J = 1.9 Hz, 2H), 7.97 (dd, J = 10.4, 2.8 Hz, 1H), 7.86 (d, J = 5.7 Hz, 1H), 7.81 (dd, J = 11.7, 6.6 Hz, 1H), 7.54-7.63 (m, 1H), 5.09-5.16 (m, 1H), 3.03 (s, 3H), 2.09 (t, J = 12.9 Hz, 2H), 1.78 (dd, J = 12.9, 3.8 Hz, 2H), 1.55 (s, 6H), 1.51 (s, 6H) |
| 431 | LC-MS: 414 [M + H]⁺. ¹H NMR (500 MHz, DMSO-d₆) δ: 9.24-9.35 (m, 1H), 8.43-8.58 (m, 1H), 8.22 (d, J = 1.6 Hz, 2H), 8.06 (dd, J = 9.1, 1.9 Hz, 1H), 7.87 (dd, J = 12.1, 6.5 Hz, 1H), 7.83 (dd, J = 11.5, 6.5 Hz, 1H), 7.37 (d, J = 9.5 Hz, 1H), 5.77 (tt, J = 10.7, 4.1 Hz, 1H), 2.33 (dd, J = 13.1, 3.9 Hz, 2H), 1.84 (dd, J = 12.9, 11.3 Hz, 2H), 1.54 (s, 6H), 1.52 (s, 6H) |
| 435 | LC-MS: 378 [M + H]⁺. ¹H NMR (500 MHz, methanol-d₄) δ: 8.57-8.58 (m, 1H), 8.55 (d, J = 5.0 Hz, 1H), 8.45 (s, 2H), 8.05-8.10 (m, 1H), 7.95-7.99 (m, 1H), 7.86 (s, 1H), 7.82 (d, J = 9.5 Hz, 1H), 5.79 (tt, J = 10.4, 4.4 Hz, 1H), 2.53 (dd, J = 14.5, 4.5 Hz, 2H), 1.86-2.01 (m, 2H), 1.66 (s, 6H), 1.60 (s, 6H), (2 hydrogens corresponding to NH unobserved) |
| 437 | LC-MS: 396 [M + H]⁺. ¹H NMR (500 MHz, DMSO-d₆) δ: 9.28-9.44 (m, 1H), 8.47-8.61 (m, 1H), 8.25 (s, 2H), 8.01 (dd, J = 9.3, 2.0 Hz, 1H), 7.92 (t, J = 8.2 Hz, 1H), 7.69 (dd, J = 12.8, 1.7 Hz, 1H), 7.65 (dd, J = 8.0, 1.7 Hz, 1H), 7.34 (d, J = 9.1 Hz, 1H), 5.76 (tt, J = 10.7, 4.1 Hz, 1H), 2.33 (dd, J = 13.2, 3.9 Hz, 2H), 1.85 (dd, J = 13.2, 10.1 Hz, 2H), 1.54 (s, 6H), 1.53 (s, 6H) |

| Cpd | Data |
|---|---|
| 440 | LC-MS: 359 [M + H]$^+$. $^1$H NMR (500 MHz, methanol-d$_4$) δ: .06 (d, J = 10.1 Hz, 1H), 7.78 (dd, J = 9.5, 6.3 Hz, 1H), 7.32 (d, J = 9.8 Hz, 1H), 6.58-6.76 (m, 2H), 5.11 (tt, J = 12.0, 4.1 Hz, 1H), 3.02 (s, 3H), 1.73 (dd, J = 12.9, 3.5 Hz, 2H), 1.63 (t, J = 12.5 Hz, 2H), 1.43 (s, 6H), 1.27 (s, 6H), (1 hydrogen corresponding to NH unobserved) |
| 441 | LC-MS: 364 [M + H]$^+$. $^1$H NMR (500 MHz, DMSO-d$_6$) δ: 1.33 (d, J = 6.62 Hz, 6H) 1.65 (q, J = 12.40 Hz, 2H) 2.42 (d, J = 12.61 Hz, 2H) 3.38-3.50 (m, 2H) 5.48 (s, 1H) 6.51-6.63 (m, 1H) 7.42-7.57 (m, 3H) 7.80 (d, J = 1.58 Hz, 1H) 8.09 (d, J = 8.83 Hz, 1H) 8.50 (d, J = 9.46 Hz, 1H) 8.61 (d, J = 2.52 Hz, 1H) 8.76 (br s., 1H) 9.12 (br s., 1H) 13.18 (s, 1H) |
| 442 | LC-MS: 379 [M + H]$^+$. $^1$H NMR (500 MHz, DMSO-d$_6$) δ: 8.42 (s, 1H), 8.28 (dd, J = 1.6, 0.9 Hz, 1H), 8.03 (dd, J = 9.1, 1.6 Hz, 1H), 7.95 (s, 1H), 7.67 (d, J = 9.1 Hz, 1H), 7.14 (d, J = 9.1 Hz, 1H), 5.03-5.17 (m, 1H), 4.19 (s, 3H), 2.94 (s, 3H), 1.49-1.58 (m, 2H), 1.37-1.48 (m, 2H), 1.27 (s, 6H), 1.10 (s, 6H), (1 hydrogen corresponding to NH unobserved) |
| 443 | LC-MS: 366 [M + H]$^+$. $^1$H NMR (500 MHz, methanol-d$_4$) δ: 8.35 (s, 1H), 8.31 (dd, J = 1.6, 0.9 Hz, 1H), 8.11 (d, J = 9.1 Hz, 1H), 7.99 (dd, J = 9.1, 1.9 Hz, 1H), 7.75 (dt, J = 9.1, 0.9 Hz, 1H), 7.21 (d, J = 9.5 Hz, 1H), 5.81 (tt, J = 11.2, 4.1 Hz, 1H), 4.27 (s, 3H), 2.28 (dd, J = 12.6, 4.1 Hz, 2H), 1.48 (t, J = 12.3 Hz, 2H), 1.41 (s, 6H), 1.30 (s, 6H), (1 hydrogen corresponding to NH unobserved) |
| 445 | LC-MS: 379 [M + H]$^+$. $^1$H NMR (500 MHz, acetone-d$_6$) δ: 8.52 (dt, J = 7.0, 1.1 Hz, 1H), 8.13 (dt, J = 8.8, 1.3 Hz, 1H), 7.66 (d, J = 9.8 Hz, 1H), 7.28 (ddd, J = 9.0, 6.8, 1.3 Hz, 1H), 7.13 (d, J = 9.5 Hz, 1H), 6.89 (td, J = 6.9, 1.4 Hz, 1H), 5.22 (tt, J = 12.3, 3.5 Hz, 1H), 3.04 (s, 3H), 2.63 (s, 3H), 1.67 (dd, J = 12.3, 3.5 Hz, 2H), 1.56 (t, J = 12.3 Hz, 2H), 1.36 (s, 6H), 1.18 (s, 6H), (1 hydrogen corresponding to NH unobserved) |
| 446 | LC-MS: 352 [M + H]$^+$. $^1$H NMR (500 MHz, acetone-d$_6$) δ: 9.14 (dd, J = 1.6, 0.9 Hz, 1H), 7.98 (dd, J = 9.5, 1.9 Hz, 1H), 7.94 (t, J = 0.9 Hz, 1H), 7.89 (d, J = 9.5 Hz, 1H), 7.63 (dt, J = 9.5, 0.8 Hz, 1H), 7.60 (d, J = 1.3 Hz, 1H), 7.14 (d, J = 9.5 Hz, 1H), 5.34 (tt, J = 12.6, 3.5 Hz, 1H), 1.67 (dd, J = 12.3, 3.8 Hz, 2H), 1.55 (t, J = 12.1 Hz, 2H), 1.36 (s, 6H), 1.17 (s, 6H), (1 hydrogen corresponding to NH unobserved) |
| 447 | LC-MS: 394 [M + H]$^+$. $^1$H NMR (500 MHz, acetone-d$_6$) δ: 8.47 (d, J = 2.5 Hz, 1H), 8.05 (d, J = 9.1 Hz, 1H), 7.98 (d, J = 8.5 Hz, 1H), 7.76 (d, J = 1.9 Hz, 1H), 7.70 (d, J = 2.2 Hz, 1H), 7.59 (dd, J = 8.5, 2.2 Hz, 1H), 7.06 (d, J = 9.1 Hz, 1H), 6.57 (dd, J = 2.4, 1.7 Hz, 1H), 5.85 (tt, J = 11.3, 4.1 Hz, 1H), 2.21 (dd, J = 12.1, 3.9 Hz, 2H), 2.04-2.08 (m, 2H), 1.35 (s, 6H), 1.18 (s, 6H), (2 hydrogens corresponding to OH and NH unobserved) |
| 452 | LC-MS: 409 [M + H]$^+$. $^1$H NMR (500 MHz, acetone-d$_6$) δ: 7.59 (dd, J = 8.5, 6.0 Hz, 1H), 7.46 (s, 2H), 7.31 (dd, J = 10.1, 2.5 Hz, 1H), 7.15 (td, J = 8.5, 2.5 Hz, 1H), 7.04 (d, J = 9.5 Hz, 1H), 6.91 (d, J = 9.5 Hz, 1H), 5.23 (tt, J = 12.3, 2.8 Hz, 1H), 3.00 (s, 3H), 1.65 (dd, J = 12.3, 3.5 Hz, 2H), 1.51 (t, J = 12.1 Hz, 2H), 1.33 (s, 6H), 1.15 (s, 6H), (2 hydrogens corresponding to NH unobserved) |
| 455 | LC-MS: 344 [M + H]$^+$. $^1$H NMR (500 MHz, methanol-d$_4$) δ: 8.17 (d, J = 9.5 Hz, 1H), 7.66 (d, J = 8.8 Hz, 1H), 7.19 (d, J = 9.5 Hz, 1H), 6.44 (dd, J = 8.7, 2.4 Hz, 1H), 6.41 (d, J = 2.5 Hz, 1H), 5.71 (tt, J = 11.0, 3.8 Hz, 1H), 2.23 (dd, J = 12.6, 4.1 Hz, 2H), 1.40-1.47 (m, 2H), 1.39 (s, 6H), 1.27 (s, 6H), (3 hydrogens corresponding to OH and NH unobserved) |
| 456 | LC-MS: 425 [M + H]$^+$. $^1$H NMR (500 MHz, DMSO-d$_6$) δ: 9.23-9.39 (m, 1H), 8.39-8.52 (m, 1H), 8.26 (s, 2H), 8.00-8.08 (m, 1H), 7.93 (s, 1H), 7.81-7.85 (m, 1H), 7.78 (d, J = 7.9 Hz, 1H), 7.63 (d, J = 8.2 Hz, 1H), 4.95-5.03 (m, 1H), 3.08 (s, 3H), 2.13 (t, J = 12.9 Hz, 2H), 1.81 (dd, J = 12.9, 3.5 Hz, 2H), 1.56 (s, 6H), 1.52 (s, 6H) |
| 458 | LC-MS: 414 [M + H]$^+$. $^1$H NMR (500 MHz, DMSO-d$_6$) δ: 8.70-9.36 (m, 1H), 8.29 (s, 2H), 7.85 (d, J = 9.1 Hz, 1H), 7.60 (d, J = 9.5 Hz, 1H), 7.33-7.39 (m, 1H), 5.59-5.68 (m, 1H), 2.24-2.33 (m, 2H), 1.72-1.82 (m, 2H), 1.50 (s, 6H), 1.48 (s, 6H), (2 hydrogens corresponding to NH unobserved) |

Example 7 (Compound 434)

6-[2-Methoxy-6-(1H-pyrazol-4-yl)pyridin-3-yl]-N-methyl-N-(2,2,6,6-tetramethylpiperidin-4-yl) pyridazin-3-amine hydrochloride 6-(2-Methoxy-6-(1-(tetrahydro-2H-pyran-2-yl)-1H-pyrazol-4-yl)pyridin-3-yl)-N-methyl-N-(2,2,6,6-tetramethylpiperidin-4-yl)pyridazin-3-amine (6 mg) was dissolved in 1 mL of 4N HCl/dioxane and the resulting mixture was stirred at RT for 20 minutes. The mixture was evaporated and triturated with ether to provide 6-(2-methoxy-6-(1H-pyrazol-4-yl)pyridin-3-yl)-N-methyl-N-(2,2,6,6-tetramethylpiperidin-4-yl)pyridazin-3-amine 4 mg, 75%).

LC-MS: 422 [M+H]$^+$. $^1$H NMR (500 MHz, methanol-d$_4$) δ: 8.42-8.47 (m, 1H), 8.33-8.42 (m, 2H), 8.09-8.17 (m, 1H), 7.99-8.08 (m, 1H), 7.50-7.56 (m, 1H), 5.0 (m, 1H), 4.16 (s, 3H), 3.20 (s, 3H), 1.94-2.15 (m, 4H), 1.65 (s, 6H), 1.57 (s, 6H)

Example 8 (Compound 460)

3-{6-[Methyl(2,2,6,6-tetramethylpiperidin-4-yl)amino]pyridazin-3-yl}-6-(1H-pyrazol-4-yl)pyridin-2-ol hydrochloride Step 1: 6-Chloro-N-methyl-N-(2,2,6,6-tetramethylpiperidin-4-yl)pyridazin-3-amine (280 mg, 1.0 mmol) was dissolved in 10 mL, a mixture of dioxane and water (4:1). To the solution was added sodium carbonate (190 mg, 3 eq), (6-chloro-2-methoxypyridin-3-yl)boronic acid (190 mg, 1 eq) and Pd(Ph$_3$P)$_4$ (70 mg, 0.1 eq). The reaction mixture was stirred at 90° C. for 16 h, then applied to a column and purified using DCM/MeOH to yield (133 mg, 55%) 6-(6- chloro-2-methoxypyridin-3-yl)-N-methyl-N-(2,2,6,6-tetramethylpiperidin-4-yl)pyridazin-3-amine.

LC-MS: 390 [M+H]$^+$. $^1$H NMR (500 MHz, DMSO-d$_6$) δ: 8.25 (d, J=7.88 Hz, 1H), 7.83 (d, J=9.77 Hz, 1H), 7.24 (d, J=7.88 Hz, 1H), 7.11 (d, J=9.77 Hz, 1H), 5.00-5.24 (m, 1H), 3.93 (s, 3H), 2.87-2.96 (m, 3H), 1.40-1.57 (m, 4H), 1.21-1.29 (m, 7H), 1.10 (br s, 6H

Step 2: 6-(6-Chloro-2-methoxypyridin-3-yl)-N-methyl-N-(2,2,6,6-tetramethylpiperidin-4-yl)pyridazin-3-amine (90 mg) was dissolved in a mixture of dioxane and water (4:1, 5 mL). To the solution was added sodium carbonate (100 mg, 3 eq), 1-(tetrahydro-2H-pyran-2-yl)-4-(4,4,5,5-tetramethyl-1,3,2-dioxaborolan-2-yl)-1H-pyrazole (70 mg, 1.1 eq) and Pd(Ph$_3$P)$_4$ (27 mg, 0.1 eq). The reaction mixture was stirred at 90° C. for 16 h, then purified by column chromatography using DCM/MeOH to yield 80 mg (68%) of 6-(2-methoxy-6-(1-(tetrahydro-2H-pyran-2-yl)-1H-pyrazol-4-yl)pyridin-3-yl)-N-methyl-N-(2,2,6,6-tetramethylpiperidin-4-yl)pyridazin-3-amine.

Step 3: 6-(2-Methoxy-6-(1-(tetrahydro-2H-pyran-2-yl)-1H-pyrazol-4-yl)pyridin-3-yl)-N-methyl-N-(2,2,6,6-tetramethylpiperidin-4-yl)pyridazin-3-amine (45 mg) was dissolved in 4 mL of 4N HCl/dioxane and the resulting mixture was heated for 2 hours at 60° CF. The resulting mixture was evaporated and triturated with ether to provide 3-(6-(methyl (2,2,6,6-tetramethylpiperidin-4-yl)amino)pyridazin-3-yl)-6-(1H-pyrazol-4-yl)pyridin-2-ol (24 mg, 61%).

LC-MS: 408 [M+H]$^+$; NMR (500 MHz, methanol-d$_4$) δ: 8.62-8.69 (m, 1H), 8.55-8.61 (m, 1H), 8.39 (s, 2H), 7.95-8.06 (m, 1H), 7.04-7.14 (m, 1H), 5.02-5.24 (m, 1H), 3.18 (s, 3H), 2.03 (s, 4H), 1.67 (s, 6H), 1.57 (s, 6H)

Using the procedure described for Example 8 above, an additional compound described herein may be prepared by substituting the appropriate starting materials reagents, and reaction conditions, obtaining compounds such as those selected from:

| Cpd | Data |
|---|---|
| 461 | LC-MS: 395 [M + H]$^+$. $^1$H NMR (500 MHz, methanol-d$_4$) δ: 8.46 (d, J = 9.5 Hz, 1H), 8.33-8.42 (m, 1H), 8.29 (d, J = 7.6 Hz, 1H), 8.10-8.23 (m, 1H), 7.20 (d, J = 9.1 Hz, 1H), 6.86 (d, J = 7.3 Hz, 1H), 5.84 (tt, J = 10.4, 3.8 Hz, 1H), 2.49 (dd, J = 13.9, 4.1 Hz, 2H), 1.86 (dd, J = 13.9, 10.4 Hz, 2H), 1.65 (s, 6H), 1.56 (s, 6H), (3 hydrogens corresponding to OH and NH unobserved) |

BIOLOGICAL EXAMPLES

The following in vitro biological examples demonstrate the usefulness of the compounds of the present description for treating Huntington's disease.

To describe in more detail and assist in understanding the present description, the following non-limiting biological examples are offered to more fully illustrate the scope of the description and are not to be construed as specifically limiting the scope thereof. Such variations of the present description that may be now known or later developed, which would be within the purview of one skilled in the art to ascertain, are considered to fall within the scope of the present description and as hereinafter claimed.

Example 1

Development and Validation of Meso Scale Discovery (MSD) Assay to Quantify Mutant and Total Huntingtin Protein (HTT)—Best Pair Analysis for Endogenous HTT Detection To identify orally bioavailable small molecules useful for HTT reduction, high throughput ELISA methods to detect and measure both total HTT (wild-type and mutant) (tHTT) and mutant HTT (mHTT) in cells and tissues from HD patients and animal models are needed. The method described herein permits relatively high throughput protein measurement of tHTT and mHTT levels in cells and tissues from HD patients and in HD animal models. The ELISA method described herein enables screening of molecules for their ability to decrease the level of HTT and to identify and optimize small molecules for use in treating HD.

To determine the combination of antibodies that detect HTT (wild type and mutant) in a sensitive, high throughput format, multiple commercially available antibodies (Table 1) were screened in capture/detection combinations.
Protocol for Best Pair Analysis for Antibody Comparison in Detecting Total and Mutant HTT in Cells 1. Cells were cultured in a cell culture-compatible 96-well plate.
2. The medium was removed and 50-100 μL of lysis buffer per well (composition described below) was added to cells to provide a "cell lysate". The plate was placed on a shaker at 4° C. for 30 minutes, then stored at −20° C.
3. A Capture Antibody Diluent was prepared by diluting the capture antibody in PBS for standard plates as described in the plate layout, then 30 μL of the Capture Antibody Diluent was added per well. The plate was sealed and incubated at 4° C. overnight.
4. The plate was washed 3× with 200 μL of Wash Buffer. Blocking Buffer (150 μL per well) was added, then the plate was sealed and incubated on a plate shaker for 3-4 hours at room temperature (RT).
5. The Blocking Buffer was decanted and the plate was washed 3× with 200 μL of Wash Buffer. The cell lysate (25 μL per well) was then added. The plate was sealed and incubated at 4° C. overnight.
6. A First Detection Antibody Diluent was prepared by diluting a first detection antibody for pairing in an Assay Antibody Diluent. The plate was washed 3× with 200 μL of Wash Buffer, then 25 μL of the First Detection Antibody Diluent was added per well. The plate was sealed and incubated on a plate shaker for 1 hour at RT.
7. A Second Detection Antibody Diluent was prepared by diluting a second detection antibody for pairing in an Assay Antibody Diluent. The plate was washed 3× with 200 μL of Wash Buffer, then 25 μL of the Second Detection Antibody Diluent was added per well. The plate was sealed and incubated on a plate shaker for 1 hour at RT.

8. The Read Buffer was diluted 4×. The plate was washed 3× with 200 µL of Wash Buffer, then 150 µL of the Read Buffer was added per well. The plate were read immediately following.

The various commercially available antibodies screened in the Best Pair Analysis, providing different capture/detection combinations are shown in Table 1. The capture/detection antibody pairs evaluated are shown in Table 2. The two antibody pairs that gave the maximum spread of values (higher signal to noise ratio) were selected for polyglutamine-expanded (mHTT) and total human HTT detection.

TABLE 1

| Species | ID | Antibody Epitope |
|---|---|---|
| monoclonal mouse | MAB2166 | Huntingtin fragment from aa 181-810 as a fusion protein |
| monoclonal rat | MAB2174 | Huntingtin fusion protein 549-679, fused to Glutathione S-tranferase |
| monoclonal mouse | MAB5374 | GST fusion protein from the first 256 amino acids from human huntingtin with the deletion of the polyglutamine tract |
| goat polyclonal | sc-8767 | Peptide mapping near the N-terminus of Huntingtin of human origin (N18) |
| monoclonal mouse | P1874 | GST human Huntingtin (N-terminal fragment of 171 amino acids containing 65Q) |
| monoclonal mouse | MAB1574 | Homopolymeric glutamine stretch |
| monoclonal rabbit | #5656S | Synthetic peptide corresponding to residues surrounding Pro1220 of human huntingtin protein |
| monoclonal mouse | MW1 | DRPLA-19Q |

TABLE 2

| Pair | HTT MSD | ID | Signal to Noise ratio |
|---|---|---|---|
| Capture/Detection | Total | MAB2166/MAB2174 | 95 |
| Capture/Detection | Total | MAB2166/sc-8767 | 6 |
| Capture/Detection | Total | sc-8767/#5656 | 5 |
| Capture/Detection | Total | MAB2166/#5656S | 483 |
| Capture/Detection | Mutant | MAB5374/#5656S | 8 |
| Capture/Detection | Mutant | MAB1574/#5656S | 25 |
| Capture/Detection | Mutant | P1874/#5656S | 20 |
| Capture/Detection | Mutant | MW1/#5656S | 45 |

Characteristics for Best Pair capture/detection antibody pairs are those combinations that give minimum background and maximum signal. Such highly sensitive ELISA assays would be useful to detect HTT in the context of drug discovery for screening agents (small and large molecules and gene therapies) and for use in detecting HTT as a biomarker in clinical studies. Such capture/detection antibody pairs for quantifying total HTT are selected from MAB2166/MAB2174 and MAB2166/#5656S. Such capture/detection antibody pairs for quantifying mutant HTT are selected from MAB1574/#5656S, P1874/#5656S and MW1/#5656S. The antibody pair for mHTT (MW1/#5656S) and the other for total HTT (MAB2166/#5656S) from this analysis were further optimized and validated to provide high-throughput assays that enabled HTT detection in patient fibroblasts and lymphocytes.

The Endogenous Huntingtin Protein assay used in Example 2 was developed using the Best Pair antibodies identified in Table 2, providing highly sensitive, high-throughput detection assays for polyglutamine-expanded (mHTT) and total human HTT in multiple cell systems. The platform used for the assay is the ELISA-based Meso Scale Discovery (MSD) electrochemiluminescence assay platform.

Example 2

Endogenous Huntingtin Protein Assay

Meso Scale Discovery (MSD) 96-well or 384-well plates were coated overnight at 4° C. with MW1 (expanded polyglutamine) or MAB2166 monoclonal antibody (for capture) at a concentration of 1 µg/mL in PBS (30 µL per well). Plates were then washed three times with 300 µL wash buffer (0.05% Tween-20 in PBS) and blocked (100 µL blocking buffer; 5% BSA in PBS) for 4-5 hours at room temperature with rotational shaking and then washed three times with wash buffer.

Samples (25 µL) were transferred to the antibody-coated MSD plate and incubated overnight at 4° C. After removal of the lysates, the plate was washed three times with wash buffer, and 25 µL of #5656S (Cell signaling; rabbit monoclonal) secondary antibody (diluted to 0.25 µg/mL in 0.05% Tween-20 in blocking buffer) was added to each well and incubated with shaking for 1 Hour at room temperature. Following incubation with the secondary antibody, the wells were rinsed with wash buffer after which 25 µL of goat anti-rabbit SULFO TAG secondary detection antibody (required aspect of the MSD system) (diluted to 0.25 µg/mL in 0.05% Tween-20 in blocking buffer) was added to each well and incubated with shaking for 1 hour at room temperature. After rinsing three times with wash buffer, 150 µL of read buffer T with surfactant (MSD) were added to each empty well, and the plate was imaged on a SI 6000 imager (MSD) according to manufacturers' instructions provided for 96- or 384-well plates. The resulting $IC_{50}$ values (µM) for compounds tested are shown in Table 3.

As shown in Table 3, test compounds described herein had the following $IC_{50}$ values, an $IC_{50}$ value between >3 µM and ≤9 µM is indicated by a single star (*), an $IC_{50}$ value between >1 µM and ≤3 µM is indicated by two stars (), an $IC_{50}$ value between >0.5 µM and ≤1 µM is indicated by three stars (*), an $IC_{50}$ value between >0.1 µM and ≤0.5 µM is indicated by four stars (**) and an $IC_{50}$ value of ≤0.1 µM is indicated by five stars (***).

TABLE 3

| Cpd | IC$_{50}$ |
|---|---|
| 16 | * |
| 26 | **** |
| 31 | **** |
| 460 | * |
| 39 | * |
| 44 | ***** |
| 46 | ***** |
| 47 | **** |
| 48 | ***** |
| 51 | ***** |
| 63 | ***** |
| 64 | ***** |
| 170 | ***** |
| 176 | ***** |
| 200 | ***** |
| 207 | **** |
| 212 | ***** |
| 218 | ***** |
| 258 | **** |
| 307 | **** |
| 315 | ***** |
| 318 | ***** |
| 348 | ***** |
| 350 | ***** |
| 352 | **** |
| 393 | ***** |
| 411 | ***** |
| 412 | ***** |
| 413 | ***** |
| 414 | ***** |
| 415 | ***** |
| 416 | ***** |
| 417 | ***** |
| 418 | ***** |
| 419 | ***** |
| 420 | ***** |
| 421 | ***** |
| 422 | ***** |
| 423 | ***** |
| 424 | **** |
| 425 | **** |
| 426 | **** |
| 427 | **** |
| 428 | **** |
| 429 | **** |
| 430 | **** |
| 431 | **** |
| 432 | **** |
| 433 | **** |
| 434 | *** |
| 435 | *** |
| 436 | *** |
| 437 | ** |
| 438 | ** |
| 439 | ** |
| 440 | * |
| 441 | * |
| 442 | * |
| 443 | * |
| 444 | * |
| 445 | * |
| 446 | * |
| 447 | * |
| 448 | * |
| 449 | * |
| 450 | * |
| 451 | * |
| 451 | * |
| 452 | * |
| 454 | * |
| 455 | * |
| 456 | * |
| 456 | * |
| 456 | * |
| 457 | * |
| 458 | * |
| 459 | * |
| 460 | * |
| 461 | * |
| 462 | * |
| 463 | * |
| 464 | * |
| 465 | * |

Without regard to whether a document cited herein was specifically and individually indicated as being incorporated by reference, all documents referred to herein are incorporated by reference into the present application for any and all purposes to the same extent as if each individual reference was fully set forth herein.

Having now fully described the subject matter of the claims, it will be understood by those having ordinary skill in the art that the same can be performed within a wide range of equivalents without affecting the scope of the subject matter or embodiments described herein. It is intended that the appended claims be interpreted to include all such equivalents.

What is claimed is:

1. A compound, or a form thereof, selected from the group consisting of:
   N,2,2,6,6-pentamethyl-N-{5-[3-(1H-pyrazol-4-yl)phenoxy]-1,3,4-thiadiazol-2-yl}piperidin-4-amine, and
   N,2,2,6,6-pentamethyl-N-{5-[4-(1H-pyrazol-4-yl)phenoxy]-1,3,4-thiadiazol-2-yl}piperidin-4-amine;
   wherein a form of the compound is selected from the group consisting of a salt, clathrate, isotopologue, racemate, enantiomer, diastereomer, stereoisomer, and tautomer form thereof.

2. A compound salt, or a form thereof, selected from the group consisting of:
   N,2,2,6,6-pentamethyl-N-{5-[3-(1H-pyrazol-4-yl)phenoxy]-1,3,4-thiadiazol-2-yl}piperidin-4-amine hydrochloride, and
   N,2,2,6,6-pentamethyl-N-{5-[4-(1H-pyrazol-4-yl)phenoxy]-1,3,4-thiadiazol-2-yl}piperidin-4-amine hydrochloride;
   wherein a form of the compound salt is selected from the group consisting of a clathrate, isotopologue, racemate, enantiomer, diastereomer, stereoisomer, and tautomer form thereof.

3. A method for treating or ameliorating Huntington's Disease in a subject in need thereof comprising administering to the subject an effective amount of the compound, or form thereof, of claim 1.

4. A method for treating or ameliorating Huntington's Disease in a subject in need thereof comprising administering to the subject an effective amount of the compound salt, or form thereof, of claim 2.

5. The method of claim 3, wherein the effective amount of the compound, or form thereof, is in a range of from about 0.001 mg/kg/day to about 500 mg/kg/day.

6. The method of claim 4, wherein the effective amount of the compound salt, or form thereof, is in a range of from about 0.001 mg/kg/day to about 500 mg/kg/day.

7. A pharmaceutical composition comprising the compound of claim 1, or form thereof, in admixture with one or more pharmaceutically acceptable excipient(s).

8. A pharmaceutical composition comprising the compound salt of claim 2, or form thereof, in admixture with one or more pharmaceutically acceptable excipient(s).

* * * * *